US012773147B2

(12) United States Patent
Selvitelli et al.

(10) Patent No.: US 12,773,147 B2
(45) Date of Patent: Oct. 27, 2026

(54) MULTIPARAMETER LEAD SET AND METHODS OF USE THEREOF

(71) Applicant: KPR U.S., LLC, Mansfield, MA (US)

(72) Inventors: David M. Selvitelli, Chicopee, MA (US); Kathleen M. Tremblay, Chicopee, MA (US); Melvin A. Finke, Deland, FL (US); Erick Garstka, Chicopee, MA (US)

(73) Assignee: KPR U.S., LLC, Mansfield, MA (US)

( * ) Notice: Subject to any disclaimer, the term of this patent is extended or adjusted under 35 U.S.C. 154(b) by 466 days.

(21) Appl. No.: 17/451,446

(22) Filed: Oct. 19, 2021

(65) Prior Publication Data

US 2022/0117502 A1 Apr. 21, 2022

Related U.S. Application Data

(60) Provisional application No. 63/093,650, filed on Oct. 19, 2020.

(51) Int. Cl.

*A61B 5/273* (2021.01)
*A61B 5/0205* (2006.01)
*A61B 5/318* (2021.01)

(52) U.S. Cl.

CPC .......... *A61B 5/273* (2021.01); *A61B 5/02055* (2013.01); *A61B 5/318* (2021.01); *A61B 2562/222* (2013.01); *A61B 2562/225* (2013.01)

(58) Field of Classification Search

CPC ..... A61B 5/02055; A61B 5/273; A61B 5/318; A61B 5/28; A61B 2562/222; A61B 2562/225; A61B 2562/227

See application file for complete search history.

(56) References Cited

U.S. PATENT DOCUMENTS

| | | | | |
|---|---|---|---|---|
| 5,343,869 | A * | 9/1994 | Pross | G16H 15/00 600/513 |
| 5,402,884 | A | 4/1995 | Gilman et al. | |
| 5,491,299 | A * | 2/1996 | Naylor | A61B 5/303 174/105 R |
| 7,104,801 | B1 | 9/2006 | Brodnick et al. | |
| 7,403,808 | B2 | 7/2008 | Istvan et al. | |
| 11,224,373 | B2 * | 1/2022 | Verbakel | A61B 5/303 |

(Continued)

FOREIGN PATENT DOCUMENTS

| | | | | |
|---|---|---|---|---|
| CN | 106129744 A | * 11/2016 | | A61B 5/0402 |
| JP | 3007818 U | 2/1995 | | |

(Continued)

*Primary Examiner* — Amanda L Steinberg
*Assistant Examiner* — Laura Hodge
(74) *Attorney, Agent, or Firm* — ArentFox Schiff LLP

(57) ABSTRACT

A multiparameter lead set, method of use, and method of assembling or re-processing a multiparameter lead set. The multiparameter lead set includes a first patient lead for monitoring a first health indicator of a patient. The first patient lead further includes a first lead interconnection feature. The lead set further includes a second patient lead for monitoring a second health indicator of the patient. The second patient lead further include a second lead interconnection feature. The second lead interconnection feature and the first lead interconnection feature are interconnectable to removably connect a first portion of the first patient lead to a second portion of the second patient lead.

19 Claims, 44 Drawing Sheets

(56) References Cited

U.S. PATENT DOCUMENTS

| | | | | |
|---|---|---|---|---|
| 11,817,660 | B1* | 11/2023 | Ghaffari | H01R 13/6277 |
| 2006/0161068 | A1 | 7/2006 | Hastings et al. | |
| 2006/0178030 | A1* | 8/2006 | Lund | H01B 9/003<br>439/287 |
| 2009/0301754 | A1* | 12/2009 | Morley-Smith | H01B 7/40<br>29/745 |
| 2012/0197144 | A1 | 8/2012 | Christ et al. | |
| 2016/0120434 | A1 | 5/2016 | Park et al. | |
| 2020/0138288 | A1* | 5/2020 | Al-Ali | A61B 5/002 |
| 2021/0196192 | A1* | 7/2021 | Piraino | A61B 5/339 |

FOREIGN PATENT DOCUMENTS

| | | | |
|---|---|---|---|
| JP | 2008142544 | A | 6/2008 |
| JP | 2019526323 | A | 9/2019 |
| WO | 2018/033503 | A1 | 2/2018 |

* cited by examiner

MULTIPARAMETER LEAD SET AND METHODS OF USE THEREOF

CLAIM OF PRIORITY UNDER 35 U.S.C § 119

The present Application for Patent claims priority to U.S. Provisional Application No. 63/093,650, entitled "MULTIPARAMETER LEAD SET AND METHODS OF USE THEREOF," filed on Oct. 19, 2020 and assigned to the assignee hereof and hereby expressly incorporated by reference.

FIELD OF THE INVENTION

Aspects of the present disclosure relate to multiparameter lead sets and cable and connection management for use with a variety of sensing devices within a medical system, such as with physiologic monitoring systems, and methods of use thereof.

BACKGROUND

When a patient requires monitoring for observation, treatment, or a combination of both, such as in a medical environment, e.g., a hospital, nursing home, or assisted living facility, the patient's vital signs and other health indicators may be monitored in order to continually and accurately assess the patient's well-being. One such vital sign is the monitoring of the heart via an electrocardiogram, which may be commonly referred to as an EKG and/or ECG. To monitor events of the heart via an EKG, a series of 3, 5, 6, 10, or 14 or more electrodes may be placed on a patient to sense electrical signals corresponding to activity of a patient's heart. For example, each of the electrodes may be used to allow the charge carriers (electrons) within the electrodes to communicate with the charge carriers (ions) within the body via electrochemical exchange. Thus, placing the EKG electrodes on the body surface of a patient allows for voltage changes within the body to be recorded and/or displayed to a heath professional after adequate amplification of the signal.

SUMMARY

This summary is provided to introduce a selection of concepts in a simplified form that are further described below in the DETAILED DESCRIPTION. This summary is not intended to identify key features of the claimed subject matter, nor is it intended to be used as an aid in determining the scope of the claimed subject matter.

In various aspects of the present disclosure, multiparameter lead sets including a plurality of monitoring devices (also interchangeably referred to herein as "patient connectors") that may be attached to a patient and electronically communicate with a patient monitor via a cable system are described, in addition to methods of use thereof. The lead sets may include a variety of sensors and/or other devices that are attachable or otherwise connectable to patient to provide health indicators, such as one or more temperature sensors, a plurality of electrodes or electrode connectors configured to selectively mount to electrodes for monitoring the electrical activity of the heart, and/or an $SpO_2$ or other sensor for monitoring patient blood oxygen saturation levels. The multiparameter lead set may have a single or multiple lead connectors configured be connectable to a single or multiple monitoring stations. The single or multiple connectors may consolidate the connection of multiple monitoring devices and/or leads for use with the single or multiple monitoring stations.

In one aspect of the present disclosure, a multiparameter lead set is disclosed. The multiparameter lead set may include a first patient lead for monitoring a first health indicator of a patient, the first patient lead extending between a first lead distal end and a first lead proximal end. The first patient lead may further include a first patient connector at the first lead distal end that is configured to be attached to a patient for monitoring the first health indicator of the patient and a first lead connector at the first lead proximal end. The first patient lead may further include a first lead interconnection feature. The multiparameter lead set may further include a second patient lead for monitoring a second health indicator of the patient, the second patient lead extending between a second lead distal end and a second lead proximal end. The second patient connector at the second lead distal end may be configured to be attached to the patient for monitoring the second health indicator of the patient; and may be connected to a second lead connector at the second lead proximal end. The second patient lead may further include a second lead interconnection feature, wherein the first lead interconnection feature and the second lead interconnection feature are interconnectable to removably connect a first portion of the first patient lead to a second portion of the second patient lead. For example, the first patent lead may have a series of 3, 5, 6, 10, or 14 ECG patient connectors at a distal end, a first lead connector at a proximal end; and a first wire or series of wires connecting the ECG patient connectors and the first lead connector. The second patient lead may have a temperature sensor at a distal end, a second lead connector at a proximal end, and a second wire or series of wires connecting the temperature sensor and the second patient connector. In the aforementioned example, at least a section of the first wire and second wire and/or first lead connector and second lead connector include interconnection features allowing for the first patient lead and second patient lead to be connectable/disconnectable from one another.

In one aspect of the present disclosure, a method of monitoring at least two health indicators of a patient is disclosed. The method includes connecting a first patient connector of a first patient lead to the patient, wherein the first patient lead is for monitoring a first one of the at least two health indicators of the patient and includes a first lead interconnection feature that is configured to be connectable to and disconnectable from a second patient lead via a first interconnection feature of the first patient lead and a second lead interconnection feature of the second patient lead. The method further includes a step of connecting a second patient connector of the second patient lead to the patient, wherein the second patient lead is for monitoring a second one of the at least two health indicators of the patient. The method further comprises connecting the first lead interconnection feature to the second lead interconnection feature or partially disconnecting the first interconnection feature from the second interconnection feature, and connecting a first lead connector of the first lead and a second lead connector of the second lead to at least one monitoring device.

In one aspect of the present disclosure, a method of assembling or reconstructing a multiparameter lead set is disclosed. The lead set comprises a first type of patient lead for monitoring a first health indicator of a patient and a second type of patient lead for monitoring a second health indicator of a patient that is connectable to and disconnectable from the first type of patient lead. The first type of patient lead comprises a first patient connector and a first lead connector and the second type of patient lead comprises a second patient connector and a second lead connector. The method of assembling or reconstructing comprises the steps of: selecting a plurality of leads for the lead set for assembling or reconstructing, wherein the plurality of leads comprises one of the first type of patient lead and one of the second type of patient lead; disconnecting the one of the first type of patient lead and the one of the second type of patient lead if the one of the first type of patient lead and one of the second type of patient lead are not already separated; and sanitizing, sterilizing and/or high level disinfection (HLD) the one of the first type of patient lead and the one of the second type of lead.

Additional advantages and novel features of these aspects will be set forth in part in the description that follows, and in part will become more apparent to those skilled in the art upon examination of the following or upon learning by practice of the present disclosure.

BRIEF DESCRIPTION OF THE DRAWINGS

The novel features believed to be characteristic of aspects of the present disclosure are set forth in the appended claims. In the description that follows, like parts are marked throughout the specification and drawings with the same numerals, respectively. The drawing figures are not necessarily drawn to scale and certain figures may be shown in exaggerated or generalized form in the interest of clarity and conciseness. The present disclosure itself, however, as well as a preferred mode of use, further objects and advantages thereof, will be best understood by reference to the following detailed description of illustrative aspects of the disclosure when read in conjunction with the accompanying drawings, wherein:

DETAILED DESCRIPTION

Figure 1:
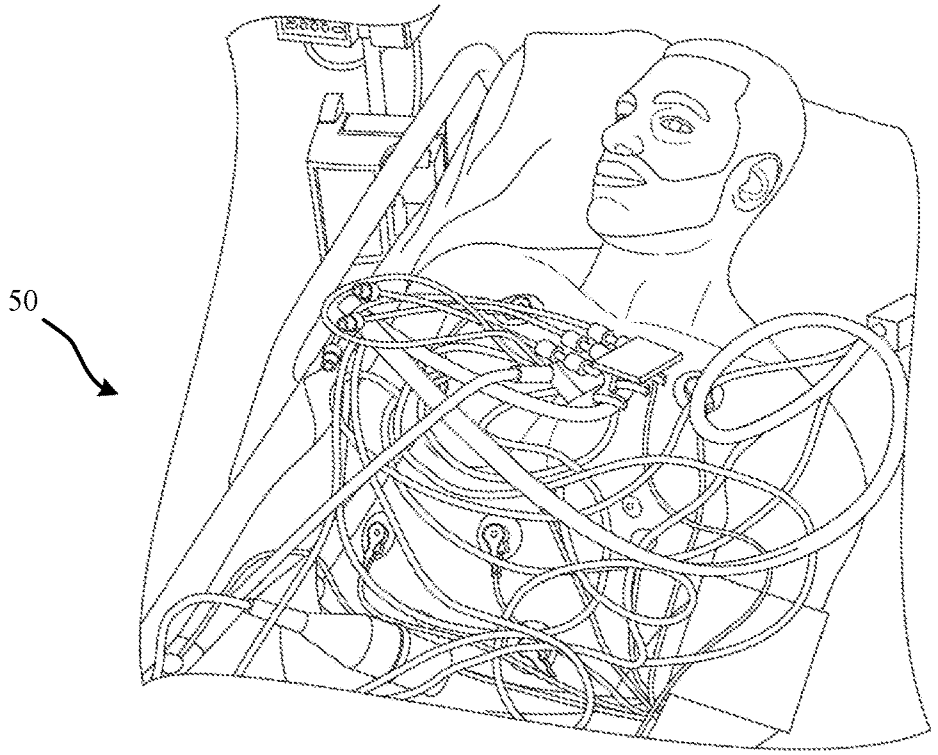
FIG. 1 Related Art
FIG. 1 illustrates an example of patient with a number of monitoring devices or other patient leads connected in accordance with the related art.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details.

For context, a broad overview is provided of aspects of the present disclosure and the advantages the present disclosure provides. This overview, and the detailed description that follows, been presented for purposes of illustration and description. It is not intended to be exhaustive nor to limit the present disclosure to the forms described. Numerous modifications are possible in light of the above teachings, including a combination of the abovementioned aspects. Some of those modifications have been discussed and others will be understood by those skilled in the art. The various aspects were chosen and described in order to best illustrate the principles of the present disclosure and various aspects as are suited to the particular use contemplated. The scope of the present disclosure is, of course, not limited to the examples or aspects set forth herein, but can be employed in any number of applications and equivalent devices by those of ordinary skill in the art. Rather, it is hereby intended the scope be defined by the claims appended hereto.

When a patient requires monitoring for observation, treatment, or a combination of both, such as in a medical environment, e.g., a hospital, nursing home, or assisted living facility, the patient's vital signs and other health indicators may be monitored to assess the patient's well-being. In such practice, various health indicators, including body temperature, blood oxygen saturation levels, pulse, respiration rate, blood pressure (e.g., non-invasive blood pressure or NIBP), and electrical activity of the heart (e.g., via an electrocardiogram or "EKG" or "ECG"), to name a few examples, may be monitored via a single or plurality of different medical devices. However, each device may be designed to measure a single indicator. For example, an EKG monitoring device may be used for monitoring a patient's heart functions and/or pulse and may include a number of leads connected to an EKG monitoring station or other monitoring device. The temperature of the patient may be monitored via a separate lead and/or another device connected to a temperature monitoring station and/or the aforementioned monitoring device. Further, the pulse oximetry or oxygen saturation of a patient's blood may be monitored using a blood oxygen monitoring lead and/or device connected to a blood oxygen monitoring station and/or the aforementioned monitoring station. Similarly, blood pressure of the patient may be monitored using either another device and/or another lead.

Thus, in some cases, as shown in FIG. 1, a number of separate wires leads, and/or tubes may be connected at one end of each to various locations on a patient's body and from the other end to a single or various different monitoring devices, either directly or via intermediate connection devices. This large number of separate cables, leads, and/or connectors may cause cable management issues, especially with patients who require numerous additional connections to equipment, such as tubes used for intravenous therapy, catheters, and/or breathing tubes, to name a few examples. Patients may also need to be moved from a private room, for example, to another section of the facility, such as for a procedure or testing. In such situations, disconnecting and/or reconnecting a large number of connectors, tube, and/or leads may be inconvenient and in a worst case scenario may result in errors due to a medical employee miss-connecting a device and/or forgetting to connect or disconnect a device. Further, such connecting and disconnecting may increase the risk of contamination of such device and/or cross-contamination of patients. The present disclosure provides numerous examples of various features, systems, and methods that may improve both the efficiency and safety of connecting and/or reconnecting a number of such devices. Further, the present disclosure provides numerous examples of cable or lead sets that provide a consolidated cable and/or lead set for the monitoring of multiple parameters. In some examples, a consolidated cable, lead, and/or tube management system may allow for cables, leads and/or tubes to be fully or partially disconnected and/or reconnected for cable management and/or refurbishment, recycling, or high level disinfecting (HLD)/sanitization, to name a few example advantages. Consolidating or otherwise joining multiple cables, lead sets, and/or tubes, via an interconnection feature and/or series of interconnection features may further reduce the number cables, leads, and/or tubes that are required to handled or connected when monitoring a patient.

Aspects of the present disclosure may also decrease the occurrence of contamination and/or Hospital Acquired Infections (HAI's) due to the handling and contamination of cables, leads, and/or tubes, such as may result from contacting areas that have not been high level disinfecting (HLD). For example, when a patient is moved, multiple individual tubes, leads, and/or cables may each need to be disconnected from a first set of monitoring devices and then reconnected with a second set of monitoring devices at the new location. In such situations, both the disconnecting of the aforementioned cables, tubes and/or leads with the first set of monitoring devices and the re-connecting various connectors with the second set of devices may cause contamination. For example, a medical employee may contaminate the cables, tubes, or leads and then directly contaminate the first or second sets of monitoring devices by contacting such devices. Or, for example, if the patient is moved hastily, unintentional contamination of a monitoring device may occur when a medical employee quickly unplugs a lead, cable, and/or tube from the monitoring device and inadvertently contacts the monitoring device, for example, with contaminated gloves. Further, when the connectors are reconnected when a patient moves to a second location, contamination may occur as a result of contact with contaminated items in other sections of the medical facility. In addition, while monitoring devices may be re-used for monitoring another patient after being high level disinfecting (HLD) following use with a first patient, it may be difficult to fully high level disinfecting (HLD) such a monitoring devices or to verify that a device has been properly disinfected, due to the overall geometry of the device and/or to complexity in disinfecting the connection portions of the device. Risks of such contamination may be increased for patients in medical settings because of a depressed capacity for a proper immune response, such as due to the nature of the treatment of their initial illness, the nature of the initial illness itself, or some combination of both causes.

Figure 2:
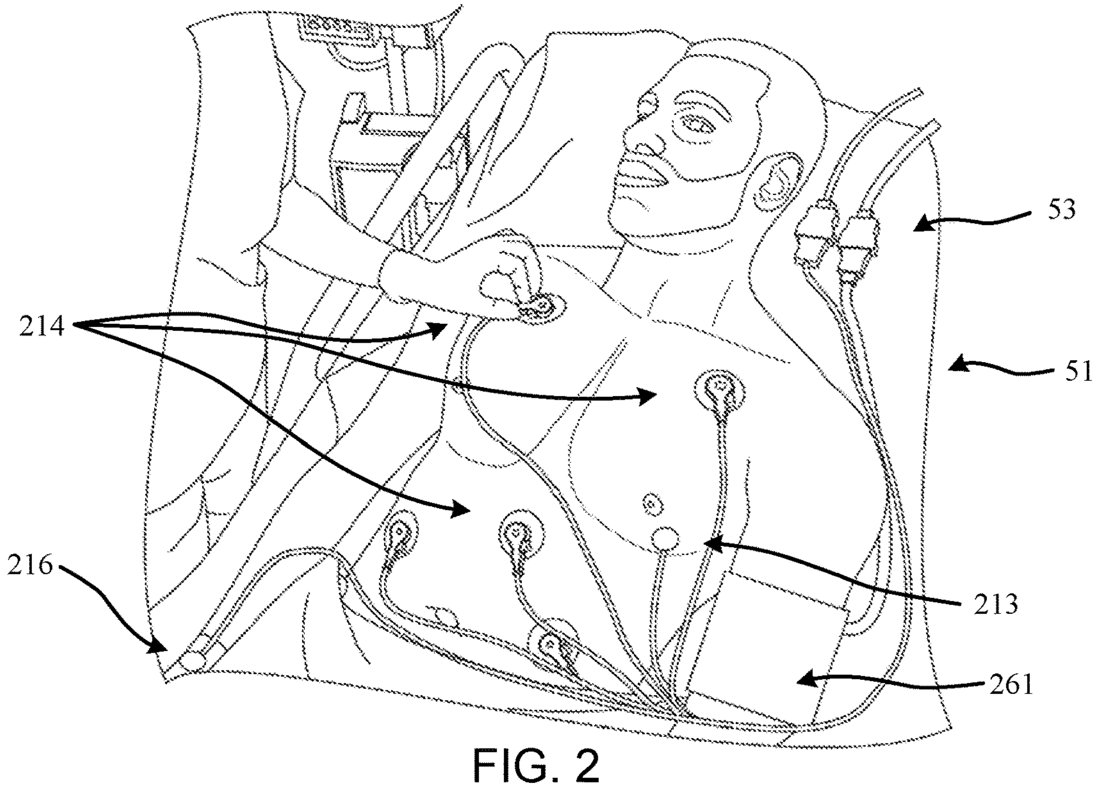
FIG. 2 illustrates one example of a patient with a number of monitoring devices and other leads connected according to aspects of the present disclosure.

The current disclosure provides additional apparatuses and methods for decreasing risk of contamination by consolidating a number of leads into a lead set via interconnection features that allow individual leads of a lead set to be fully connected, disconnected or partially connected or disconnected. To provide a broad overview and example, FIG. 2 shows one example of the organization of multiple cables, tubes or other leads (some of which are shown in FIG. 1) via aspects described in the present disclosure. For example, a first set of patient connectors 214 may be ECG connectors that may be connected at various locations on a patient's body to monitor electrical activity of the heart. In addition a second patient connector may, for example, be an oxygen saturation ($SpO_2$) sensor 216 for monitoring a patient's blood oxygen saturation. A third patient connector may for example be a temperature sensor 213 for monitoring a patient's temperature. A fourth patient connector may for example be a non-invasive blood pressure monitoring device (NIBP) 261. In the related art, one problem that may occur when monitoring a number of patient parameters, cables, leads, and tubes may become tangled or otherwise disorganized. Further, as described above, a problem may arise due to each one of the patient connectors requiring an individual connector to be connected to a single or multiple monitoring devices. As shown in FIG. 2, among other advantages, by providing interconnection features as described herein, the leads, wires, and tubes associated with each patient connector may be connected or otherwise consolidated and the number of connectors 53 reduced, which may provide for increased comfort of the patient and reduce the likeliness of tangles or other management issues that may result in problems such as discomfort, contamination, and/or leads being damaged or otherwise inadvertently pulled off of a patient's body in the related art methods. By providing a lead set in which a variety of patient connectors may be used, resulting in a minimum number of intermediate devices and separate locations/lead sets may be required for connection to a monitoring device, the number and types of locations for which contamination occur may be significantly reduced. Further, aspects of the present disclosure may also reduce such risks by providing a single consolidated feature (e.g., an adaptor or multiparameter input device) that may be mounted or otherwise maintained at a location remote from the monitoring device and/or devices, so as to further reduce the likelihood of spread of contamination. Thus, in addition to the improved efficiency of connection and use of such lead sets provided by aspects of the current disclosure, the disclosed features may also decrease the chances of contamination or HAIs, among other advantages.

I. TERMINOLOGY

Throughout the disclosure, the terms substantially or approximately may be used as a modifier for a geometric relationship between elements or for the shape of an element or component. While the terms substantially or approximately are not limited to a specific variation and may cover any variation that is understood by one of ordinary skill in the art to be an acceptable variation, some examples are provided as follows. In one example, the term substantially or approximately may include a variation of less than 10% of the dimension of the object or component. In another example, the term substantially or approximately may include a variation of less than 5% of the object or component. If the term substantially or approximately is used to define the angular relationship of one element to another element, one non-limiting example of the term substantially or approximately may include a variation of 5 degrees or less. These examples are not intended to be limiting and may be increased or decreased based on the understanding of acceptable limits to one of skill in the relevant art.

For purposes of the disclosure, directional terms are expressed generally with relation to a standard frame of reference when the system and apparatus described herein is installed in an in-use orientation. Further, in order to provide context to the current disclosure, a broad overview of the discovered deficiencies of various systems and an example implementation of the current disclosure and the advantages provided by the disclosure are described below. Further details of example implementations of the current disclosure are described in detail with reference to the figures below.

Terms such as a, an, and the are not intended to refer to only a singular entity, but include the general class of which a specific example may be used for illustration. The terms a, an, and the may be used interchangeably with the term at least one. The phrases at least one of and comprises at least one of followed by a list refers to any one of the items in the list and any combination of two or more items in the list. All numerical ranges are inclusive of their endpoints and non-integral values between the endpoints unless otherwise stated.

The terms first, second, third, and fourth, among other numeric values, may be used in this disclosure. It will be understood that, unless otherwise noted, those terms are used in their relative sense only. In particular, in some aspects certain components may be present in interchangeable and/or identical multiples (e.g., pairs). For these components, the designation of first, second, third, and/or fourth may be applied to the components merely as a matter of convenience in the description of one or more of the aspects of the disclosure.

Throughout the disclosure, the terms reprocess, refurbish, and reconstruct are used. While generally the terms may be used interchangeably, in one example, the term refurbish or reprocess may include method steps such as inspecting, cleaning, disinfecting or sanitizing, high level disinfecting, and/or testing. Further, the term reconstructing may include method steps other than inspecting, cleaning, disinfecting or sanitizing, high level disinfection, and/or testing, such as repair of connectors, wires, and/or conduits, replacing an adhereable media portion or a hydrogel or other patient contact surface, replacing a cover, and/or replacing a connector or sensor connector or a portion of the connector or sensor. In one example, an apparatus subjected to reconstruction may been subject to additional processing or repair beyond reprocessing. However, the aforementioned terms and definitions are merely provided as examples.

II. EXAMPLES a. Monitoring Lead Sets and Multiparameter Adapters

Figure 3:
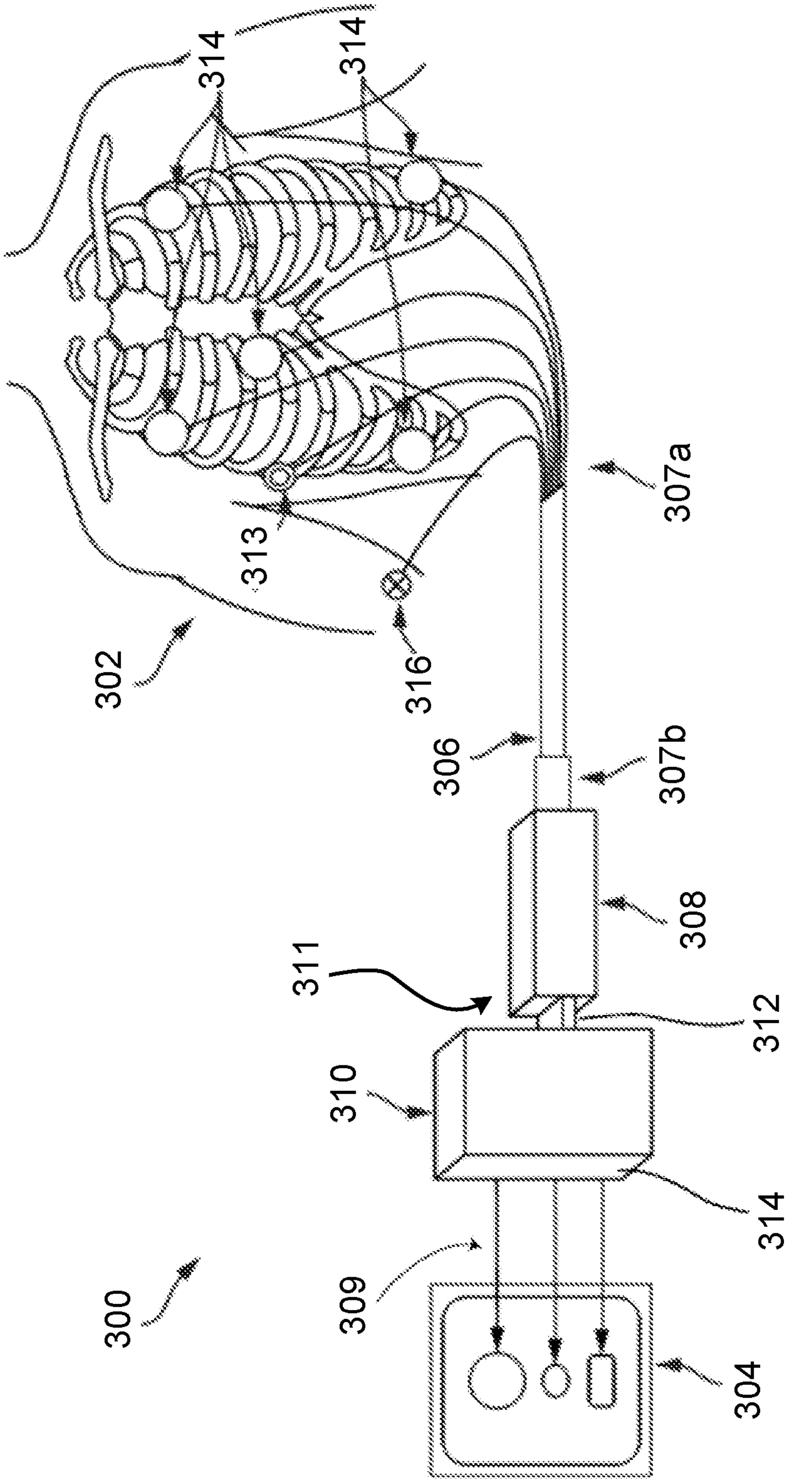
FIG. 3 illustrates an example multiparameter lead set selectively connected with a multiparameter lead set adapter according to aspects of the present disclosure.

According to various aspects of the present disclosure, FIG. 3 illustrates an example multiparameter lead set 300 that comprises a plurality of monitoring devices 302 coupled to a monitoring station 304. The lead set 300 may include a combination of different types of monitoring devices 302 that measure or monitor a plurality of different parameters (e.g., patient health indicators). The monitoring station 304 may further include a display to display one or more of the plurality of different parameters and may include a warning system and/or alarm to warn a medical employee if anyone or a combination of the different parameters fall outside of a typical and/or safe range. The monitoring station 304 may receive signals from the monitoring devices 302 via coupling facilitated by a cable section 306, which may hereinafter also be interchangeably referred to as a "lead," process the signals, and output readable and/or otherwise interpretable data. In order to continuously or non-continuously monitor a plurality of different parameters associated with the monitoring devices, one or more portions (the "patient connectors") of the monitoring devices 302 may be selectively placed in direct contact with the patient or may be connectable to a patch or electrode that is in direct contact with the patient, for example. Placement may constitute direct attachment to various locations on the patient's skin, such as on the chest, circumvention of various limbs, such as an arm or finger, or insertion into the patient, such as via an intravenous needle or tube (e.g., a catheter or other device).

FIG. 3 illustrates a single set of examples of monitoring devices 302 that may be used. Such monitoring devices 302 may include as patient connectors a single or plurality of temperature sensor(s) or temperature sensor connector(s) 313 that measure (or monitor) core body temperature and a plurality of electrodes 314 and/or connection components for use therewith. Such electrodes 314 may be configured to be attached to a patient's skin (e.g., see various features of an example electrode shown in FIGS. 19A-21) in order to measure (or monitor) the electrical activity of the heart. Yet another example patient connector may be a pulse oximetry sensor or connector 316 that measures (or monitors) blood oxygen saturation levels and/or pulse. In one aspect, instead of the patient connectors, such as the temperature sensor 313, and/or the pulse oximetry sensor 316, or other blood oxygen sensor being directly incorporated into the multiparameter lead set 300 as shown, the lead set 300 may, for example, include one or more lead connectors that are connectable to a respective temperature sensor, pulse oximetry or other blood oxygen saturation sensor, or other patient connector. Further, rather than the lead set 300 being connected directly to such patient connectors (e.g., sensors 313, 316), the leads may be coupled wirelessly. For example, one or more leads in the lead set terminate at a wireless device (e.g., a Bluetooth device or a radiofrequency identification (RFID) device) that in turn enables a wireless communication with a corresponding wireless component of the patient connectors (e.g., sensors 313, 316). It is noted that the aforementioned examples are not limiting; for example, the patient connectors may also include one or more blood pressure cuffs configured to monitor blood pressure, catheters configured to monitor blood pressure, catheters or other devices configured to measure and monitor the depth of anesthesia, and devices configured to monitor carbon dioxide levels, among other devices.

While each patient connector may have its own separate respective cable connection ("monitoring lead" that provides coupling to and communication with the monitoring station 304, as shown in FIG. 3, aspects of the present disclosure provide for the plurality of such monitoring leads to be organized or configured to suit a user's need. For example, the plurality of monitoring leads may be included in a ribbonized or partially ribbonized portion, rather than solely being provided as separated monitoring leads. As another example, the plurality of monitoring leads may be enclosed partially or wholly within a single flexible casing. When the monitoring leads include a partially ribbonized or completely ribbonized, portion, or are contained in a single flexible casing ("cable section" 306), such arrangement may increase the operability of lead set 300 by reducing the probability of entanglement of the ribbonized or encased portion (cable section 306) during use, while also increasing the customizability of lead set 300 for application to patients of different sizes and positions. For example, when cable section 306 is ribbonized and/or partially ribbonized, individual monitoring leads in the cable ribbon may be selectively separated from one another to allow a medical employee and/or patient to provide suitable separation among any one of the plurality of patient connectors (e.g., electrode connectors 314, temperature sensor 313, and/or blood oxygen saturation sensor and/or connector 316), for example when the aforementioned patient connectors are attached at different locations on a patient's body.

The cable section 306, as shown in FIG. 3, has two opposite ends, a first end or distal end 307*a* end and a second end or proximal end 307*b*. When ribbonized in this cable section 306, the first end 307*a* may be configured to have a single or multiple monitoring interface connectors 308; however, if the monitoring leads are only partially ribbonized or non-ribbonized in this cable section 306, the first end 307*a* may comprise multiple monitoring interface connectors 308, which may include a first monitoring interface connector and a second monitoring interface connector, for example. Throughout the disclosure, the term monitoring interface connector and patient connector may be used interchangeably. As described in further detail with reference to FIGS. 9-14C below, the monitoring lead connector 308 may include any number of individual connectors (e.g., a first monitoring interface connector or second monitoring interface connector) that are selectively connectable to from a single connector via first lead interconnection feature. With regard to the second end 307*b*, if this cable section 306 is non-ribbonized or partially ribbonized, the second end 307*b* may be configured to be spliced from a single cable into multiple ends in order to facilitate physical connection and electrical communication with the monitoring devices 302. As explained in further detail below, either a ribbonized cable, a single cable, and/or individual cables or any combination thereof may be completely or partially separated and re-connected via an interconnection feature or series of interconnection features. Further details of the interconnection features are described with reference to FIGS. 9-13 and 15A-17D below.

The monitoring leads, including the aforementioned cables, leads, or tubes, temperature sensor(s) and/or connector(s) 313, electrode connector(s) and/or sensor(s) and/or pulse oximetry sensor(s) or connector(s) 316 and/or connectors or interfaces described above or throughout the present disclosure may be configured to include visual indicators that allow for quick verification of connection points and components such as easy-read labeling or unique colors for specific monitoring leads matching same color patient connectors. In various aspects, monitoring leads for the monitoring devices 302 may have distinct or differing geometries, colors, etc. to indicate its corresponding function as described in greater detail herein. For example, temperature sensor(s) or connector(s) 313 and/or associated temperature patch (described in further detail with respect to FIGS. 5, 6, 8, and 19A-23 below) may be colored blue, whereas electrode connectors 314 and/or the associated electrodes to be adhered to the patient's body may be colored white. In an example implementation, different monitoring devices may be implemented with different geometries to provide tactile differences and/or differences in connection interfacing. In another example usable with any of the aforementioned visual indicators, each one of the monitoring devices may for example include a connection interface that is specific to and only connectable to the correct connection point or terminal. For example, the temperature sensor or connector 313 may have a first type of connection interface for connecting to a thermal patch and/or thermal sensor, and the electrode connectors 314 may have a second type of connection interface for connecting to electrodes connected or adhered to a patient's skin, and the first type of connection interface may not be connectable to the second type of interface and vise-versa. Similarly, the oxygen saturation connector 316 may include a third type of connector interface that is not connectable to the first or second type of connection interface. The aforementioned visual indicators and/or connection interfaces may allow a medical professional to more efficiently connect monitoring devices 302 to a patient and/or prevent a medical professional from making errors when connecting monitoring devices 302 to a patient. Further, in another example implementing the aforementioned tactile differences, the temperature sensor connector 313 may for example have ridges or other surface irregularities, and the electrode connectors 314 may be smooth. Providing tactile differences may further improve a medical professional's ability to efficiency connect the lead set 300 to a patient in a proper manner and/or to reduce the chances that leads are incorrectly connected.

In one example implementation in accordance with aspects of the present disclosure, the cable section 306 may comprise a combination of electrically conductive material disposed within an insulating material, such as polyvinyl chloride, glass, rigid laminate, varnish, resin, or rubber, or some combination thereof, and may be partially or fully electromagnetically shielded to decrease the likelihood of electromagnetic interference during the monitoring of the electrical activity of the heart, for example. Further, both cable section 306 and monitoring devices 302 may be comprised of relatively inexpensive materials, and for at least this reason may be configured to be disposed of after a single use. However, in another example implementation cable section 306 may be configured to be reused among a plurality of different patients, after disinfection, sterilization, and/or high level disinfection (HLD), for example. One example of reconstructing and/or reuse of cable section 306 is described in further detail with respect to FIG. 18. Because cable section 306 and monitoring devices 302 are the components of lead set 300 most likely to be in direct contact with the patient to which they are applied and/or to others contacting the lead set, the example implementation in which both monitoring devices 302 and cable section 306 are single-use disposable and/or reprocessable after a single patient use may result in reduced likelihood of cross-contamination in a medical environment and thus also decrease the spread of HAIs among patients (e.g., by reducing the amount of materials, devices, and otherwise within the medical environment that are exposed to a plurality of different patients and environments).

In order to facilitate the interoperation of the cable section 306 and monitoring station 304, the cable section 306 may be gathered, organized, and positioned (or combined) and connected or otherwise placed in electrical or other signal continuity with an interface connector, also interchangeably referred to herein as a "pigtail." For purposes of this disclosure, a monitoring lead connector 308 may include any device or configuration that allows multiple inputs (e.g., cables) to be combined into a single interface. In a practical example, the monitoring devices 302, each with their own respective cable (i.e., the cable section 306), are combined into monitoring lead connector 308 monitoring and/or a plurality lead connectors (e.g., a first lead connector and a second lead connector) that are joinable to form monitoring lead connector 308. Thereafter, the monitoring lead connector 308 is connected to the monitoring station 304 directly or via a multiparameter input device connector 312 of a multiparameter input device 310. The monitoring lead connector 308 may include a number of terminals that correspond to each of the monitoring devices allowing for a single connector to be connected and/or disconnected instead of the more tedious connection of individual connectors associated with each monitoring lead. Thus, the aforementioned monitoring lead connector 308 may allow the lead set 300 to more easily be selectively connectable to the multiparameter input device 310 via the multiparameter input device connector that facilitates a connection (e.g., electrical, physical) between monitoring station 304 (e.g., via the monitoring lead connector 308 where applicable) and the monitoring station 304. Thus, the monitoring lead connector 308 may improve the efficiency of connecting and/or disconnecting the monitoring devices 302 from a monitoring station 304 and/or the multiparameter input device310 (if applicable). Further, by consolidating a number of connectors into a single monitoring lead connector 308, the risk of contamination may decrease by preventing the handling of multiple connectors and/or contact of multiple connectors with patient surroundings. In one example, the monitoring lead connector 308 may be modular and include multiple connecters interfaced or otherwise connectable to form a single larger connector, which may be customizable based on the number and type of patient monitoring devices 302 in lead set 300. Additional examples of such a modular monitoring lead connector 308 are shown in and described with reference to FIGS. 9-14C below.

As shown in FIG. 1, the single and/or joined cable section 306 may, for example, be connected to the multiparameter input device 310. The multiparameter input device 310 may include (e.g., near monitoring lead connector interface 311) that is connectable to monitoring lead connector 308 that is connectable to monitoring station 304, which may be interchangeably referred to throughout the specification and claims as a monitoring device or monitor. It is noted that while a single monitoring station 304 is shown, the multiparameter input device may be connectable to a multiple monitoring stations or devices, depending on patient monitoring requirements. Thus, the multiparameter input device 310 may allow for a single connection interface or connector that prevents or reduces the likelihood of a technician having to unplug or plug-in multiple connectors in to a single or multiple monitoring devices. As shown in the example implementation in FIG. 3, the multiparameter input device 310 may include a multiparameter input device connector 312 that is connectable to the cable section 306 via the pigtail and thus provides continuity, and/or other signal or fluid communication between the monitoring devices 302 and multiparameter input device 310. The multiparameter input device 310 may be connectable to a monitoring station 304 and/or multiple monitoring stations via a single or multiple monitoring station connectors 309. Thus, the multiparameter input device 310 may make the implementation of lead set 300 simpler and easier to clean/handle by, for example, providing a single location and a single point of physical and/or electrical connection for the cable section 306. As a result, each individual variety of monitoring devices 302 thereby does not need to be separately connected with monitoring station 304.

In various aspects, the multiparameter input device 310 may be configured to remain with monitoring station 304 and related equipment to allow use with a different lead set 300 for each patient, for example, even if a plurality of different models of monitoring station 304 are implemented within the same medical environment. In such aspects, the monitoring lead connector 308 of lead set 300 may be configured to accompany a single patient, along with the cable section 306 and monitoring devices 302, as they and the patient move from location to location within the medical environment. This ease in portability simplifies the preparation process required, which may especially be useful with patients who need significant monitoring to undergo different procedures or diagnostic tests, for example. This configuration may also reduce the amount of time spent sterilizing, disinfecting, or high level disinfecting (HLD) components that are re-used for multiple patients (e.g., the monitoring station 304) between patients or may result in less exposure of such devices to contaminants in the medical setting. Further, multiparameter input device 310 may provide a remote connection between monitoring station 304 and lead set 300, which may prevent direct contact with the monitoring station 304 when connecting and/or disconnecting the lead set 300 from multiparameter input device 310.

As described above, the lead set 300, including the monitoring lead connector 308, cable section 306, and monitoring devices 302may be disposable and/or capable of being reprocessed or otherwise recycled or re-used after processing and/or single patient use.

The monitoring lead connector 308 and/or multiparameter input device 310 and/or multiparameter input device connector 312 may comprise a material of sufficiently rigid structure, such as plastics, composites, or durable rubber or semi-elastic materials such as thermoplastic polyurethane or other thermoplastic elastomers, that may increase the ease of handling connection and use with lead set 300 by a medical professional. The monitoring lead connector 308 may also include serrations or other anti-slip surface geometries, coating, and/or coverings that may improve a medical professional's grip on the pigtail and otherwise prevent slipping or dropping of the monitoring lead connector 308. The monitoring lead connector 308 may also be coated, treated, and or comprised of anti-bacterial and/or anti-microbial agent known in the art, which may include but is not limited to isothiazolinone treatments, zinc pyrithione, thiabendazole and silver antimicrobial products, to name a few examples.

The multiparameter input device 310 may be comprised of a similar or different sufficiently rigid material as listed above. In addition, the multiparameter input device 310 may additionally be treated, coated, and or comprised of any known anti-bacterial and/or anti-microbial agent. Further, the multiparameter input device 310 may include a rigid or semi-rigid mount (not shown). In another example, the multiparameter input device 310 may be rigidly connectable to a mount (not shown) located at or proximal to a monitoring station 304 and/or remote from monitoring station 304 and may be removeably connected to the mount. The aforementioned examples may allow a medical professional to easily connect the monitoring lead connector 308 to or remove the interface connector from the multiparameter input device 310. For example, by rigidly or semi-rigidly mounting multiparameter input device 310 to a monitoring station 304 and/or remotely from monitoring station 304, a medical professional is able to connect or remove the monitoring lead connector 308 from the multiparameter input device 310 with one hand and may further allow the medical professional to avoid contacting the multiparameter input device 310 when connecting the monitoring lead connector 308, which may further reduce a risk of contamination and decrease costs and time associated with high level disinfection (HLD) or sterilization.

Figure 11:
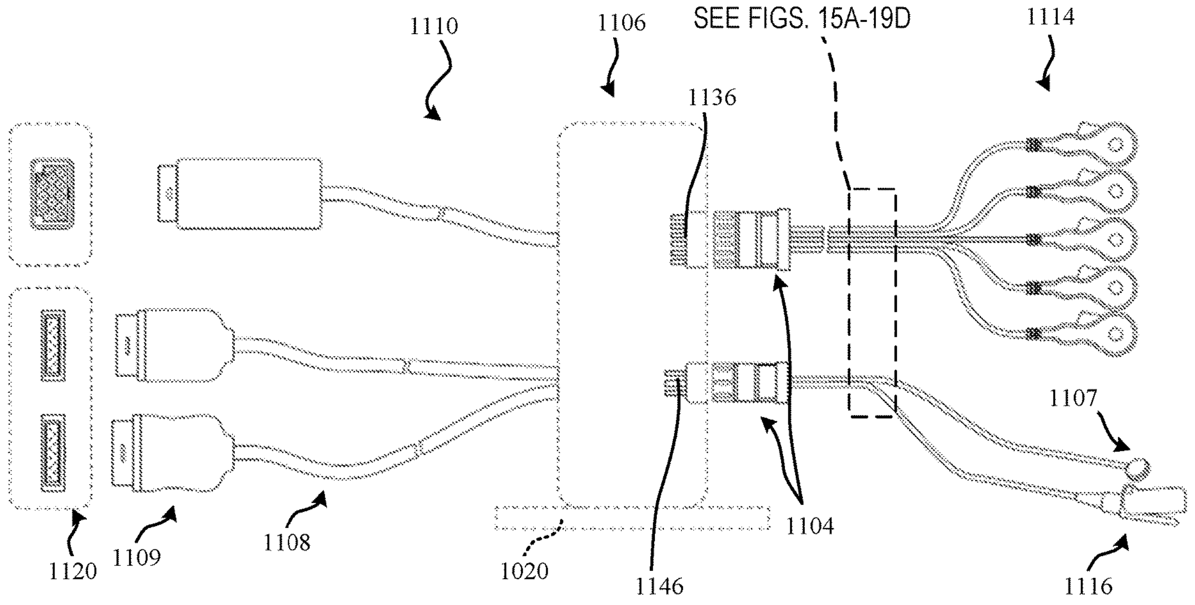
FIG. 11 illustrates an example of a multiparameter lead set and multiparameter input device according to aspects of the present disclosure.

The monitoring lead connector 308 may, for example, be configured as a male style multi-pin connector configured to recieveably interface with female connector of the multiparameter input device 310 (e.g., similar to the configuration shown in FIGS. 4 and 12-14C). Of course, the aforementioned example may be reversed, as well, with the monitoring lead connector 308 having a female style connector and the multiparameter input device 310 having a male-style connector (e.g., as shown in FIG. 3). In another example, the multiparameter input device 310 may include a printed circuit board (PCB) or other flat-surface interface with multiple terminals (e.g. as shown in FIG. 11), and the monitoring lead connector 308 may be configured to receive at least a portion of or the entire PCB or other flat-surface interface when connecting the monitoring lead connector 308 and multiparameter input device 310. The aforementioned example may further improve ease of high level disinfecting and/or sanitizing the multiparameter input device 310 due, for example, to ease of cleaning a flat or semi-flat surface. Further examples of such a configuration are described with reference to FIG. 11 below.

Figure 4:
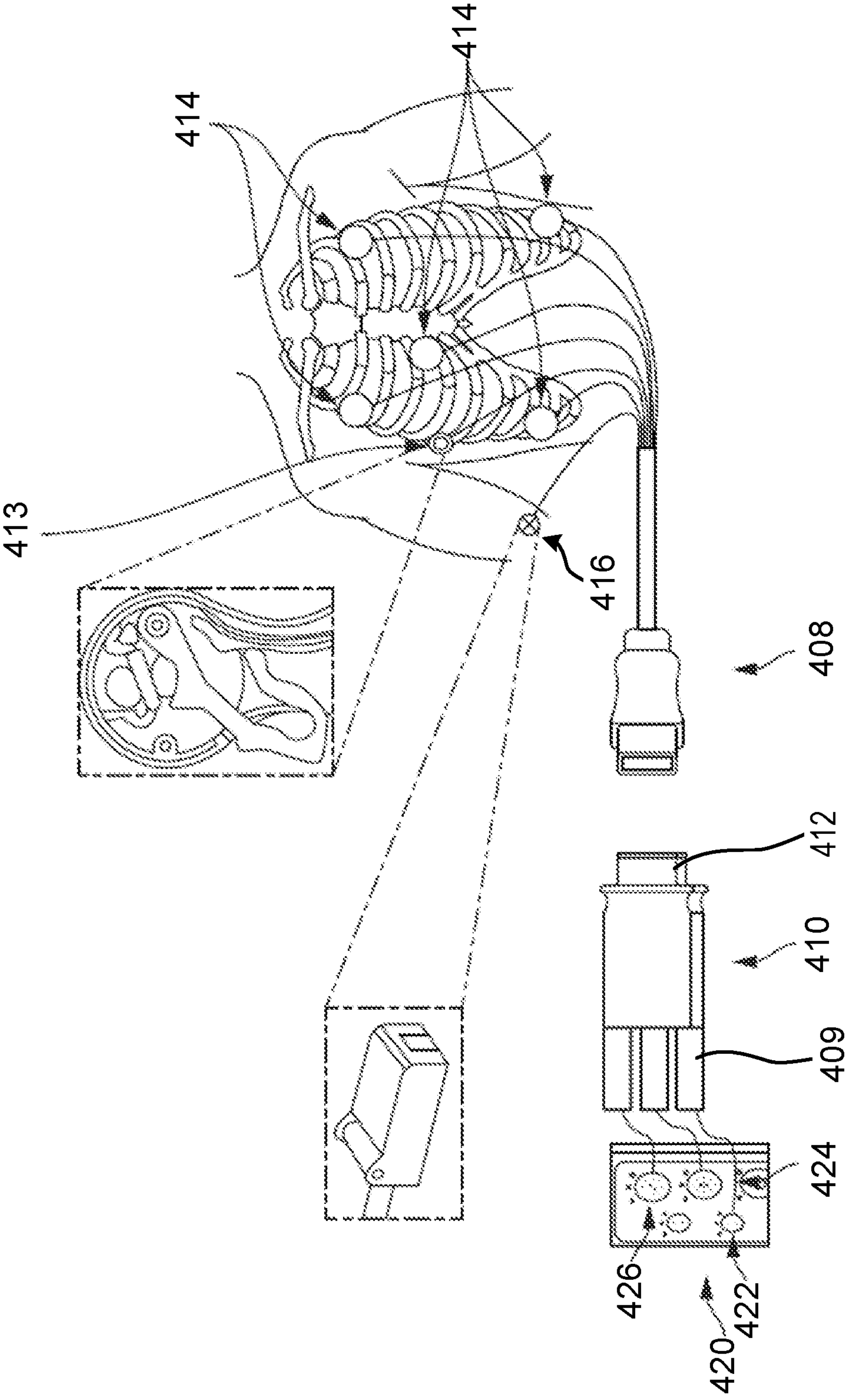
FIG. 4 illustrates various details of an example multiparameter lead set selectively connectable with a multiparameter lead set adapter according to aspects of the present disclosure.

FIG. 4 illustrates various additional features of an example multiparameter lead set 408 (hereinafter "lead set"), in accordance with aspects of the present disclosure. The lead set 408 may include a plurality of electrocardiogram connectors and/or pads 414, wherein electrode pads 414 are configured to monitor electrical activity of the heart of a patient. The electrode pads 414 may for example be adhereable to a patient's skin with a removable connector connected thereto. The electrode connectors and/or pads 414 may be similar to or identical to the electrode connectors 314 and electrodes that may be adhered to a patient's skin along the lines as shown and described with relation to FIG. 3. The lead set 400 may further include a temperature sensor and/or connector 413 and/or temperature connector configured to connect to or otherwise be in signal communication with a temperature sensor and/or connector 413, wherein the temperature sensor and/or connector 413 may be configured to monitor either core or surface temperature of a patient, for example. In one example, the temperature sensor and/or connector 413 and/or temperature connector may be similar to or identical to the temperature sensor 313 described with respect to FIG. 3. The lead set 400 may further include a blood oxygen sensor and/or connector 416, which may, for example, be or include a pulse oximetry sensor, wherein a pulse oximetry sensor connected via connector 416 may be configured to monitor blood oxygen saturation levels or pulse of the patient. The blood oxygen sensor and/or connector may also be similar to or identical to the pulse oximetry sensor or connector 316 described with respect to FIG. 3. The electrode connectors 414, temperature sensor and/or connector 413, and pulse oximetry sensor connected via connector 416 may also be configured to be selectively connectable to a multiparameter input connector 412 of a multiparameter input device 410. In the example shown in FIG. 4, the pulse oximetry sensor connected via connector 416 may be or include a Nellcor™ SpO2 sensor, as manufactured by Medtronic, of Minneapolis, Minnesota. In another example, connector 416 may be replaced with a directly connected or communicatively coupled blood oxygen saturation sensor, such as a pulse oximetry sensor or SpO2 sensor or other similarly functioning sensor known in the art. Further, the multiparameter input device 410 may be configured to couple electrode connectors 414, temperature sensor and/or connector 413, and pulse oximetry sensor via single or multiple monitoring station connectors (e.g., 426 and 422) connected to the multiparameter input device 410 via a cable or series of cables (e.g., 424) to a monitoring station 420, which may monitor multiple parameters, and/or to multiple monitors (not shown), via organizing the interoperation of devices 414, 413, and via connector 416 with corresponding ports, such as an electrocardiogram port 424, a temperature port 422, and an oxygen saturation level port 426, wherein ports 424, 422, and 426 are disposed within multiparameter monitoring station 420.

Figure 5:
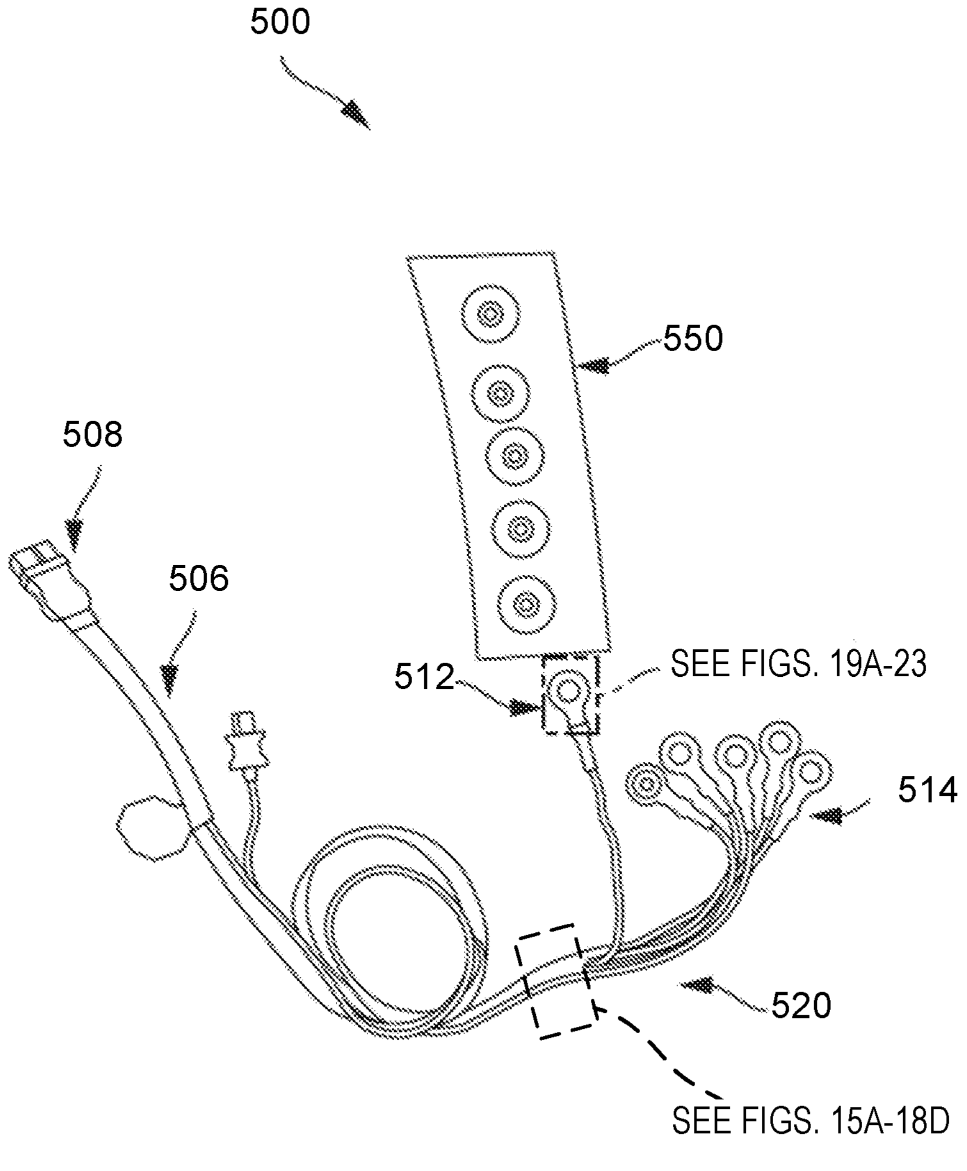
FIG. 5 illustrates various lead related features for an example multiparameter lead set according to aspects of the present disclosure.

FIG. 5 illustrates various example features of an example lead set 500, in accordance with aspects of the present disclosure. The lead set 500 may include a temperature sensor 512 (which may be similar or identical to the temperature sensor and/or connector configuration in FIGS. 3 and 4 above) and a plurality of electrode connectors 514 connectable to corresponding electrode pads 550. Further, example lead set 500 includes a monitoring lead connector 508 and ribbonized cable 506, wherein monitoring lead connector 508 and cable 506 are configured to electrically and physically connect to a monitor system (e.g., similar to as shown in FIG. 1) either with an adapter (e.g., multiparameter input device 310 or 410 shown in FIGS. 3 and 4, respectively) or via direct or signal coupling to a monitor (e.g., monitoring station 304 or 420 in FIGS. 3 and 4, respectively). Further, cable 506 of FIG. 5 may include a separation section 520, wherein each of the leads in the ribbon is separated or separable and/or re-connectable as described in further detail below. The length of the separated section 520 may be varied to accommodate the size and positioning on the patient of the temperature sensor 512 and electrode connectors 514 being applied, for example, simply by further separating one or more of the ribbonized segments of cable as needed. In another example, a visual indicator, such as a light-emitting diode (LED) indicator light may be implemented in order to signal whether monitoring lead connector 508 is correctly connected and/or interoperating (e.g., by determining if a circuit is completed) with an adapter (e.g., multiparameter input device 310 or 410 shown in FIGS. 3 and 4, respectively), as well as whether temperature sensor 512 and/or electrode connectors 514 are maintaining electrical connection or other coupling/communication with a patient monitor (e.g., monitoring station 304 or 420 in FIGS. 3 and 4, respectively).

The aforementioned multiparameter input device and/or monitoring lead connector 508 may also include surface geometries and/or interfacing surfaces that promote the correct connection between the monitoring lead connector 508 and the multiparameter input device. For example, the multiparameter input device and/or monitoring lead connector 508 may have cross-sections that allow the two to be connected only in a certain orientation and so that each only interoperates with its designated connector. The multiparameter input device and/or the monitoring lead connector 508 may also, for example, be color coded or have the same or other similar or corresponding/complementary color or colors in order to allow a medical professional to quickly and efficiently identify a correct connector and/or orientation of the two connectors. The aforementioned multiparameter input device may connect to a single monitoring station and/or multiple monitoring stations (e.g., as described with reference to FIGS. 3 and 4 above). The connectors may include any of the features described above, including color coding, differing geometries, and/or tactile qualities to assist a medical professional with making the proper connections between the multiparameter input device and the monitoring station or multiple monitoring stations. An example of this variation is representatively illustrated in FIG. 3, as reflected in the differing shaped and sized circular, oval, and rectangular ports shown within monitoring station (e.g., 304 in FIG. 3). Other, non-limiting examples are shown and described below with respect to FIGS. 9-13.

Figure 6:
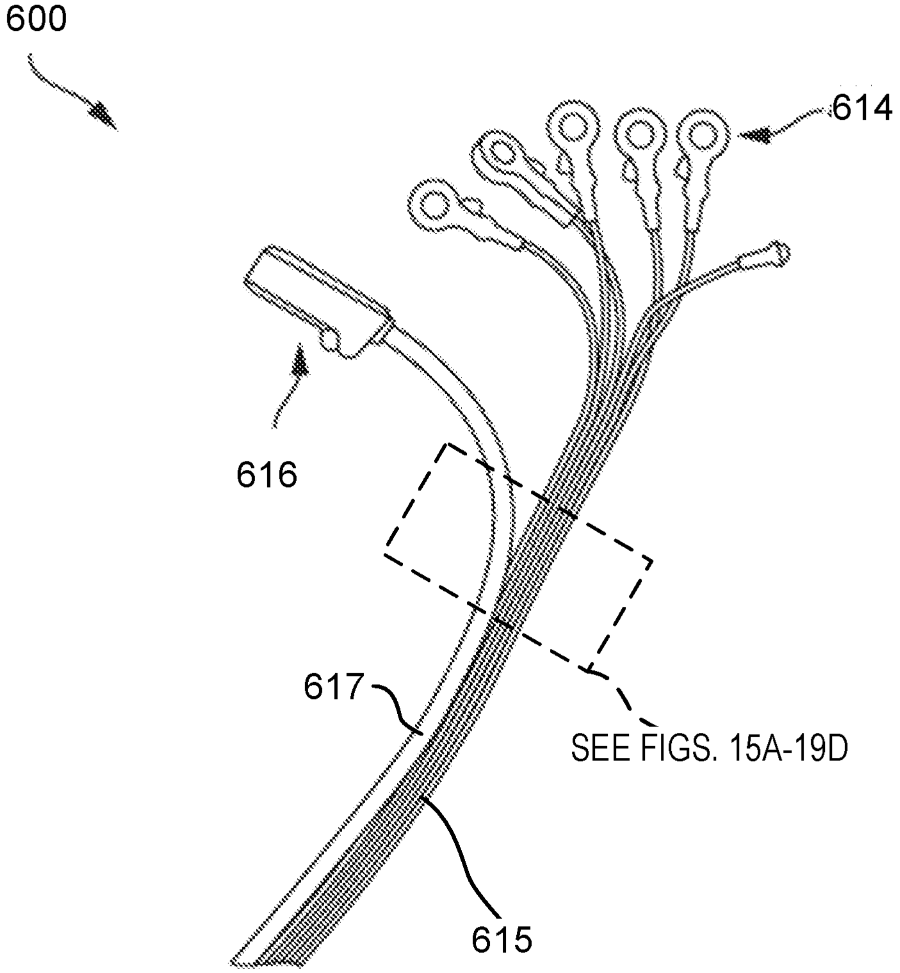
FIG. 6 illustrates a perspective view of an example $SpO_2$ sensor lead according to aspects of the present disclosure.

FIG. 6 illustrates various features of another example lead set 600, in accordance with aspects of the present disclosure, wherein lead set 600 comprises an oxygen saturation level sensor or connector 616 for connection with an oxygen saturation level sensor (not shown) and a plurality of EKG electrode connectors 614, which may be configured to connect to electrodes that are adhered to a patient's skin. In one example, the electrode connectors 614 may be EKG electrodes that are configured to directly adhere to a patient's skin. Oxygen saturation sensor or connector 616 may include or be configured to interoperate with a variety of different oxygen saturation level sensors currently available on the market, such as the Nellcor™ $SpO_2$ sensor manufactured by Medtronic of Minneapolis, Minnesota. As described in further detail below with reference to FIGS. 15A-17D, any one or a combination of the EKG electrode connector leads 615 and/or the oxygen saturation connector lead 617 may be partially and/or fully connectable and disconnectable along the length of each respective lead via an interconnection feature or features as described in further detail below.

Figure 7:
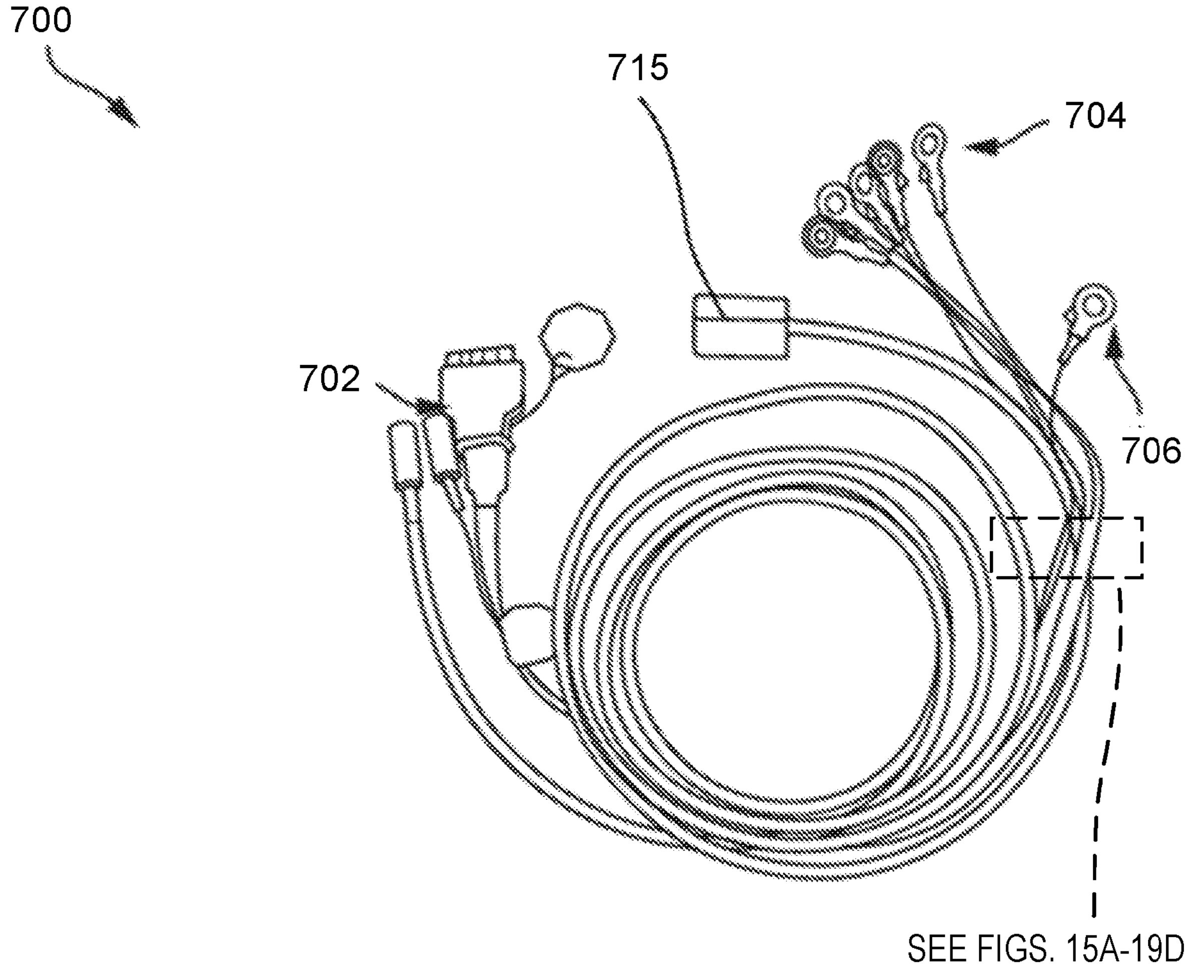
FIG. 7 illustrates an example multiparameter lead set incorporating a Nellcor™ $SpO_2$ sensor, KDL Multiparameter adaptor, five electrode pad devices, and a temperature sensor device, according to aspects of the present disclosure.

FIG. 7 illustrates various features of another example lead set according to various aspects of the present disclosure. As shown in FIG. 7, the example lead set 700 may comprise a KDL Multiparameter connector 702 and an additional series of connectors, which may be connected to a separate monitoring station or stations than multiparameter connector 502. The aforementioned example may be useful, for example, if EKG functions are monitored on a first monitoring device and temperature and oxygen saturation are monitored on a separate monitoring device or devices. The lead set further may include five electrode connection devices 704, for example, which may be connectable to respective electrodes that are adhered or otherwise in contact with a patient's skin. The lead set may further include a Nellcor™ $SpO_2$ sensor device 715, and a temperature sensor device 706. Features of the aspects shown in FIG. 7 may be combined with or otherwise usable with any of the aspects described herein. In addition, as described in further detail below with reference to FIGS. 15A-17D, any one or a combination of the leads may be partially and/or fully connectable and disconnectable along the length of each respective lead via an interconnection feature or features as described in further detail below.

Figure 8:
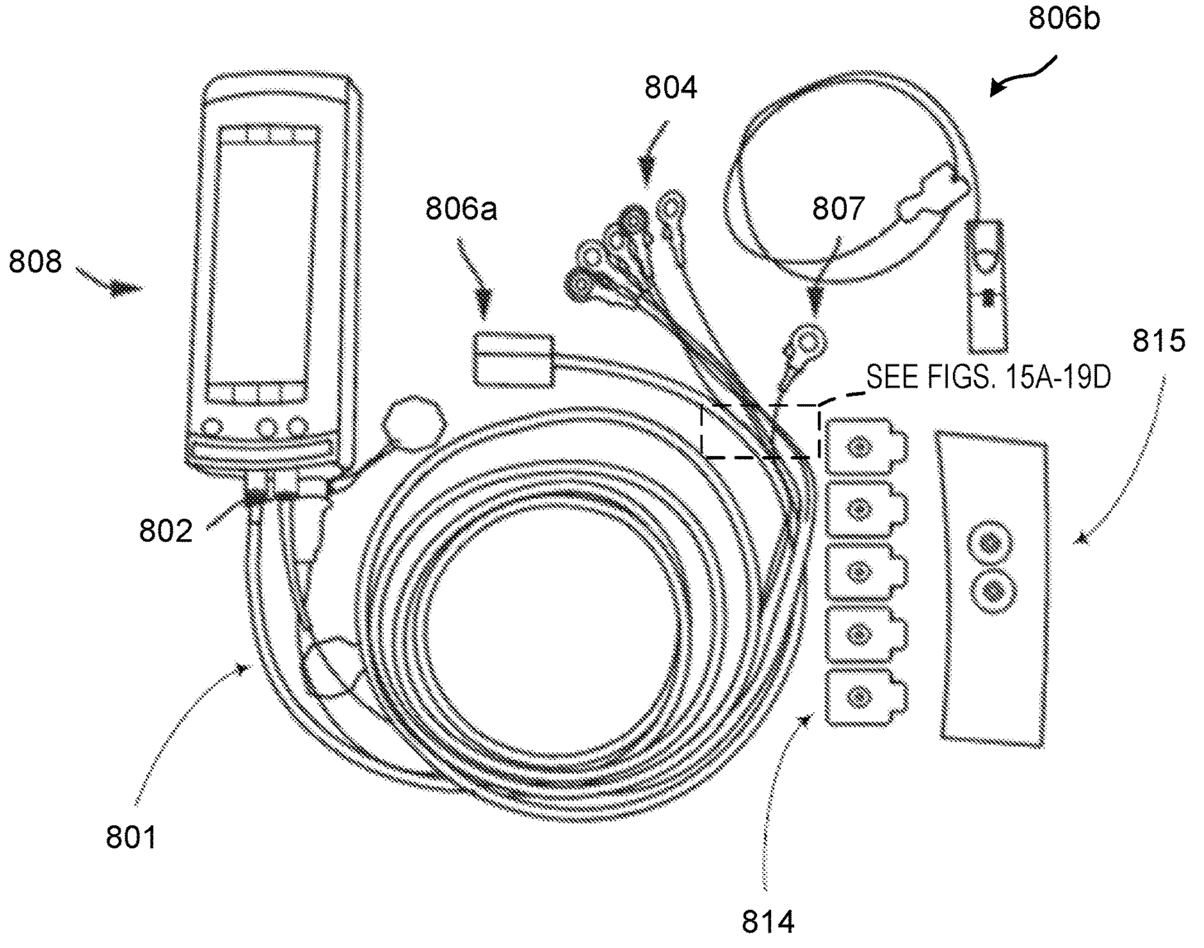
FIG. 8 illustrates various features for another example multiparameter lead set system that includes a multiparameter monitor, according to aspects of the present disclosure.

Turning to FIG. 8, an example multiparameter lead kit 801 comprising various features in accordance with aspects of the present disclosure is shown. The lead set 801 may include any of the applicable features described throughout this disclosure, including but not limited to the features shown in FIG. 8. For example, the lead set 801 may include, a lead set connector or connectors 802 and five electrode connectors 804, which are configured to be connected to electrodes 814 that are adhered to a patient's skin. The lead set 801 may further include an 402 sensor connector 806*a* configured to be connected to a $SpO_2$ sensor 806*b*. The lead set 801 may further include a temperature sensing device or connector 807, which may be connectable to a single or multiple temperature patches 815. In the example shown, the lead set 801 is connectable to a multiparameter monitor 808. While five electrode connectors 804 are illustrated in FIG. 6, there may be more or less than five electrode connectors 804 implemented within lead set 801. In some examples, the lead set 801 may include three electrode connectors, six electrode connectors, ten electrode connectors, or twelve electrode connectors. Accordingly, when provided as a kit, an appropriate corresponding number of electrodes 814 may be provided. Features of the aspects shown in FIG. 8 may be combined with or otherwise usable with any of the aspects described herein. In addition, as described in further detail below with reference to FIGS. 15A-17D, any one or a combination of the leads may be partially and/or fully connectable and disconnectable along the length of each respective lead via an interconnection feature or features as described in further detail below.

Figure 9:
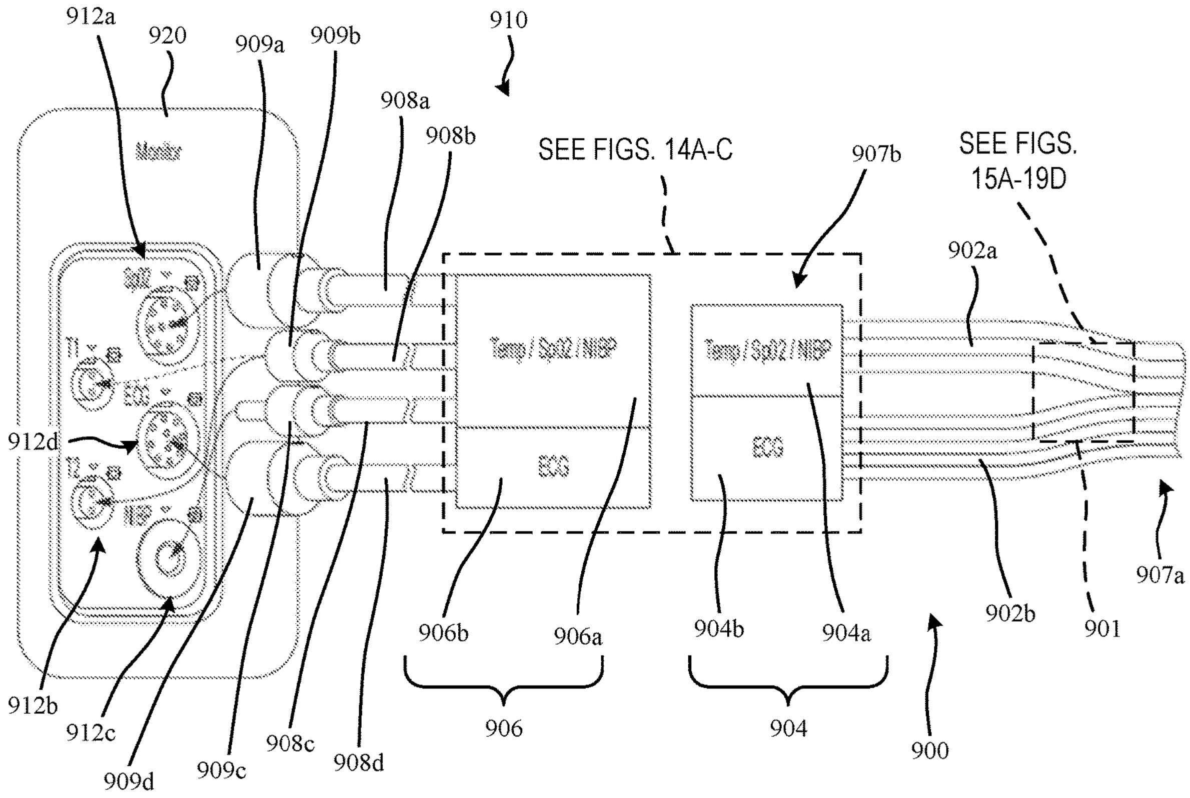
FIG. 9 illustrates an example multiparameter lead set and multiparameter input device according to aspects of the present disclosure.

FIG. 9 shows one example of a lead set 900 and a multiparameter input device usable with aspects of the current disclosure. The lead set 900 may for example include a first cable 902*a*. It is noted that, while a first cable 902*a* is referenced, such a cable is not limited to a single cable or lead, and may for example include multiple cables or tubes which may, for example, be ribbonized or individually connectable and/or disconnectable via disconnection features, such as along the lines as described in further detail with respect to FIGS. 15A-17D below. A first cable 902*a* of the lead set 900 may be configured to provide signals or otherwise communicate a first set of patient health indicators to a monitor or series of monitors 920. As shown in FIG. 9, the first patient health indicator(s) may for example include the monitoring of electrical activity of the patients, for example, via an ECG. The first cable 902*a* may be connected to a first lead connector 904*a* at a lead proximal end 907*b* and may be connected to patient connectors (not shown in FIG. 9) at a lead distal end 907*a* of the first lead cable 902*a*. While not shown in FIG. 9, one example of a patient connector or connectors may include connector(s) for monitoring heart activity of a patient (e.g., an electrocardiogram, which may be commonly referred to as an EKG and/or ECG, examples of which are shown as references 214, 314, 414, 514, 614, and/or 804 in FIGS. 2, 3, 4, 5, and 6, respectively).

A second cable 902*b*, tube, or series of cables and/or tubes 902*b* may be configured to provide signals or otherwise communicate a second set of patient health indicators to a monitor or series of monitors 920. As shown in the non-limiting example in FIG. 9, the second set of heath indicators may, for example, reflect a temperature, oxygen saturation and/or blood pressure of a patient. The second cable 902*b* may be connected to a second lead connector 904*b* at the lead proximal end 907*b* and may be connected to patient connectors (not shown in FIG. 9) at a lead distal end 907*a* of the second lead cable 902*b*. While not shown in FIG. 9, one example of a patient connector or connectors may include one or more connector(s) and/or sensor(s) for monitoring a temperature of a patient (e.g., a temperature sensor patch and/or connector similar to those described as references 213, 313, 413, 512, and 706 in FIGS. 2, 3, 4, 5, and 7, respectively. Another example of a patient connector, which may be useable in combination with the examples described throughout the present disclosure, may include a connector or series of connectors and/or device or series of devices for measuring pulse oximetry or oxygen saturation (402) of a patient's blood (e.g., a pulse oximetry sensor or 402 sensor as shown in and described with reference to references 216, 416, 616 in FIGS. 2, 4, and 6, respectively). Another example of a patient connector, which may be useable alternative to or in combination with the examples described throughout the present disclosure may include a non-invasive blood pressure (NIBP) device or connectable NIBP device. For example, a patient's blood pressure may be monitored periodically via a cuff or other such device placed around a patient's finger or arm (e.g., reference 261 in FIG. 2). The blood pressure monitoring device may, for example, measure pressure by any configuration or features known in the art and may output an electrical signal that varies based on a patient's blood pressure. In one example, as described in further detail with respect to FIG. 13, the blood pressure monitoring device may be connected to the monitor 920 via a tube providing fluid communication between the monitoring device placed on the patient (e.g., cuff 261 in FIG. 2) and the monitor 920. It is noted that the aforementioned monitoring parameters are provided as examples and not intended to be limiting. Aspects of the current disclosure are applicable with any known patient monitoring system, including any individual lead or lead set that requires contact or other types of connection to a patient at a proximal end and is connected (e.g., electrically, via a fluid connection, and/or optically) to a monitoring device. Each of the first lead connector 904*a* and the second lead connector 904*b* may be connectable to and disconnectable from a corresponding first multiparameter connector 906*a* and second multiparameter connector 906*b* of a multiparameter input device 910. The first lead connector 904*a* and/or second lead connector 904*b* may be or include separate connectors and/or may be modular so as to be connectable to one another to form a single lead connector 904. Similarly, the first multiparameter input device connector 906*a* and second multiparameter input device connector 906*b* may be or include separate connectors and/or may be modular so as to be connectable to one another to form a single multiparameter input device connector 906.

As shown in FIG. 9, the multiparameter input device 910 may include a series of monitor side connectors, which may include but are not limited to an oxygen saturation ($SpO_2$) connector 909*a* configured to be connected to a monitor $SpO_2$ port 912*a*, a single or plurality of temperature sensor monitor connectors 909*b* configured to be connected to a single or plurality of monitor temperature port(s) 912*b*, a blood pressure (NIBP) monitor connector 909*c* that may be configured to be connected to a monitor NIBP port 912*c*. Further, the multiparameter input device may include ECG monitor connector 909*d* that is configured to be connected to a monitor ECG port.

Accordingly, by consolidating the connectors into just two connectors, or a single connector comprised of multiple connectors connected to one another, a technician or other medial provisional may more easily connect and/or disconnect the lead set 900 from the multiparameter input device without having to separately remove or re-connect individual connectors (e.g., connector 909*a*, 909*b*, 909*c*, and 909*d*) from the monitor 920. As mentioned above, the aforementioned structure increases efficiency by reducing the need for a technician or other medial professional to disconnect and/reconnect multiple cables, and thus may prevent cables from being improperly connected and/or fumbling with cables, which, among other things, may result in excessive contact between the technician and the monitor 920. The consolidation of multiple cables into a single or plurality of connectors may especially provide advantages in an urgent or otherwise rushed scenario where a patient, with several leads connected at various location so the patient's body may need to be quickly connected and/or disconnected from a monitoring device. Further the aforementioned structure may provide a decreased chance of contamination of the monitor 920 or other devices that may be re-used amongst multiple patients, to name one example advantage.

As described in further detail with reference to FIGS. 15A-19D, any one or combination of the aforementioned example monitoring leads may include an interconnection feature that allows the cables to be connected and/or disconnected from one another along the length of the cable or tube. For example, the ECG cable or second cable shown in FIG. 9 may be a ribbonized and include, for example, a set of 3, 5, 6, 10, or 14 cables that correspond to each electrode or other device placed on or otherwise interacting with a patient. The ribbonized cable may allow for each cable to be permanently connected or selectively separable by a user to allow for proper placement of each electrode on a patient. The set of 5, 6, 10, or 14 cables may be selectively connectable and disconnectable either along the entire length of the cable or a section of the cable to any one or a combination of the aforementioned temperature, $SpO_2$, and/or NIBP cable(s) via interconnection features such as those described with reference to FIGS. 15A-17D below. In one aspect, any one or any combination of the cables shown in FIG. 9 may be connectable, disconnectable and/or partially connectable and disconnectable to allow for customization and/or organization of the leads depending on patient need and/or the location of each monitoring device on or relative to a patient. Further, as described with respect to FIGS. 14A-14C below, either one or both of the multiparameter input device connector 906 and/or the lead set connector 904 may include interconnection features to create a single connector from multiple connectors. For example the first lead connector may be connectable to the second lead connector 904*b* via one or more interconnection features described with relation to FIGS. 14A-14C. Similarly, the first multiparameter connector 906*a* and the second multiparameter connector 906*b* may be connectable via the aforementioned (and below described) interconnection features to form a single unitized multiparameter connector 906. Along with the aforementioned advantages, the interconnection features may provide the ability to customize the lead set 900 and/or multiparameter input device 910 based on the need of a specific patient. Further, the ability to connect/disconnect individual features of the lead set 900 and/or multiparameter input device 906 may allow for reconstructing and/or refurbishing of either one of or both of the multiparameter input device 910 or the lead set 900, while also allowing for efficient inspection and replacement of components and/or to improve efficiency of sanitizing or high level disinfecting (HLD) components, to name a few advantages.

Figure 10A:
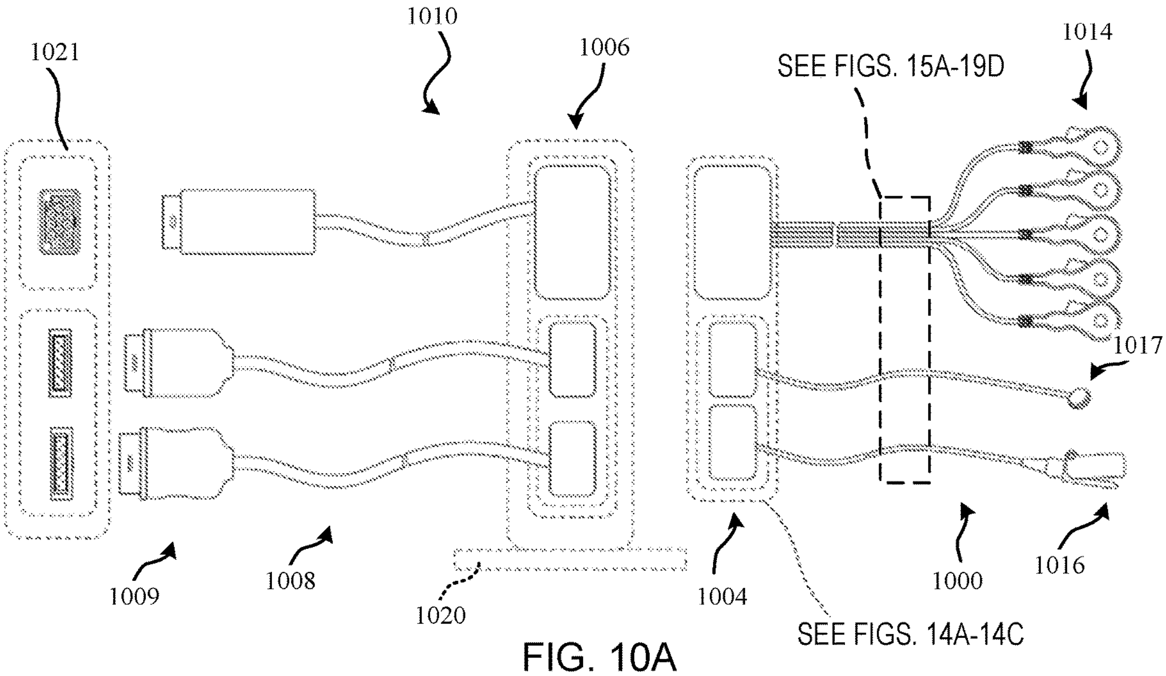
FIG. 10A illustrates an example multiparameter lead set and multiparameter input device according to aspects of the present disclosure.
Figure 10B:
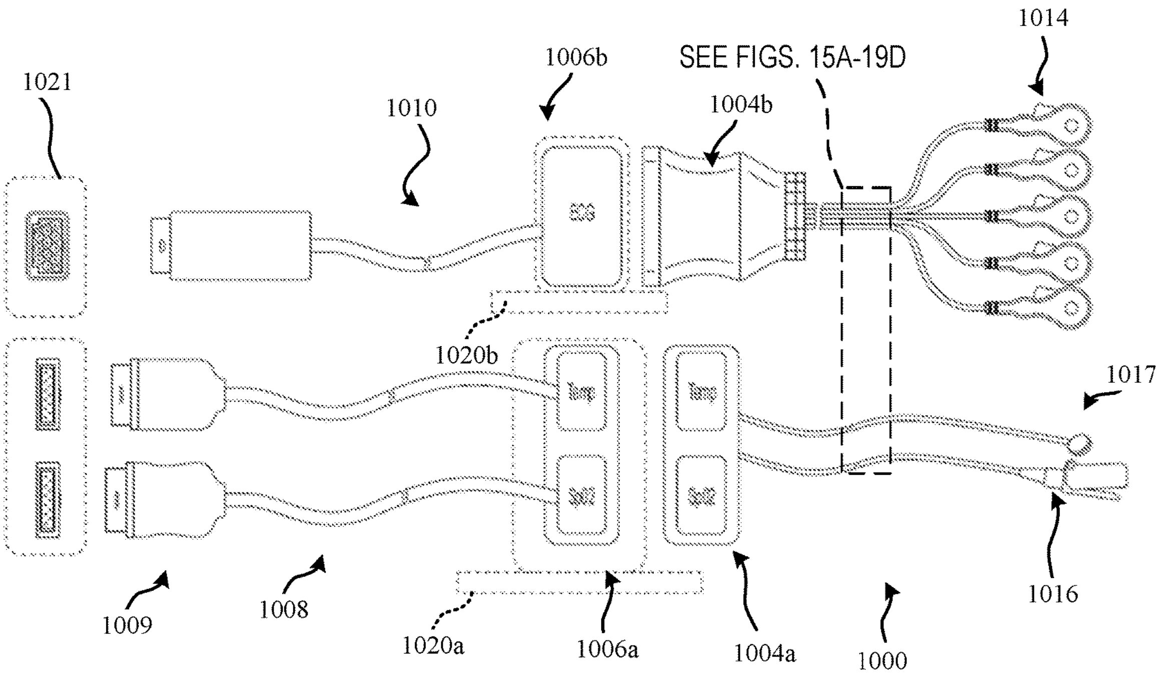
FIG. 10B illustrates an example multiparameter lead set and multiparameter input device according to aspects of the present disclosure.

FIGS. 10A and 10B show example configurations for a lead set 1000 and multiparameter input device 1010. Because several features and details are in common or similar to the features discussed with reference to FIGS. 1-9 above, only additional features required for the understanding of the present disclosure are described further below. FIG. 10A shows one example of a lead set with at least a first patient connector (e.g., a series of ECG connectors 1014) and second patient connector (e.g., at least one of or both of a temperature sensor 1017 and/or an $SpO_2$ sensor or connector 1016). In the example shown in FIG. 10A, both the first patient connector and the second patient connector are connected to a single lead set connector 1004. The single lead set connector 1004 is configured to connect to multiparameter input device 1006, which may, for example, be mounted or permanently via a mount 1020. In one aspect, the multiparameter input device 1006 may be mounted at a location remote from a single or multiple monitoring device(s) having monitoring connectors 1021. The multiparameter input device may have a series of monitor side leads 1008 and monitor connectors 1009 configured to be connected to respective ports on the monitoring device 1021. The mounting of the multiparameter input device 1006 via mount 1020 may enable a technician or other user to connect lead set 1000 with a single hand, for example, without having to individually connect a connector corresponding with each patient connector individually to the monitoring device 1021. Thus, the aforementioned disclosed aspects may prevent cables from being improperly connected and/or fumbling with cables, which may result in excessive contact between the technician and the monitor 1021, among other disadvantages. The consolidation of multiple cables and enablement of one-handed connection/disconnection of the lead set 1000 may especially provide advantages in an urgent or otherwise rushed scenario where a patient, with several leads connected at various location to the patient's body, for example, may need to be quickly connected and/or disconnected from a monitoring device. Further the aforementioned structure may decreased the likelihood of contamination of the monitor or monitors 1020 or other devices that may be re-used amongst multiple patients, to name another example potential advantage.

FIG. 10B shows another aspect of the present disclosure. Similarly to FIG. 10B, details of similar components to those described above are not repeated for the sake of clarity. FIG. 10B, shows another aspect in which the first patient connector (e.g., a series of ECG connectors 1014) and second patient connector (e.g., at least one of or both of a temperature sensor 1017 and/or an $SpO_2$ sensor or connector 1016) are provided with a separate first lead connector 1004*b* and second lead connector 1004*a*. The first lead connector 1004*b* and second lead connector 1004*a* may, for example, be connectable to a respective first multiparameter connector 1006*b* and second multiparameter connector 1006*a*. Similar to the single multiparameter input connector 1006 described above, each of the first multiparameter connector 1006*b* and second multiparameter connector 1006*a* may, for example, be mounted or permanently via a respective first mount 1020*b* and second mount 1020*a*. The first multiparameter input device connector 1006*b* and second multiparameter input device connector 1006*a* may also be mounted at a location remote from a single or multiple monitoring device(s) 1021 having monitoring connectors as shown in FIGS. 10A-B. The multiparameter input device may have a series of monitor side leads 1008 and monitor connectors 1009 configured to be connected to respective ports on the monitoring device 1021. The mounting of the multiparameter input device 1006 via mount 1020 allows for a technician or other user to connect the first lead set connector 1004*b* and the second lead set connector 1004*a* with a single hand, for example, without having to individually connect a connector corresponding with each patient connector individually to the monitoring device 1021. Along with the advantages noted above, the aforementioned separate first lead set connector 1004*b*, second lead set connector 1004*a*, first input multiparameter input device connector 1006*b* and/or second multiparameter input device connector 1006*a* may for example be useful when a first set of monitoring parameters (e.g., requiring the first lead set connector 1004*b*) or a second set of monitoring parameters (e.g., requiring the second lead set connector 1004*a*) is more commonly used or required than the other of the first set of monitoring parameters and second set of monitoring parameters. Thus, the aforementioned disclosed aspects may prevent cables from being improperly connected and/or fumbling with cables which may result in excessive contact between the technician and the monitor 1021.

FIG. 11 shows example configurations for a lead set 1100 and multiparameter input device 1110. Because several features and details are in common or similar to the features discussed with reference to FIGS. 1-10 above, only features required for the understanding of the additional disclosed aspects are described below. FIG. 11 shows one example of a lead set with at least a first patient connector (e.g., a series of ECG connectors 1114) and second patient connector (e.g., at least one of or both of a temperature sensor 1107 and/or an 402 sensor or connector 1116). In the example shown in FIG. 11, both the first patient connector and the second patient connector are connected to a single lead set connector (not shown) or lead set connectors 1104. The lead set connector(s) 1104 may be configured to connect to multiparameter input device 1106, which may for example be mounted or permanently via a mount 1020. In one aspect, the multiparameter input device 1006 may be mounted at a location remote from a single or multiple monitoring device (s) having monitoring ports 1120. The multiparameter input device may have a series of monitor side leads 1108 and monitor connectors 1109 configured to be connected to respective monitoring device ports 1120. In the aspect shown in FIG. 11, the multiparameter input device may include a printed circuit board (PCB) or flat-style first connector 1136 and second connector 1146 with individual terminals that are configured to provide continuity between the multiparameter input device 1106 and the monitoring device ports 1120 when the leadset connectors 1104 are connected to the first multiparameter input device connector 1146 and the second multiparameter input device connector 1136. In addition to the advantages note above, a lead set and multiparameter input device in accordance with this aspect of the present disclosure may further improve efficiency of high level disinfecting (HLD) and/or sterilizing components. For example, because the PCB or flat style connectors form a substantially flat surface, they may be easily cleaned, sanitized, and/or high level disinfecting (HLD) when compared to a traditional connector that may have surface features or concavities that may be more difficult to access or clean. In additional aspects, the first connector 1136 and second connector 1146 may be formed as a single PCB or flat style connector, and the lead set connectors 1104 may be formed as a single connector and/or as two separate connectors that are connectable into a single connector via the interconnection features, for example, as described with respect to FIGS. 14A-14C below.

Figure 12:
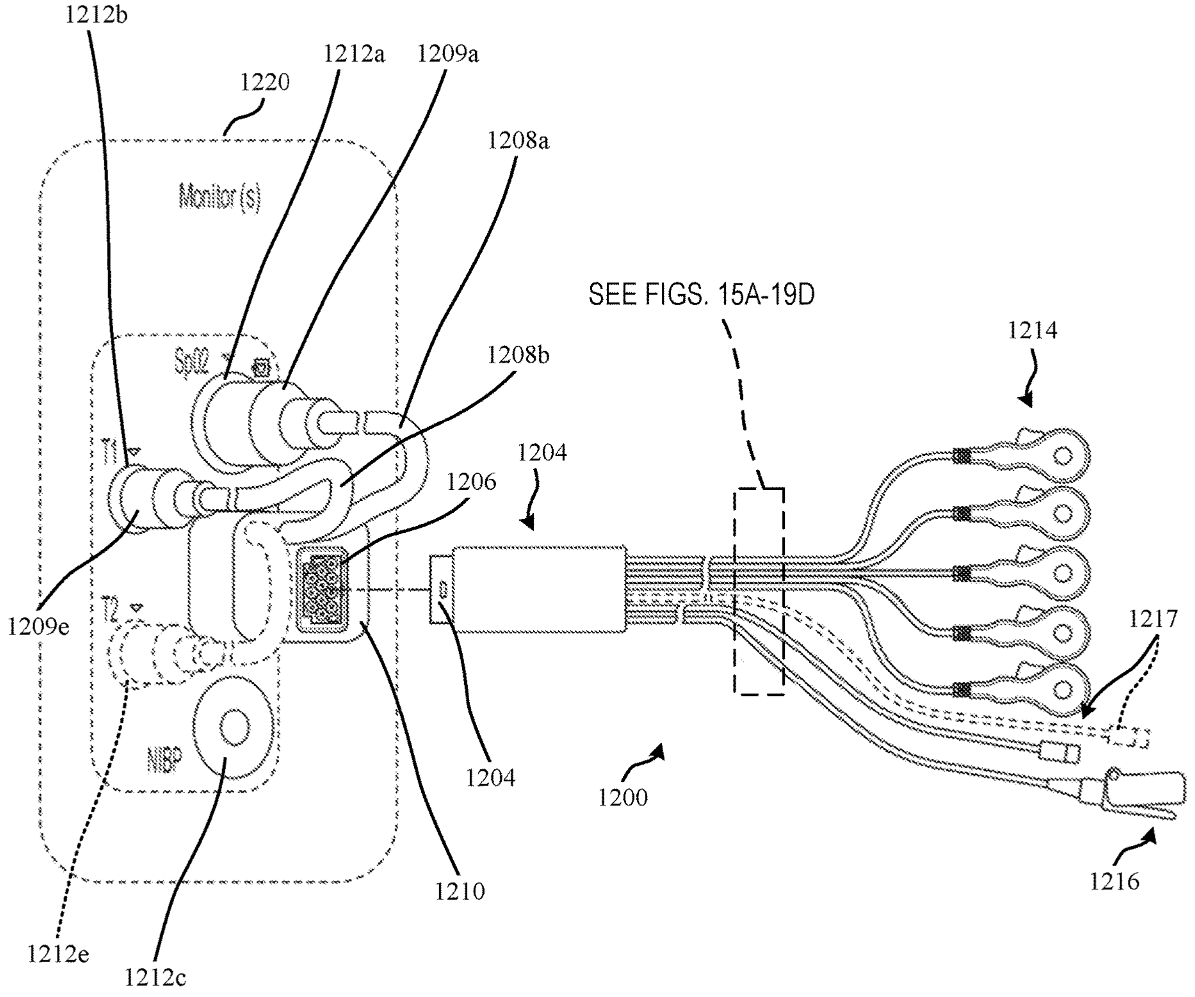
FIG. 12 illustrates an example of a multiparameter lead set and multiparameter input device that is configured to be connected and mounted to a monitoring device according to aspects of the present disclosure.

FIG. 12 shows additional aspects usable with the features described throughout the present disclosure. The multiparameter input device 1210 may for example be connectable to and supported by a first port of the monitoring device 1220 as shown in FIG. 12. For example, the multiparameter input device 1210 may be connectable to an ECG port (hidden from view in FIG. 12—example ECG port 912*d* shown in FIG. 9). The multiparameter input device 1210 may include any number of monitor side connectors. For example, once the multiparameter input device 1210 is connected to the ECG port of the monitoring device 1220 as shown in FIG. 12, a series of monitor side connectors, which may include but are not limited to an oxygen saturation ($SpO_2$) connector 1209*a* configured to be connected to a monitor $SpO_2$ port 1212*a* and a single or plurality of temperature sensor connectors 1209*e*, 1212*e*, which may be configured to be connected to a single or plurality of monitor temperature port(s) (e.g., temperature port 1212*b*). Thus, a lead set 1200, with a single lead set connector 1204 that provides contacts for communication with a number of patient connectors (e.g., ECG connectors 1214, a first and/or second temperature sensor 1217 and/or an 402 device 1216) may be connectable and disconnectable from the monitoring device 1220 via a single connection port 1206 at the multiparameter input device 1210 instead of requiring connection of multiple connectors directly to the monitoring device 1220. As shown in FIG. 12, the lead set connector 1204 may be formed as a male-style multi-terminal connector that is connectably receivable to a female-style multi-terminal connector 1206. While one example of a multiparameter input device connector 1206 and lead set connector 1204 is shown, it is noted that any type of suitable connector may be used; for example any of the connectors or ports described throughout this disclosure may be usable with the aspects described in conjunction with FIG. 12. Further, the lead set connector 1204 may, for example, be or include a modular connector that is formed of a plurality of smaller connecters connected to one another via interconnection features (e.g., as described in conjunction with FIGS. 14A-14C). In addition, the interconnection features described in conjunction with FIGS. 15A-18D may be usable with any one or combination of the leads connecting the patient side connectors (e.g., ECG connectors 1214, temperature sensors 1217 and/or 402 device 1216) to the lead set connector 1204.

Figure 13:
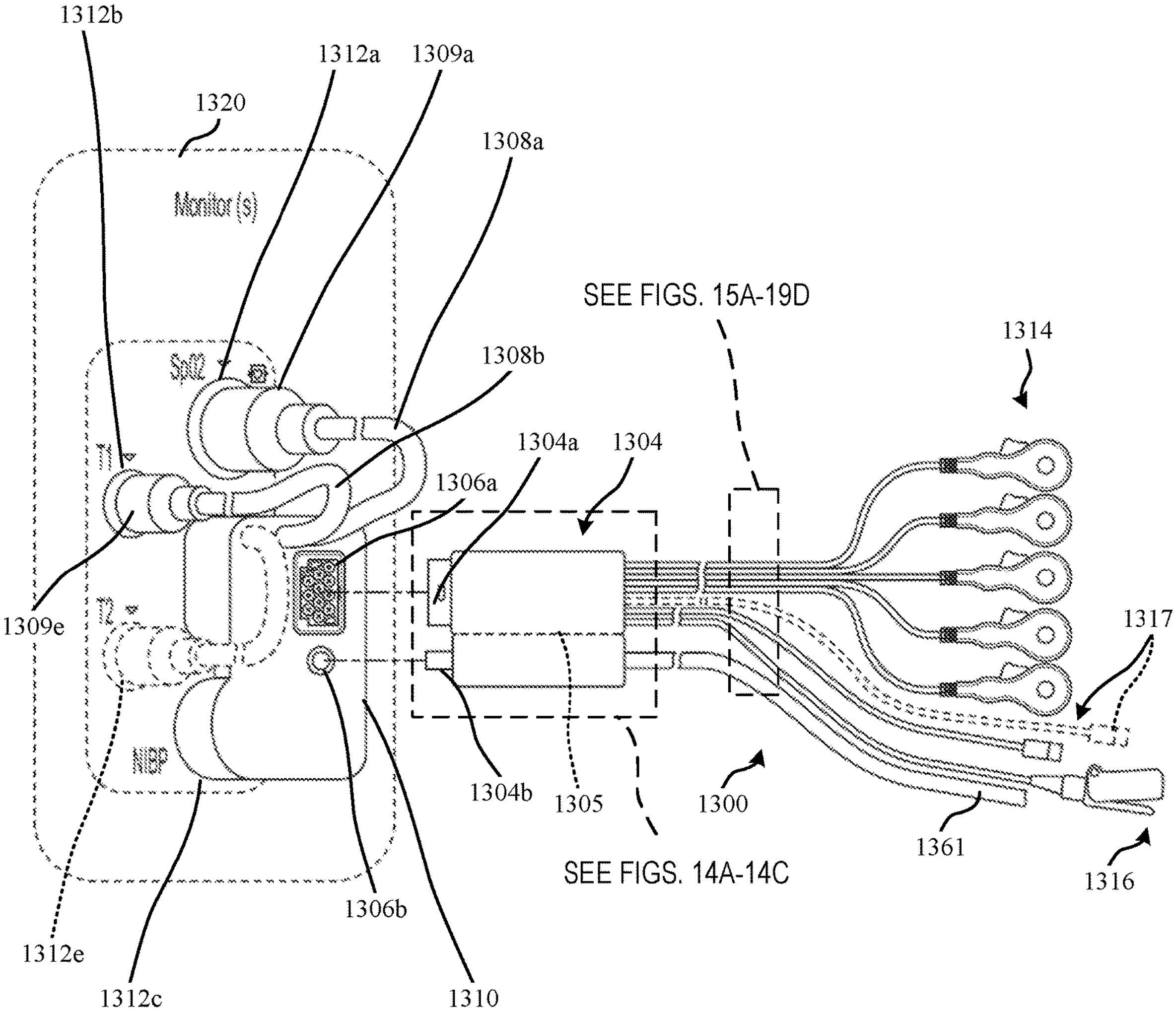
FIG. 13 illustrates an example of a multiparameter lead set and a multiparameter input device with a non-invasive blood pressure provision according to aspects of the present disclosure.

FIG. 13 shows some features that are similar the aspects of the present disclosure described with respect to FIG. 12, features and details that are in common or similar to the features discussed with reference to FIG. 12, above are only detailed as required for understanding of the additional features shown. FIG. 13 shows a multiparameter input device 1310 and lead set 1300 that is similar to the multiparameter input device 1204 and lead set 1200 in FIG. 12 with the addition of an non-invasive blood pressure (NIBP) port 1310*b* integrated into the multiparameter input device 1304. Thus, the multiparameter input device 1304 may be connectable and/or supported by a NIBP port and a ECG port (both hidden from view) of the monitor 1320. In one aspect, the NIBP port may be a tube or other connector for receiving a fluid (e.g., air). In the aforementioned aspect, the multiparameter input device 1310 provides fluid communication between a NIBP connector 1304*b* of the lead set connector and the NIBP port (hidden from view—example shown as reference 1212*c* of FIG. 12) of the monitor 1320. Thus, in addition to the aspects described with respect to FIG. 12 above, the lead set 1300 may include a lead set connector 1304*a* corresponding to a blood pressure monitoring device (not shown) connected to the lead set connector 1304 via tube 1361. As shown in FIG. 13, the lead set connector 1304 may be formed as a male-style multi-terminal connector that includes a series of terminals 1304*a* and a tube or fluid connector 1304*b* connectably receivable to a female-style multi-terminal connector 1206*a* and fluid port 1306*b* for providing fluid communication between the monitor 1320 and the lead set 1300. While one example of a multiparameter input device connector 1306 and lead set connector 1304*a* and/or 1304*b* is shown, it is noted that any type of suitable connector may be used, for example any of the connectors or ports described throughout this disclosure may be usable with the aspects described in conjunction with FIG. 12. Further, the lead set connector 1204 may for example be a modular connector that is formed of a plurality of smaller connecters connected to one another via interconnection features (e.g., as described in conjunction with FIGS. 14A-14C). For example, as shown in FIG. 13, the lead set connector 1304 may comprise a first lead set connector 1304*a* associated with ECG, temperature, and $SpO_2$ signals and a second lead set connector 1304*b* that is associated with a NIBP of a patient. The first lead set connector 1304*a* and second lead set connector 1304*b* may be connectable and disconnectable via an interconnection feature or features 1305.

Figure 14A:
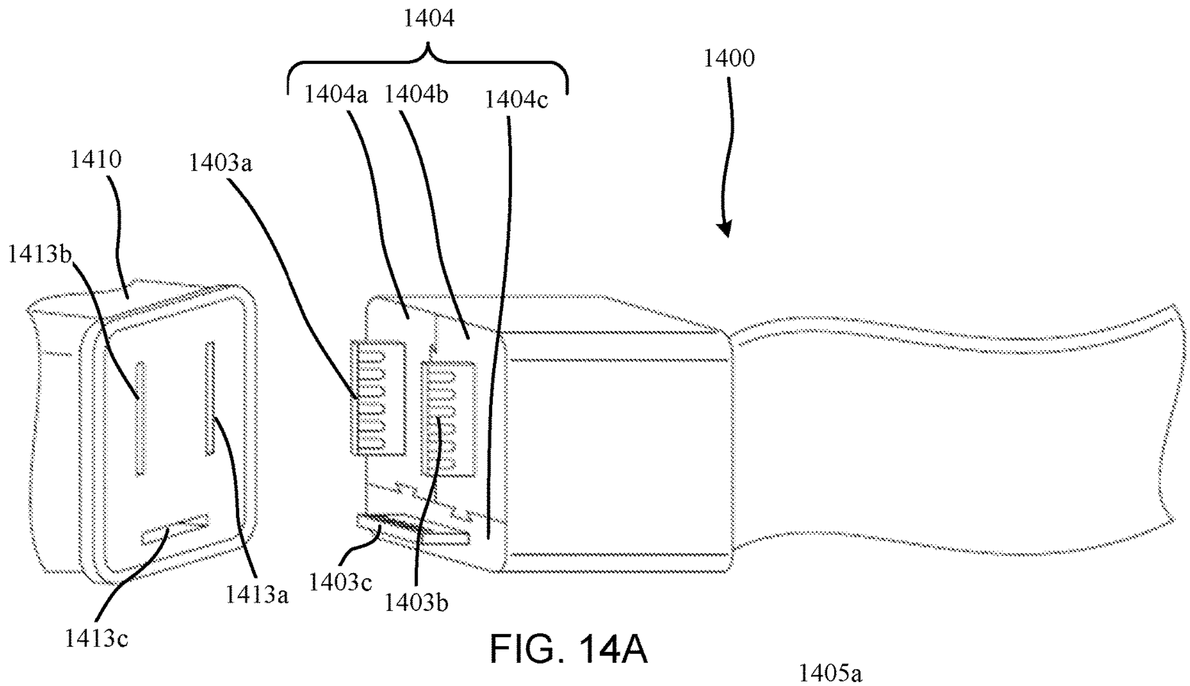
FIG. 14A illustrates an example of a modular connector usable with aspects of the present disclosure.
Figure 14B:
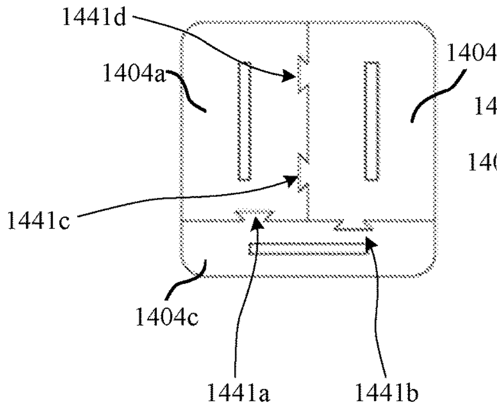
FIG. 14B illustrates an contact configuration usable with the modular connector of FIG. 14A.
Figure 14C:
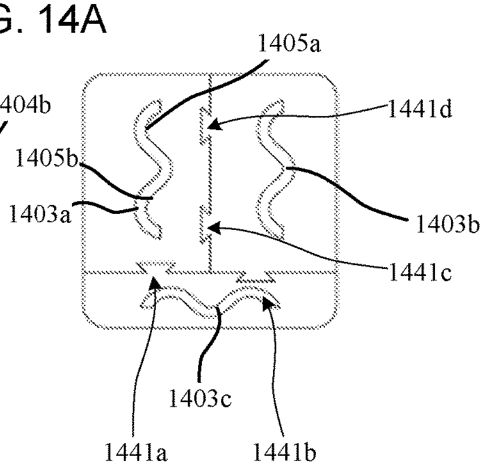
FIG. 14C illustrates a contact configuration usable with the modular connector of claim 14A.
Figure 15A:
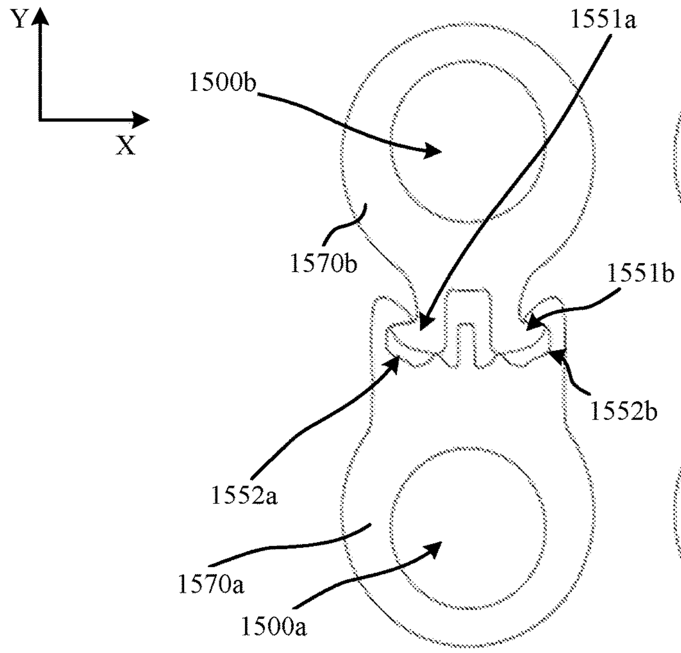
FIGS. 15A-15D show lead interconnection features usable with aspects of the present disclosure.
Figure 15B:
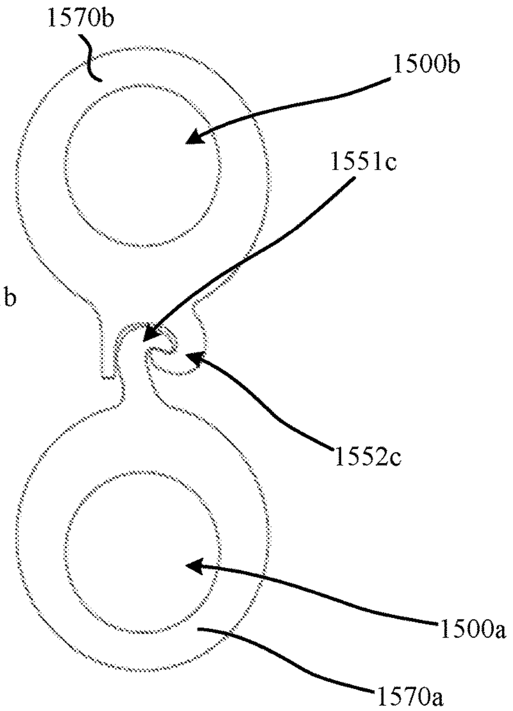
Figure 15C:
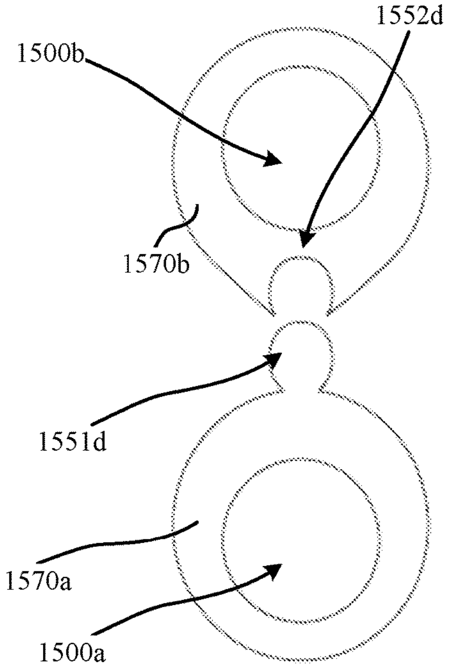
Figure 15D:
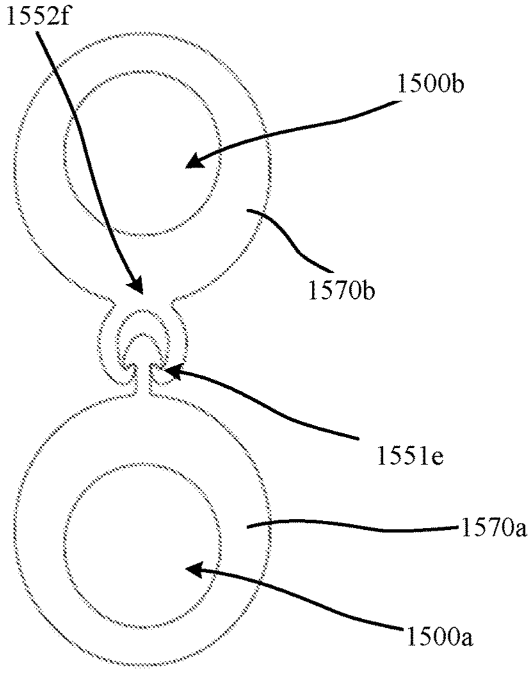

FIGS. 14A-14C show examples of lead set connector interconnection features that are usable with any of the aspects described throughout the present disclosure. As shown in FIG. 14A, a lead set 1400 may include a lead set connector 1404. The lead set connector 1404 may for example be modular and comprised of multiple connectors (e.g., 1404*a*, 1404*b*, and 1404*c*) that are connectable via interconnection features 1441*a*, 1441*b*, 1441*c*, and 1441*d*. Each of the multiple connectors 1404*a* 1404*b* and/or 1404*c* may be associated with or connected to any one or a combination of the patient connectors described throughout the present disclosure. For example, a first lead set connector 1404*a* may have a first contact terminal 1403*a* that provides continuity or otherwise provides signal communication or other coupling from a patient temperature sensor or temperature sensors (e.g., temperature sensors 1217 or 1317 in FIGS. 12 and 13, respectively) via a cable or cables connected therebetween. A second lead set connector 1404*b* may for example have a second contact terminal 1403*b* that provides continuity or otherwise provides signal communication or other coupling with an ECG or series of ECG connectors (e.g., ECG connectors 1214 and 1314 in FIGS. 12 and 13, respectively). A third lead set connector 1404*c* may for example have a third contact terminal 1403*c* that provides continuity or otherwise provides signal communication or other coupling with an $SpO_2$ connector or device (e.g., 402 device 1216 and 1316 in FIGS. 12 and 13). Each one of the first contact terminal 1403*a*, second contact terminal 1403*b*, and/or third contact terminal 1403*c* may be configured to interface with a respective first multiparameter input device interface 1413*a*, second multiparameter input device interface 1414*b*, and/or third multiparameter input device interface 1413*c* of a multiparameter input device 1410. connectors may be used.

As shown in the example in FIG. 14B, the interconnection features may, for example, include an insertable portion that is configured to be captively received by a receiving portion (e.g., a dovetail shaped portion 1441*a*-144*d* that is configured to be received by a correspondingly shaped receiving portion as shown in FIGS. 14A-C). However, the interconnection features are not limited by the example shown in FIG. 14A-C and may include any suitable interface for connecting multiple connectors. As another example, interconnection features may, for example, be or include a snap-fit interface and/or a magnetic interface, to name a few additional examples. Thus, a multiparameter lead set (e.g., 200 in FIG. 2, 300 in FIG. 3, 408 in FIG. 4, 500 in FIG. 5, 600 in FIG. 6, 700 in FIG. 7, 900 in FIG. 9, 1000, in FIGS. 10A-B, 1200 in FIG. 12, and 1300, in FIG. 13) may be or include a modular connector that allows for removal or non-inclusion of a specific lead set connector if a specific monitoring parameter is not required. For example, in the example described above, if $SpO_2$ monitoring is not required, the third lead set connector 1404*c* may be removed or excluded from the lead set. Further, the aforementioned modular construction allows for a lead set to be efficiently reprocessed by removal of a specific lead set connector if, for example, only one of the leads of the lead set is damaged or worn. Further, the aforementioned modular construction allows for a lead set to be separated or partially separated, which may, for example, improve efficiency when high level disinfecting (HLD) or sanitizing lead set during reconstructing or refurbishing.

FIG. 14C shows alternative aspects that may be usable with any of the features described throughout the present disclosure. As shown in FIG. 14C, any one or a combination of the first contact terminal 1403*a*, second contact terminal 1403*b*, and/or the third contact terminal 1403*c* may, for example be, in a patterned configuration (e.g., a patterned terminal). Example patterned configurations include, but are not limited to curved, contoured, circular, or angled (e.g., zig-zag, square, etc.) geometry. As illustrated in FIG. 14C, the patterned terminals 1403*a*-1403*c* are configured in a series of curves or undulations. Typically, the patterned terminals are configured to fit within correspondingly shaped respective receiving portions of the multiparameter input device 1410. One advantage of the patterned terminals is that they may further assist a technician or user with orienting the connector with respect to the multiparameter input device.

One additional advantage of the patterned terminals is that various geometry configurations may provide additional structural rigidity or modulus to the terminal to reduce the possibility of damage to the terminal during use. Yet another advantage of the patterned terminal (e.g., as shown in FIGS. 14B-C is the ability to position specific leads of the contact terminal in sections of the curved or otherwise patterned contact terminal that are less likely to be contacted by a technician or patient during use.

For example, terminals that are likely to have current running therethrough may be located in concave portions (e.g., first concave portion 1405*a* or second concave portion 1405*b* in FIG. 14C), or any other section of the contact terminal that are shielded or otherwise geometrically structured to prevent contact between a lead or plurality of leads from a technician or patient, for example to prevent unintentional grounding of specific lead. In other aspects, the multiparameter input device 1410 and/or lead set connector may for example include patterns or corresponding matching/complementing colors that provide either tactile or visual indication that each lead set connector 1404 is oriented correctly with respect to the multiparameter input device.

It is noted that the aforementioned configuration is provided as an example, and while three modular connectors 1404*a-c* are shown in FIG. 14A-C, any suitable number of modular connectors are usable with aspects of the current disclosure. For example, instead of three modular connectors, the lead set connector 1404 may instead include two modular connectors or more than three modular connectors. In addition, while FIGS. 14A-C show contact terminals 1413*a-c* as female-style receiving portions and contact terminals 1403*a-c* as male-style connectors, all or any combination of the contact terminals 1413*a-c* or receiving portions 1403*a-c* may be reversed (e.g., contact terminals 1413*a-c* may be male-style connectors and contact terminals 1403*a-c* may be female-style receiving portions).

FIGS. 15A-15D show cross-sectional views of example interconnection features useable with aspects of the present disclosure described throughout the present disclosure. The interconnection feature(s), which may be interchangeably referred to as interconnection interfaces(s) throughout the present disclosure, may include an interconnection feature either extending along the length of the lead 1500*b* (e.g., along a Z axis in FIGS. 15A-D) or at set intervals thereof. It is noted that the term lead as used throughout the specification may comprise any one or a combination of wires, tubes, or optical fibers. The first interconnection feature may be formed as a protrusion or series of protrusions (e.g., protrusions 1551*a-e*), which in some aspects may be hook shaped (e.g., 1551*c*) or semi-hook shaped (e.g., 1551*a*, 1551*b*, 1551*e*). The protrusion of the interface may be configured to be captively received by a corresponding concave portion or other aspect of a receiving portion (e.g., 1552*a-e*) of a second interconnection feature that extends along the length of or at set intervals of the second lead 1500*a*. In some aspects the concave portion or other receiving portion may include a hook shaped or semi-hook shaped portion or region (e.g., 1552*a*, 1552*b*, 1552*c*, or 1552*e*) that is configured to engage with a corresponding protrusion of the first interconnection feature (e.g., protrusions 1551*a-e*). The interconnection features described above may form a portion of the outer jacket or coating 1570*a-b* of a leads 1500*a-b*. The interconnection features described above may be formed of a sufficiently rigid yet flexible or elastic material, for example, that allows for the interconnection features to engage when a user or machine forces two or more of the cable(s) and/or tube(s) together. The interconnection features described above may likewise be formed of a sufficiently rigid yet flexible or elastic material that allows for the interconnection features to disengage when a user or machine applies sufficient separation force to the two or more cable(s) and/or tube(s). It is noted that while only two leads (e.g., cables, tubes, or optical fibers) 1500*a-b* are shown in FIGS. 15A-D, the aforementioned aspects are applicable to the connection of any suitable number of leads. For example, the first lead 1500*b* and/or second lead 1500*b* may include a second interconnection feature so that an additional lead may be connected thereto.

Some examples of materials used to form the interconnection features are polyethylene, or more specifically linear low density polyethylene, high-density polyethylene, a bicarbonate, a nylon, and polypropylene, thermoplastic elastomer (TPE), polyvinyl chloride (PVC), Silicone, Urethane or any combination of the aforementioned materials or known materials to facilitate interconnect features with ergonomic characteristics to name a few examples. The aforementioned interconnection features allow any one or a combination of the individual or groups of leads (e.g., wires, tubes, optical fiber(s)) of lead sets describe with respect to FIGS. 2-14 to be connected and/or partially connected along the length of the lead for management purposes. For example, in one aspect any one or a combination of leads (e.g., wires, tubes, optical fiber(s)) of a lead set (e.g., lead set 200 in FIG. 2, 300 in FIG. 3, 408 in FIG. 4, 500 in FIG. 5, 600 in FIG. 6, 700 in FIG. 7, 900 in FIG. 9, 1000, in FIGS. 10A-B, 1200 in FIG. 12, and 1300, in FIG. 13) may be assembled at manufacture so as to be pre-connected using the aforementioned interconnection features and then may be selectively disconnected either entirely or along a portion of the length of the lead set. Likewise, a lead may be re-connected either partially or along the length of the lead if needed. Thus, the aforementioned aspects allow a technician or other user to customize the lead set configuration based on a patient's needs and/or other requirements. Further, the aforementioned aspects allow a lead set to be either partially or completely disassembled for refurbishing or reconstructing.

Figure 16A:
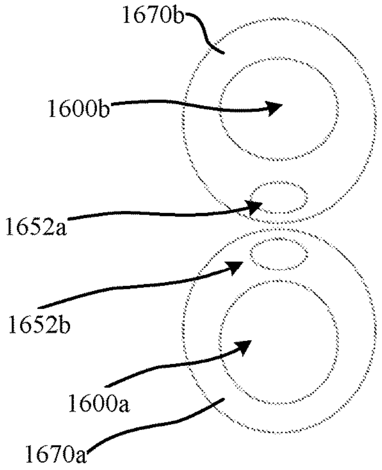
FIGS. 16A-16F show lead interconnection features usable with aspects of the present disclosure.
Figure 16B:
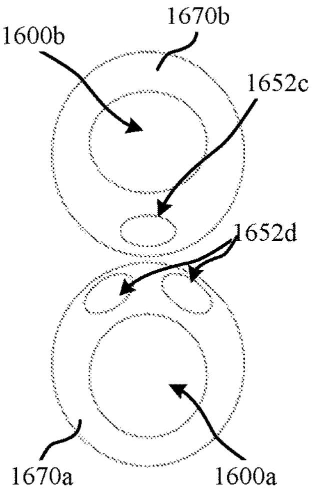
Figure 16C:
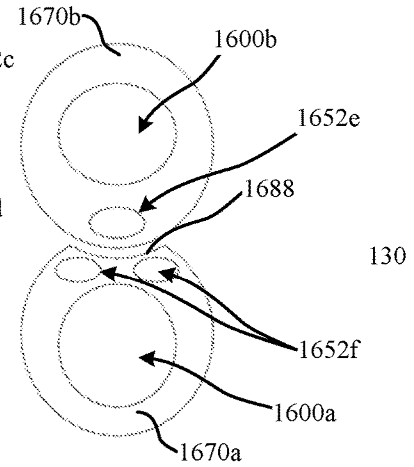
Figure 16D:
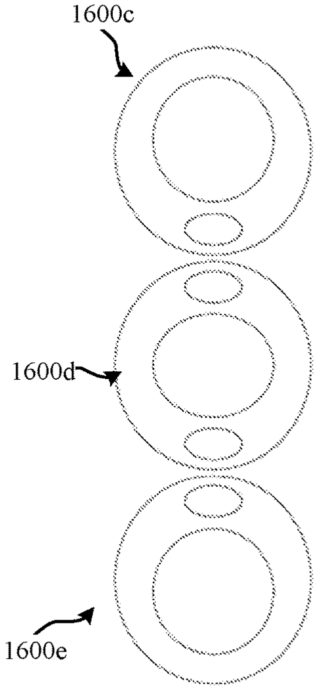
Figure 16E:
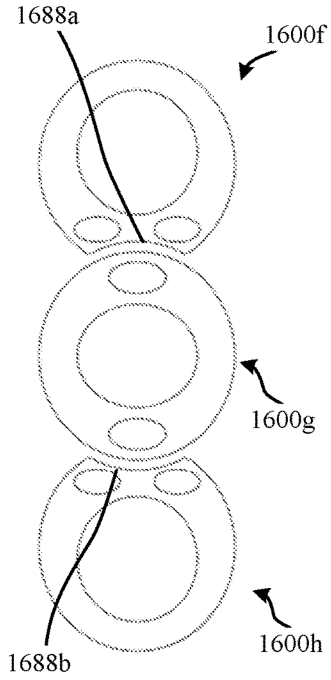

FIGS. 16A-16F show cross-sectional views of example magnetic interconnection features useable with aspects of the present disclosure described throughout the present disclosure. The interconnection feature(s), which may be interchangeably referred to as interconnection interfaces(s) throughout the present disclosure, may include an interconnection feature either extending along the length of the lead 1600*b* (e.g., along a Z axis in FIG. 15A-D) or at set intervals thereof. The first interconnection feature may be formed as magnetic strip (e.g., 1652*a*, 1652*c*, and/or 1652*e*) and/or as magnets embedded within or otherwise disposed within or on the jacket or outer coating 1670*a* of the lead. The magnetic strip and/or magnets (e.g., 1652*a*, 1652*c*, and/or 1652*e*) may comprise any magnetic configuration known in the art that provides an attractive force to a second magnetic strip and/or magnets (e.g., 1652*b*, 1652*d* and/or 1652*f*) of a second interconnection feature of a second lead 1600*a*. For example, the first interconnection feature (1652*a*, 1652*c*, and/or 1652*e*) may comprise ferrite particles within a thermoplastic binder or polymer composite. The second interconnection feature 1652*b*, 1652*d* and/or 1652*f* may, for example, be comprised of a ferromagnetic material (e.g., iron within a thermoplastic binder) so that the first interconnection feature provides a magnetic force to connect the first lead 1670*b* to the second lead 1670*a*. Another example may have interconnection features that use a magnetic structure that results in a "one-sided flux" in each interconnection feature—for example a Halback array. For example, the first and/or second interconnection features 1652*a*, 1652*c*, and/or 1652*e* and/or 1652*b*, 1652*d* and/or 1652*f* may comprise an array of ferrite particles within a binder with arranged so as to augment the magnetic field on one side of the array while cancelling the field to near zero on the other side, so that the portion of the first interconnection feature 1652*a*, 1652*c*, and/or 1652*e* that faces the second interconnection feature 1652*b*, 1652*d* and/or 1652*f* provides a magnetic attraction force that is opposite the field provided by the second interconnection feature 1652*b*, 1652*d* and/or 1652*f* (due to a similar array, but with an opposite magnetic field augmented in the second interconnection feature), to name another example configuration. FIGS. 16B-16F provide additional example configurations of magnetic interconnection features. For example, as shown in FIG. 16B, the second lead 1600*a* may, for example, include two interconnection features 1652*d* that may ensure that the first lead 1600*b* and the second lead 1600*a* remain in a particular orientation with respect to one another. In another example, as shown in FIG. 16C, the second lead 1600*a* may, for example, include a concave section 1688 that extends long the length of the lead and that is configured to receive a curved outer surface of the first lead 1600*b* to further ensure that the first lead 1600*b* and second lead 1600*a* remain in a specific orientation when the first lead interconnection feature 1652*c* and the second lead interconnection features 1652*d* are attracted via a magnetic attraction force. The aforementioned interconnection features may allow any one or a combination of the individual or groups of leads (e.g., wires, tubes, optical fiber(s)) of lead sets described with respect to FIGS. 2-14 to be connected along the length of the lead for lead management purposes. For example, in one aspect, any one or a combination of leads (e.g., wires, tubes, optical fiber(s)) of a lead set (e.g., lead set 200 in FIG. 2, 300 in FIG. 3, 408 in FIG. 4, 500 in FIG. 5, 600 in FIG. 6, 700 in FIG. 7, 900 in FIG. 9, 1000, in FIGS. 10A-B, 1200 in FIG. 12, and 1300, in FIG. 13) may come pre-connected using the aforementioned interconnection features and then may be selectively disconnected or removed from the lead set. Likewise a lead may be reconnected if needed. Thus, the aforementioned aspects allow a technician or user to customize the lead set configuration based on a patient's needs. Further, the aforementioned aspects allow a lead set to be either partially or completely disassembled for refurbishing or reconstructing. In one aspect, the leadset or leads may for example include small magnets spaced at designated intervals extruded into the wall of the lead that may interact with magnets and/or a magnetic substance in other leads.

Figure 16F:
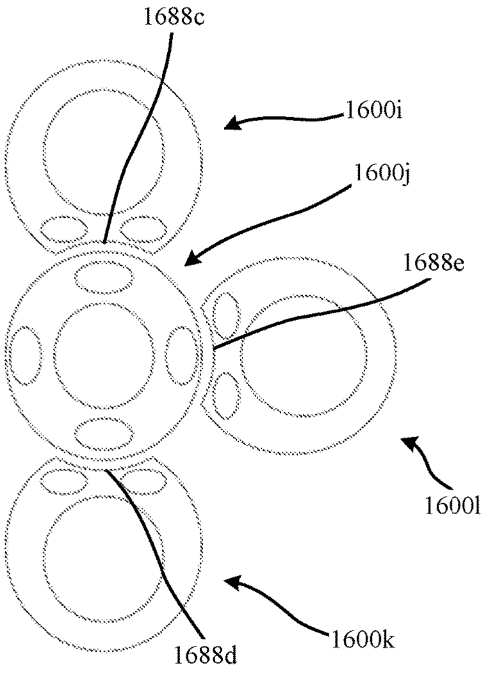

The aforementioned examples are not intended to be limiting. For example, while only two leads are shown in FIGS. 16A-16C, the interconnection features may be applied to lead set with three leads 1600*c*-1600*e* as shown in FIG. 16D and 1600*f*-1600*h* in FIG. 16E, or four leads 1600*i*-16001 as shown in FIG. 16F. Further any one or a combination of the leads may include a concave section (e.g., 1688*a*-*b* in FIG. 16E and 1688*c*-*e* as shown in FIG. 16F) to further ensure that each individual lead maintains a specific orientation when connected via the interconnection features (s). Further, it is noted that while FIGS. 16A-F show the interconnection features embedded within the jacket or outer coating of the lead sets, additional alternative configurations are usable with aspects of the present disclosure.

Figure 17A:
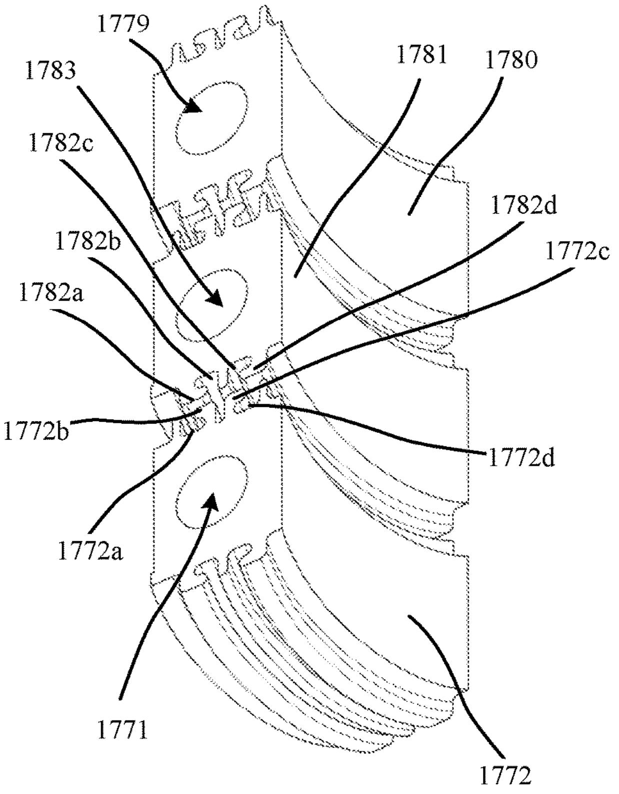
FIGS. 17A-17B show lead interconnection features useable with aspects of the present disclosure.

FIG. 17A shows a perspective cross section views of a series of cables or leads (e.g., 1779, 1783, and 1771) that have outer jackets or coverings (e.g., 1780, 1781, and 1772) with example interconnection features useable with aspects of the present disclosure. The interconnection feature(s), which may be interchangeably referred to as interconnection interfaces(s), may include an interconnection feature either extending along the length of each of the jackets or coverings 1780, 1781, and 1772 or at set intervals thereof. It is noted that the term lead as used throughout the specification may comprise any one or a combination of wires, tubes, or optical fibers. The first interconnection feature may be formed as a protrusion or series of protrusions (e.g., protrusions 1782*a*, 1782*d*, 1772*b*, and/or 1772*c*), which in some aspects may be hook shaped or semi-hook shaped. The protrusion of the interface may be configured to be captively received by a corresponding concave portion or other aspect of a receiving portion (e.g., 1782*b*, 1782*c*, 1772*a*, and/or 1772*d*) of a second interconnection feature that extends along the length of or at set intervals of a second lead. For example, as shown in FIG. 17A, a first lead 1783 and second lead 1771 may have a corresponding first interconnection feature and second interconnection feature. The first interconnection feature of the first lead 1783 may for example include a first hook shaped protrusion 1782*a*, a second hook shaped protrusion 1782*a*, and a first receiving portion 1782*a* as a hook shaped channel and a second receiving portion 1782*c* as a second hook shaped channel. The second lead 1771 may have a second interconnection feature with a second interconnection feature first receiving portion 1772*a* as a hook shaped channel configured to captively receive the first hook shaped protrusion 1782 of the first connection interface and a second interconnection feature second receiving portion 1772*d* as a second hook shaped channel configured to captively receive the second hook shaped protrusion 1782*a* of the first interconnection feature. The second interconnection feature may further include a second interconnection feature first hook shaped protrusion 1772*b* and/or second interconnection feature second hook shaped protrusion 1772*c* configured to be captively received by the first receiving portion 1782*a* and a second receiving portion 1782*c* of the first connection interface. As shown in FIG. 17A, an outer jacket 1780 of a third lead 1779 may have a similar connection interface allowing the third lead 1779 to be connected to the first lead 1783, for example. While only three leads are shown in FIG. 17A, any number of leads may be connected in a similar fashion and employing similar connection features to those described above. The interconnection features described above may be formed of a sufficiently rigid yet flexible or elastic material, for example, that allows for the interconnection features to engage when a user or machine forces two or more of the cable(s) and/or tube(s) together. The interconnection features described above may likewise be formed of a sufficiently rigid yet flexible or elastic material that allows for the interconnection features to disengage when a user or machine applies sufficient separation force to the two or more cable(s) and/or tube(s). In one example, a connection device or devices may be used to assist with and/or may be required to connect and/or disconnect the aforementioned interconnection features. In one example, the connection device may be slid along the outer surface of two or more leads to cause the first connection interface to engage with the second connection interface and/or to allow any number of cables to be connected to one another.

Figure 17B:
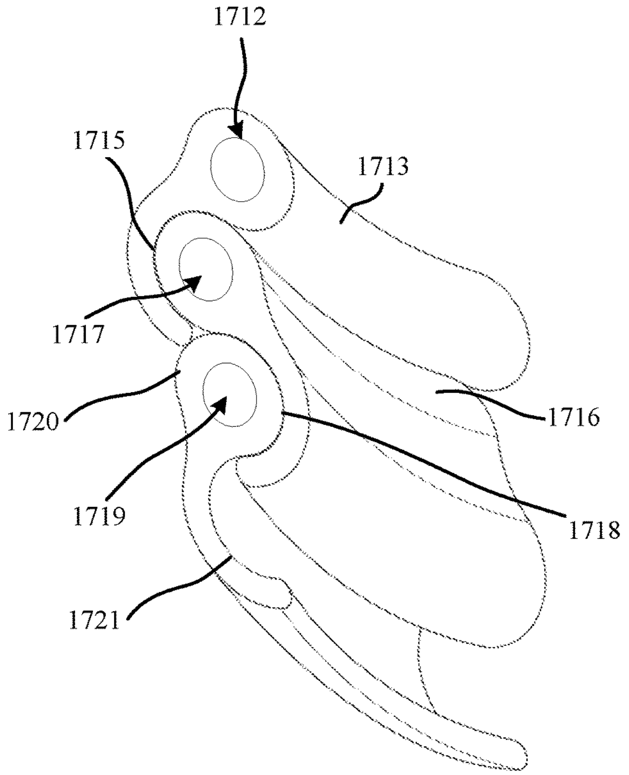

FIG. 17B shows a perspective cross section views of a series of cables or leads (e.g., 1712, 1717, and 1719) that have outer jackets or coverings (e.g., 1713, 1716, and 1720) with example interconnection features useable with aspects of the present disclosure. The interconnection feature(s), which may be interchangeably referred to as interconnection interfaces(s), may include an interconnection feature either extending along the length of each of the jackets or coverings 1713, 1716 and/or 1720 or at set intervals thereof. The first interconnection feature 1715 may be formed as a channel or concave portion configured to receive a second interconnection feature, which may for example be the outer rounded or otherwise convex surface 1715 of a second lead 1717. Similarly, the second lead 1717 may include an interconnection feature 1718 configured to receive an outer rounded or otherwise convex surface of a third lead 1719. While only three leads are shown in FIG. 17B, any number of leads may be connected in a similar fashion and employing similar connection features (e.g., to an interconnection feature 1721 of the third lead 1719, for example) to those described above. The interconnection features described above may be formed of a sufficiently rigid yet flexible or elastic material, for example, that allows for the interconnection features to engage when a user or machine forces two or more of the cable(s) and/or tube(s) together. The interconnection features described above may likewise be formed of a sufficiently rigid yet flexible or elastic material that allows for the interconnection features to disengage when a user or machine applies sufficient separation force to the two or more cable(s) and/or tube(s). In one example, a connection device or devices may be used to assist with and/or may be required to connect and/or disconnect the aforementioned interconnection features. In one example, the connection device may be slid along the outer surface of two or more leads to cause the first connection interface to engage with the second connection interface and/or to allow any number of cables to be connected to one another. In addition, the aspects shown in FIG. 17B may additionally be usable with and may include any one or a number of the magnetic features shown and discussed with respect to FIGS. 16A-16F and/or 19A-19D, for example.

Figure 18:
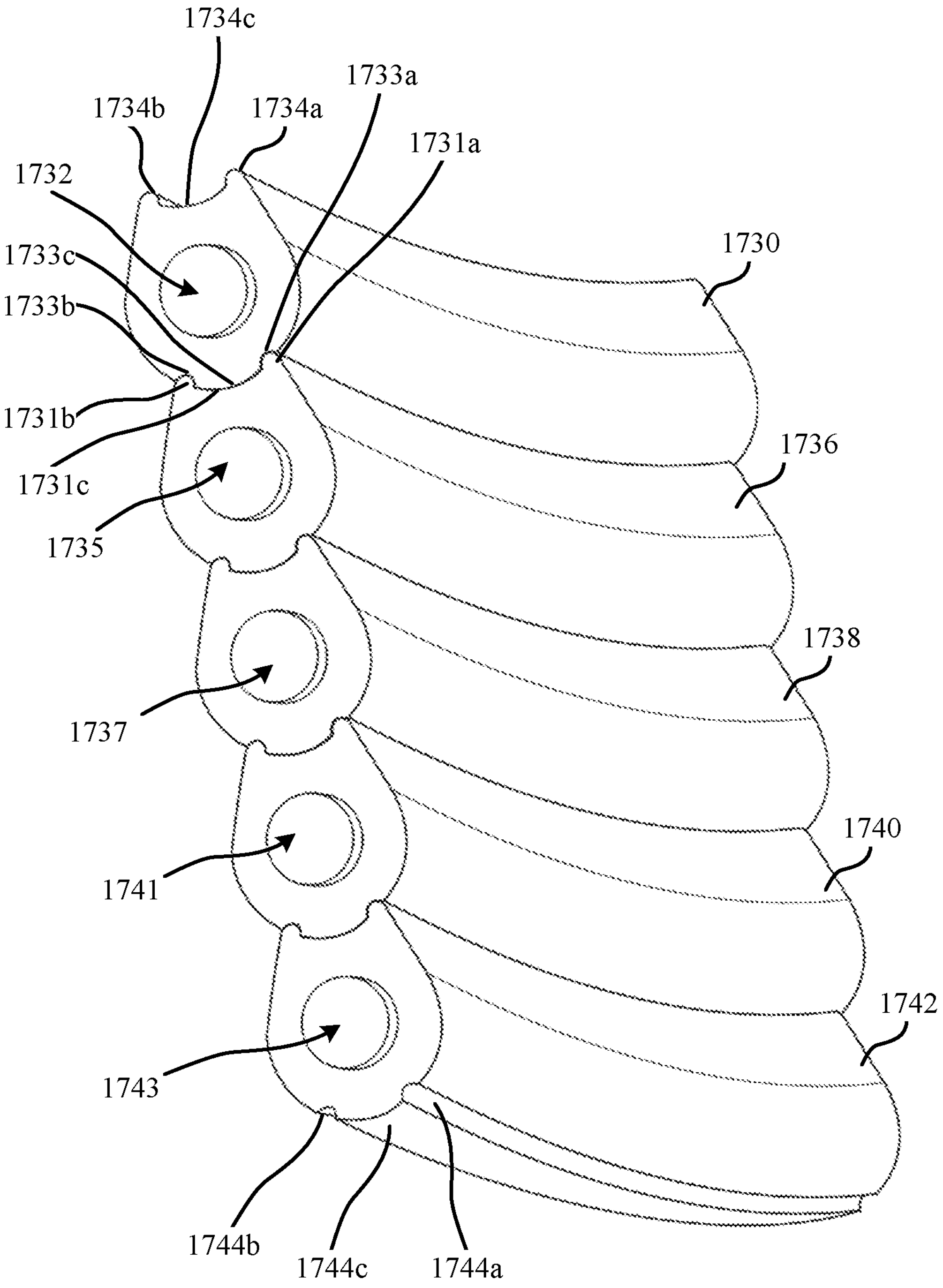
FIG. 18 shows lead interconnection features usable with aspects of the present disclosure.

FIG. 18 shows a perspective cross section views of a series of cables or leads (e.g., 1732, 1735, 1737, 1741, and 1743) that have outer jackets or coverings (e.g., 1730, 1736, 1738, 1740, and 1742) with example interconnection features useable with aspects of the present disclosure. The interconnection feature(s), which may be interchangeably referred to as interconnection interfaces(s), may include an interconnection feature either extending along the length of each of the jackets or coverings 1730, 1736, 1738, 1740, and 1742 as shown in FIG. 18 or at set intervals thereof. It is noted that the term lead as used throughout the specification may comprise any one or a combination of wires, tubes, or optical fibers. As shown in the example in FIG. 18, an interconnection feature may be formed as a protrusion or series of protrusions (e.g.,1734*a-b*, 1731*a-b*). The protrusion of the interconnection feature may have a concave section (e.g., 1734*c*, 1731*c*) therebetween and may be configured to captively received a convex portion (e.g., 1733*c* and/or 1744*c*) while the protrusions (e.g.,1734*a-b*, 1731*a-b*) are received by two receiving channels (e.g., 1733*a-c*, 1744*a-b*) of an interconnection feature of a second lead. The aforementioned features may allow multiple leads to be stacked or otherwise connected to one another. Any one or a combination of the aforementioned aspects may additionally include any one or a combination of the magnetic features shown and discussed with respect to FIGS. 16A-16F and/or 19A-19D, for example. Any one or a combination of the protrusion or series of protrusions (e.g.,1734*a-b*, 1731*a-b*), the concave section(s) (e.g., 1734*c*, 1731*c*), and/or convex portion(s) (e.g., 1733*c* and/or 1744*c*) and/or two receiving channels (e.g., 1733*a-c*, 1744*a-b*) may have any or combination of the magnetic features described hereinthroughout employed therein. While only five leads are shown in FIG. 18, any number of leads may be connected in a similar fashion and employing similar connection features to those described above. The interconnection features described above may be formed of a sufficiently rigid yet flexible or elastic material, for example, that allows for the interconnection features to engage when a user or machine forces two or more of the cable(s) and/or tube(s) together. The interconnection features described above may likewise be formed of a sufficiently rigid yet flexible or elastic material that allows for the interconnection features to disengage when a user or machine applies sufficient separation force to the two or more cable(s) and/or tube(s). In one example, a connection device or devices may be used to assist with and/or may be required to connect and/or disconnect the aforementioned interconnection features. In one example, the connection device may be slid along the outer surface of two or more leads to cause the first connection interface to engage with the second connection interface and/or to allow any number of cables to be connected to one another.

Some examples of materials used to form any of the interconnection features described above are polyethylene, or more specifically linear low density polyethylene, high-density polyethylene, a bicarbonate, a nylon, and polypropylene, thermoplastic elastomer (TPE), polyvinyl chloride (PVC), Silicone, Urethane or any combination of the aforementioned materials or known materials to facilitate interconnect features with ergonomic characteristics to name a few examples. The aforementioned interconnection features allow any one or a combination of the individual or groups of leads (e.g., wires, tubes, optical fiber(s)) of lead sets describe with respect to FIGS. 2-14 to be connected and/or partially connected along the length of the lead for management purposes. For example, in one aspect any one or a combination of leads (e.g., wires, tubes, optical fiber(s)) of a lead set (e.g., lead set 200 in FIG. 2, 300 in FIG. 3, 408 in FIG. 4, 500 in FIG. 5, 600 in FIG. 6, 700 in FIG. 7, 900 in FIG. 9, 1000, in FIGS. 10A-B, 1200 in FIG. 12, and 1300, in FIG. 13, lead set 1950 in FIG. 19E below, and/or lead set 1960 in FIG. 19F below) may be assembled at manufacture so as to be pre-connected using the aforementioned interconnection features and then may be selectively disconnected either entirely or along a portion of the length of the lead set. Likewise, a lead may be re-connected either partially or along the length of the lead if needed. Thus, the aforementioned aspects allow a technician or other user to customize the lead set configuration based on a patient's needs and/or other requirements. Further, the aforementioned aspects allow a lead set to be either partially or completely disassembled for refurbishing or reconstructing.

Figure 19A:
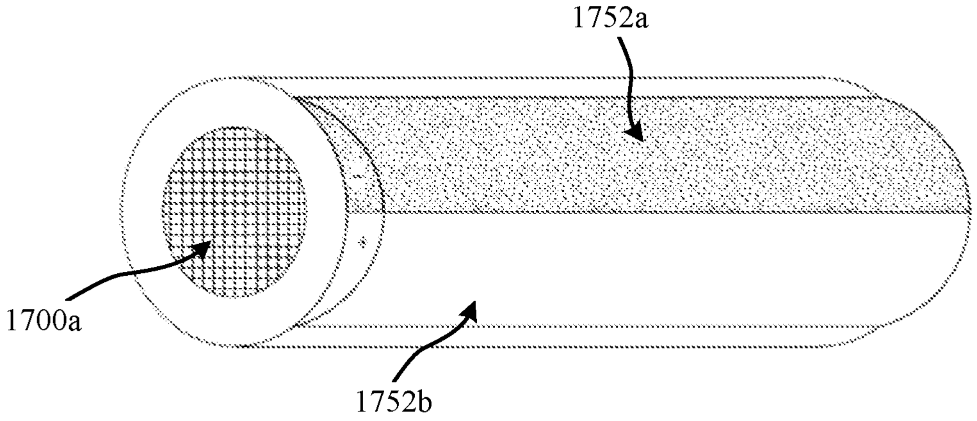
FIGS. 19A-19D show lead interconnection features usable with aspects of the present disclosure.
Figure 19B:
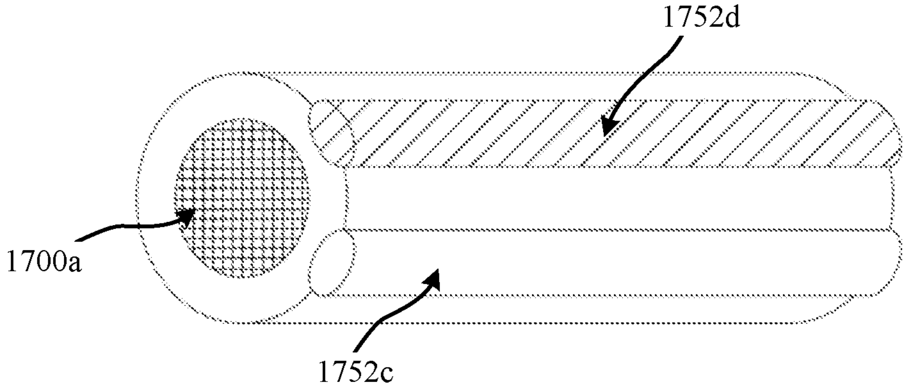
Figure 19C:
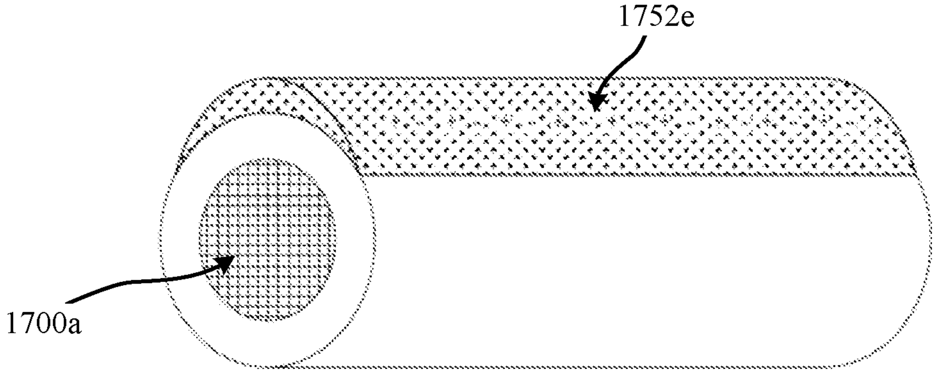
Figure 19D:
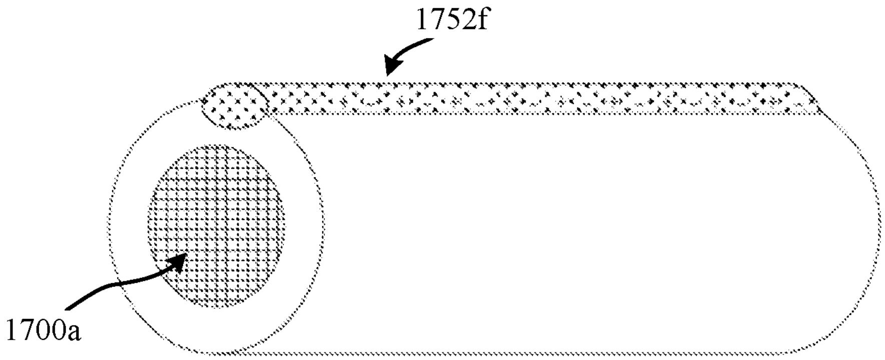

FIG. 19A shows one example of lead 1700*a* having a magnetic interconnection feature disposed on the outside thereof. In the example shown in FIG. 19A, the magnetic interconnection feature may for example include a thermoplastic or other binder material with ferrite or other magnetic or ferromagnetic particles embedded therein. For example, if magnetic particles are used, ferrite particles may be oriented so that that the majority of first poles of the ferrite particles face a first direction in first section 1752*a* (e.g., so that a net magnetic force is south) and so that the majority of second poles of the ferrite particles face the first direction in a second section 1752*b* (e.g., so that the net magnetic force is north). The aforementioned example may be known as a Halbach array. The aforementioned configuration may allow for a second lead (not shown) that includes either a ferromagnetic section or a similar interconnection feature configuration (with opposite poles) to be magnetically attracted to the lead 1700*a* in a desired orientation. FIG. 19B shows another alternative configuration with a first interconnection section 1752*d* and second interconnection section 1752*c* partially embedded within the lead 1700*a*. The first interconnection section 1752 and second interconnection section 1752 may be separated so that a second lead (not shown)

connects via a specific orientation with respect to the first lead 1700*a* and may further prevent the first lead 1700*a* and the second lead from twisting around one-another or otherwise tangling. FIGS. 19C and 19D shown two additional configurations with a magnetic interconnection feature 1752*e* and/or 1752*f* either adhered or otherwise connected to the outer surface of the first lead 1700*a* and/or partially embedded within the outer jacket of the first lead 1700*a*. As mentioned above, while only individual leads are shown in FIGS. 19A-19D, any number of leads may be connected in a similar fashion and employing similar connection features to those described above.

Figure 19E:
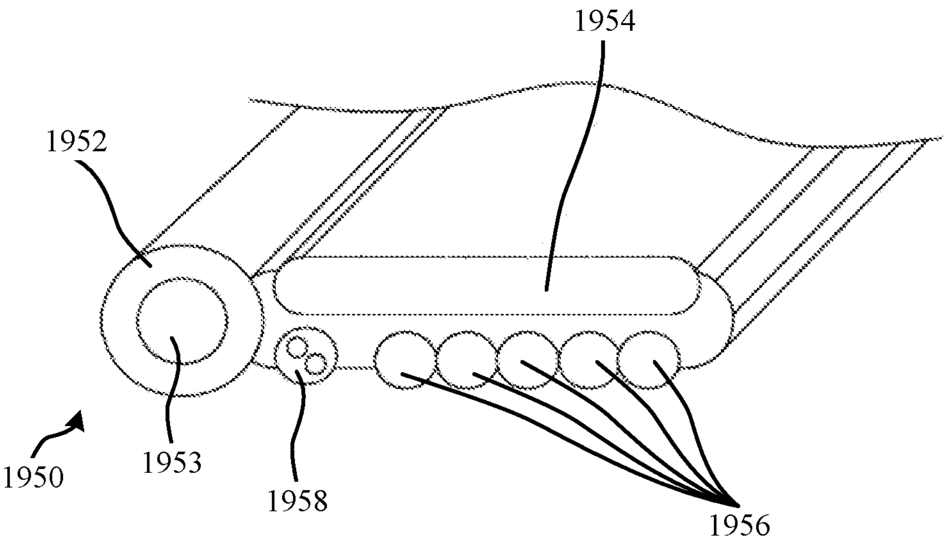
FIGS. 19E-19F show lead interconnection features usable with aspects of the present disclosure.

FIG. 19E shows a cross section of one example leadset 1950 having a series of tubes and/or wires that are configured to span at least partially between a series of patient connectors or sensors (e.g., any one or combination of the patient-side connectors or sensors described throughout this disclosure) and any one or combination of the multiparameter input device connector(s) and/or monitors described throughout this disclosure). As shown in FIG. 19E, the leadset 1950 may have a flat-like shape and may include any one or a combination of a series of EKG or ECG cables or leads 1956, a $SpO_2$ cable or lead(s) 1954, a temperature sensor cable or lead(s) 1958, and/or a non-invasive blood pressure conduit "NIBP" 1952 having a fluid (e.g., air) lumen for providing a fluid pathway between a pump/monitoring device and a patient side connector and/or blood pressure monitoring device. Any one or combination of the individual leads or cables described above may incorporate the interconnection features above with respect to FIGS. 14A-19D to allow for selective disconnection and/or connection of the individual leads or cables for the leadset 1950.

Figure 19F:
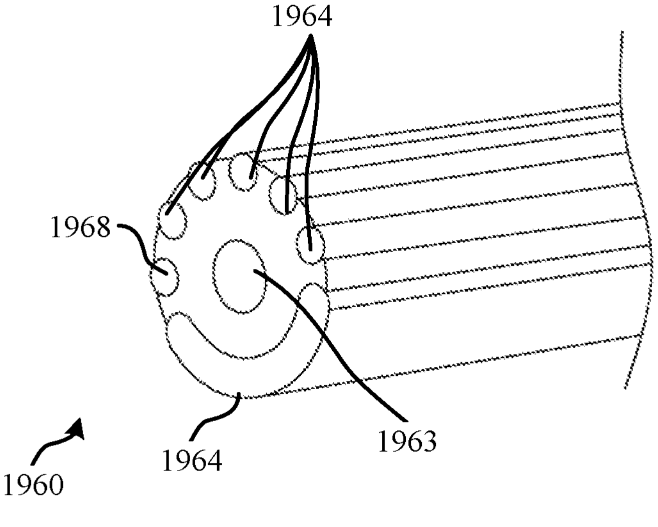

FIG. 19F shows a cross-section of another example leadset 1960 having a series of tubes and/or wires that are configured to span at least partially between a series of patient connectors or sensors (e.g., any one or combination of the patient-side connectors or sensors described throughout this disclosure) and any one or combination of the multiparameter input device connector(s) and/or monitors described throughout this disclosure). As shown in FIG. 19F, the leadset 1960 may have a round overall shape and may include any one or a combination of a series of EKG or ECG cables or leads 1966, an SpO2 cable or lead(s) 1964, a temperature sensor cable or lead(s) 1968, and/or a non-invasive blood pressure conduit "NIBP" 1963 as a fluid (e.g., air) lumen for providing a fluid pathway between a pump/monitoring device and a patient side connector and/or blood pressure monitoring device. Any one or combination of the individual leads or cables described above may incorporate the interconnection features above with respect to FIGS. 14A-19D to allow for selective disconnection and/or connection of the individual leads or cables for the leadset 1960.

b. Reconstructing Method For Lead Sets and Multiparameter Adapters

Figure 20:
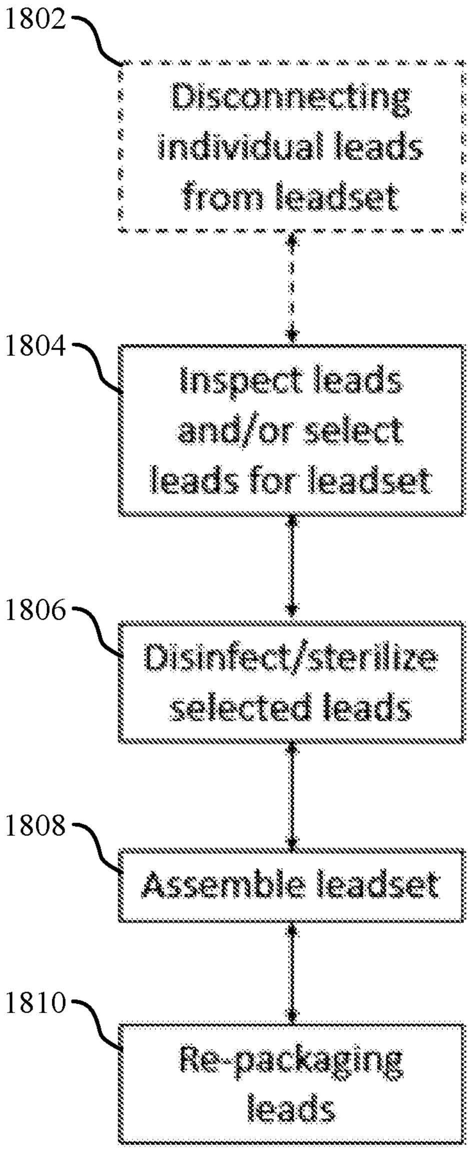
FIG. 20 illustrates a method of assembling or reconstructing a multiparameter lead set.

The aspects disclosed above may be especially useful for the selective refurbishing, reprocessing, and/or reconstructing of the lead sets described herein. FIG. 20 shows one example of a refurbishing and/or reconstructing process in accordance with one aspect of the present disclosure. As shown in FIG. 20, once a lead set is used, the lead set may, for example, be reprocessed or sent to a reconstructing facility. During reconstructing, a first type of patient connector, associated lead and/or lead set connector may be disconnected from a lead set or separated from the lead set 1802. In one example, the lead set may comprise at least a first lead, patient connector, and lead connector associated with a first patient health indicator and may be connected via an interconnection feature to at least a second lead, patient connector, and lead connector associated with a first patient health indicator. To give one specific example, the first type of patient connector may be an ECG connector or series of connectors (e.g., 314 in FIG. 3, 414 in FIG. 4, 514 in FIG. 5, 614 in FIG. 6, 704 in FIG. 7, 804 in FIG. 8, 1014 in FIGS. 10A-B, 1114 in FIG. 11, 1214 in FIG. 12, and 1314 in FIG. 13), and a lead connecting the first type of patient connector to a first lead set connector (e.g., 904*b* in FIG. 9, 1004*b* in FIG. 10, 1136 in FIG. 11, and 1304 in FIG. 13). The second type of patient connector may be a temperature sensor or series of sensors or connectors (e.g., 213 in FIG. 2, 313 in FIG. 3, 413 in FIG. 4, 512 in FIG. 5, 706 in FIG. 7, 807 in FIG. 8, 1017 in FIGS. 10A-B, 1117 in FIG. 11, 1217 in FIG. 12, and 1317 in FIG. 13) and a second lead connecting the second type of patient connector to the second lead set connector (e.g., 904*a* in FIG. 9, and 1104 in FIG. 11). In one example, the first type of leadset may for example be refurbished or reconstructed by any one or combination of a cleaning step, a sanitization or sterilization step, or a high level disinfection step. As discussed in further detail below, in the aforementioned example, the second type of patient lead and/or patient connector may require additional steps to sufficiently refurbish or reconstruct beyond the aforementioned cleaning step, sanitization or sterilization step, or high level disinfection step. The first lead and/or second lead may be connected via any one or a combination of the interconnection features described with respect to FIGS. 15A-19D, and/or the first lead set connector and second lead set connector may be connected via any one of the interconnection features described with respect to FIGS. 15A-19D. Using the aforementioned non-limiting example, the first lead set and second lead set and/or first lead set connector and second lead set connector may be disconnected from one another if they are not already disconnected at 1802. In one example, a disconnection device may be assist with or may be required to disconnect the aforementioned connection features. In one example, the disconnection device may be slid along the outer surface of two or more leads to cause the first interconnection interface to disengage from the second interconnection interface and/or to allow any number of cables to be disconnected from one another. The aforementioned disconnection of the interconnection features via a disconnection device may be completed manually via a technician or worker and/or may be completed via an automated or machine-assisted process.

After the first lead set is disconnected from the second lead set the individual leads, patient connectors and/or sensors and/or the lead set connectors may be inspected or tested to ensure proper function 1804. If it is determined at 1804 that a specific lead of the lead set is damaged or does not function properly, the lead or a component of the lead may be replaced and/or repaired as necessary.

After the leads are inspected and/or tested at 1804, the leads may be sterilized or high level disinfectied (HLD) 1806 either before or after the lead set is assembled at 1808. The lead set may be assembled by re-connecting or connecting or otherwise engaging the interconnection features of the leads and/or the interconnection features of the lead set connectors. In one example, a connection device or devices may assist with or may be required to connect the aforementioned interconnection features. In one example, the connection device may be slid along the outer surface of two or more leads to cause the first connection interface to engage with the second connection interface and/or to allow any number of cables to be connected to one another. The aforementioned disconnection via a disconnection device may be completed manually via a technician or worker and/or may be completed via an automated or machine-assisted process.

The lead set may be re-packaged at 1810 after re-assembly 1808 so that the lead set may be re-used. While general steps are noted above, it is understood that the aforementioned process may be varied without departing from the scope of the present disclosure. For example, high level disinfecting (HLD)/sterilization 1806 may be repeated after the lead set is repackaged, or the lead set may be high level disinfecting (HLD) and/or sterilized 1806 only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets.

c. Temperature Sensor and Electrode Connector Usable with Monitoring Lead Sets

Figure 21A:
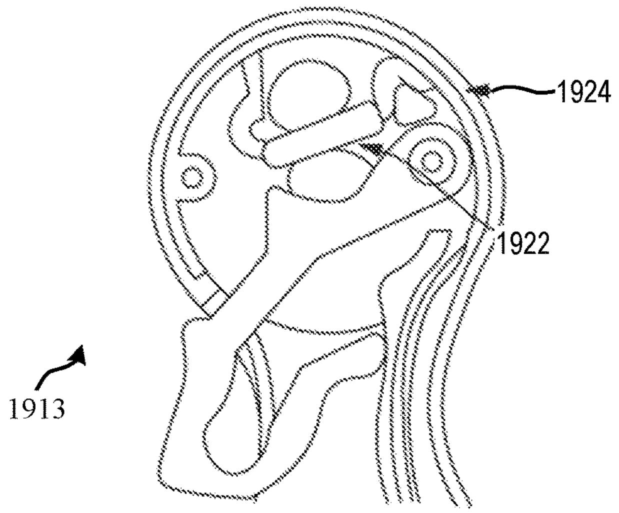
FIGS. 21A-21C illustrate an example temperature sensor device and patches according to aspects of the present disclosure.
Figure 21B:
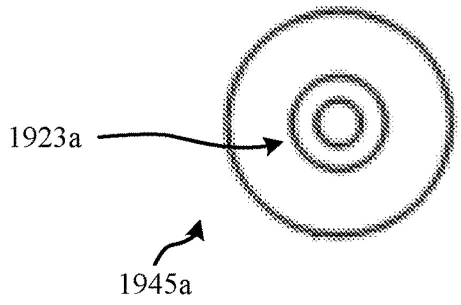
Figure 21C:
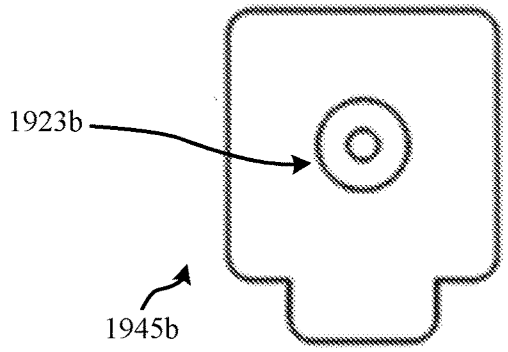

FIG. 21A illustrates a close-up cutaway view of an example temperature connector and sensor 1913, similar to the sensors shown in FIGS. 4 and 5. The temperature sensor 1913 may be configured for use with a temperature patch 1945*a* and 1945*b* in FIGS. 21B and 21C, respectively. The temperature patches 1945*a* and 1945*b* may, for example, be or include heat conductive material bodies placed in direct contact with the skin of the patient. The heat conductive material body may include a metal or other readily heat conducting material, and may be used with a hydrogel placed between the body and the patient's skin, which, in addition to facilitating the conduct of heat from the skin, may also provide adhesive properties to help maintain positioning of the heat conducting material body throughout the duration of patient monitoring. The heat conductive material body may be in thermal communication with a temperature sensor connection post 1923*a* or 1923*b* of the temperature patch and thus may then be placed in thermal and/or electrical communication with a temperature sensing device 1922, such as a thermistor within the sensor 1913. The temperature sensing device 1922 (FIG. 21A), such as a thermistor, which may have a resistance that varies as a function of the temperature. The device 1922 may then vary in resistance with the temperature of the heat conductive material or thermal conductive body in contact with the skin of the patient. In addition, to further increase the accuracy of the measurement provided by the temperature sensor 1913, hydrogel may be added so as to surround the heat conducting material body and/or other portions of the overall sensor 1913 (FIG. 21A). In another example, temperature sensing may occur in the temperature patches 1923*a* (FIG. 21B) and/or 1923*b* (FIG. 21C) instead of or in combination with the aforementioned temperature sensing in connector 1913 (FIG. 21A). In this aspect, the temperature patches 1945*a* (FIG. 21B) and/or 1945*b* (FIG. 21C) may have a thermistor embedded therein, and the post 1923*a* (FIG. 21B) and/or 1923*b* (FIG. 21C) may provide signal communication and/or signal continuity or other coupling between a temperature sensor in the patch 1945*a* (FIG. 21B) and/or 1945*b* (FIG. 21C) and a monitoring device.

Alternatively, or in addition to use of a material such as hydrogel, a foam, plastic, or paper cover placed over the sensor 1913 of FIG. 21A may also act as an insulator and help protect or stabilize the emplaced temperature sensor 1913. To further validate the measurement made by temperature sensor 1913, outer sensor body 1924 (also interchangeably referred to herein as a "housing") of sensor 1913 may also include a reflective coating to mitigate the effects of radiative cooling or heating.

Patient body temperature may alternatively be monitored by other devices and/or methods, such as by use of a temperature sensing Foley catheter. Additionally, both a catheter and a temperature sensor may be implemented within any of the lead sets described throughout the specification, so that two different temperature measurements may be obtained. These two different measurements may correspond respectively to the difference in measuring the core temperature and surface temperature of the patient, for example.

Figure 22A:
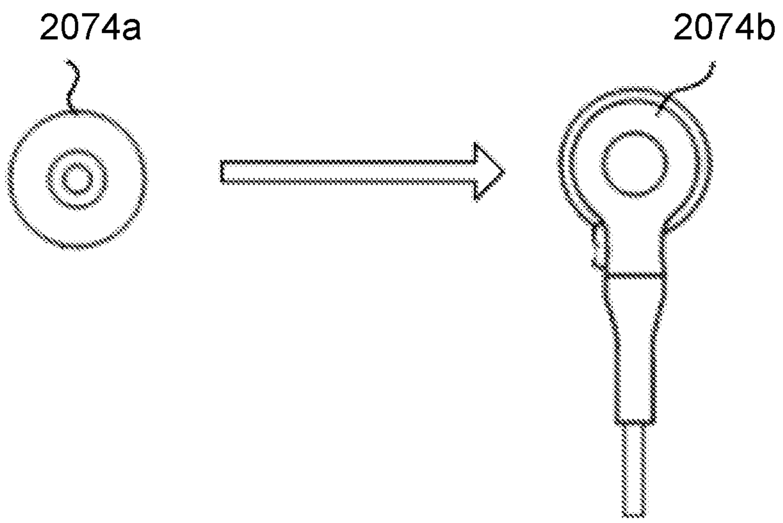
FIGS. 22A-22B illustrate an example electrode pad device and an example temperature sensor device attached to a patient, according to aspects of the present disclosure.
Figure 22B:
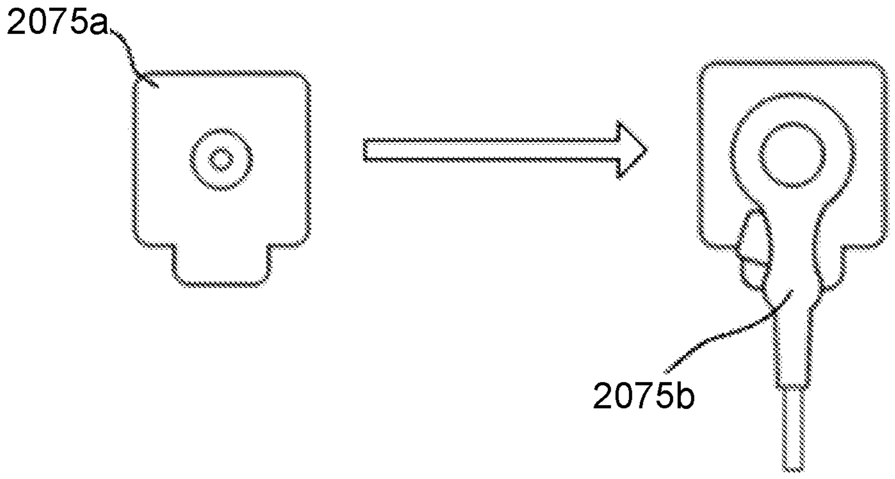

According to various aspects of the present disclosure, FIGS. 22A and 22B illustrate various images of an example implementation of monitoring devices and methods of connecting monitoring devices to a patient. For example, as shown in FIG. 22A the monitoring devices may include a temperature sensing device and/or thermal patch 2074*a*, which may be adhered or otherwise emplaced on a patient's body. Once the temperature sensing device and/or thermal patch 2074*a* is emplaced, a temperature sensing device and/or connector 2074*b* may be removably connectable to the patch 2074*a*. FIG. 20B also illustrates an electrode connector 2075*b* that is selectively connectable to an electrode pad 2075*a* which may be adhered or otherwise emplaced on a patient, for example.

Figure 22C:
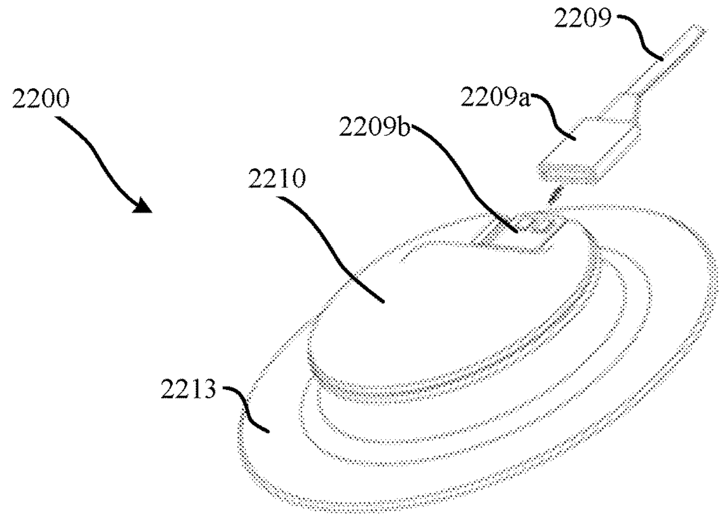
FIG. 22C illustrates a temperature sensor system according to aspects of the disclosure.
Figure 22D:
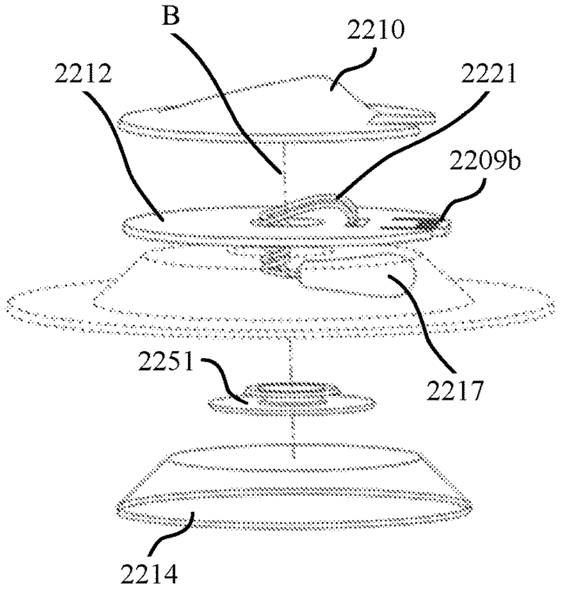
FIG. 22D is an exploded view of the temperature sensor system of FIG. 22C according to aspects of the disclosure.
Figure 22E:
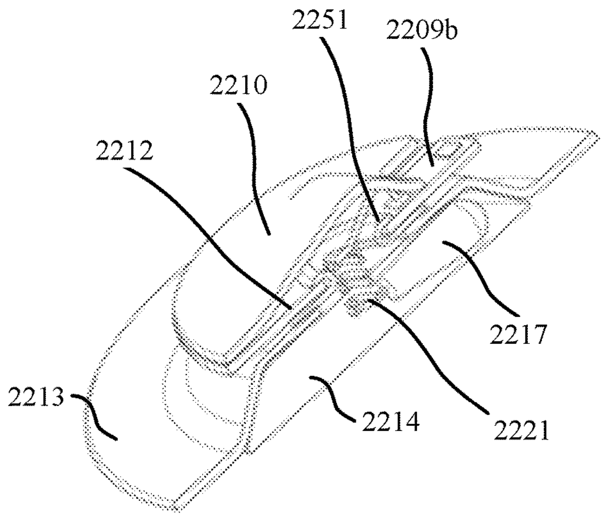
FIG. 22E is a cross-section view of the temperature sensor of FIGS. 22C and 22D according to aspects of the disclosure.

FIGS. 22C-22E show examples of a temperature sensor 2200 usable with aspects of the disclosure. The temperature sensor 2200 may be analogous with temperature sensor 213 in FIG. 2, may replace connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, for example. The temperature sensor 2200 may also be usable with or refurbished or reprocessed in accordance with any one or combination of steps described in FIGS. 27-30 described below. The temperature sensor 2300 may for example have a temperature sensor housing or first insulating cover 2210. The temperature sensor housing or insulated cover may for example be formed of a rigid or semi-rigid plastic or insulating flexible plastic of foam. The temperature sensor may for example further include a support member 2212, which may for example be formed of a rigid, semi-rigid, or flexible circuit board. In one aspect, the support member may include a card-style or flat connector 2209*b* configured to be connected to a leadset connector 2209. In another aspect, the temperature sensor may be directly connected to a leadset wire 2209, for example. The leadset wire and/or temperatures sensor wire 2209 may for example be in electrical and/or signal communication with a temperature sensor member 2217 either via the support member 2212 and/or may be directly connected to the leadset connector 2209 or the connector 2209*b*. In one example, the temperature sensor member 2217 may for example be a thermistor, which may have a resistance that varies as a function of the temperature. Thus, the temperature sensor 2200 may then vary in resistance with the temperature of the heat conductive material or thermal conductive body 2214 in contact with the skin of the patient. The thermal conducive body 2214 may for example be a thermally conductive material such as a hydrogel and may have the temperature sensor member 2217 embedded therein. In one example, the temperature sensor 2200 may further comprise a grommet 2251 configured to allow the terminals or wires connecting the temperature sensor member 2217 to pass therethrough. The grommet 2251 may be configured to fit within an opening of the support member 2212. In one example, the grommet 2215 may be configured to be rotatable within the opening of the support member 2212 which allows for the first insulating cover 2210 and the support member support member 2212 and wire or cable 2209 connected thereto to at least partially rotate with respect to the thermal conductive body 2214 about axis B (FIG. 22D). This at least partial rotation allows for the cable 2209 to be rotated or otherwise re-arranged while the thermal conductive body 2214 is emplaced or adhered to a patients skin. This rotation may improve patient comfort, allow for improved cable management and/or to prevent inadvertent removal of the temperature sensor 2200 from a patients skin.

As shown in FIG. 22C-22E, the temperature sensor may further include a second insulating cover 2213. The second insulating cover may for example be formed of a be formed of a rigid or semi-rigid plastic or insulating flexible plastic of foam. Further, the second insulating cover 2213 may further include an opening configured to receive have the grommet 2251 passed therethrough. In one aspect, the temperature sensor 2200 may be refurbished or reprocessed either by replacing the thermal conductive body 2214 and/or second insulating cover 2213 after use or by removing the second insulating cover 2213 from the temperature sensor 2200 and replacing the thermal conductive body 2214 with a new heat conductive media. For example, in the example implementation with a hydrogel as thermal conductive body 2214, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. In one example, the second insulating cover 2213 with the hydrogel removed may be used as a mold or partial mold and may be refilled or otherwise have the thermal conductive body 2214 replaced during reconstructing. I none aspect, a release film (not shown) that is configured to seal or partially seal the thermal conductive body 2214 from the environment may be placed over and/or adhered to the thermal conductive body 2214 and or the thermal conductive body 2214 and second insulating cover 2213. Further examples of such a reconstructing or refurbishing are described with respect to FIGS. 27-29 below. In one example implementation, the temperature sensor 2200 may be sealed in a pouch or other containment portion that has a low vapor transmission rate. In one example, only the temperature sensor 2200 of a leadset may be sealed in a low vapor transmission rate pouch. In one example, the oxygen saturation sensor may be sealed within a low vapor transmission rate pouch that is sealingly engaged with or sealed around the cable of the temperature sensor 2200 another example, the temperature sensor may be sealed in a low vapor transmission rate pouch while the leadset (and temperature sensor with low vapor transmission pouch) is sealed or otherwise contained therein.

Figure 22F:
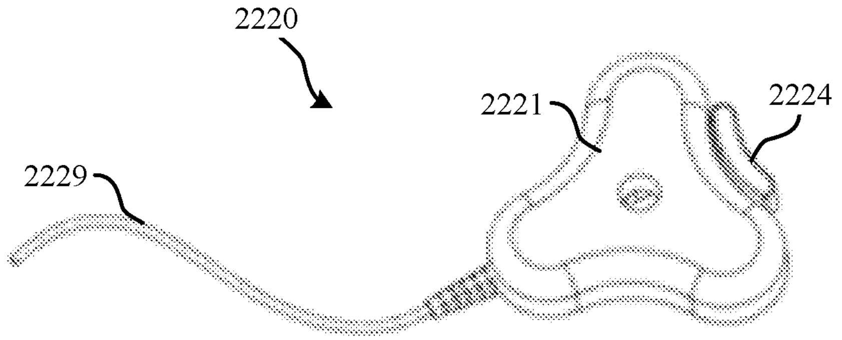
FIGS. 22F-22*i* illustrate an example temperature sensor device and patches according to aspects of the present disclosure.

FIGS. 22F-22 show an example temperature connector and sensor 2220, similar to the sensors shown in FIGS. 4 and 5. The temperature sensor 2220 may be configured for use with a temperature patch 2225*a* and 2225*b* in FIGS. 22H and 22*i*. The temperature patches 2225*a* and 2225*b* may, for example, be or include heat conductive material bodies placed in direct contact with the skin of the patient. The heat conductive material body may include a metal, hydrogel or substrate thereof or may include any other readily heat conducting material, and may be used with a hydrogel placed between the body and the patient's skin, which, in addition to facilitating the conduct of heat from the skin, may also provide adhesive properties to help maintain positioning of the heat conducting material body throughout the duration of patient monitoring. The heat conductive material body may be in thermal communication with a temperature sensor connection post 2223*a* and/or 2223*b* of the temperature patch and thus may then be placed in thermal communication with a temperature sensor within the connector 2220. The temperature sensor may be similar to temperature sensor 1922 (FIG. 21A), and may be a thermistor as described above. The engagement activation portion 2224 may be configured cause an engagement portion to biasingly engage with a temperatures sensor connection post 2223*a* and/or 2223*b* to fixedly connect the body 2221 of the connector 2220 to a temperature patch 2225*a* and/or 2225*b*.

Figure 22G:
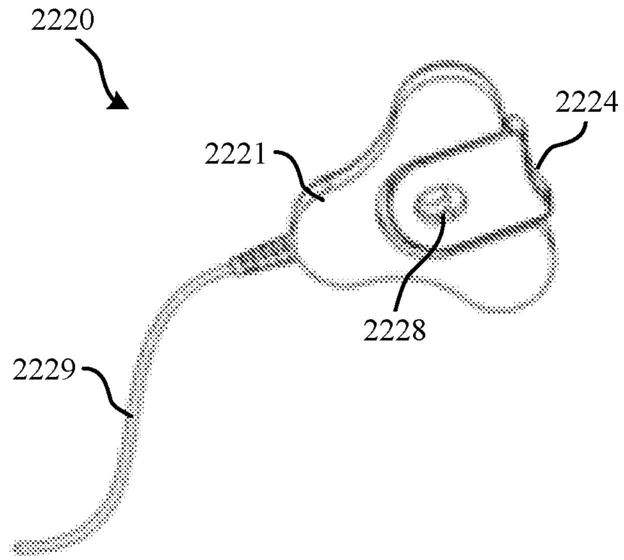
Figure 22H:
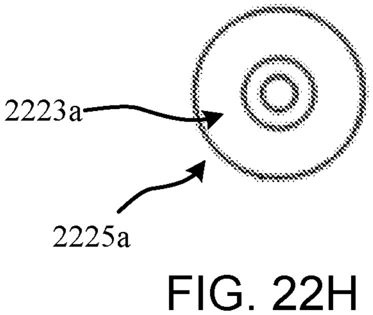
Figure 22I:
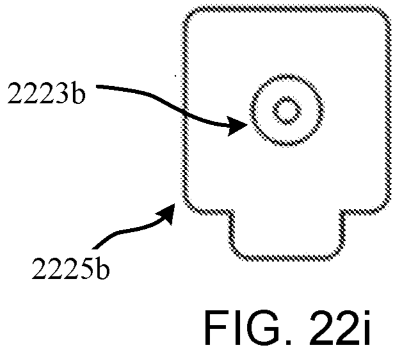

In another example, temperature sensing may occur in the temperature patches 2225*a* and/or 2225*b* instead of or in combination with the aforementioned temperature sensing in connector 2220. In this aspect, the temperature patches 2225*a* and/or 2225*b* may have a thermistor embedded therein, and the post 2225*a* and/or 2225*b* may provide signal communication and/or signal continuity or other coupling between a temperature sensor in the patch 2225*a* and/or 2225*b* and a monitoring device. As shown in FIGS. 22F and 22G, the temperature connector and/or sensor housing 2221 may for example have a different shape to indicate that the connector/sensor of the leadset is for detecting a patient's temperature. In another example usable with the aforementioned implementation, the temperature connector and/or sensor housing 2221 may for example have a different color, texture or other indicator to convey to a user that the connector/sensor of the leadset is used for temperature detection (e.g., instead of as a ECG or other patient sensor or connector). In some examples, the temperature patches 2225*a* and 2225*b* may be color or pattern matched to the temperature connector and/or sensor housing to further assist a user in connecting a leadset to a patient.

Figure 23A:
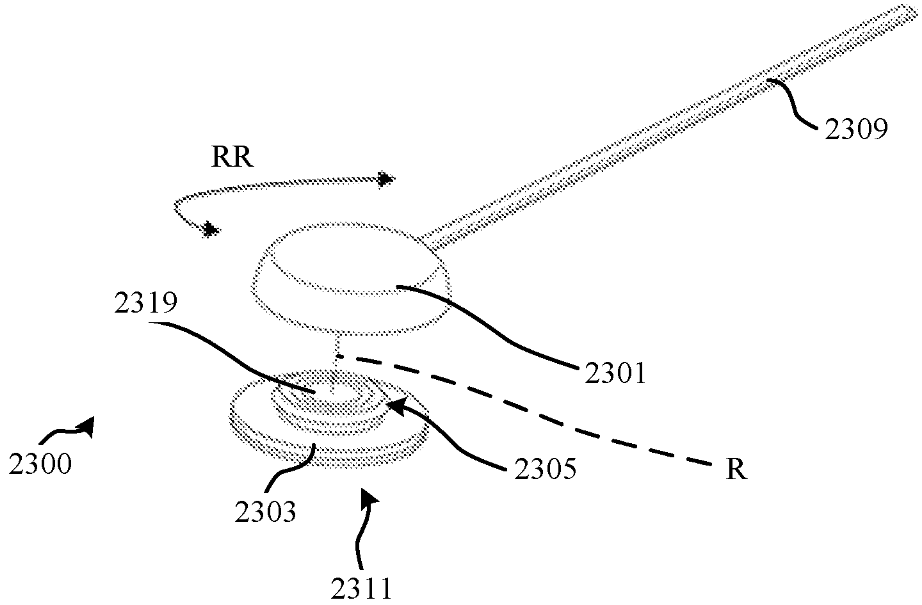
FIG. 23A is a partially exploded view of an example temperature sensor system according to aspects of the disclosure.
Figure 23B:
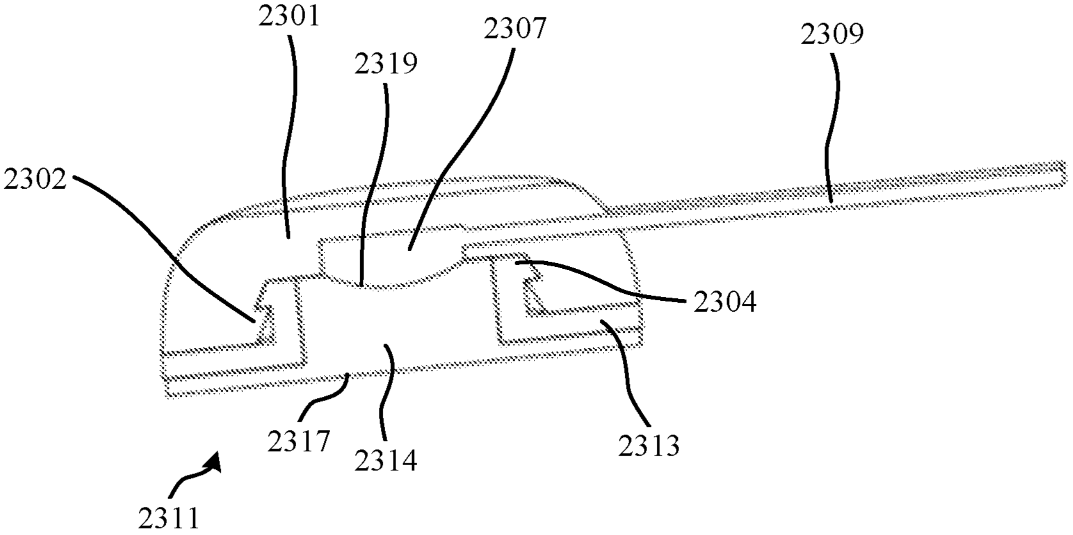
FIG. 23B is a cross section view of the temperature sensor system of FIG. 23A according to aspects of the disclosure.

FIGS. 23A and 23B show examples of a temperature sensor 2300 usable with aspects of the disclosure. In one example, the temperature sensor 2300 may be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, for example. The temperature sensor 2300 may for example have a temperature sensor housing 2301. The temperature sensor outer housing may have connected thereto or embedded therein a temperature sensor portion 2307 which may be a temperatures sensor casing having a temperature sensing device, such as a thermistor as the temperature sensor portion 2307 or within the temperature sensor casing. The temperature sensor portion 2307 may be configured to be in electrical communication or signal communication with a monitoring device or station via a cable 2309, which may be part of any of the aforementioned lead sets described throughout this specification. For example, while not shown in FIGS. 23A and 23B, the opposite end of the cable 2308 may for example have a terminal or other electrical connection as part of a lead set connector as described in the aspects throughout this disclosure. Further, the cable 2309 may have any one or a combination of the interconnection features described above with respect to FIGS. 15A-19F. In another aspect the cable 1209 may be molded, extruded, or otherwise permanently connected to other cables of a leadset (e.g., one or more ECG cables, one or more Oxygen Saturation cables, and/or any monitoring cable known in the art) to form a single bundle or group of cables thus eliminating or reducing cable clutter. In another aspect the cable 2309 may for example include just a single cable with a connector at the terminal end thereof that is configured to connect to be placed in signal communication with a monitoring or display device. The temperature sensor housing 2301 may further be configured to receiveably engage a heat conductive portion 2311. Throughout the disclosure, the heat conductive portion may be interchangeably referred to as a connection portion or adhesive media portion. The heat conductive portion 2311 may for example provide a thermal connection or communication between a patient's skin and the temperature sensor portion 2307 by providing a thermal path between the patients skin at or proximal to first surface 2317 and the temperature sensor portion 2307.

The heat conductive portion 2311 may for example include a heat conductive portion housing 2313 configured to house or otherwise be connected to a heat conductive media portion 2314. In one example, the heat conductive portion housing 2313 may be an annular structure with an opening at the first end that is dimensioned to receive a portion of the temperature sensor portion 2307 and an opening with flat surface configured to support a heat conductive media portion 2314. The heat conductive media portion 2314 may be configured to fill or otherwise contact the inner surfaces of the heat conductive portion housing 2313 as shown in FIG. 23B. In one example, the heat conductive media portion 2314 may for example be a hydrogel or other heat-conductive media having a first surface 2317 configured to be emplaced or adhered to a patients skin and a second surface 2319 configured to contact the temperature sensor portion 2307. Thus the heat conductive media portion 2314 may be configured to provide thermal communication between the temperature sensor portion 2307 and a patients skin. In the examples described throughout the disclosure, the heat conductive media may function to provide a thermal path and/or may function as an adhesive or adhereable surface that is configured to adhere or otherwise emplace a sensor or connector on a patients skin. Accordingly, the heat conducive portion a or heat conductive media may be interchangeable referred to an adhereable portion, adhesive media portion or adhereable media portion throughout the disclosure.

In one example implementation, the heat conductive portion 2311 may be configured to be receiveably engaged within a concave portion of the temperature sensor housing 2301 via interaction between temperature sensor housing engagement members 2302 and heat conductive media portion engagement member 2304. In one example, the temperature sensor housing engagement members 2302 and heat conductive media portion engagement member 2304 may for example be annular grooves configured to engage with one another as shown in the cross-section in FIG. 23B. One example of an annular groove may for example have a tooth-shaped cross section as shown in FIG. 23B. As described in further detail below with respect to example implementations shown in FIGS. 28A-C, any one or a combination of the temperature sensor housing engagement members 2302 and heat conductive media portion engagement member 2304 may for example be configured to break or otherwise be separated or permanently deformed if the heat conductive portion 2311 is separated from the temperature sensor housing 2301 and a refurbishing or reconstructing method or system according to an aspect of the disclosure may be used to repair or replace the deformed or broken temperature sensor housing engagement members 2302 and/or heat conductive media portion engagement member 2304. In another example, any one or a combination of the temperature sensor housing engagement members 2302 and/or heat conductive media portion engagement member(s) 2304 may be configured to elastically deform to allow for the re-engageable separation of the heat conductive portion 2311 and the temperature sensor housing 2301. In one example, the interaction between the temperature sensor housing engagement members 2302 and heat conductive media portion 2314 may for example allow the temperature sensor housing 2301 to rotate about axis R with respect to the heat conductive portion 2311 as indicated by arrow(s) RR. Thus, the interaction between the heat conductive media portion 2314 and the temperature sensor housing engagement members 2302 may cause the heat conductive portion 2311 to be captively connected to the temperature sensor housing 2301 and temperature sensor portion 2307 while still allowing rotation in direction RR which allows for the cable 2309 to be rotated or otherwise re-arranged while the first surface 2317 is emplaced or adhered to a patients skin. This rotation may improve patient comfort, allow for improved cable management and/or prevent inadvertent removal of the temperature sensor 2300 from a patients skin.

In one example implementation, the temperature sensor 2300 may be reconstructed or reprocessed either by replacing the heat conductive portion 2311 after use or by removing the heat conductive media portion 2314 from the 2313 and replacing the heat conductive media portion 2314 with a new heat conductive media. For example, in the example implementation with a hydrogel as the heat conductive media portion 2314, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation.

In one example, the heat conductive portion housing 2413 with the hydrogel removed may be used as a mold or partial mold and may be refilled or otherwise have the heat conduction media portion 2414 replaced during reconstructing. Further examples of such a reconstructing or refurbishing are described with respect to FIGS. 27-29 below.

Figure 24A:
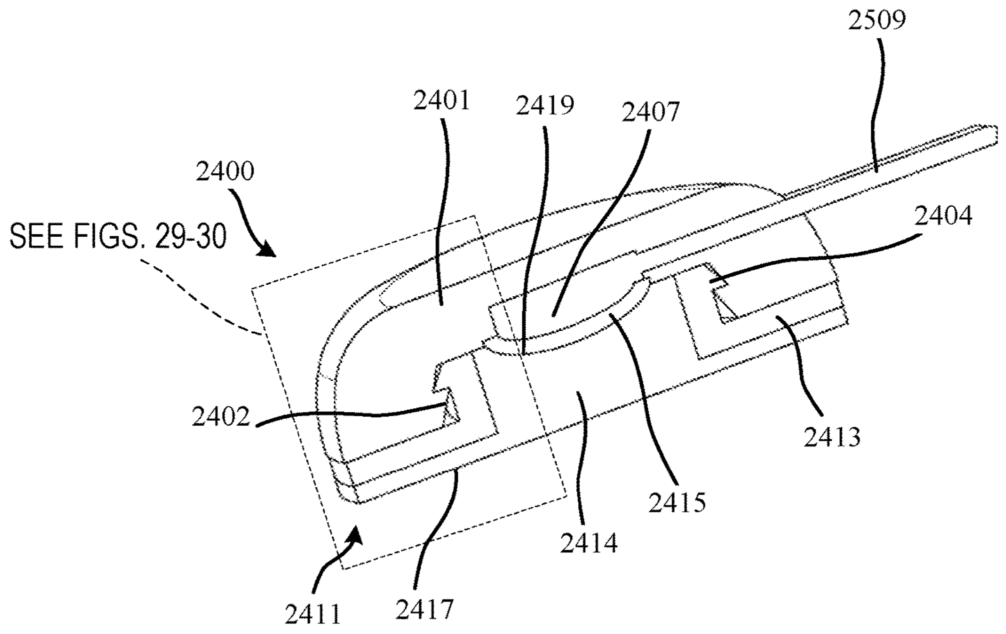
FIG. 24A is a cross section view of a temperature sensor system according to aspects of the disclosure.
Figure 24B:
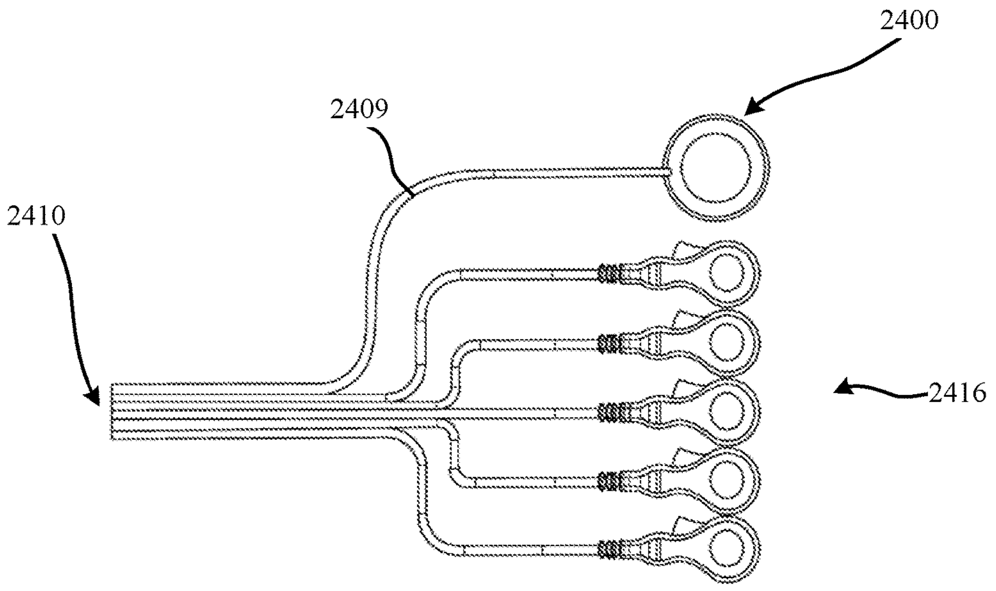
FIG. 24B illustrates a temperature sensor used with a multiparameter lead set according to aspects of the disclosure.

FIGS. 24A and 24B show example implementations of a temperature sensor 2400 and a leadset according to aspects of the disclosure. In one example, the temperature sensor 2400 may be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, and/or temperature sensor 2300 in FIGS. 23A and 23B for example. The temperature sensor 2400 may for example have a temperature sensor housing 2401. The temperature sensor housing 2401 may have connected thereto or embedded therein a temperature sensor portion 2407 which may be a temperatures sensor casing having a temperature sensing device, such as a thermistor as the temperature sensor portion 2407 or within the temperature sensor casing. The temperature sensor portion 2407 may be configured to be in electrical communication or signal communication with a monitoring device or station via a cable 2409, which may be part of any of the aforementioned lead sets described throughout this specification. One example of such a leadset 2416 is shown in FIG. 24B and may include any one or a combination of additional patient physiological sensors. For example, the leadset 2416 may include any number of one or more ECG cables, one or more Oxygen Saturation cables, and/or any monitoring cable known in the art or described throughout this disclosure. While not shown in FIGS. 24A and 24B, the opposite end of the cable 2409 or leadset cable(s) 2410 may for example have a terminal or other electrical connection as part of a lead set connector as described in the aspects throughout this disclosure. Further, the cable 2409 and/or leadset cable(s) 2410 may have any one or a combination of the interconnection features described above with respect to FIGS. 15A-19F. In another aspect, the cable 2409 may be molded, extruded, or otherwise permanently connected to other cables of a leadset (e.g., as shown in FIG. 24B to one or more ECG cables, and/or one or more Oxygen Saturation cables, and/or any monitoring cable known in the art) to form a single bundle or group of cables thus eliminating or reducing cable clutter. In another aspect the cable 2409 may for example include just a single cable with a connector at the terminal end thereof that is configured to connect to be placed in signal communication with a monitoring or display device. The temperature sensor housing 2401 may further be configured to receiveably engage a heat conductive portion 2411. Throughout the disclosure, the heat conductive portion may be interchangeably referred to as a connection portion. The heat conductive portion 2411 may for example provide a thermal connection or communication between a patient's skin and the temperature sensor portion 2407 by providing a thermal path between the patients skin at or proximal to first surface 2417 and the temperature sensor portion 2307.

The heat conductive portion 2411 may for example include a heat conductive portion housing 2413 configured to house or otherwise be connected to a heat conductive media portion 2414. In one example, the heat conductive portion housing 2413 may be an annular structure with an opening at the first end that is dimensioned to receive a portion of the temperature sensor portion 2407 and an opening with flat surface configured to support a heat conductive media portion 2414. The heat conductive media portion 2414 may be configured to fill or otherwise contact the inner surfaces of the heat conductive portion housing 2413 as shown in FIG. 24A. In one example, the heat conductive media portion 2414 may for example be a hydrogel or other heat-conductive media having a first surface 2417 configured to be emplaced or adhered to a patients skin and a second surface 2419 configured to contact the temperature sensor portion 2407. Thus the heat conductive media portion 2314 may be configured to provide thermal communication between the temperature sensor portion 2407 and a patients skin.

In one example implementation, the heat conductive portion 2411 may be configured to be receiveably engaged within a concave portion of the temperature sensor housing 2401 via interaction between temperature sensor housing engagement members 2402 and heat conductive media portion engagement member 2404. In one example, the temperature sensor housing engagement members 2402 and heat conductive media portion engagement member 2404 may for example be annular grooves configured to engage with one another as shown in the cross-section in FIG. 24A. One example of an annular groove may for example have a tooth-shaped cross section as shown in FIG. 24A. As described in further detail below with respect to example implementations shown in FIGS. 28A-C, any one or a combination of the temperature sensor housing engagement members 2402 and heat conductive media portion engagement member 2404 may for example be configured to break or otherwise be separated or permanently deformed if the heat conductive portion 2411 is separated from the temperature sensor housing 2401 and a refurbishing or reconstructing method or system according to an aspect of the disclosure may be used to repair or replace the deformed or broken temperature sensor housing engagement members 2402 and/or heat conductive media portion engagement member 2404. In another example, any one or a combination of the temperature sensor housing engagement members 2402 and/or heat conductive media portion engagement member(s) 2404 may be configured to elastically deform to allow for the re-engageable separation of the heat conductive portion 2411 and the temperature sensor housing 2401. In one example, the interaction between the temperature sensor housing engagement members 2402 and heat conductive media portion 2414 may for example allow the temperature sensor housing 2401 to rotate about axis R (e.g., as shown in FIG. 23A) with respect to the heat conductive portion 2411 as indicated by arrow(s) RR (FIG. 23A). Thus, the interaction between the heat conductive media portion 2414 and the temperature sensor housing engagement members 2402 may cause the heat conductive portion 2411 to be captively connected to the temperature sensor housing 2401 and temperature sensor portion 2407 while still allowing rotation in direction RR which allows for the cable 2409 to be rotated or otherwise re-arranged while the first surface 2417 is emplaced or adhered to a patients skin. This rotation may improve patient comfort, allow for improved cable management and/or prevent inadvertent removal of the temperature sensor 2400 from a patients skin.

In the example shown in FIG. 24A, the temperature sensor 2400 may further comprise a lubricant 2415 which may further improve the heat conductive portions 2411 ability rotate with respect to the temperature sensor housing 2401 and cable 2409 while being captively connected to the temperature sensor housing 2401 and temperature sensor portion 2407. Further, the lubricant 2415 may further improve the heat transfer characteristics between the heat conductive media portion 2414 and the temperature sensor portion 2407. While any known lubricant may be used. One example of a lubricant usable with the set temperature sensor 2400 may include but is not limited to a thermally conductive silicone grease or oil or the like.

In one example, the heat conductive media portion 2414 and the temperature sensor portion 2407 and/or the temperature sensor housing 2401 may be configured to have a space or reservoir therebetween for containing lubricant 2415. In one example, there may be a space or cavity formed between the heat conductive media portion 2414 and the temperature sensor portion 2407 and/or the temperature sensor housing 2401 if a lubricant 2415 is not present. In one example implementation, the temperature sensor 2400 may be reconstructed or reprocessed either by replacing the heat conductive portion 2411 after use or by removing the heat conductive media portion 2414 from the 2413 and replacing the heat conductive media portion 2414 with a new heat conductive media. For example, in the example implementation with a hydrogel as the heat conductive media portion 2414, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. In one example, the heat conductive portion housing 2413 with the hydrogel removed may be used as a mold or partial mold and may be refilled or otherwise have the heat conductive media portion 2414 replaced during reconstructing. In another implementation usable with the aforementioned implementations a replacement lubricant 2415 may be placed on either one or both of the temperature sensor portion 2407 and/or the heat conductive portion 2411 during reconstructing or refurbishing. Further examples of such a reconstructing or refurbishing are described with respect to FIGS. 27-29 below.

Figure 25:
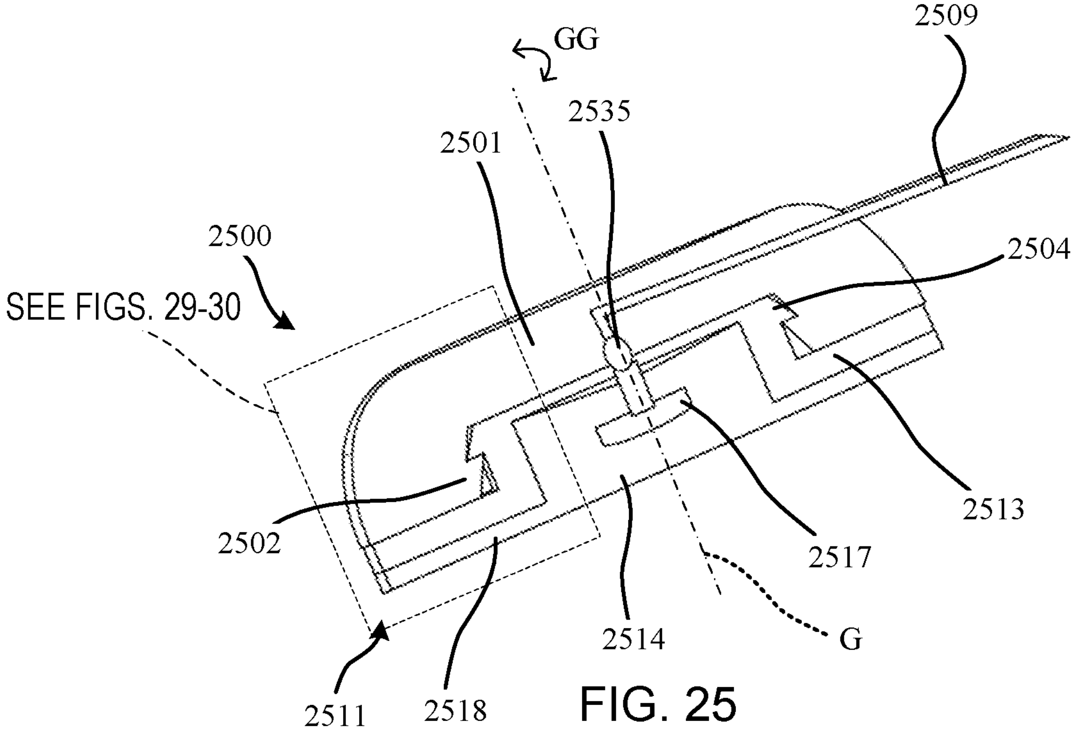
FIG. 25 is a cross section view of a temperature sensor system according to aspects of the disclosure.

FIG. 25 shows one example implementations of a temperature sensor 2500 according to aspects of the disclosure. In one example, the temperature sensor 2500 may be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, temperature sensor 2300 in FIGS. 23A and 23B, and/or temperature sensor 2400 in FIGS. 24A and 24B, for example. The temperature sensor 2500 may for example have a temperature sensor housing 2501. The temperature sensor housing 2501 may have connected thereto or embedded therein a swivel or rotatable connector 2535, the rotatable connector 2535 may for example be series of rotatable terminals or a rotatable connector known in the art. In one example, the rotatable connector 2535 may instead be a non-rotatable or only partially rotatable connector or terminal device for providing signal communication between a temperature sensor portion 2407 and a cable 2509. In the example implementation wherein the rotatable connector 2535 is rotatable, the heat conductive portion 2511 may be configured to rotate with respect to the temperature sensor housing 2501 about axis G in directions GG.

The temperature sensor 2500 may further include temperature sensor portion 2517 which may be a temperatures sensor casing having a temperature sensing device, such as a thermistor as the temperature sensor portion 2517 or within the temperature sensor casing. The temperature sensor portion 2517 may be configured to be in electrical communication or signal communication with a monitoring device or station via a cable 2509 via the rotatable connector 2535. The cable 2509 may be part of any of the aforementioned lead sets described throughout this specification and may include any one or a combination of additional patient physiological sensors. For example, the leadset 2416 may include any number of one or more ECG cables, one or more Oxygen Saturation cables, and/or any monitoring cable known in the art or described throughout this disclosure. While not shown FIG. 25, the opposite end of the cable 2509 may for example have a terminal or other electrical connection as part of a lead set connector as described in the aspects throughout this disclosure. Further, the cable 2509 may have any one or a combination of the interconnection features described above with respect to FIGS. 15A-19F. In another aspect, the cable 2509 may be molded, extruded, or otherwise permanently connected to other cables of a leadset (e.g., as shown in FIG. 24B to one or more ECG cables, and/or one or more Oxygen Saturation cables, and/or any monitoring cable known in the art) to form a single bundle or group of cables thus eliminating or reducing cable clutter. In another aspect the cable 2509 may for example include just a single cable with a connector at the terminal end thereof that is configured to connect to be placed in signal communication with a monitoring or display device. The temperature sensor housing 2501 may further be configured to receiveably engage a heat conductive portion 2511. Throughout the disclosure, the heat conductive portion may be interchangeably referred to as a connection portion. The heat conductive portion 2511 may for example provide a thermal connection or communication between a patient's skin and the temperature sensor portion 2517 by providing a thermal path between the patients skin at or proximal to first surface 2518 and the temperature sensor portion 2517. The heat conductive portion 2511 may for example include a heat conductive portion housing 2513 configured to house or otherwise be connected to a heat conductive media portion 2514 having the temperature sensor portion 2517 embedded or otherwise disposed therein. In one example, the heat conductive portion housing 2513 may be an annular structure with an opening at the first end that is dimensioned to receive a portion of the temperature sensor portion 2517 and an opening with flat surface configured to support a heat conductive media portion 2514. The heat conductive media portion 2514 may be configured to fill or otherwise contact the inner surfaces of the heat conductive portion housing 2513 as shown in FIG. 25. In one example, the heat conductive media portion 2514 may for example be a hydrogel or other heat-conductive media having a first surface 2518 configured to be emplaced or adhered to a patients skin and having the temperature sensor portion 2517 embedded therein or otherwise surrounded by the heat conductive media portion 2514. Thus the heat conductive media portion 2314 may be configured to provide thermal communication between the temperature sensor portion 2517 and a patients skin.

In one example implementation, the heat conductive portion 2511 may be configured to be receiveably engaged within a concave portion of the temperature sensor housing 2501 via interaction between temperature sensor housing engagement members 2502 and heat conductive media portion engagement member 2504. In one example, the temperature sensor housing engagement members 2502 and heat conductive media portion engagement member 2504 may for example be annular grooves configured to engage with one another as shown in the cross-section in FIG. 25. One example of an annular groove may for example have a tooth-shaped cross section as shown in FIG. 25. As described in further detail below with respect to example implementations shown in FIGS. 28A-C, any one or a combination of the temperature sensor housing engagement members 2502 and heat conductive media portion engagement member 2504 may for example be configured to break or otherwise be separated or permanently deformed if the heat conductive portion 2511 is separated from the temperature sensor housing 2501 and a refurbishing or reconstructing method or system according to an aspect of the disclosure may be used to repair or replace the deformed or broken temperature sensor housing engagement members 2502 and/or heat conductive media portion engagement member 2504. In another example, any one or a combination of the temperature sensor housing engagement members 2502 and/or heat conductive media portion engagement member(s) 2504 may be configured to elastically deform to allow for the re-engageable separation of the heat conductive portion 2511 and the temperature sensor housing 2501. In one example, the interaction between the temperature sensor housing engagement members 2502 and heat conductive media portion 2514 may for example allow the temperature sensor housing 2501 to rotate about axis G with respect to the heat conductive portion 2511 as indicated by arrow(s) GG. Thus, the interaction between the heat conductive media portion 2514 and the temperature sensor housing engagement members 2502 may cause the heat conductive portion 2511 to be captively connected to the temperature sensor housing 2501 and temperature sensor portion 2517 while still allowing rotation in directions GG which allows for the cable 2509 to be rotated or otherwise re-arranged while the first surface 2517 is emplaced or adhered to a patients skin. This rotation may improve patient comfort, allow for improved cable management and/or prevent inadvertent removal of the temperature sensor 2500 from a patients skin.

In one example implementation, the temperature sensor 2500 may be refurbished or reprocessed either by replacing the heat conductive portion 2511 and/or the heat conductive media portion 2514 after use or by removing the heat conductive media portion 2514 from the heat conductive portion housing 2513 and/or from around the temperature sensor portion temperature sensor portion 2517 and replacing the heat conductive media portion 2514 with a new heat conductive media and/or replacing the heat conductive media portion 2514. For example, in the example implementation with a hydrogel as the heat conductive media portion 2514, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. In one example, the heat conductive portion housing 2513 with the hydrogel removed may be used as a mold or partial mold either while attached to the temperature sensor housing 2501 or separated from the temperature sensor housing 2501 and may be refilled or otherwise have the heat conductive media portion 2514 replaced during reconstructing. In one example, the heat conductive portion housing 2513 may be left installed or re-installed into the temperature sensor housing 2501 and the hydrogel or other conductive media may be refilled so as to encompass or otherwise surround and/or cure around temperature sensor portion 2517.

Figure 26:
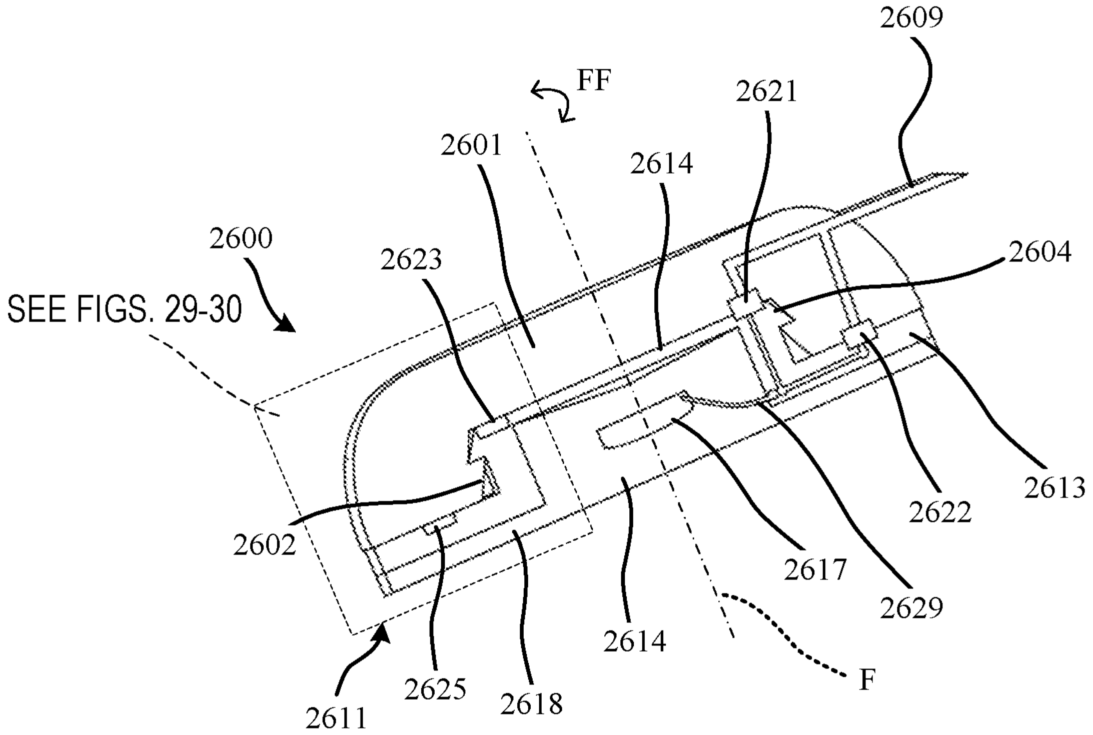
FIG. 26 is a cross section view of a temperature sensor system according to aspects of the disclosure.

FIG. 26 shows one example implementations of a temperature sensor 2600 according to aspects of the disclosure. In one example, the temperature sensor 2600 may for example be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, temperature sensor 2300 in FIGS. 23A and 23B, temperature sensor 2400 in FIGS. 24A and 24B, and/or temperature sensor 2500 in FIG. 25, for example. The temperature sensor 2600 may for example have a temperature sensor housing 2601. The temperature sensor housing 2601 may have connected thereto or embedded therein a first terminal and/or a second terminal 2621 and 2622 that are configured to provide electrical communication or signal communication between the first and/or second terminal(s) 2621 and 2622, a temperature sensor portion 2617 and a cable 2609.

The temperature sensor 2600 may further include temperature sensor portion 2617 which may be a temperatures sensor casing having a temperature sensing device, such as a thermistor as the temperature sensor portion 2617 or within the temperature sensor casing. The temperature sensor portion 2617 may be configured to be in electrical communication or signal communication with a monitoring device or station via the first and/or second terminals 2621 and 2622 and cable 2509. The cable 2609 may be part of any of the aforementioned lead sets described throughout this specification and may include any one or a combination of additional patient physiological sensors. For example, the leadset may include any number of one or more ECG cables, one or more Oxygen Saturation cables, non-invasive blood pressure monitoring passage and/or any monitoring cable known in the art or described throughout this disclosure. While not shown FIG. 26, the opposite end of the cable 2609 may for example have a terminal or other electrical connection as part of a lead set connector as described in the aspects throughout this disclosure. Further, the cable 2609 may have any one or a combination of the interconnection features described above with respect to FIGS. 15A-19F. In another aspect, the cable 2609 may be molded, extruded, or otherwise permanently connected to other cables of a leadset (e.g., as shown in FIG. 24B to one or more ECG cables, one or more non-invasive blood pressure passages or cables and/or one or more Oxygen Saturation cables, and/or any monitoring cable known in the art) to form a single bundle or group of cables thus eliminating or reducing cable clutter. In another aspect, the cable 2609 may for example include just a single cable with a connector at the terminal end thereof that is configured to connect to be placed in signal communication with a monitoring or display device. The temperature sensor portion 2617 may for example be part of a heat conductive portion 2611 which may be configured to be receiveably engaged with the temperature sensor housing 2601. Throughout the disclosure, the heat conductive portion may be interchangeably referred to as a connection portion.

The heat conductive portion 2611 may for example provide a thermal connection or communication between a patient's skin and the temperature sensor portion 2617 by providing a thermal path between the patients skin at or proximal to first surface 2618 and the temperature sensor portion 2617. As shown in FIG. 26, the temperature sensor portion 2617 may be embedded or otherwise surrounded by a heat conductive media portion 2614. The heat conductive portion 2611 may for example include a heat conductive portion housing 2613 configured to house or otherwise be connected to a heat conductive media portion 2614 having the temperature sensor portion 2617 embedded or otherwise disposed therein. In one example, the heat conductive portion housing 2613 may be an annular structure and an opening with flat surface configured to support a heat conductive media portion 2614. The heat conductive media portion 2614 may be configured to fill or otherwise contact the inner surfaces of the heat conductive portion housing 2613 as shown in FIG. 26. In one example, the heat conductive media portion 2614 may for example be a hydrogel or other heat-conductive media having a first surface 2618 configured to be emplaced or adhered to a patients skin and having the temperature sensor portion 2617 embedded therein or may otherwise be configured to surround the temperature sensor portion 2617. Thus the heat conductive media portion 2614 may be configured to provide thermal communication between the temperature sensor portion 2617 and a patients skin.

The heat conductive portion 2611 may further include one or more heat conductive portion terminals 2625 and/or 2623 that may be configured to engage with or otherwise provide an electrical or signal communication with the first and/or second terminal(s) 2622 and 2621. Either one of or both of the one or more heat conductive portion terminals 2625 and/or 2623 may have an annular or circular contact surface configured to engage with or otherwise contact a respective one of the first and/or second terminal(s) 2622 and/or 2621 regardless of the rotational orientation of the heat conductive portion 2611 with respect to the temperature sensor housing 2601. This allows for electrical or signal communication between the temperature sensor portion 2617 and the cable 2609 while still allowing the temperature sensor housing 2601 to rotate about axis F with respect to the heat conductive portion 2611 as indicated by arrow(s) FF. Thus, the interaction between the heat conductive media portion 2614 and the temperature sensor housing engagement members 2602 may cause the heat conductive portion 2611 to be captively connected to the temperature sensor housing 2601 and temperature sensor portion 2617 while still allowing rotation in directions FF which allows for the cable 2609 to be rotated or otherwise re-arranged while the first surface 2618 is emplaced or adhered to a patients skin. In another aspect, instead of the one of or both of the one or more heat conductive portion terminals 2625 and/or 2623 may have an annular or circular contact surface, one of or both of the first terminal and/or second terminal(s) 2621 and/or 2622 may have an annular or circular contact surface configured to engage with or otherwise contact a respective one of the one of or both of the one or more heat conductive portion terminals 2625 and/or 2623 regardless of the rotational orientation of the heat conductive portion 2611 with respect to the temperature sensor housing 2601. Similarly, any combination of or both of the heat conductive portion terminals 2625 and/or 2623 and/or the first and/or second terminals 2621 and/or 2622 may be configured to have a circular or annular contact surface. It is noted that any one or a combination of the first terminal 2621, second terminal 2622, a first heat conductive portion terminal 2623 and/or a second heat conductive terminal portion 2625 may be formed as a conducive leaf spring or other self-biasing structure that ensures that the terminal is in constant contact with the respective terminal and to ensure that there is constant electrical and/or signal communication between terminals that provide continuity between the temperature sensor portion 2617 and the cable 2609.

In one example implementation, the heat conductive portion 2611 may be configured to be receiveably engaged within a concave portion of the temperature sensor housing 2601 via interaction between temperature sensor housing engagement members 2602 and heat conductive media portion engagement member 2604. In one example, the temperature sensor housing engagement members 2602 and heat conductive media portion engagement member 2604 may for example be annular grooves configured to engage with one another as shown in the cross-section in FIG. 26. One example of an annular groove may for example have a tooth-shaped cross section as shown in FIG. 26. As described in further detail below with respect to example implementations shown in FIGS. 28A-C, any one or a combination of the temperature sensor housing engagement members 2602 and heat conductive media portion engagement member 2604 may for example be configured to break or otherwise be separated or permanently deformed if the heat conductive portion 2611 is separated from the temperature sensor housing 2601 and a refurbishing or reconstructing method or system according to an aspect of the disclosure may be used to repair or replace the deformed or broken temperature sensor housing engagement members 2602 and/or heat conductive media portion engagement member 2604. In another example, any one or a combination of the temperature sensor housing engagement members 2602 and/or heat conductive media portion engagement member(s) 2604 may be configured to elastically deform to allow for the re-engageable separation of the heat conductive portion 2611 and the temperature sensor housing 2601. In one example, the interaction between the temperature sensor housing engagement members 2602 and heat conductive media portion 2614 may for example allow the temperature sensor housing 2601 to rotate about axis F with respect to the heat conductive portion 2611 as indicated by arrow(s) FF. Thus, the interaction between the heat conductive media portion 2614 and the temperature sensor housing engagement members 2602 may cause the heat conductive portion 2611 to be captively connected to the temperature sensor housing 2601 and temperature sensor portion 2617 while still allowing rotation in directions GG which allows for the cable 2609 to be rotated or otherwise re-arranged while the first surface 2617 is emplaced or adhered to a patients skin. This rotation may improve patient comfort, allow for improved cable management and/or prevent inadvertent removal of the temperature sensor 2600 from a patients skin.

In one example implementation, the temperature sensor 2600 may be refurbished or reprocessed either by replacing the heat conductive portion 2611 and/or the heat conductive media portion 2614 after use or by removing the heat conductive media portion 2614 from the heat conductive portion housing 2613 and/or from around the temperature sensor portion temperature sensor portion 2617 and replacing the heat conductive media portion 2614 with a new heat conductive media and/or replacing the heat conductive media portion 2614. For example, in the example implementation with a hydrogel as the heat conductive media portion 2614, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. In one example, the heat conductive portion housing 2613 with the hydrogel removed may be used as a mold or partial mold either while attached to the temperature sensor housing 2601 or separated from the temperature sensor housing 2601 and may be refilled or otherwise have the heat conductive media portion 2614 replaced during reconstructing. In one example, the heat conductive portion housing 2613 may be left installed or re-installed into the temperature sensor housing 2601 and the hydrogel or other conductive media may be refilled so as to encompass or otherwise surround and/or cure around temperature sensor portion 2617.

c. Reconstructing Method For Lead Sets and Temperature Sensor(s)

Along with the refurbishing, reprocessing, and/or reconstructing aspects described above with respect to FIG. 20, one aspect of the disclosure includes a method and/or process for refurbishing, reprocessing, and/or reconstructing a temperature sensor according to aspects of the disclosure. While it is noted that aspects described below describe refurbishing, reprocessing, and/or reconstructing of a temperature sensor, the aspects described below may be combined with refurbishing and/or reconstructing of lead sets described above for example, the aforementioned aspects, e.g., the temperature sensor that is refurbished, reprocessed, and/or reconstructed may for example be connected to and refurbished, reprocessed, and/or reconstructed with a lead set described throughout this disclosure. The lead set may, for example, be reprocessed or sent to a reconstructing facility. During this process, a first type of patient connector, associated lead and/or lead set connector may be disconnected from a lead set or separated from the lead set. In one example, the lead set may comprise at least a first lead, patient connector, and lead connector associated with a first patient health indicator and may be connected via an interconnection feature to at least a second lead, patient connector, and lead connector associated with a first patient health indicator. To give one specific example, the first type of patient connector may be an ECG connector or series of connectors (e.g., 314 in FIG. 3, 414 in FIG. 4, 514 in FIG. 5, 614 in FIG. 6, 704 in FIG. 7, 804 in FIG. 8, 1014 in FIGS. 10A-B, 1114 in FIG. 11, 1214 in FIG. 12, and 1314 in FIG. 13), and a lead connecting the first type of patient connector to a first lead set connector (e.g., 904*b* in FIG. 9, 1004*b* in FIG. 10, 1136 in FIG. 11, and 1304 in FIG. 13). The second type of patient connector may be a temperature sensor or series of sensors or connectors (e.g., 213 in FIG. 2, 313 in FIG. 3, 413 in FIG. 4, 512 in FIG. 5, 706 in FIG. 7, 807 in FIG. 8, 1017 in FIGS. 10A-B, 1117 in FIG. 11, 1217 in FIG. 12, and 1317 in FIG. 13) and a second lead connecting the second type of patient connector to the second lead set connector (e.g., 904*a* in FIG. 9, and 1104 in FIG. 11). In one example, the first type of leadset may for example be refurbished or reconstructed by any one or combination of a cleaning step, a sanitization or sterilization step, or a high level disinfection step. As discussed in further detail below, in the aforementioned example, the second type of patient lead and/or patient connector may require additional steps to sufficiently refurbish or reconstruct beyond the aforementioned cleaning step, sanitization or sterilization step, or high level disinfection step. The first lead and/or second lead may be connected via any one or a combination of the interconnection features described with respect to FIGS. 15A-19D, and/or the first lead set connector and second lead set connector may be connected via any one of the interconnection features described with respect to FIGS. 15A-19D. Using the aforementioned non-limiting example, the first lead set and second lead set and/or first lead set connector and second lead set connector may be disconnected from one another if they are not already disconnected. In one example, a disconnection device may be assist with or may be required to disconnect the aforementioned connection features. In one example, the disconnection device may be slid along the outer surface of two or more leads to cause the first interconnection interface to disengage from the second interconnection interface and/or to allow any number of cables to be disconnected from one another. The aforementioned disconnection of the interconnection features via a disconnection device may be completed manually via a technician or worker and/or may be completed via an automated or machine-assisted process.

Figure 27:
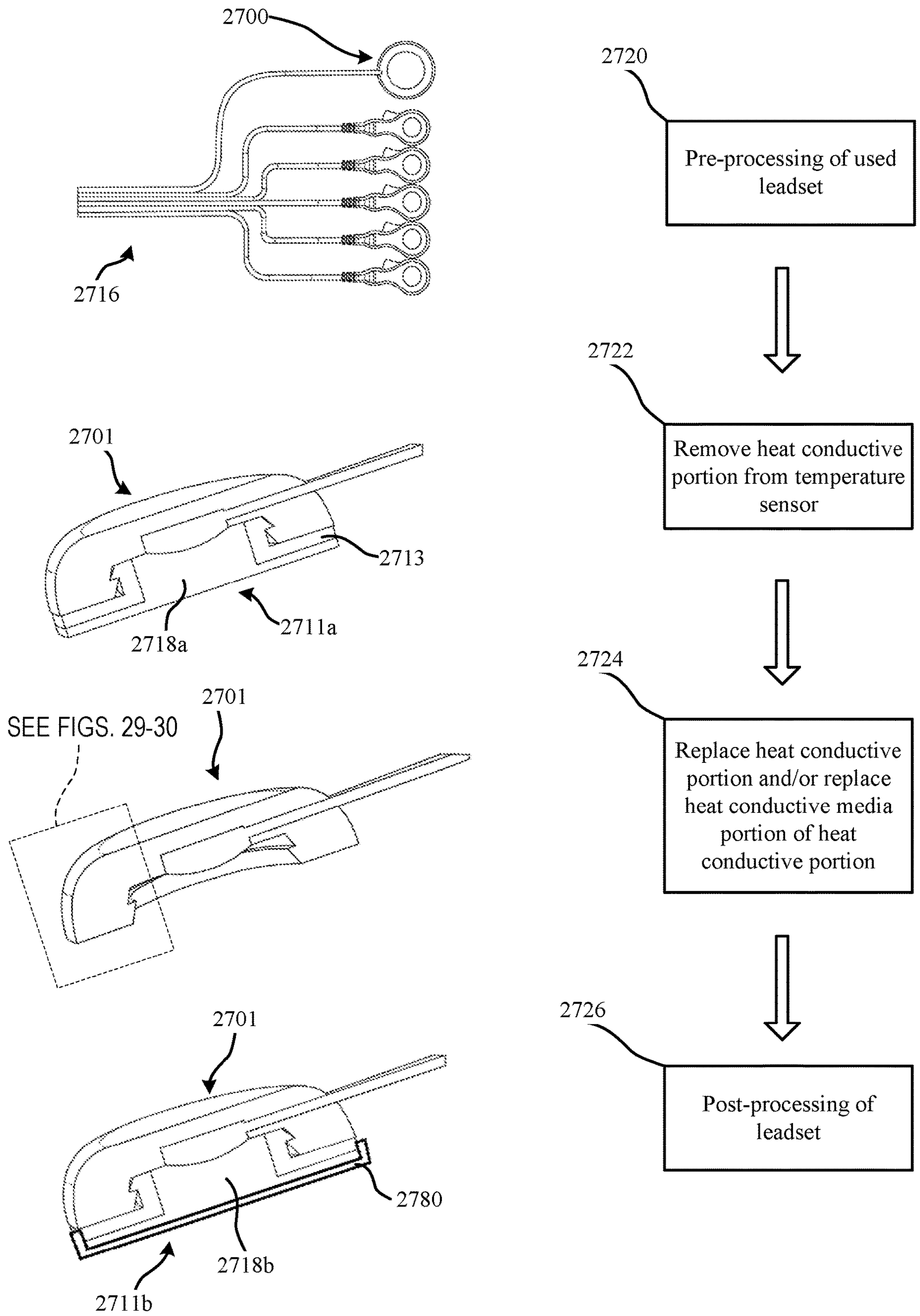
FIG. 27 illustrates a method of reconstructing a multiparameter lead set that includes a temperature sensor system according to aspects of the disclosure.

As shown in FIG. 27, in another aspect that is usable as an alternative to or with any one or combination of the steps described above, the temperature sensor 2700 may be refurbished, reprocessed, and/or reconstructed. In one aspect, the temperature sensor 2700 may be part of a leadset 2716. While leadset 2716 shown in FIG. 27 shows five (5) ECG connectors or sensors it is noted that anyone or combination of the patient monitoring sensors or connectors described throughout the disclosure (e.g., non-invasive blood pressure, oxygen saturation) or that are known in the art may be implemented into the leadset and may be part of the process according to aspects of the disclosure. In one example, the temperature sensor 2700 may for example be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, temperature sensor 2300 in FIGS. 23A and 23B, temperature sensor 2400 in FIGS. 24A and 24B, and/or temperature sensor 2500 in FIG. 25 or temperature sensor 2600 in FIG. 26 for example. As shown in FIG. 27, in one example of a method, a used leadset (e.g., leadset 2617) having a temperature sensor (e.g., temperature sensor 2700) may be subject to pre-processing at step 2720. While not intended to be limiting, some examples of pre-processing may include any one or a combination of one or more cleanings, sterilization and/or high level disinfection (HDL) processes. As mentioned above, in some examples, the pre-processing step 2720 may also include replacement of component(s), cable(s), and/or tube(s) if during inspection it is deemed such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 2720, a used heat conductive portion 2711*a* may be removed from the temperature sensor housing 2701. In some aspects, the removal of the used heat conductive portion 2711*a* from the temperature sensor housing 2701 may require a specialized tool or other device to allow for separation of the temperature sensor housing 2701 and the heat conductive portion 2711*a*. In one example, a machine, robot, or other automated process may be used to separate the temperature sensor housing 2701 and the heat conductive portion 2711*a*. After the used heat conductive portion 2711*a* is separated from the temperature sensor housing 2701, a new heat conductive portion 2711*b* may be installed into the temperature sensor housing 2701. As shown in FIG. 27, at step 2726, the new heat conductive portion 2711*b* may already have a release liner 2780 for protecting the heat conductive media portion. The release liner 2780 may for example indicate that the temperature sensor has been properly reprocessed, refurbished, and/or reconstructed and/or may help to protect the heat conductive media portion from contamination. In the example mentioned above wherein the heat conductive media portion is a hydrogel, the release liner 2780 may for example prevent drying or loss of moisture of the hydrogel. While not intended to be limiting, the release liner may for example include any one or combination of a foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET). The release liner 2780 may for example be configured to be easily removable by an end user and may include a tab or other such feature to assist with or improve efficiency of pulling-off or otherwise removing the release liner 2780 from the temperature sensor 2700.

In one example implementation, the temperature sensor 2700 may be sealed in a pouch or other containment portion that has a low vapor transmission rate. In one example, only the temperature sensor 2700 of a leadset may be sealed in a low vapor transmission rate pouch. In one example, the temperature sensor may be sealed within a low vapor transmission rate pouch that is sealingly engaged with or sealed around the cable of the temperature sensor. In another example, the temperature sensor may be sealed in a low vapor transmission rate pouch while the leadset (and temperature sensor with low vapor transmission pouch) is sealed or otherwise contained therein.

In another aspect, instead of replacing the used heat conductive portion 2711*a* with a new heat conductive portion 2711*b* that either already has a release liner 2780 installed and/or has a release liner 2780 installed after installation into the temperature sensor housing 2701, the used heat conductive media portion 2718*a* may be removed from the heat conductive media portion housing 2713 and replaced with a new heat conductive media portion 2718*b*. For example, if the heat conductive media portion 2718 is a hydrogel, the hydrogel maybe removed either with the heat conductive media portion housing 2713 still attached to the temperature sensor housing 2701 or may be removed after the heat conductive media portion housing 2713 is removed from the temperature sensor housing 2701. The hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. Once they hydrogel is removed from the heat conductive media portion housing 2713, the hydrogel may be replaced. In one example, the hydrogel may be replaced by using the heat conductive media portion housing 2713 as a mold and providing and curing hydrogel in the heat conductive media portion housing 2713. After the hydrogel is cured the release liner 2780 may be provided. In another example, the release liner 2780 may be provided or otherwise connected to the heat conductive media portion housing 2713 and may serve as part of the mold that is configured to have the hydrogel cured therein.

After step 2724, the temperature sensor 2700, leadset 2716, any additional patient monitoring sensors or connectors that are part of the leadset and/or one or more of the leadset connectors 1204 may be subject to post-processing. Some example of post-processing steps may include but are not limited to: additional cleaning, sterilization and/or high level disinfection (HDL) processes; one or more Ethylene oxide treatment(s). In some examples the post-processing step 2724 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 2716 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned process in combination with the various other features of the lead set described herein may provide for a reduction in waste and/or cost by allowing for efficient reprocessing, reconstructing and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned reconstructing or refurbishing steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 28:
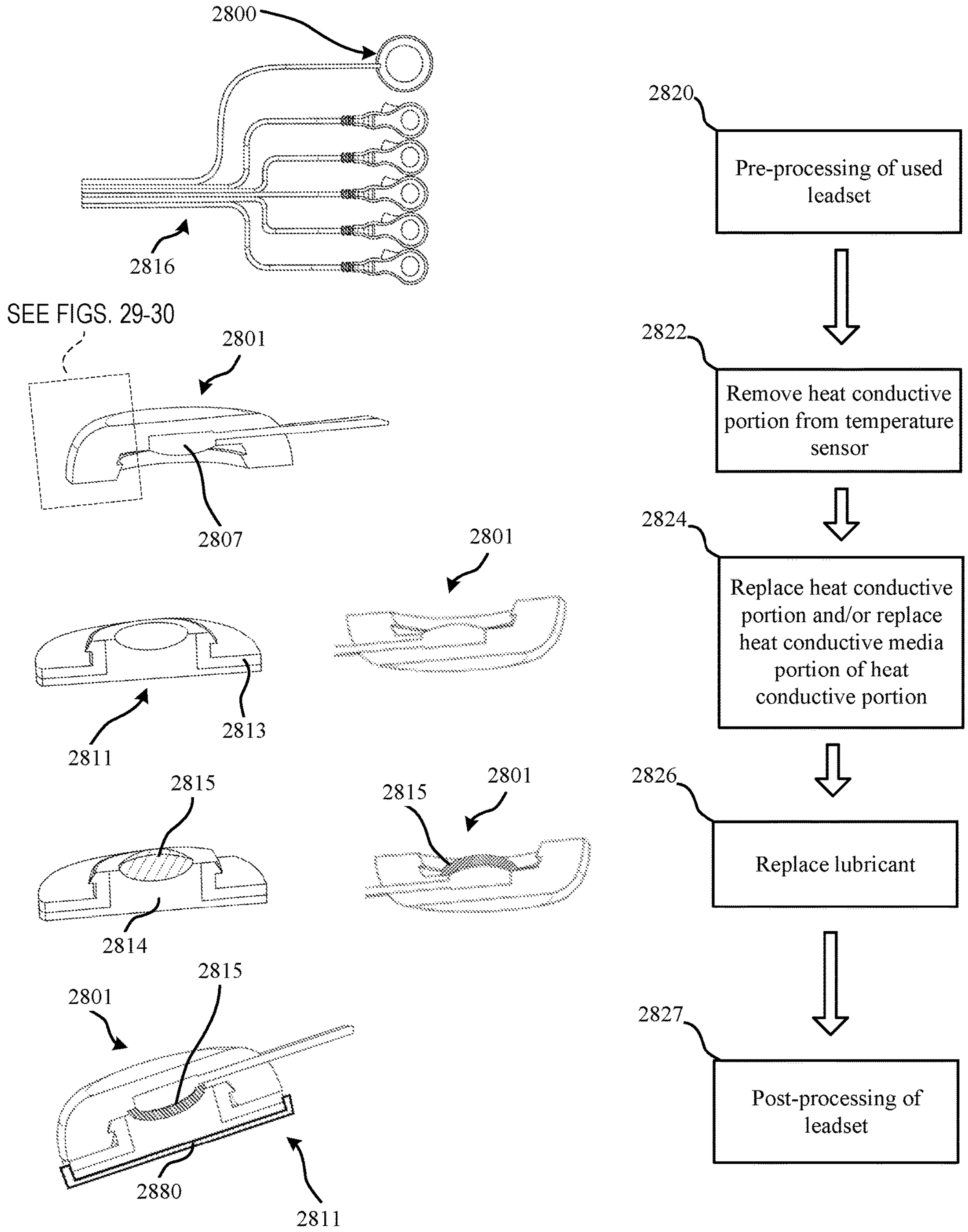
FIG. 28 illustrates a method of reconstructing a multiparameter lead set that includes a temperature sensor system according to aspects of the disclosure.

Turning to FIG. 28, in another aspect that is usable as an alternative to or with any one or combination of the steps described above, the temperature sensor 2800 may be reprocessed, refurbished and/or reconstructed. In one aspect, the temperature sensor 2800 may be part of a leadset 2816. While leadset 2816 shown in FIG. 28 shows five (5) ECG connectors or sensors it is noted that anyone or combination of the patient monitoring sensors or connectors described throughout the disclosure (e.g., non-invasive blood pressure, oxygen saturation) or that are known in the art may be implemented into the leadset and may be part of the process according to aspects of the disclosure. In one example, the temperature sensor 2800 may for example be analogous with temperature sensor 213 in FIG. 2, connector 314 in FIG. 3, connector 413 in FIG. 4, temperature sensor 512 in FIG. 5, temperature sensor device 706 in FIG. 7, connector 807 in FIG. 8, temperature sensor 1017 in FIGS. 10A and 10B, temperature sensor 1107 in FIG. 11, temperature sensor 1217 in FIG. 12, temperature sensor 1317 in FIG. 13, temperature sensor 2300 in FIGS. 23A and 23B, temperature sensor 2400 in FIGS. 24A and 24B, temperature sensor 2500 in FIG. 25, temperature sensor 2600 in FIG. 26, and/or temperature sensor 2700 in FIG. 27, for example. As shown in FIG. 28, in one example of a method, a used leadset (e.g., leadset 2816) having a temperature sensor (e.g., temperature sensor 2800) may be subject to pre-processing at step 2820. While not intended to be limiting, some examples of pre-processing may include any one or a combination of one or more cleanings, sterilization and/or high level disinfection (HDL) processes. As mentioned above, in some examples, the pre-processing step 2820 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 2820, a used heat conductive portion may be removed from the temperature sensor housing 2801. In some aspects, the removal of the used heat conductive portion and the temperature sensor housing 2801 may require a specialized tool or other device to allow for separation of the temperature sensor housing 2701 and the heat conductive portion. In one example, a machine, robot, or other automated process may be used to separate the temperature sensor housing 2801 and the heat conductive portion. After the used heat conductive portion is separated from the temperature sensor housing 2801, a new heat conductive portion 2811 may be prepared for installation into the temperature sensor housing 2801 at step 2824.

In step 2829, a lubricant 2815 may be re-installed to either one of or both of the new heat conductive portion 2811 and/or the temperature sensor housing 2801. As described above with respect to FIG. 24A, a lubricant 2815 may further improve the heat transfer characteristics between the heat conductive media portion 2814 and the temperature sensor portion 2807. While any known lubricant may be used, one example of a lubricant usable with the set temperature sensor 2400 may include but is not limited to a thermally conductive silicone grease or oil or the like. The lubricant 2815 may for example be applied to the a reservoir or other designated space provided on the conductive media portion 2814 and/or the temperature sensor housing 2801. In one example, the new heat conductive portion 2811 may then be installed into the temperature sensor housing 2801 so that the lubricant 2815 occupies a space or cavity formed between the heat conductive media portion 2814 and the temperature sensor portion 2807 as shown in FIG. 28.

As shown in FIG. 28, the new heat conductive portion 2811 may already have a release liner 2880 for protecting the heat conductive media portion 2814. The release liner 2880 may for example indicate that the temperature sensor has been properly reprocessed, refurbished and/or reconstructed and/or may help to protect the heat conductive media portion from contamination. In the example mentioned above wherein the heat conductive media portion is a hydrogel, the release liner 2880 may for example prevent drying or loss of moisture of the hydrogel. While not intended to be limiting, the release liner may for example include any one or combination of a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET). The release liner 2780 may for example be configured to be easily removable by an end user and may include a tab or other such feature to assist with or improve efficiency of pulling-off or otherwise removing the release liner 2880 from the temperature sensor 2800. In one example implementation, the temperature sensor 2800 may be sealed in a pouch or other containment portion that has a low vapor transmission rate. In one example, only the temperature sensor 2800 of a leadset may be sealed in a low vapor transmission rate pouch. In one example, the oxygen saturation sensor may be sealed within a low vapor transmission rate pouch that is sealingly engaged with or sealed around the cable of the temperature sensor 2800 another example, the temperature sensor may be sealed in a low vapor transmission rate pouch while the leadset (and temperature sensor with low vapor transmission pouch) is sealed or otherwise contained therein.

In another aspect, instead of replacing the used heat conductive portion 2811 with a new heat conductive portion that either already has a release liner 2880 installed and/or has a release liner 2880 installed after installation into the temperature sensor housing 2801, the used heat conductive media portion may be removed from the heat conductive media portion housing and replaced with a new heat conductive media portion. For example, if the heat conductive media portion 2814 is a hydrogel, the hydrogel maybe removed either with the heat conductive media portion housing 2813 still attached to the temperature sensor housing 2801 or may be removed after the heat conductive media portion housing 2813 is removed from the temperature sensor housing 2801. The hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. Once they hydrogel is removed from the heat conductive media portion housing 2813, the hydrogel may be replaced. In one example, the hydrogel may be replaced by using the heat conductive media portion housing 2813 as a mold and providing and curing hydrogel in the heat conductive media portion housing 2813. After the hydrogel is cured the release liner 2880 may be provided. In another example, the release liner 2880 may be provided or otherwise connected to the heat conductive media portion housing 2813 and may serve as part of the mold that is configured to have the hydrogel cured therein.

After step 2827, the temperature sensor 2800, leadset 2816, any additional patient monitoring sensors or connectors that are part of the leadset and/or one or more of the leadset connectors may be subject to post-processing. Some example of post-processing steps may include but are not limited to: additional cleaning, sterilization and/or high level disinfection (HDL) processes; one or more Ethylene oxide treatment(s). In some examples the post-processing step 2824 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 2716 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 29:
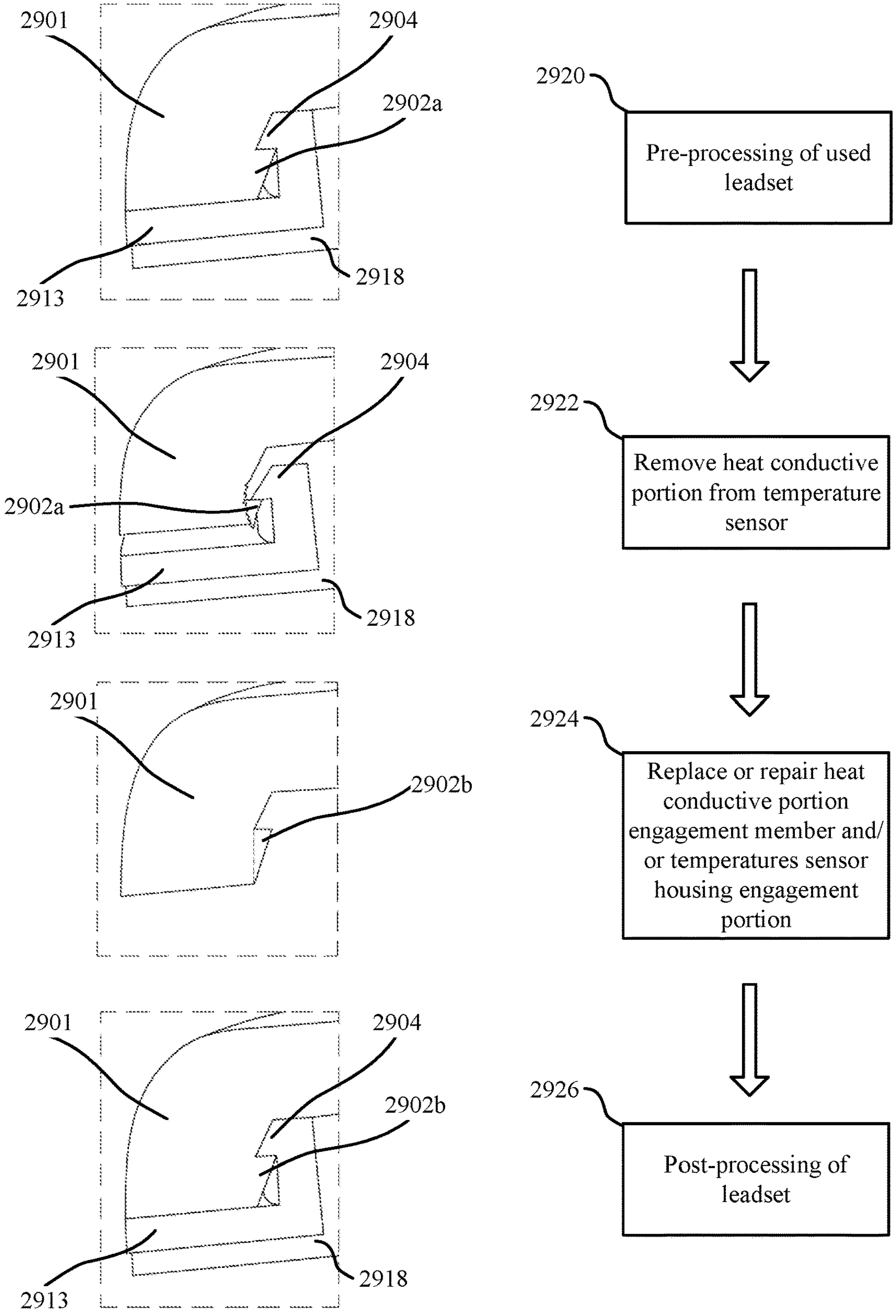
FIG. 29 illustrates a method of reconstructing a temperature sensor system usable with a multiparameter lead set according to aspects of the disclosure.

FIG. 29 shows one example reconstructing method that is usable with temperature sensor 2300 in FIGS. 23A and 23B, temperature sensor 2400 in FIGS. 24A and 24B, temperature sensor 2500 in FIG. 25, temperature sensor 2600 in FIG. 26, temperature sensor 2700 in FIG. 27 and/or temperature sensor 2800 in FIG. 28. As noted above with respect to FIGS. 27 and 28, a temperature sensor described herein may be refurbished, reprocessed, and/or reconstructed via any one of or any combination of the steps described above with respect to FIGS. 27 and 28. In addition to the steps described above, the steps in FIGS. 29 and 30 may be carried out in addition to the steps described above with respect to FIGS. 27 and 28. When the heat conductive media portion housing 2913 and/or the heat conductive media portion 2918 is removed from the temperature sensor housing 2901, any one or a combination of the temperature sensor housing engagement members 2902 and heat conductive media portion engagement member 2904 may for example break or otherwise separate or permanently deform or may be configured to break or otherwise be separated or permanently deformed. One example of a method is shown in FIG. 29. In the example shown in FIG. 29 a temperature sensor and/or a leadset containing or incorporating a temperature sensor may be subject to pre-processing in step 2920. Pre-processing may include but is not limited to any one or a combination of one or more cleanings, sterilization and/or high level disinfection (HDL) processes. As mentioned above, in some examples, the pre-processing step 2920 may also include replacement of component(s), cable(s), and/or tube(s) if during inspection it is deemed that such replacement is needed.

After pre-processing, the media portion housing 2913 of the heat conductive portion may be removed for either replacement and/or for replacement or refilling of a heat conductive media (e.g., hydrogel) 2918 using any one of the steps, methods, or apparatuses described above. When the heat conductive portion is removed, the temperature sensor housing engagement members 2902*a* may break or otherwise be removed from the temperature sensor housing 2901. After the heat conductive portion is removed from the temperature sensor housing 2901, the temperature sensor housing engagement 2902*a* that was broken or otherwise removed during separation may be replaced with a replacement temperature sensor housing engagement members 2902*b* in step 2924. Some examples of replacement may include but are not limited to re-molding of temperature sensor housing engagement members 2902*b*, removal of any excess portion of the of the broken temperature sensor housing engagement portion and adhering or otherwise connecting a new engagement member 2902*b* to the temperature sensor housing 2901. Some examples of adhering or otherwise connecting a new engagement member may include but are not limited to gluing using an adhesive, resin, or epoxy; ultrasonic or friction welding; melting a portion of the temperature sensor housing 2901 and/or the replacement member 2902*b* and allowing re-solidification thereof; and/or tapping and threading a new engagement member 2902*b*. In one example, the new engagement member 2902*b* may for example be formed of a material having different properties. For example, the new engagement member 2902*b* may be formed of a material having any one or a combination of a toughness that is greater than the previous temperature sensor housing engagement members 2902*a*, a flexibility that is greater than the previous temperature housing engagement members 2902*a*, a stiffness or rigidity that is greater than the previous temperature housing engagement members 2902*a*. In one example, the new engagement member 2902*b* may for example have an indicator that allows a technician or user to identify that the temperature sensor has been refurbished, reprocessed and/or reconstructed and/or has had the temperature sensor housing engagement members 2902 replaced. Some examples of indicators include a material with a different color, pattern, and/or texture to name a few examples.

As shown in FIG. 29, once the heat conductive portion engagement member and/or temperature sensor housing engagement portion is replaced, the temperature sensor and/or leadset having the temperature sensor connected thereto may be subject to post-processing in step 2926. Some examples of post-processing steps may include but are not limited to: additional cleaning, sterilization and/or high level disinfection (HDL) processes; one or more Ethylene Oxide treatment(s). In some examples the post-processing step 2926 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset and/or temperature sensor may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/ sterilization may be repeated after the lead set is repackaged, or the lead set may be high level disinfected (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets.

Figure 30:
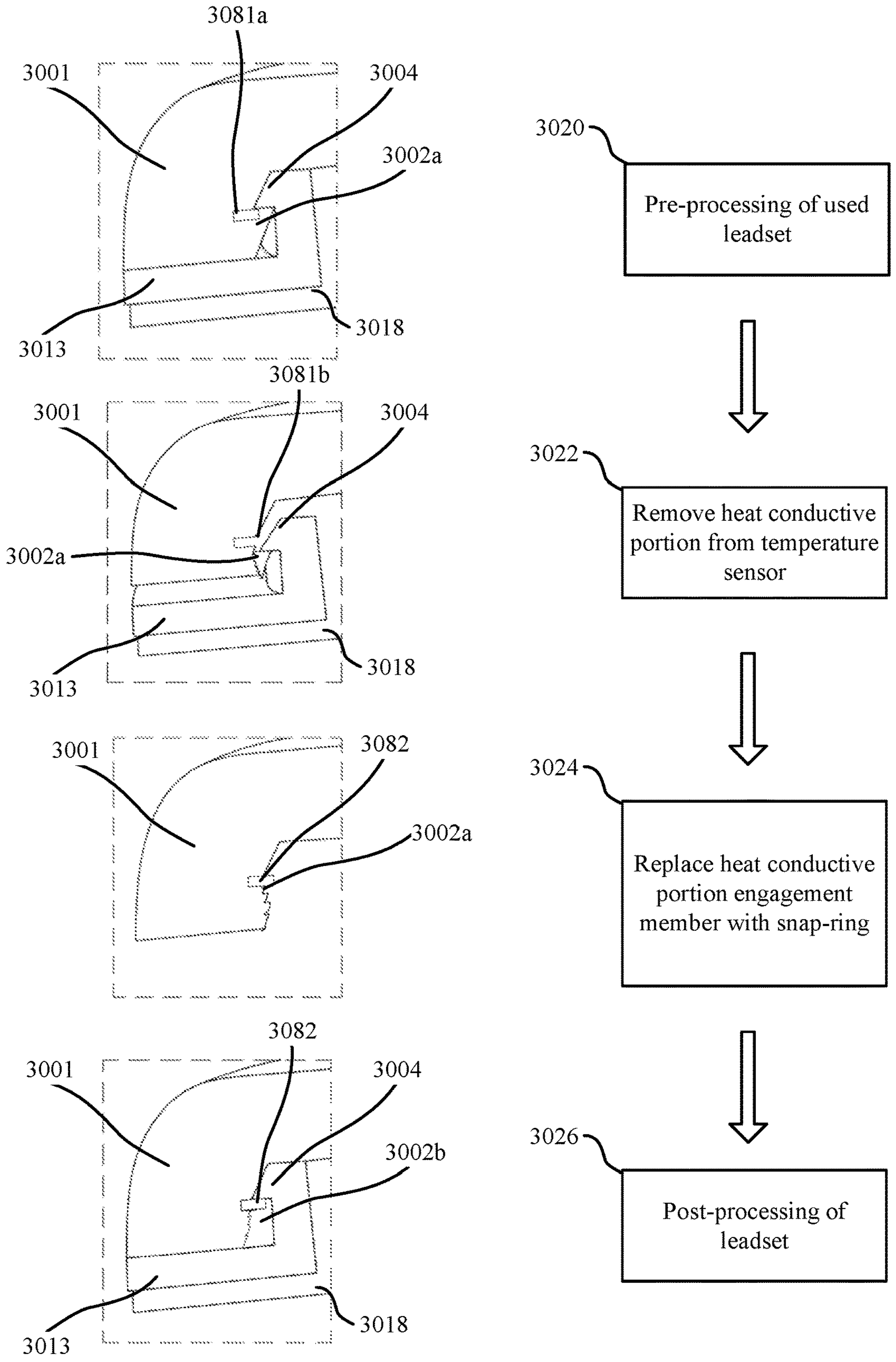
FIG. 30 illustrates a method of reconstructing a temperature sensor system usable with a multiparameter lead set according to aspects of the disclosure.

FIG. 30 shows one example reconstructing method wherein a snap-ring or other engageable replacement temperature sensor housing engagement member is used to refurbish or reconstruct a broken or otherwise separated temperatures sensor housing engagement member 3002*a*. The aspects described are is usable with and may be analogous with the temperature sensor 2300 in FIGS. 23A and 23B, temperature sensor 2400 in FIGS. 24A and 24B, temperature sensor 2500 in FIG. 25, temperature sensor 2600 in FIG. 26, temperature sensor 2700 in FIG. 27 and/or temperature sensor 2800 in FIG. 28. As noted above with respect to FIGS. 27 and 28, a temperature sensor described herein may be refurbished, reprocessed, and/or reconstructed via any one of or any combination of the steps described above with respect to FIGS. 27 and 28. In addition to the steps described above, the steps in FIG. 30 may be carried out in addition to the steps described above with respect to FIGS. 27 and 28.

In one aspect of the disclosure, the temperature sensor housing 3001 may for example include a channel or opening 3081*a* therein that is configured to receiveably engage with or receive a portion of a snap-ring or other engagement feature of a replacement temperature sensor housing engagement member 3082 after a previous temperature housing engagement members 3002*a* are broken or otherwise removed.

As shown in step 3020 of FIG. 30, the heat conductive media portion housing 3013 and/or the heat conductive media portion 3018 is removed from the temperature sensor housing 3001, any one or a combination of the temperature sensor housing engagement members 3002 and heat conductive media portion engagement member 3004 may for example break or otherwise separate or permanently deform, or may be configured to break or otherwise be separated or permanently deformed. In the example shown in FIG. 30 a temperature sensor and/or a leadset containing or incorporating a temperature sensor may be subject to pre-processing in step 3020. Pre-processing may include but is not limited to any one or a combination of one or more cleanings, sterilization and/or high level disinfection (HDL) processes. As mentioned above, in some examples, the pre-processing step 3020 may also include replacement of component(s), cable(s), and/or tube(s) if during inspection it is deemed that such replacement is needed.

After pre-processing, the media portion housing 3013 of the heat conducive portion may be removed for either replacement and/or for replacement or refilling of a heat conductive media (e.g., hydrogel) 3018 using any one of the steps, methods, or apparatuses described above. When the heat conductive portion is removed, the temperature sensor housing engagement members 3002*a* may break or otherwise be removed from the temperature sensor housing 3001, which may expose the channel or opening 3081*b* as shown in FIG. 30. After the heat conductive portion is removed from the temperature sensor housing 3001, a snap ring 3082 or other replacement engagement member may be installed into the channel or opening 3081*b* as shown in step 3024. In one example, the snap ring 3082 or other replacement engagement member may be installed via a tool that compresses the snap ring to decrease the other diameter thereof. Once the snap ring 3082 or other replacement engagement member is aligned within the channel or opening 3081 the snap ring may 3082 may be released, thus casing the outer diameter of the snap ring 3082 to increase and be captively engaged with the channel or opening 3081*b*.

The new engagement member or snap ring 3082 may for example be formed of a material having different properties. For example, the new engagement member 3082 may be formed of a material having any one or a combination of a toughness that is greater than the previous temperature sensor housing engagement members 3002*a*, a flexibility that is greater than the previous temperature housing engagement members 3002*a*, a stiffness or rigidity that is greater than the previous temperature housing engagement members 3002*a*. In one example, the replacement engagement member or snap ring 3082 may for example be formed of a metal such as stainless steel. In one example, the new engagement member 3082 may for example have an indicator that allows a technician or user to identify that the temperature sensor has been refurbished, reprocessed and/or reconstructed and/or has had the temperature sensor housing engagement members 3002*a* replaced. Some examples of indicators include a material with a different color, pattern, and/or texture to name a few examples.

In one example implementation, the temperature sensor may be sealed in a pouch or other containment portion that has a low vapor transmission rate. In one example, only the temperature sensor of a leadset may be sealed in a low vapor transmission rate pouch. In one example, the oxygen saturation sensor may be sealed within a low vapor transmission rate pouch that is sealingly engaged with or sealed around the cable of the temperature sensor another example, the temperature sensor may be sealed in a low vapor transmission rate pouch while the leadset (and temperature sensor with low vapor transmission pouch) is sealed or otherwise contained therein.

As shown in FIG. 30, once the heat conductive portion engagement member and/or temperature sensor housing engagement portion is replaced, the temperature sensor and/or leadset having the temperature sensor connected thereto may be subject to post-processing in step 3026. Some examples of post-processing steps may include but are not limited to: additional cleaning, sterilization and/or high level disinfection (HDL) processes; one or more Ethylene Oxide treatment(s). In some examples the post-processing step 3026 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset and/or temperature sensor may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets.

d. Oxygen Saturation Sensor(s) Usable with Monitoring Lead Sets

Figure 31A:
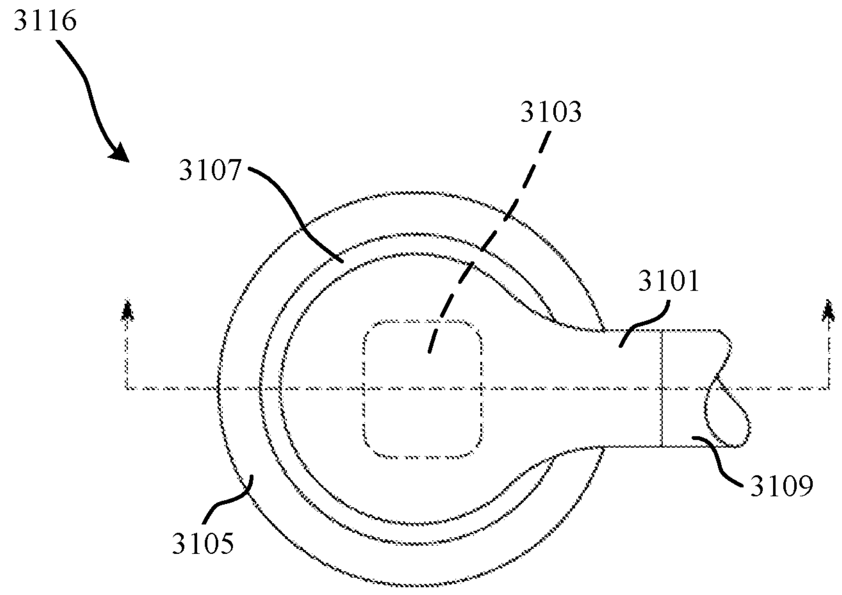
FIG. 31A is a top view of an oxygen saturation sensor usable with a multiparameter lead set according to aspects of the disclosure.
Figure 31B:
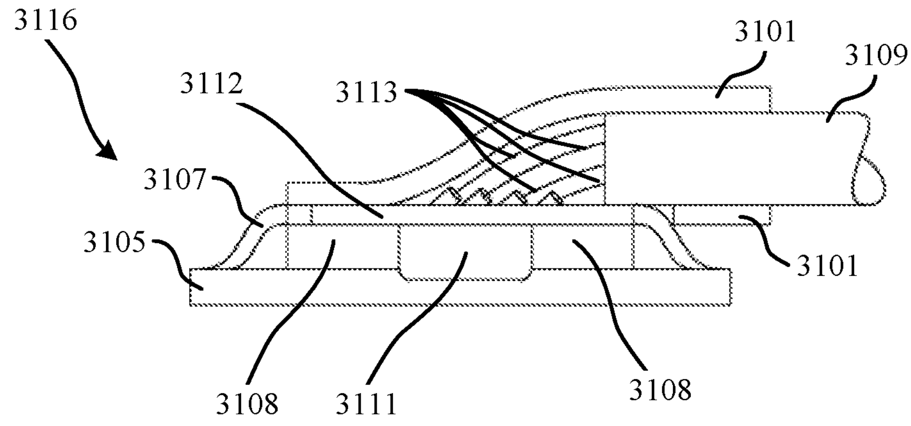
FIG. 31B is side cross-section view of the oxygen saturation sensor of FIG. 31A.
Figure 31C:
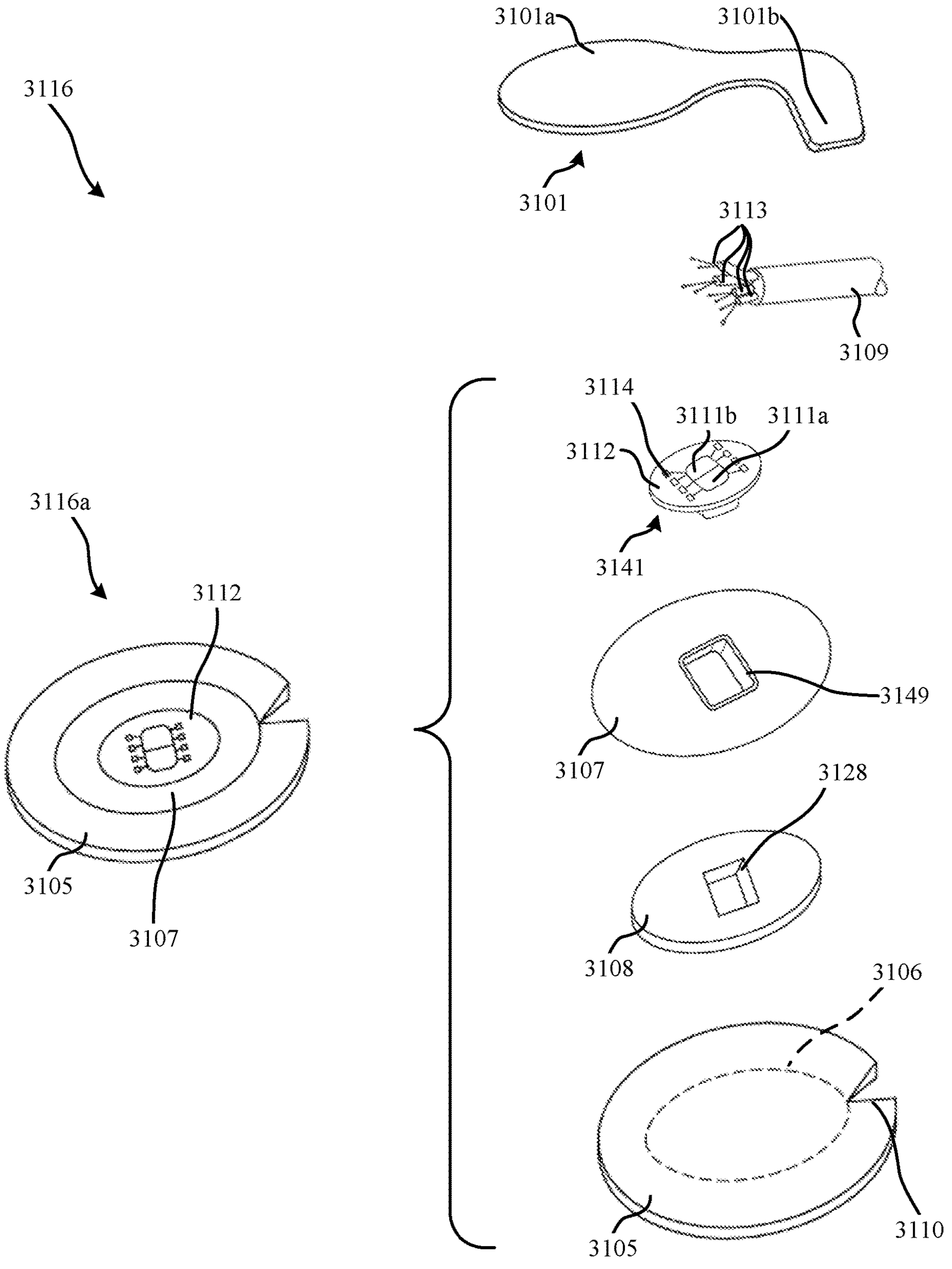
FIG. 31C is a disassembled or pre-assembled view of the oxygen saturation sensor of FIGS. 31A and 31B.

Any one or a combination of the lead sets described herein may include a oxygen saturation sensor, which may be interchangeably referred to as a pulse oximetry sensor. The oxygen saturation sensor may be configured to determine or output a signal that indicates one of or both of a pulse rate (PR) of a patient and peripheral capillary oxygen saturation ($SpO_2$) one of the patient monitoring leads. One example of an oxygen saturation sensor 3116 is shown in FIG. 31A-31C. The oxygen saturation sensor 3116 may for example be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, for example.

In one example, the oxygen saturation sensor 3116 may for example be configured to provide a reflectance-based $SpO_2$ and/or PR of a patent when emplaced upon or adhered a patients skin. In one example, the oxygen saturation sensor 3016 may be configured to be adhered to a patients armpit and/or forehead. In the example shown in FIGS. 31A-31C, the oxygen saturation sensor 3116 may have an adhereable portion 3108 that may be configured to be adhered to and/or may be configured to be re-adhereable after removal from a patients skin. Providing a re-adhereable adhereable portion

3108 allows for the sensor to be removed and replaced as needed which may improve convenience by not requiring a new leadset or new adhesive every time the sensor is removed from the patient. In one example, the adhereable portion 3108 may for example be a hydrogel or other adhesive or otherwise re-adhereable media (e.g., a pressure sensitive adhesive or foam tape).

As best shown in FIG. 31C, the adhereable portion 3108 may for example include an adhereable portion opening 3128 configured to prevent blockage of a sensor portion (e.g., 3111*a* and 3111*b*) of the sensor 3116. The sensor 3116 may further include a cable or lead 3109 having a plurality of wires or conduits 3113 configured to provide electrical or signal communication between the sensor assembly 3141 and a monitor (e.g., monitor or monitoring devices 304 in FIG. 1, 420 in FIG. 4, 808 in FIG. 8, 920 in FIG. 9, 2021 in FIGS. 10A and 10B, 1120 in FIG. 11, 1220 in FIG. 12, 1320 in FIG. 13, and/or any monitoring or display device or devices known in the art.

The oxygen saturation sensor 3116 shown in FIGS. 31A-31C further includes a sensor assembly 3141 having an emitter portion and a receiver portion 3111*b* and/or 3111*a*. In one example, the emitter portion may for example emit photoplethysmographic pulses in two ore more wavelengths, which may for example be in the red and infrared regions. The receive portion may for example measure or provide an output or change in resistance or current that changes in response to light absorption to indicate perfusion of blood to the dermis and subcutaneous tissues of the skin. The oxygen saturation sensor assembly 3141 may include any known oxygen saturation or pulse oximetry configuration. In one example, the oxygen saturation sensor assembly 3141 may for example include a known reflectance based pulse oximetry configuration. As shown in FIGS. 31A-31C, the components (e.g., the emitter and/or receiver portions 3111*a* and/or 3111*b*) of the oxygen saturation sensor assembly 3141 may for example be mounted or otherwise connected or embedded into a circuit board, flexible circuit board, or semi-flexible circuit board 3112. It is noted that in one aspect the oxygen saturation sensor assembly 3141 may for example include a flexible or semi-flexible circuit board which may improve durability of the assembly and/or may provide improved comfort to the patient wearer. The semi-flexible circuit board 3112 may for example include a series of connection portions 3114 configured to have the individual wires 3113 of the lead 3109 connected thereto. In one example, the connection portions 3114 may for example include a series of solder pads configure to have individual wires 3113 of the lead 3109 soldered thereto. In another example, the connection portions 3114 may for example be a connector or other connection portion configured to be removably connected to, permanently connected to, or semi-permanently connected to the individual wires 3113 of the lead 3109. As described in further detail below, the connection portions 3114 and/or wires 3113 may be configured to be de-soldered and re-soldered and/or disconnected and re-connected during a reconstruction process.

The oxygen saturation sensor 3116 may further include an inner cover 3107, the inner cover may for example have an inner cover opening 3149 that is configured to align with or otherwise correspond with the opening 3128 of the adhereable portion 3108 in order to prevent obstruction of the emission and receiver portion 3111*a* and 3111*b*. The inner cover 3107 may for example be formed of a thin flexible or laminate material. For example, the inner cover 3107 may for example be formed of any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as paper, cellulose, rayon, or any combination thereof. In one example, the inner cover 3107 may for example be formed of any material with a low moisture vapor transmission rate. The inner cover opening 3149 may for example have inner walls that are heat sealed, bonded to, or welded to the inner cover 3107. In one example, the inner cover 3107 may be configured to seal or otherwise engage with a release liner portion 3105, so that when engaged, the adhereable portion 3108 is substantially sealed from the external environment. In addition, the walls of the adhereable portion opening 3128 may for example further engage with the release liner portion 3105, and thus cause the adhereable portion 3108 to be substantially or completely sealed from the external environment. The aforementioned sealing may ensure that the oxygen saturation sensor 3116 remains sanitary until use. Further, in the aforementioned example wherein the adhereable portion 3108 comprises a hydrogel, the inner cover 3107 and the release liner portion 3105 may prevent the hydrogel from dying out or otherwise losing moisture prior to use due to exposure to the surrounding environment.

As shown in FIGS. 31A-31C, the oxygen saturation sensor 3116 may further include a release layer or release portion 3105. The release portion 3105 may be configured to be removably adhered to or otherwise sealed to the inner cover 3107 as best shown in the cross-section in FIG. 31B. The interaction between the inner cover 3107 and the release liner portion 3105 may prevent the hydrogel from dying out or otherwise losing moisture prior to use due to exposure to the surrounding environment. The release portion 3105 may further include a tear away seam 3106. The tear away seam may for example include any on or a combination of a perforation, a heat seam, and/or trench or groove with a decrease in thickness of material that allows for the controlled tearing away of the release liner portion 3105 by causing separation of the material that forms the release liner portion at the tear away seam 3106. The release liner portion 3105 may further include a pull-tab or notch 3110 that allows a user to grip a portion of the release liner portion 3105 and tear away the release liner by causing a separation at seam 3106. In another example, the seam 3106 may be omitted and the release liner portion 3105 may be configured to be separated from the inner cover 3107 and/or the adhereable portion 3108 when removing the release liner portion 3105 when the oxygen saturation sensor 3116 is to be used. The release liner portion 3105 may for example be formed of any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof.

In one example implementation, the oxygen saturation sensor 3116 may be sealed in a pouch or other containment portion that has a low vapor transmission rate. In one example, only the oxygen saturation sensor 3116 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3116 In another example, the oxygen saturation sensor may be sealed in a low vapor transmission rate pouch while the leadset (and oxygen saturation sensor with low vapor transmission pouch) is sealed or otherwise contained therein.

The oxygen saturation sensor 3116 may further include a cover 3101 with a cable and sensor assembly cover portion 3101*a* and a cable cover and/or strain relief portion 3101*b*. The cover 3101 may be configured to be adhered to or otherwise bonded or connected to the semi-flexible circuit board 3112 and/or the inner cover 3107 to provide an outer cover for the casing and to protect the internal components of the oxygen saturation sensor 3116. In the example shown in FIGS. 31A-31C, the relief portion 3101*b* may be configured to be wrapped around the lead 3109 thus providing a cover to protect the interface between the individual wires 3113 and the semi-flexible circuit board 3112 and to provide strain relief (e.g., to protect the individual wires 3113 from excessive bending or kinking). The relief portion 3101*b* may for example be configured to completely wrap around or partially wrap around the lead 3109 and may be adhered to or otherwise connected to the lead 3109. In one example, the cover 3101 may for example be formed of a foam. In one example the foam may for example be liquid impervious or liquid resistant and may have an adhesive backing that is configured to adhere to at least one of or the combination of the lead 3109, the semi-flexible circuit board 3112 and/or the inner cover 3107. In one example, the foam that forms the cover 3101 may for example improve patient comfort by providing a more forgiving surface (e.g., softer and more pliable) than is typically used to form an oxygen saturation sensor. The foam outer surface may for example provide greater comfort to a wearer that for example has the oxygen saturation sensor 3116 applied to or adhered to their armpit.

In one example of the disclosure, a manufacturing method for manufacturing or assembling a leadset with a oxygen saturation sensor or a manufacturing method for manufacturing or assembling an oxygen saturation sensor or replacement oxygen saturation sensor is disclosed. With reference to FIG. 31C, an oxygen saturation sensor may be assembled by connecting or adhering an adhereable portion 3108 to the bottom face of a semi-flexible circuit board 3112 of a oxygen saturation sensor assembly 3141. A inner cover 3107 may be applied to the oxygen saturation sensor assembly 3141 so that the receiver portion and emitter portion 3111*a* and 3111*b* protrude through the inner cover opening 3149 and the adhereable portion opening 3128 and are not blocked by either one of the inner cover 3107 and the adhereable portion 3108. The release liner 3106 maybe applied or adhered to at least one of the inner cover 3107 and/or the adhereable portion 3108 with the 3106 facing downwards and away from the adhereable portion 3108 to prevent the seam 3106 from compromising the seal between the release liner portion 3105 and the adhereable portion 3108 and/or the inner cover 3107. In one example implementation, the components and assembly described above may for example be referred to herein as an oxygen saturation sensor device 3116*a*. The sensor may for example include an connection portions 3114 lead 3109

The oxygen saturation sensor device 3116*a* may for example further be connected to a lead 3109 by soldering or otherwise connecting the individual wires 3113 of the lead 3109 to the connection portions 3114 of the oxygen saturation sensor device 3116*a*. The interface between the semi-flexible circuit board 3112, the lead 3109 and/or the inner cover 3107 may then be covered by adhering the cover 3101 to the oxygen saturation sensor device 3116*a* and by wrapping the relief portion 3101*b* of the cover 3101 around the lead 3109. In one example, the cover 3101 may for example have an adhesive with a release liner (not shown) disposed on a bottom surface thereof and the release liner may be removed to expose the adhesive before applying the cover 3101 to the oxygen saturation sensor device 3116*a* and/or the lead 3109 as described above.

As described in further detail with respect to FIGS. 34 and 35 below, the leadset and/or the oxygen saturation sensor 3116 may be subject to a reconstruction method. In one example, a used oxygen saturation sensor may be replaced with a new oxygen saturation sensor device 3116*a* by removing the cover 3101, removing the lead 3109 from the oxygen saturation sensor assembly 3141 and a new or replacement oxygen saturation sensor device 3116*a* may be connected to the lead 3109 and a new cover 3101 applied thereto. In another example, the oxygen saturation sensor 3116 may be subject to a cleaning or disinfection process and the adhereable portion 3108 and/or the release liner portion 3105 may be replaced to reconstruct the oxygen saturation sensor 3116 and/or the lead set.

FIGS. 32A-32D show another example of an oxygen saturation sensor, which may be configured to determine or provide a signal communicating indicating at least one of or both of a pulse rate (PR) of a patient and peripheral capillary oxygen saturation (402) at one of the patient monitoring leads. The example oxygen saturation sensor 3216 described below with respect to FIGS. 31A-31C may for example be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, for example.

Figure 32A:
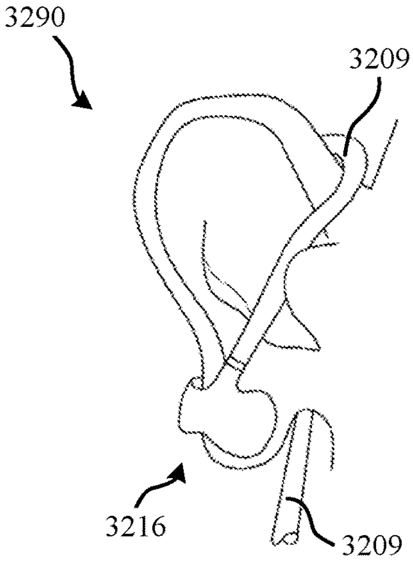
FIG. 32A is a view of an oxygen saturation sensor usable with a multiparameter lead set according to aspects of the disclosure.
Figure 32B:
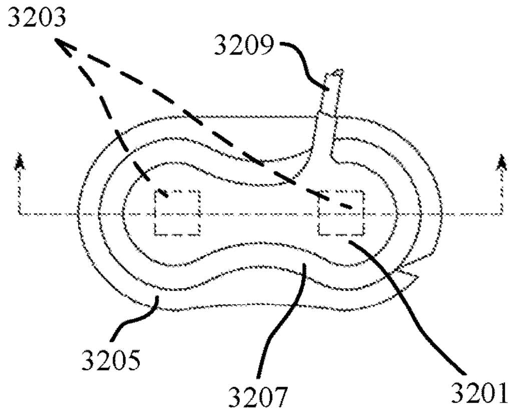
FIG. 32B is a top view of the oxygen saturation sensor of FIG. 32A.
Figure 32C:
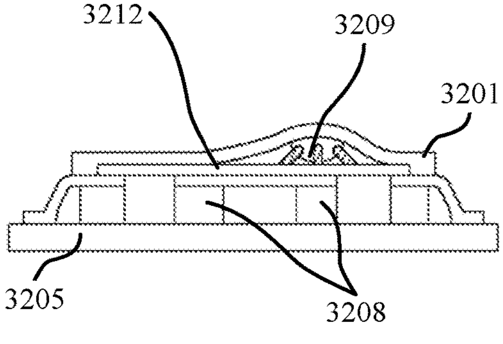
FIG. 32C is a side cross-section view of the oxygen saturation sensor of FIGS. 32A and 32B.

The oxygen saturation sensor 3216 may for example be configured to provide a transmissive pulse oximetry 402 and/or PR of a patent when emplaced upon or adhered in a folded over configurations as shown in FIG. 32A onto a patients earlobe. It is noted that while an earlobe is shown in FIG. 32A, a oxygen saturation sensor 3216 according to aspects of the disclosure may for example be adhered alternatively to a patients finger for example.

As shown in FIG. 32A, in one example implementation the oxygen saturation sensor 3216 may for example be folded over and adhered to lobe of a patient's ear 3290 so that one of an emission portion and/or receiving portion(s) 3203 has a patients earlobe therebetween. The oxygen saturation sensor 3116 may have an adhereable portion 3208 that may be configured to be adhered to and/or may be configured to be re-adhereable after removal from a patients skin. Providing a re-adhereable adhereable portion 3108 allows for the sensor to be removed and replaced as needed which may improve convenience by not requiring a new leadset or new adhesive every time the oxygen saturation sensor 3216 is removed from the patient. In one example, the adhereable portion 3208 may for example be a hydrogel or other adhesive or otherwise re-adhereable media (e.g., a pressure sensitive adhesive or foam tape).

Figure 32D:
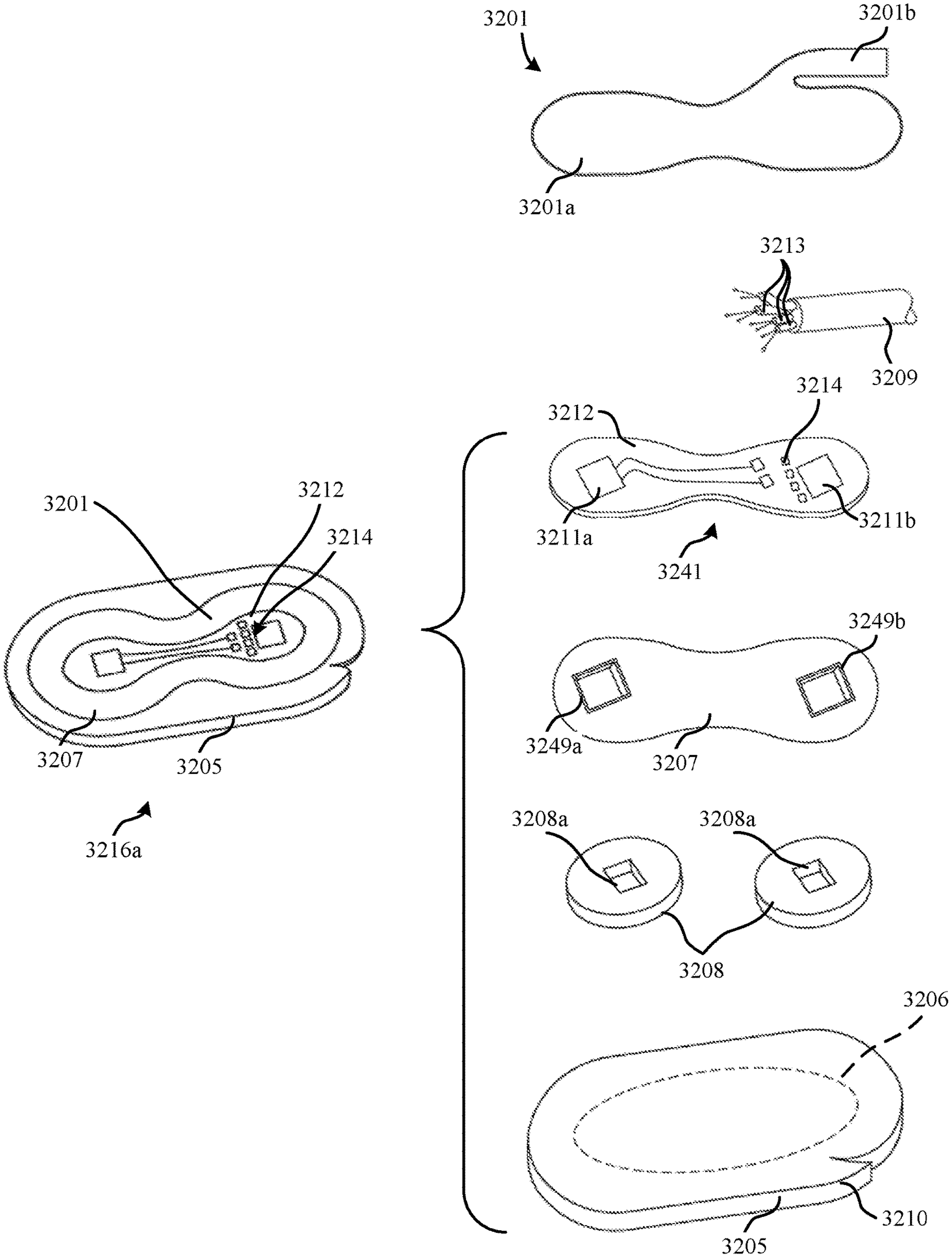
FIG. 32D is a disassembled or pre-assembled view of the oxygen saturation sensor of FIGS. 32A-32C.

As best shown in FIG. 32D, the adhereable portion 3208 may for example comprise a plurality of adhereable portion(s) 3208, each having an adhereable portion opening 3208*a* and 3208*b* configured to prevent blockage of a sensor portion (e.g., 3211*a* and 3211*b*) of the oxygen saturation sensor 3216. The oxygen saturation sensor 3216 may further include a cable or lead 3209 having a plurality of wires or conduits 3213 configured to provide electrical or signal communication between the sensor assembly 3241 and a monitor (e.g., monitor or monitoring devices 304 in FIG. 1, 420 in FIG. 4, 808 in FIG. 8, 920 in FIG. 9, 2021 in FIGS. 10A and 10B, 1120 in FIG. 11, 1220 in FIG. 12, 1320 in FIG. 13, and/or any monitoring or display device or devices known in the art.

As mentioned above, the oxygen saturation sensor 3216 shown in FIGS. 32A-32D further includes a sensor assembly 3241 having an emitter portion and a receiver portion 3211*b* and/or 3211*a*. In one example, the emitter portion may for example emit pulses in one or more wavelengths, which may for example be in the red and infrared regions. The receive portion may for example measure or provide an output or change in resistance or current in response to light detected at the receiving portion to indicate perfusion of blood. The oxygen saturation sensor assembly 3241 may include any known oxygen saturation or pulse oximetry configuration. In one example, the oxygen saturation sensor assembly 3241 may for example include a known transmissive based pulse oximetry configuration. As shown in FIGS. 32A-32D, the components (e.g., the emitter and/or receiver portions 3211*a* and/or 3211*b*) of the oxygen saturation sensor assembly 3241 may for example be mounted or otherwise connected or embedded into a flexible circuit board 3212. It is noted that in one aspect the oxygen saturation sensor assembly 3141 may for example include a flexible or semi-flexible circuit board which allows the s ear 3290 to be folded over a patient earlobe or finger for example. The flexible or semi-flexible circuit board may also improve durability of the assembly and/or may provide improved comfort to the patient wearer. The flexible circuit board 3212 may for example include a series of connection portions 3214 configured to have the individual wires 3213 of the lead 3209 connected thereto. In one example, the connection portions 3214 may for example include a series of solder pads configured to have individual wires 3213 of the lead 3209 soldered thereto. In another example, the connection portions 3214 may for example be a connector or other connection portion configured to be removably connected to, permanently connected to, or semi-permanently connected to the individual wires 3213 of the lead 3209. As described in further detail below, the connection portions 3214 and/or wires 3213 may be configured to be de-soldered and re-soldered and/or disconnected and re-connected during a reconstruction process.

The oxygen saturation sensor 3216 may further include an inner cover 3207, the inner cover may for example have a series of inner cover opening(s) 3249*a* and 3249*b* configured to align with or otherwise correspond with the openings 3208*a* and 3208*b* of the adhereable portion 3208 in order to prevent obstruction of the emission and receiver portion 3211*a* and 3211*b*. The inner cover 3207 may for example be formed of a thin flexible or laminate material. For example, the inner cover 3207 may for example be formed of any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as paper, cellulose, rayon, or any combination thereof. In one example, the inner cover 3207 may for example be formed of any material with a low moisture vapor transmission rate. The inner cover openings 3249*a* and/or 3249*b* may for example have inner walls that are heat sealed, bonded to, or welded to the inner cover 3207. In one example, the inner cover 3207 may be configured to seal or otherwise engage with a release liner portion 3205, so that when engaged, the adhereable portion 3208 is substantially sealed from the external environment. In addition, the walls of the adhereable portion openings 3249*a* and/or 3249*b* may for example further engage with the release liner portion 3205, and thus cause the adhereable portion 3208 to be substantially or completely sealed from the external environment. The aforementioned sealing may ensure that the oxygen saturation sensor 3216 remains sanitary until use. Further, in the aforementioned example wherein the adhereable portion 3208 comprises a hydrogel, the inner cover 3207 and the release liner portion 3205 may prevent the hydrogel from dying out or otherwise losing moisture prior to use due to exposure to the surrounding environment.

As shown in FIGS. 32A-32D, the oxygen saturation sensor 3216 may further include a release layer or release portion 3205. The release portion 3205 may be configured to be removably adhered to or otherwise sealed to the inner cover 3207 as best shown in the cross-section in FIG. 32C. The interaction between the inner cover 3207 and the release liner portion 3205 may prevent the hydrogel from dying out or otherwise losing moisture prior to use due to exposure to the surrounding environment. The release portion 3205 may further include a tear away seam 3206. The tear away seam may for example include any on or a combination of a perforation, a heat seam, and/or trench or groove with a decrease in thickness of material that allows for the controlled tearing away of the release liner portion 3205 by causing separation of the material that forms the release liner portion at the tear away seam 3206. The release liner portion 3205 may further include a pull-tab or notch 3210 that allows a user to grip a portion of the release liner portion 3205 and tear away the release liner by causing a separation at seam 3206. In another example, the seam 3206 may be omitted and the release liner portion 3205 may be configured to be separated from the inner cover 3207 and/or the adhereable portion 3208 when removing the release liner portion 3205 when the oxygen saturation sensor 3216 is to be used. The release liner portion 3205 may for example be formed of any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof. The release liner portion 3205 may for example be formed as a rigid or semi-rigid card-type sheet.

In one example implementation, the oxygen saturation sensor 3216 may be sealed in a pouch or other containment portion that has a low vapor transmission rate. In one example, only the oxygen saturation sensor 3216 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3216 In another example, the oxygen saturation sensor may be sealed in a low vapor transmission rate pouch while the leadset (and oxygen saturation sensor with low vapor transmission pouch) is sealed or otherwise contained therein.

The oxygen saturation sensor 3216 may further include a cover 3201 with a cable and sensor assembly cover portion 3201*a* and a cable cover and/or strain relief portion 3201*b*. The cover 3201 may be configured to be adhered to or otherwise bonded or connected to the semi-flexible circuit board 3212 and/or the inner cover 3207 to provide an outer cover for the casing and to protect the internal components of the oxygen saturation sensor 3216. In the example shown in FIGS. 32A-32D, the relief portion 3201*b* may be configured to be wrapped around the lead 3209 thus providing a cover to protect the interface between the individual wires 3213 and the semi-flexible circuit board 3212 and to provide strain relief (e.g., to protect the individual wires 3213 from excessive bending or kinking). The relief portion 3201*b* may for example be configured to completely wrap around or partially wrap around the lead 3209 and may be adhered to or otherwise connected to the lead 3209. In one example, the cover 3201 may for example be formed of a foam. In one example the foam may for example be liquid impervious or liquid resistant and may have an adhesive backing that is configured to adhere to at least one of or the combination of the lead 3209, the semi-flexible circuit board 3212 and/or the inner cover 3207. In one example, the foam that forms the cover 3201 may for example improve patient comfort by providing a more forgiving surface (e.g., softer and more pliable) than is typically used to form an oxygen saturation sensor. The foam outer surface may for example provide greater comfort to a wearer. In one example of the disclosure, a manufacturing method for manufacturing or assembling a leadset with a oxygen saturation sensor or a manufacturing method for manufacturing or assembling an oxygen saturation sensor or replacement oxygen saturation sensor is disclosed. With reference to FIG. 32D, an oxygen saturation sensor may be assembled by connecting or adhering an adhereable portion 3208 to the bottom face of a semi-flexible circuit board 3212 of an oxygen saturation sensor assembly 3241. A inner cover 3207 may be applied to the oxygen saturation sensor assembly 3241 so that the receiver portion and emitter portion 3211*a* and 3211*b* protrude through the inner cover openings 3249*a* and 3249*b* and the adhereable portion openings 3208*a* and 3208*b* and are not blocked by either one of the inner cover 3207 and the adhereable portion 3208. The release liner 3206 maybe applied or adhered to at least one of the inner cover 3207 and/or the adhereable portion 3208 with the 3206 facing downwards and away from the adhereable portion 3208 to prevent the seam 3206 from compromising the seal between the release liner portion 3205 and the adhereable portion 3208 and/or the inner cover 3207. In one example implementation, the components and assembly described above may for example be referred to herein as an oxygen saturation sensor device 3216*a*.

Figure 33:
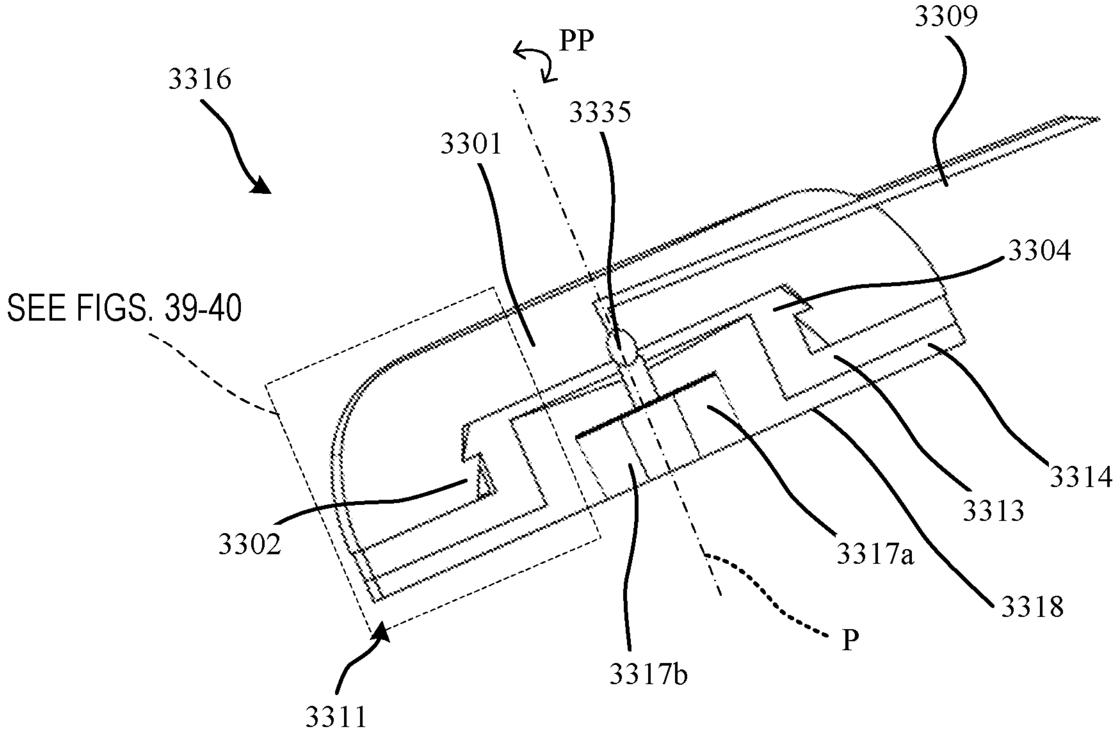
FIG. 33 is a side cross-section view of an oxygen saturation sensor usable with a multiparameter leadset according to aspects of the disclosure.

The oxygen saturation sensor device 3216*a* may for example further be connected to a lead 3209 by soldering or otherwise connecting the individual wires 3213 of the lead 3209 to the connection portions 3214 of the oxygen saturation sensor device 3216*a*. The interface between the semi-flexible circuit board 3212, the lead 3209 and/or the inner cover 3207 may then be covered by adhering the cover 3201 to the oxygen saturation sensor device 3216*a* and by wrapping the relief portion 3201*b* of the cover 3201 around the lead 3209. In one example, the cover 3201 may for example have an adhesive with a release liner (not shown) disposed on a bottom surface thereof and the release liner may be removed to expose the adhesive before applying the cover 3201 to the oxygen saturation sensor device 3216*a* and/or the lead 3209 as described above. As described in further detail with respect to FIGS. 36 and 37 below, the leadset and/or the oxygen saturation sensor 3216 may be subject to a reconstruction method or process. In one example, a used oxygen saturation sensor may be replaced with a new oxygen saturation sensor device 3216*a* by removing the cover 3201, removing the lead 3209 from the oxygen saturation sensor assembly 3241 and a new or replacement oxygen saturation sensor device 3216*a* may be connected to the lead 3209 and a new cover 3201 applied thereto. In another example, the oxygen saturation sensor 3216 may be subject to a cleaning or disinfection process and the adhereable portion 3208 and/or the release liner portion 3205 may be replaced to reconstruct the oxygen saturation sensor 3216 and/or the lead set. FIG. 33 shows one example implementations of an oxygen saturation sensor 3316 according to aspects of the disclosure. The oxygen saturation sensor 3316 may be configured to determine or output a signal that indicates one of or both of a pulse rate (PR) of a patient and peripheral capillary oxygen saturation ($SpO_2$) one of the patient monitoring leads. The oxygen saturation sensor 3316 may for example be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, for example.

The oxygen saturation sensor 3316 may for example be configured to provide a reflectance-based $SpO_2$ and/or PR of a patent when emplaced upon or adhered a patients skin. In one example, the oxygen saturation sensor 3316 may be configured to be adhered to a patients armpit and/or forehead. In the example shown in FIG. 33, the oxygen saturation sensor 3316 may have an adhereable portion 3108 that may be configured to be adhered to and/or may be configured to be re-adhereable after removal from a patients skin. Providing a re-adhereable adhereable portion 3314 allows for the sensor to be removed and replaced as needed which may improve convenience by not requiring a new leadset or new adhesive every time the sensor is removed from the patient. In one example, the adhereable portion 3314 may for example be a hydrogel or other adhesive or otherwise re-adhereable media (e.g., a pressure sensitive adhesive or foam tape). The oxygen saturation sensor 3316 may for example have an oxygen sensor housing 3301. The temperature sensor housing 3301 may have connected thereto or embedded therein a swivel or rotatable connector 3335, the rotatable connector 3335 may for example be series of rotatable terminals or a rotatable connector known in the art. In one example, the rotatable connector 3335 may instead be a non-rotatable or only partially rotatable connector or terminal device for providing signal communication between an oxygen saturation sensor portion with an emitter and a receiver 3317*a* and 3317*b* and a cable 3309. In the example implementation wherein the rotatable connector 3335 is rotatable, an adhereable portion 3311 may be configured to rotate with respect to the oxygen saturation sensor housing 3301 about axis P in directions PP. The oxygen saturation sensor 3316 may further include an oxygen saturation sensor portion with an emitter 3317*a* and a receiver 3317*b*. In one example, the emitter portion may for example emit photoplethysmographic pulses in two or more wavelengths, which may for example be in the red and infrared regions. The receiver portion may for example measure or provide an output or change in resistance or current that changes in response to light absorption to indicate perfusion of blood to the dermis and subcutaneous tissues of the skin. The oxygen saturation sensor portion may include any known oxygen saturation or pulse oximetry configuration. In one example, the oxygen saturation portion may for example include a known reflectance based pulse oximetry configuration.

The emitter 3317*a* and receiver 3317*b* of the oxygen saturation sensor portion may be configured to be in electrical communication or signal communication with a monitoring device or station via a cable 3309 via the rotatable connector 3335. The cable 3309 may be part of any of the aforementioned lead sets described throughout this specification and may include any one or a combination of additional patient physiological sensors. For example, the leadset may include any number of one or more ECG cables, one or more temperature sensor cables, and/or any monitoring cable known in the art or described throughout this disclosure. While not shown FIG. 33, the opposite end of the cable 3309 may for example have a terminal or other electrical connection as part of a lead set connector as described in the aspects throughout this disclosure. Further, the cable 3309 may have any one or a combination of the interconnection features described above with respect to FIGS. 15A-19F. In another aspect, the cable 3309 may be molded, extruded, or otherwise permanently connected to other cables of a leadset (e.g., as shown in FIG. 24B to one or more ECG cables, and/or one or more temperature cables, and/or any monitoring cable known in the art) to form a single bundle or group of cables thus eliminating or reducing cable clutter. In another aspect the cable 3309 may for example include just a single cable with a connector at the terminal end thereof that is configured to connect to be placed in signal communication with a monitoring or display device. The oxygen saturation sensor housing 3301 may further be configured to receiveably engage an adhereable portion 3311 2511. Throughout the disclosure, the adhereable portion may be interchangeably referred to as a connection portion. The adhereable portion 2511 may for example provide an adhesive connection with a patient's skin allowing for the emitter 3317*a* and the receiver 3317*b* to be held in proximity to a patients skin. The adhereable portion 3311 may for example include an adhereable portion housing 3313 configured to house or otherwise be connected to an adhereable media portion 3314 having the emitter 3317*a* and receiver 3317*b* of the oxygen saturation sensor portion partially embedded or otherwise disposed therein. In one example, the adhereable portion 3311 may for example have an opening or void configured to allow the emitter 3317*a* and/or receiver 3317*b* to be unobstructed by the re-adhereable adhereable portion 3314. In one example, the adhereable portion housing 3313 may be an annular structure with an opening at the first end that is dimensioned to receive a portion of the emitter 3317*a* and/or receiver 3317*b* and an opening with flat surface configured to support the re-adhereable adhereable portion 3314. The re-adhereable adhereable portion 3314 may be configured to fill or otherwise contact the inner surfaces of the adhereable portion housing 3313 as shown in FIG. 33. In one example, the re-adhereable adhereable portion 3314 may for example be a hydrogel or pressure sensitive adhesive configured to be emplaced or adhered to a patients skin, for example in a patients armpit or forehead. In one example, the pressure sensitive adhesive may comprise a plurality of layers of pressure sensitive adhesive that can be peeled away once the first layer is used (e.g., once adhered to a patient and removed) to expose a new layer to be adhered to the patient.

In one example implementation, the adhereable portion 3311 may be configured to be receiveably engaged within a concave portion of the oxygen saturation sensor housing 3301 via interaction between oxygen saturation sensor housing engagement members 3302 and adhereable media portion engagement member 3304. In one example, the oxygen saturation sensor housing engagement members 3302 and adhereable media portion engagement member 3304 may for example be annular grooves configured to engage with one another as shown in the cross-section in FIG. 33. One example of an annular groove may for example have a tooth-shaped cross section as shown in FIG. 33. As described in further detail below with respect to example implementations shown in FIGS. 38-40, any one or a combination of the oxygen saturation sensor housing engagement members 3302 and adhereable media portion engagement member 3304 may for example be configured to break or otherwise be separated or permanently deformed if the adhereable portion 3311 is separated from the oxygen saturation sensor housing 3301 and a refurbishing or reconstructing method or system according to an aspect of the disclosure may be used to repair or replace the deformed or broken oxygen saturation sensor housing engagement members 3302 and/or adhereable media portion engagement member 3304.

In another example, any one or a combination of the oxygen saturation sensor housing engagement members 3302 and/or adhereable media portion engagement member 3304 may be configured to elastically deform to allow for the re-engageable separation of the adhereable portion 3311 and the oxygen saturation sensor housing 3301. In one example, the interaction between the oxygen saturation sensor housing engagement members 3302 and re-adhereable adhereable portion 3314 may for example allow the oxygen saturation sensor housing 3301 to rotate about axis P with respect to the adhereable portion 3311 as indicated by arrow(s) PP. Thus, the interaction between the re-adhereable adhereable portion 3314 and the oxygen saturation sensor housing engagement members 3302 may cause the adhereable portion 3311 to be captively connected to the oxygen saturation sensor housing 3301 while still allowing rotation in directions PP which allows for the cable 3309 to be rotated or otherwise re-arranged while the first surface 3318 is emplaced or adhered to a patients skin. This rotation may improve patient comfort, allow for improved cable management and/or prevent inadvertent removal of oxygen saturation sensor 3316 from a patients skin.

In one example implementation, the oxygen saturation sensor 3316 may be reconstructed or reprocessed either by replacing the adhereable portion 3311 and/or the re-adhereable adhereable portion 3314 after use or by removing the re-adhereable adhereable portion 3314 from the adhereable portion housing 3313 and/or from around the emitter 3317*a* and receiver 3317*b* and replacing the re-adhereable adhereable portion 3314 with a new adhereable media and/or replacing the re-adhereable adhereable portion 3314. For example, in the example implementation with a hydrogel as the re-adhereable adhereable portion 3314, the hydrogel may be removed and replaced. In one example, the hydrogel may be chemically dissolved and/or dissolved via heating using steam for example. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation.

In one example, the adhereable portion housing 3313 with the hydrogel removed may be used as a mold or partial mold either while attached to the oxygen saturation sensor housing 3301 or separated from the oxygen saturation sensor housing 3301 and may be refilled or otherwise have the re-adhereable adhereable portion 3314 replaced during reconstructing. In one example, the adhereable portion housing 3313 may be left installed or re-installed into the oxygen saturation sensor housing 3301 and the hydrogel or other conductive media may be refilled so as to encompass or otherwise surround and/or cure around the emitter 3317*a* and receiver 3317*b*.

e. Reconstructing Method For Lead Sets and Oxygen Sensor (s)

Along with the reprocessing, refurbishing and/or reconstructing aspects described above with respect to FIG. 20, one aspect of the disclosure includes a method and/or process for reprocessing, refurbishing and/or reconstructing an oxygen saturation sensor according to aspects of the disclosure. While it is noted that aspects described below describe reprocessing, refurbishing and/or reconstructing of a temperature sensor, the aspects described below may be combined with reprocessing, refurbishing and/or reconstructing of lead sets described above for example. The aforementioned aspects, e.g., the oxygen saturation sensor that is refurbished or reprocessed may for example be connected to and refurbished, reprocessed and/or reconstructed with a lead set described throughout this disclosure. The lead set may, for example, be reprocessed, refurbished, or reconstructed by sending to a reconstructing facility. During the process, a first type of patient connector, associated lead and/or lead set connector may be disconnected from a lead set or separated from the lead set. In one example, the lead set may comprise at least a first lead, patient connector, and lead connector associated with a first patient health indicator and may be connected via an interconnection feature to at least a second lead, patient connector, and lead connector associated with a first patient health indicator. To give one specific example, the first type of patient connector may be an ECG connector or series of connectors (e.g., 314 in FIG. 3, 414 in FIG. 4, 514 in FIG. 5, 614 in FIG. 6, 704 in FIG. 7, 804 in FIG. 8, 1014 in FIGS. 10A-B, 1114 in FIG. 11, 1214 in FIG. 12, and 1314 in FIG. 13), and a lead connecting the first type of patient connector to a first lead set connector (e.g., 904*b* in FIG. 9, 1004*b* in FIG. 10, 1136 in FIG. 11, and 1304 in FIG. 13). The second type of patient connector may be an oxygen saturation sensor or series of sensors or connectors (e.g., sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIGS. 32A-32D, and/or oxygen saturation sensor 3316 in FIG. 33) and a second lead connecting the second type of patient connector to the second lead set connector. In one example, the first type of leadset may for example be refurbished or reconstructed by any one or combination of a cleaning step, a sanitization or sterilization step, or a high level disinfection step. As discussed in further detail below, in the aforementioned example, the second type of patient lead and/or patient connector may require additional steps to sufficiently reconstruct beyond the aforementioned cleaning step, sanitization or sterilization step, or high level disinfection step. The first lead and/or second lead may be connected via any one or a combination of the interconnection features described with respect to FIGS. 15A-19D, and/or the first lead set connector and second lead set connector may be connected via any one of the interconnection features described with respect to FIGS. 15A-19D. Using the aforementioned non-limiting example, the first lead set and second lead set and/or first lead set connector and second lead set connector may be disconnected from one another if they are not already disconnected. In one example, a disconnection device may be assist with or may be required to disconnect the aforementioned connection features. In one example, the disconnection device may be slid along the outer surface of two or more leads to cause the first interconnection interface to disengage from the second interconnection interface and/or to allow any number of cables to be disconnected from one another. The aforementioned disconnection of the interconnection features via a disconnection device may be completed manually via a technician or worker and/or may be completed via an automated or machine-assisted process.

Figure 34:
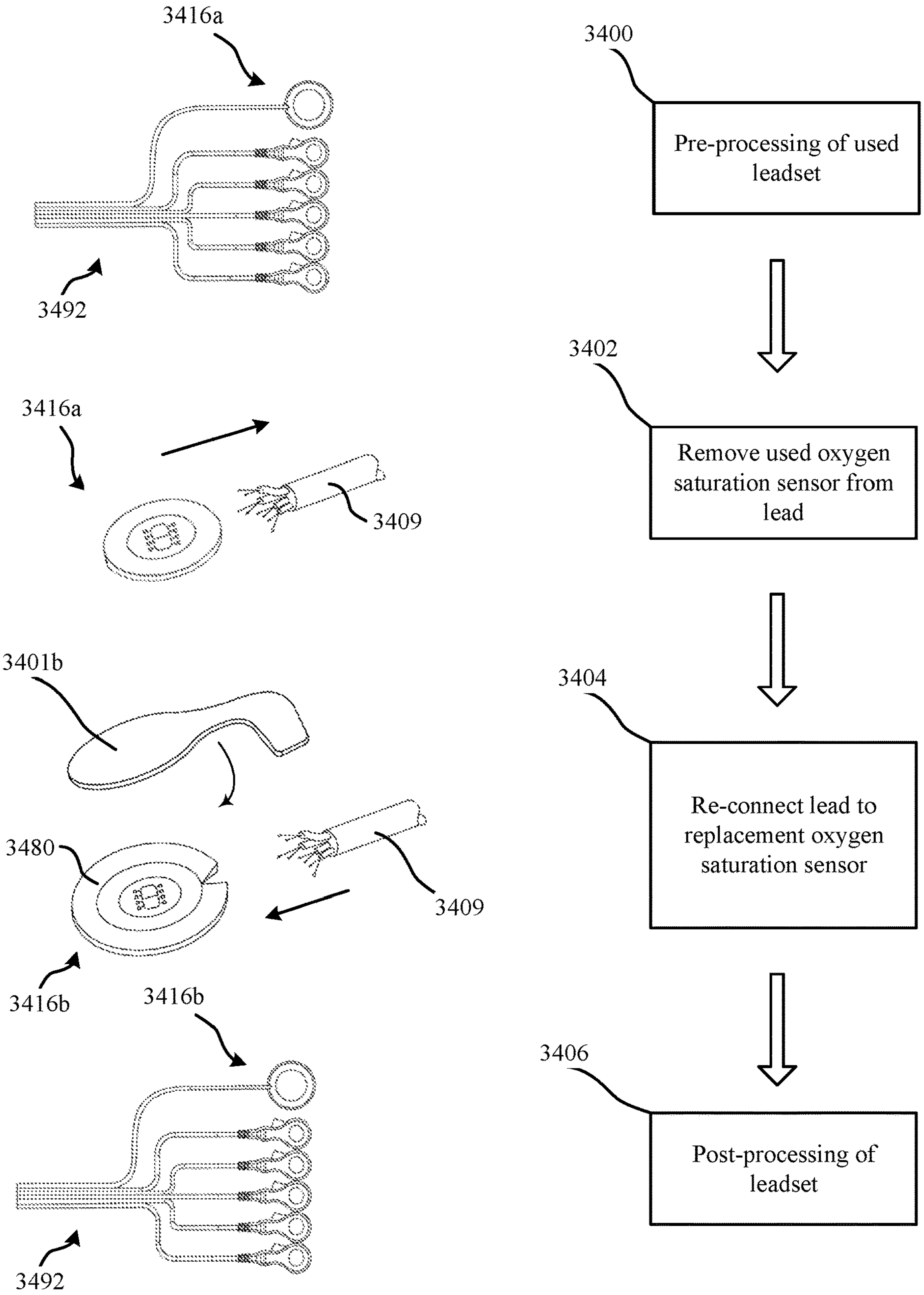
FIG. 34 illustrates a method of reconstructing a sensor system and/or multiparameter lead set according to aspects of the disclosure.

As shown in FIG. 34, in another aspect that is usable as an alternative to or with any one or combination of the steps described above, a used oxygen saturation sensor 2416*a* and/or leadset 3492 may be refurbished, reprocessed, and/or reconstructed. In one aspect, the oxygen saturation sensor 3416*a* may be part of lead set 3492. While lead set 3492 shown in FIG. 34 shows five (5) ECG connectors or sensors it is noted that any one or combination of the patient monitoring sensors or connectors described throughout the disclosure (e.g., non-invasive blood pressure, temperature) or that are known in the art may be implemented into the leadset and may be part of the process according to aspects of the disclosure. In one example, the oxygen saturation sensor 3416*a* may be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33.

As shown in FIG. 34, in one example of a method, a used leadset (e.g., leadset 3492) having an oxygen saturation sensor(e.g., oxygen saturation sensor 3416) may be subject to pre-processing at step 3400. While not intended to be limiting, some examples of pre-processing may include any one or a combination of one or more cleanings, sterilization and/or high level disinfection (HDL) processes. As mentioned above, in some examples, the pre-processing step 3400 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 3400, a used oxygen saturation sensor device 3416*a* may be removed from the lead 3409 by first removing a cover (e.g., cover 3101 in FIGS. 31A-31C and/or cover 3201 in FIGS. 32A-32D). After the cover is removed the individual wires or conduits within lead 3409 may either be de-soldered or otherwise disconnected allowing separation of the lead 3409 from a used oxygen saturation sensor device 3416*a*. In some aspects, the removal of the used oxygen saturation sensor device 3416*a* may require a specialized tool or other device to allow for separation of the individual wires, conduits and/or lead 3409 from the oxygen saturation sensor device 3416*a*. In one example, a machine, robot, or other automated process may be used to remove the cover and/or remove the individual wires, conduits and/or lead 3409 from the oxygen saturation sensor device 3416*a*. After the used oxygen saturation sensor device 3416*a* is separated from the lead 3409, a new oxygen saturation sensor device 3416*b* with a release liner installed may be installed into the lead 3409, which may be a part of the leadset 3492.

As shown at step 3404, the new oxygen saturation sensor device 3416*b* may already have a release liner 3480 for protecting the adhereable media portion. The release liner 3480 may for example indicate that the oxygen saturation sensor has been properly reprocessed and/or refurbished and/or may help to protect the adhereable media portion from contamination and/or from drying out. In the example mentioned above wherein the adhereable media portion is a hydrogel, the release liner 3480 may for example prevent drying or loss of moisture of the hydrogel.

While not intended to be limiting, The release liner may for example be formed of a lower vapor transmission rate material which may include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof.

In another aspect, instead of replacing the used oxygen saturation sensor device 3416*a* with a new oxygen saturation sensor device 3416*b* that either already has a release liner 3480 installed and/or has a release liner 3480 installed after the new oxygen saturation sensor device 3416*b* is reconnected to the lead 3409, a used adhereable media may be replaced with a new adhereable media.

In one example implementation, the oxygen saturation sensor 3416 may be sealed in a pouch or other containment portion that has a low vapor transmission rate. In one example, only the oxygen saturation sensor 3416 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3416. In another example, the oxygen saturation sensor may be sealed in a low vapor transmission rate pouch while the leadset (and oxygen saturation sensor with low vapor transmission pouch) is sealed or otherwise contained therein.

After step 3404, the oxygen saturation sensor 3416, leadset 3492, and/or any additional patient monitoring sensors or connectors that are part of the leadset and/or one or more of the leadset connectors may be subject to post-processing in step 3506. Some example of post-processing steps may include but are not limited to: additional cleaning, sterilization and/or high level disinfection (HDL) processes; one or more Ethylene oxide treatment(s). In some examples the post-processing step 3404 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 3492 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 35:
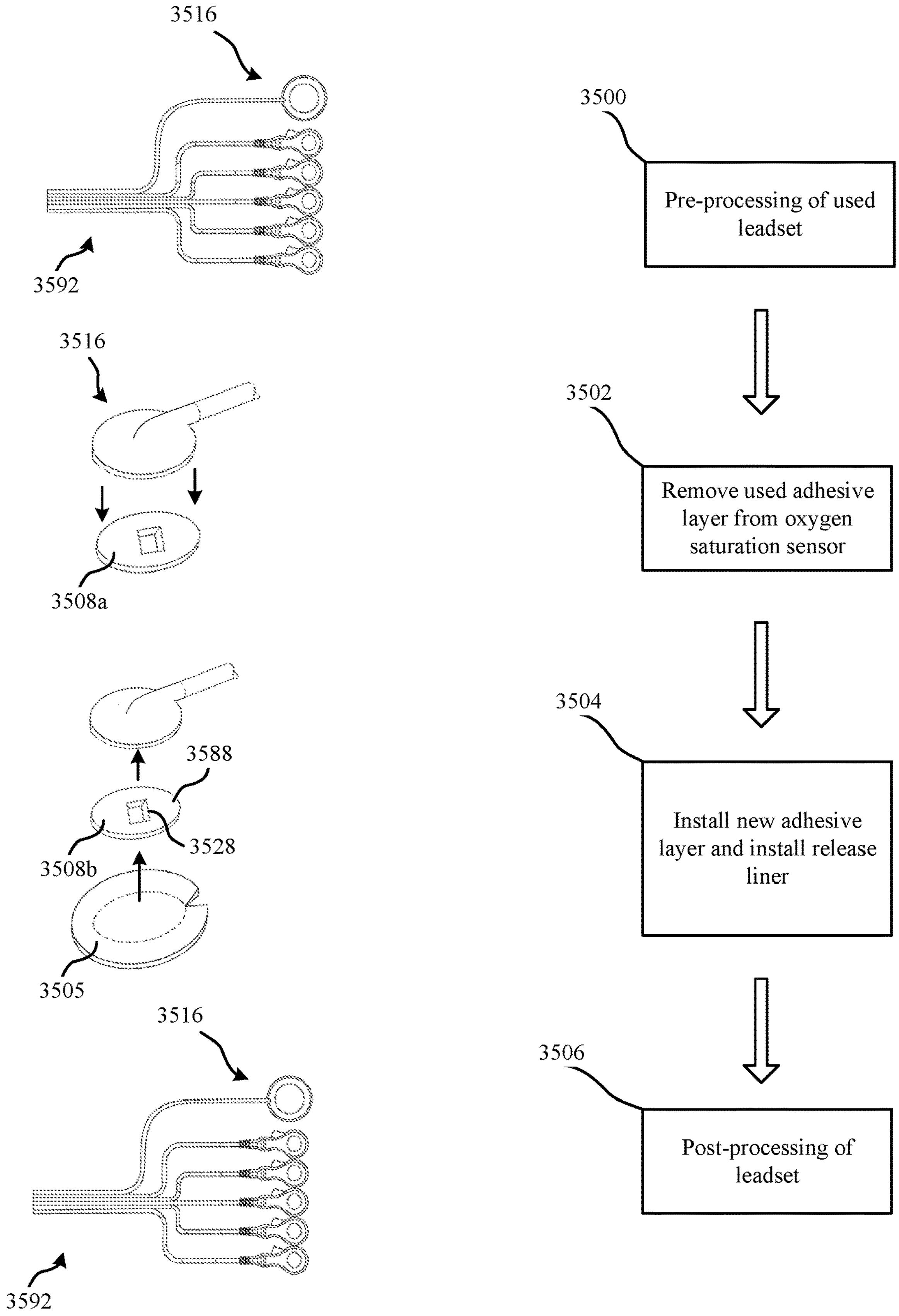
FIG. 35 illustrates a method of reconstructing a sensor system and/or multiparameter lead set according to aspects of the disclosure.

As shown in FIG. 35, in another aspect that is usable as an alternative to or with any one or combination of the steps described above, a used oxygen saturation sensor 3516*a* and/or leadset 3592 may be refurbished, reprocessed, and/or reconstructed. In one aspect, the oxygen saturation sensor 3516 may be part of lead set 3592. While lead set 3592 shown in FIG. 35 shows five (5) ECG connectors or sensors it is noted that any one or combination of the patient monitoring sensors or connectors described throughout the disclosure (e.g., non-invasive blood pressure, temperature) or that are known in the art may be implemented into the leadset and may be part of the reconstructing or refurbishing process according to aspects of the disclosure. In one example, the oxygen saturation sensor 3416*a* may be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33.

As shown in FIG. 35, in one example of a method, a used leadset (e.g., leadset 3592) having an oxygen saturation sensor (e.g., oxygen saturation sensor 3516) may be subject to pre-processing at step 3500. While not intended to be limiting, some examples of pre-processing may include any one or a combination of one or more cleanings, sterilization and/or high level disinfection (HDL) processes. As mentioned above, in some examples, the pre-processing step 3400 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 3400, an adhesive or adhereable portion 3508*a* may be removed in step 3502. After the adhereable portion 3508 is removed, the oxygen saturation sensor 3516 may be subject to any cleaning process or other process that prepares the oxygen saturation sensor 3516 for installation of a new adhereable portion 3508*b*. A new adhereable portion 3508*b* may be installed in step 3504. In one example, the new adhereable portion may be installed by removing an adhereable portion release liner (not shown) that may come preinstalled on a top surface 3588 of the new adhereable portion 3508*b* to expose an adhesive on top surface 3588. The release liner may for example include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof. Once the adhereable portion release liner is removed, the new adhereable portion 3508*b* may be aligned with and adhered to the oxygen saturation sensor 3516 so that a sensor portion aligns within an adhereable portion opening 3528 and is not obstructed by the adhereable portion.

As shown in step 3404, a release liner 3505 may be installed onto a bottom surface of the new adhereable portion 3508*b*. In another aspect, the new adhereable portion 3508*b* may already have a release liner 3505 pre-installed for protecting the adhereable media portion, in which case the aforementioned step of adding the release liner 3505 would be omitted. As mentioned above, the release liner 3505 may for example indicate that the oxygen saturation sensor has been properly reprocessed,refurbished and/or reconstructed, and/or may help to protect the adhereable media portion from contamination and/or from drying out. In the example mentioned above wherein the adhereable media portion is a hydrogel, the release liner 3505 may for example prevent drying or loss of moisture of the hydrogel.

While not intended to be limiting, The release liner may for example be formed of a lower vapor transmission rate material which may include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof.

In one example implementation, the oxygen saturation sensor 3516 may be sealed in a pouch or other containment portion that has a low vapor transmission rate. In one example, only the oxygen saturation sensor 3516 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3516. In another example, the oxygen saturation sensor may be sealed in a low vapor transmission rate pouch while the leadset (and oxygen saturation sensor with low vapor transmission pouch) is sealed or otherwise contained therein.

After step 3504, the oxygen saturation sensor 3516, leadset 3592, and/or any additional patient monitoring sensors or connectors that are part of the leadset and/or one or more of the leadset connectors may be subject to post-processing in step 3506. Some example of post-processing steps may include but are not limited to: additional cleaning, sterilization and/or high level disinfection (HDL) processes; one or more Ethylene oxide treatment(s). In some examples the post-processing step 3504 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 3492 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 36:
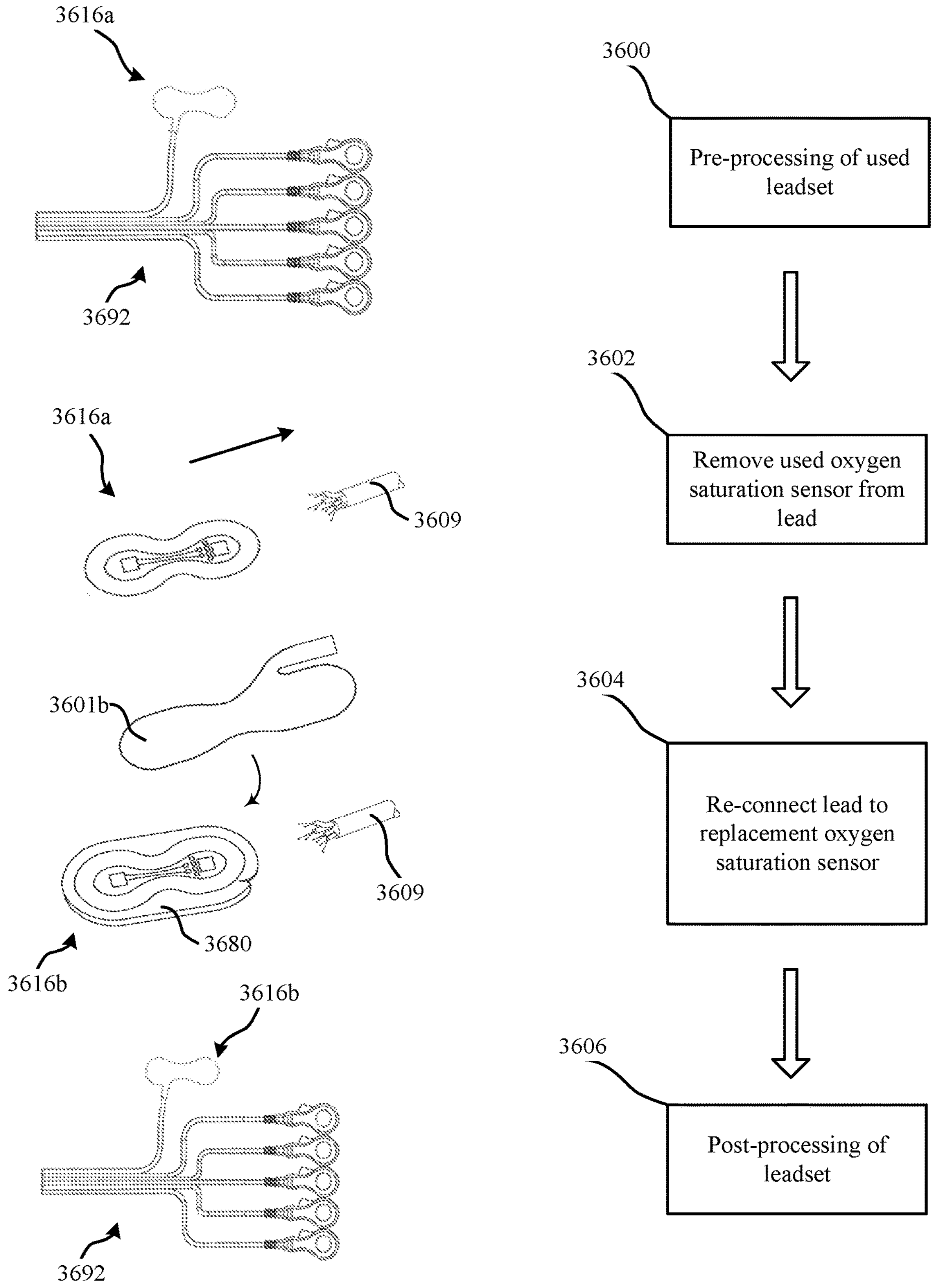
FIG. 36 illustrates a method of reconstructing a sensor system and/or multiparameter lead set according to aspects of the disclosure.

As shown in FIG. 36, in another aspect that is usable as an alternative to or with any one or combination of the steps described above, a used oxygen saturation sensor 3616*a* and/or leadset 3692 may be refurbished, reprocessed, and/or reconstructed. In one aspect, the oxygen saturation sensor 3616*a* may be part of lead set 3692. While lead set 3692 shown in FIG. 36 shows five (5) ECG connectors or sensors it is noted that any one or combination of the patient monitoring sensors or connectors described throughout the disclosure (e.g., non-invasive blood pressure, temperature) or that are known in the art may be implemented into the leadset and may be part of the process according to aspects of the disclosure. In one example, the oxygen saturation sensor 3616*a* may be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33.

As shown in FIG. 36, in one example of a method, a used leadset (e.g., leadset 3692) having an oxygen saturation sensor (e.g., oxygen saturation sensor 3616*a*) may be subject to pre-processing at step 3600. While not intended to be limiting, some examples of pre-processing may include any one or a combination of one or more cleanings, sterilization and/or high level disinfection (HDL) processes. As mentioned above, in some examples, the pre-processing step 3600 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 3600, a used oxygen saturation sensor device 3616*a* may be removed from the lead 3609 by first removing a cover (e.g., cover 3101 in FIGS. 31A-31C and/or cover 3201 in FIGS. 32A-32D). After the cover is removed the individual wires or conduits within lead 3609 may either be de-soldered or otherwise disconnected allowing separation of the lead 3609 from a used oxygen saturation sensor device 3616*a*. In some aspects, the removal of the used oxygen saturation sensor device 3616*a* may require a specialized tool or other device to allow for separation of the individual wires, conduits and/or lead 3609 from the oxygen saturation sensor device 3616*a*. In one example, a machine, robot, or other automated process may be used to remove the cover and/or remove the individual wires, conduits and/or lead 3609 from the oxygen saturation sensor device 3616*a*. After the used oxygen saturation sensor device 3616*a* is separated from the lead 3609, a new oxygen saturation sensor device 3616*b* with a release liner installed may be installed into the lead 3609, which may be a part of the leadset 3692. As shown at step 3604, the new oxygen saturation sensor device 3616*b* may already have a release liner 3680 for protecting the adhereable media portion. The release liner 3480 may for example indicate that the oxygen saturation sensor has been properly reprocessed, reconstructed and/or refurbished and/or may help to protect the adhereable media portion from contamination and/or from drying out. In the example mentioned above wherein the adhereable media portion is a hydrogel, the release liner 3480 may for example prevent drying or loss of moisture of the hydrogel. While not intended to be limiting, The release liner may for example be formed of a lower vapor transmission rate material which may include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof. In another aspect, instead of replacing the used oxygen saturation sensor device 3616*a* with a new oxygen saturation sensor device 3616*b* that either already has a release liner 3680 installed and/or has a release liner 3680 installed after the new oxygen saturation sensor device 3616*b* is reconnected to the lead 3609, a used adhereable media may be replaced with a new adhereable media.

After step 3604, the oxygen saturation sensor 3616, leadset 3692, and/or any additional patient monitoring sensors or connectors that are part of the leadset and/or one or more of the leadset connectors may be subject to post-processing in step 3606. Some example of post-processing steps may include but are not limited to: additional cleaning, sterilization and/or high level disinfection (HDL) processes; one or more Ethylene oxide treatment(s). In some examples the post-processing step 3604 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 3692 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned reconstructing or refurbishing steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 37:
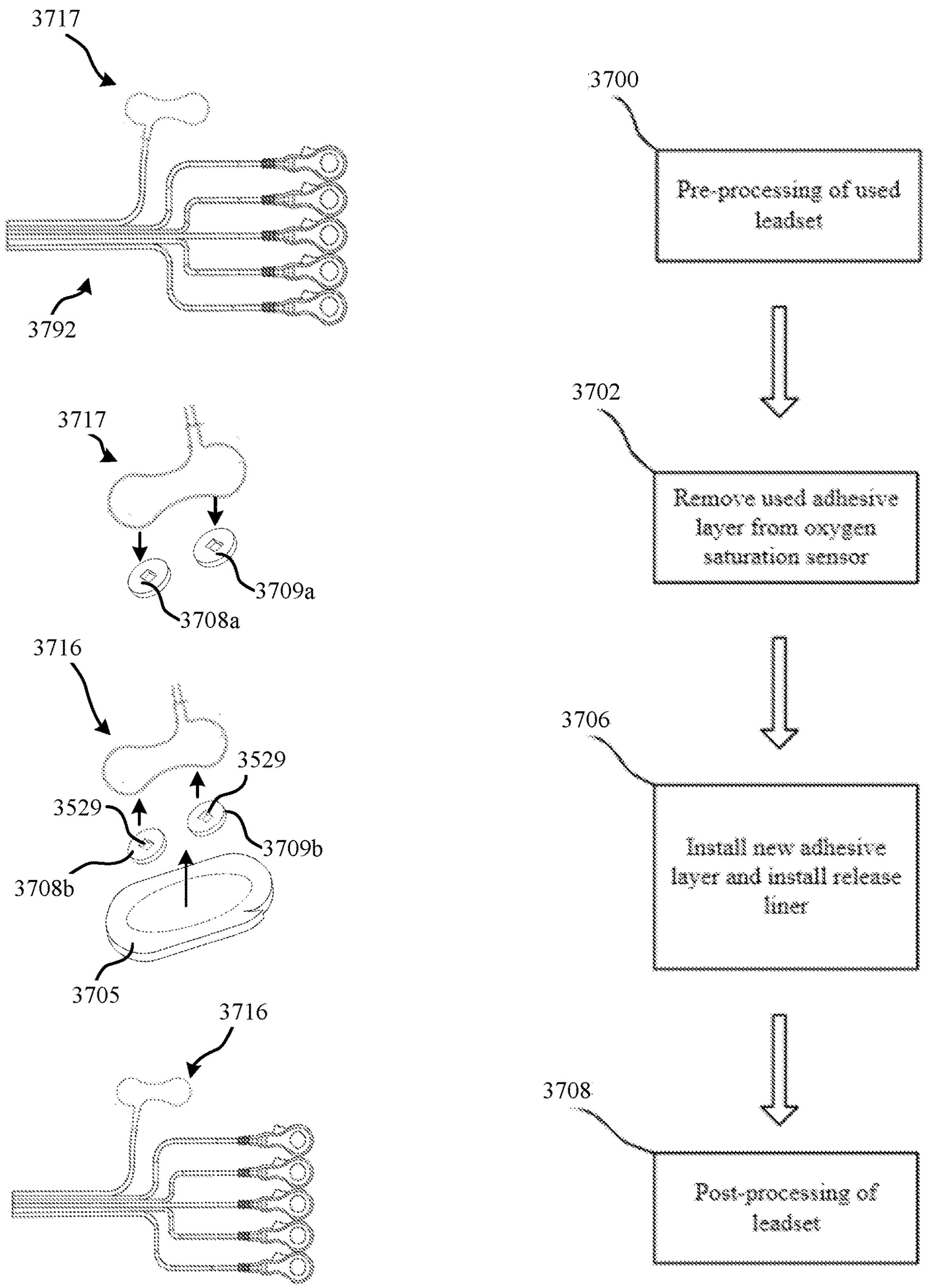
FIG. 37 illustrates a method or reconstructing a sensor system and/or multiparameter lead set according to aspects of the disclosure.

As shown in FIG. 37, in another aspect that is usable as an alternative to or with any one or combination of the steps described above, a used oxygen saturation sensor 3717 and/or leadset 3792 may be refurbished, reconstructed and/or reprocessed. In one aspect, the oxygen saturation sensor 3716 may be part of lead set 3792. While lead set 3792 shown in FIG. 37 shows five (5) ECG connectors or sensors it is noted that any one or combination of the patient monitoring sensors or connectors described throughout the disclosure (e.g., non-invasive blood pressure, temperature) or that are known in the art may be implemented into the leadset and may be part of the process according to aspects of the disclosure. In one example, the oxygen saturation sensor 3416*a* may be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33.

As shown in FIG. 37, in one example of a method, a used leadset (e.g., leadset 3792) having an oxygen saturation sensor (e.g., oxygen saturation sensor 3716) may be subject to pre-processing at step 3700. While not intended to be limiting, some examples of pre-processing may include any one or a combination of one or more cleanings, sterilization and/or high level disinfection (HDL) processes. As mentioned above, in some examples, the pre-processing step 3700 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 3700, an adhesive or adhereable portion(s) 3708*a* and 3709*a* may be removed in step 3702. After the adhereable portions 3708*a* and 3709*a* are removed, the oxygen saturation sensor 3716 may be subject to any cleaning process or other process that prepares the oxygen saturation sensor 3716 for installation of a new adhereable portion(s) 3708*b* and 3709*b*. The new adhereable portions 3708*b* and 3709*b* may be installed in step 3704. In one example, the new adhereable portion may be installed by removing an adhereable portion release liner (not shown) that may come pre-installed on a top surfaces of the new adhereable portions 3708*b* and 3709*b* to expose an adhesive on top surface of the adhereable portions 3708*a* and 3708*b*. The release liner may for example include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof. Once the adhereable portion release liners are removed, the new adhereable portions 3708*b* and 3709*b* may be aligned with and adhered to the oxygen saturation sensor 3716 so that a sensor portion aligns within adhereable portion openings 3728 and 3729 so as to not obstructed by the adhereable portion. As shown in step 3704, a release liner 3705 may be installed onto a bottom surface of the new adhereable portions 3708*b* and/or 3709*b*. In another aspect, the new adhereable portion 3508*b* may already have a release liner 3705 pre-installed for protecting the adhereable media portion, in which case the aforementioned step of adding the release liner 3705 would be omitted. As mentioned above, the release liner 3705 may for example indicate that the oxygen saturation sensor has been properly reprocessed, reconstructed, and/or refurbished and/or may help to protect the adhereable media portion from contamination and/or from drying out. In the example mentioned above wherein the adhereable media portion is a hydrogel, the release liner 3705 may for example prevent drying or loss of moisture of the hydrogel.

In one example implementation, the oxygen saturation sensor 3716 with the replacement adhereable portions 3708*a* and/or 3708*b* may be sealed in a pouch or other containment portion that has a low vapor transmission rate. In one example, only the oxygen saturation sensor 3716 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3716 In another example, the oxygen saturation sensor may be sealed in a low vapor transmission rate pouch while the leadset (and oxygen saturation sensor with low vapor transmission pouch) is sealed or otherwise contained therein.

While not intended to be limiting, The release liner and/or pouch described above may for example be formed of a lower vapor transmission rate material which may include any one or a combination (substrate) of an aluminum or metallic foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET), and/or a natural or semi-synthetic material such as, cellulose, rayon, or any combination thereof.

After step 3706, the oxygen saturation sensor 3716, leadset 33792, and/or any additional patient monitoring sensors or connectors that are part of the leadset and/or one or more of the leadset connectors may be subject to post-processing in step 3708. Some example of post-processing steps may include but are not limited to: additional cleaning, sterilization and/or high level disinfection (HDL) processes; one or more Ethylene oxide treatment(s). In some examples the post-processing step 3604 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset 3792 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned reconstructing or refurbishing steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 38:
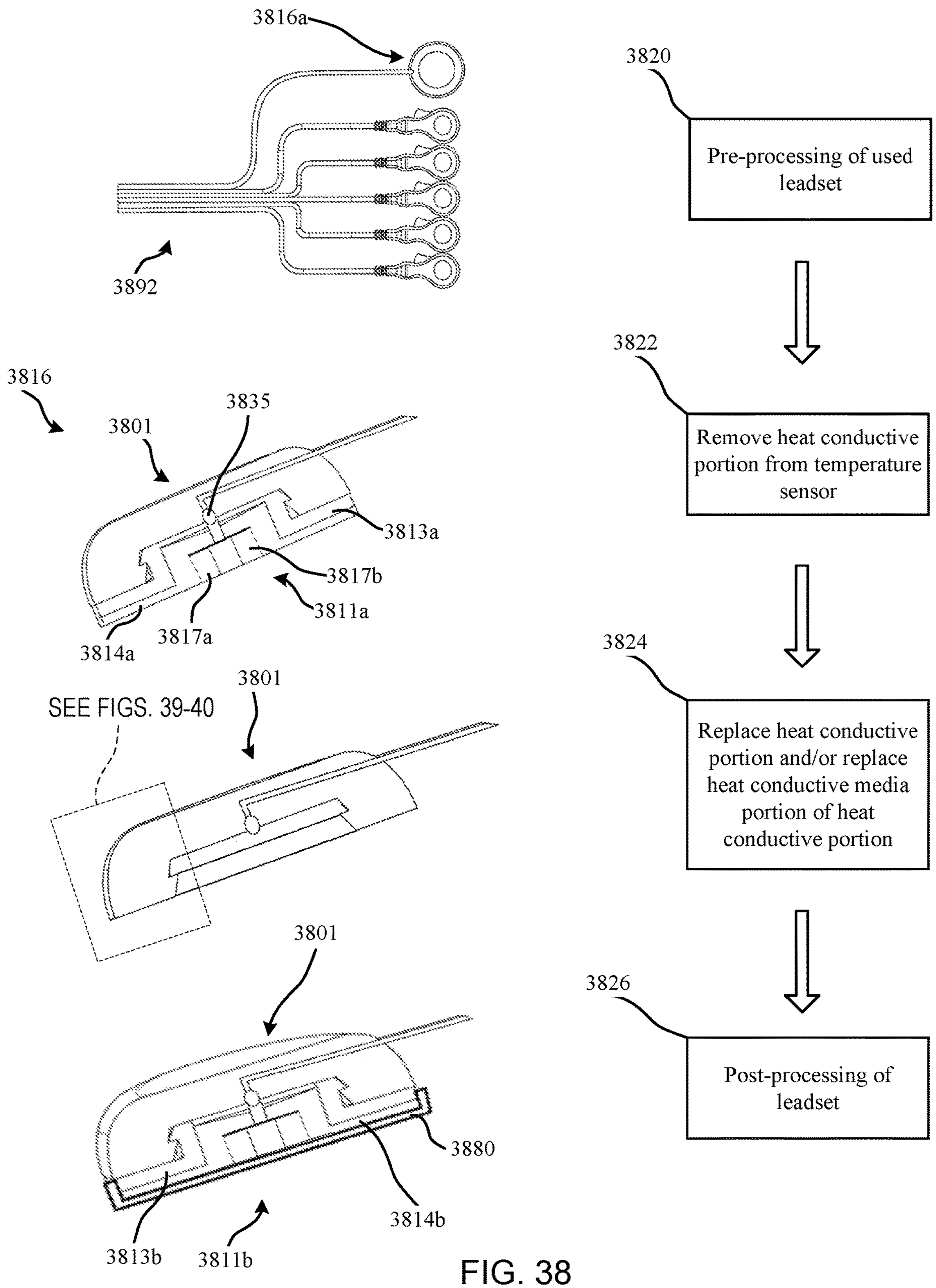
FIG. 38 illustrates a method of reconstructing a sensor system and/or multiparameter lead set according to aspects of the disclosure.

FIG. 38 shows another method in accordance with aspects of the disclosure. As an alternative to or with any one or combination of the steps described above, a used oxygen saturation sensor 3816 and/or leadset 3892 may be refurbished, reconstructed, and/or reprocessed. In one aspect, the oxygen saturation sensor 3816 may be part of lead set 3892. While lead set 3892 shown in FIG. 38 shows five (5) ECG connectors or sensors it is noted that any one or combination of the patient monitoring sensors or connectors described throughout the disclosure (e.g., non-invasive blood pressure, temperature) or that are known in the art may be implemented into the leadset and may be part of the process according to aspects of the disclosure. While it is noted that the oxygen saturation sensor 3816 described in FIG. 38 included identical or similar features to oxygen saturation sensor 3316 in FIG. 33, the oxygen saturation sensor 3816 may be analogous with or replace sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33.

As shown in FIG. 38, in one example of a method, a used leadset (e.g., leadset 3892) having an oxygen saturation sensor (e.g., oxygen saturation sensor 3816*a*) may be subject to pre-processing at step 3820. While not intended to be limiting, some examples of pre-processing may include any one or a combination of one or more cleanings, sterilization and/or high level disinfection (HDL) processes. As mentioned above, in some examples, the pre-processing step 3700 may also include replacement of component(s), cable(s), and/or tube(s) if during inspection it is deemed that such replacement is needed. Further in some aspects cables and/or tubes of the leadset may be disconnected or reconnected to form a leadset with a bundled or otherwise connected length of cable(s) and/or tube(s).

Once pre-processing of the leadset is completed in step 3820, a used adhereable portion 3811*a* with an adhereable portion housing 3813*a* may be removed from the oxygen saturation sensor housing 3801 in step 3822. In some aspects, the removal of the used adhereable portion housing 3813*a* from the oxygen saturation sensor housing 3801 may require a specialized tool or other device to allow for separation of the used adhereable portion housing 3813*a* from the oxygen saturation sensor housing 3801. As shown in the example in FIG. 38, in one example, the used adhereable portion housing 3813*a* may include an emitter portion and a receiver portion 3817*a* and 3817*b* and removal of the used adhereable portion housing 3813*a* may result in disconnection of the rotatable connector 3835. In one example, a machine, robot, or other automated process may be used to separate the oxygen saturation sensor housing 3801 and the used adhereable portion housing 3813*a*. After the used adhereable portion housing 3813*a* is separated from the oxygen saturation sensor housing 3801, a new adhereable portion 3811*b*, with a new adhereable portion housing may be installed into the oxygen saturation sensor housing 3801. As shown in FIG. 38, at step 3826, the new adhereable portion 3811*b* may already have a release liner 2880 for protecting the adhereable surface of the new adhereable portion 3811*b*. The release liner 3880 may for example indicate that the oxygen saturation sensor has been properly reprocessed, reconstructed and/or refurbished and/or may help to protect the heat conductive media portion from contamination. In the example mentioned above wherein the adhereable portion includes hydrogel, the release liner 3880 may for example prevent drying or loss of moisture of the hydrogel. While not intended to be limiting, the release liner may for example include any one or combination of a foil, a polypropylene or bi-axially oriented polypropylene film (BOPP), a polyethylene or high-density polyethylene film (HDPE), a medium density polyethylene film (MDPE), a low density polyethylene film (LDPE) and/or a polyethylene terephthalate or a polyethylene terephthalate film (PET). The release liner 3880 may for example be configured to be easily removable by an end user and may include a tab or other such feature to assist with or improve efficiency of pulling-off or otherwise removing the release liner 3880. In another aspect, instead of replacing the used adhereable portion 3811*a* with a new adhereable portion 3811*b* that either already has a release liner 3880 installed and/or has a release liner 3880 installed after installation into the oxygen saturation sensor housing 3801, the used adhesive media 3814*a* within the used adhereable portion housing 3813*a* may be removed and replaced with a new adhesive media 3814*b*. For example, if the adhesive media is a hydrogel, the hydrogel maybe removed with the used adhereable portion housing 3813*a* still attached to the oxygen saturation sensor housing 3801 or may be removed after the used adhereable portion housing 3813*a* is removed from the oxygen saturation sensor housing 3801. The hydrogel may be chemically dissolved and/or dissolved via heating using steam for example or may be manually removed via hand or by media removal. In another example, the hydrogel may be soaked or otherwise configured to absorb water or another liquid and may be removed via an alcohol, vinegar, or solutions thereof. In one example that is usable with the aforementioned examples or as an alternative to the aforementioned examples, the hydrogel may be subject to an ultrasonic cleaning or scintillation. Once the hydrogel is removed from the used adhereable portion housing 3813*a*, the hydrogel may be replaced. In one example, the hydrogel may be replaced by using used adhereable portion housing 3813*a* as a mold and providing and curing hydrogel in the used adhereable portion housing 3813*a*. After the hydrogel is cured, the release liner 3880 may be provided. In another example, the release liner 3880 may be provided or otherwise connected to the used adhereable portion housing 3813*a* and may serve as part of the mold that is configured to have the hydrogel cured therein.

In one example implementation, the oxygen saturation sensor 3816 may be sealed in a pouch or other containment portion that has a low vapor transmission rate. In one example, only the oxygen saturation sensor 3816 of a leadset may be sealed in a low vapor transmission rate pouch. In one example, the oxygen saturation sensor may be sealed within a low vapor transmission rate pouch that is sealingly engaged with or sealed around the cable of the oxygen saturation sensor 3816. In another example, the oxygen saturation sensor may be sealed in a low vapor transmission rate pouch while the leadset (and oxygen saturation sensor with low vapor transmission pouch) is sealed or otherwise contained therein.

After step 3824, the oxygen saturation sensor 3816, leadset 3892, and/or any additional patient monitoring sensors or connectors that are part of the leadset and/or one or more of the leadset connectors may be subject to post-processing in step 3826. Some example of post-processing steps may include but are not limited to: additional cleaning, sterilization and/or high level disinfection (HDL) processes; one or more Ethylene oxide treatment(s). In some examples the post-processing step 3826 may also include testing and/or replacement of component(s), cable(s), and/or tube(s) if it is deemed that such replacement is needed. Further in some aspects cables and/or tubes of the leadset may be reconnected or otherwise bundled and/or joined as described throughout the disclosure to form a leadset with a bundled or otherwise connected length of cable(s) and/or tube(s). In some aspects the leadset 3792 may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets. Any one of or any combination of the aforementioned steps may be completed manually via a technician or worker and/or may be completed by an automated or machine-assisted process. Further it is noted that the order of the steps above are not intended to be limiting and the order may be changed without departing from the scope of the disclosure. The steps described above may also be combined with or otherwise incorporate steps or other aspects described above with respect to FIG. 20.

Figure 39:
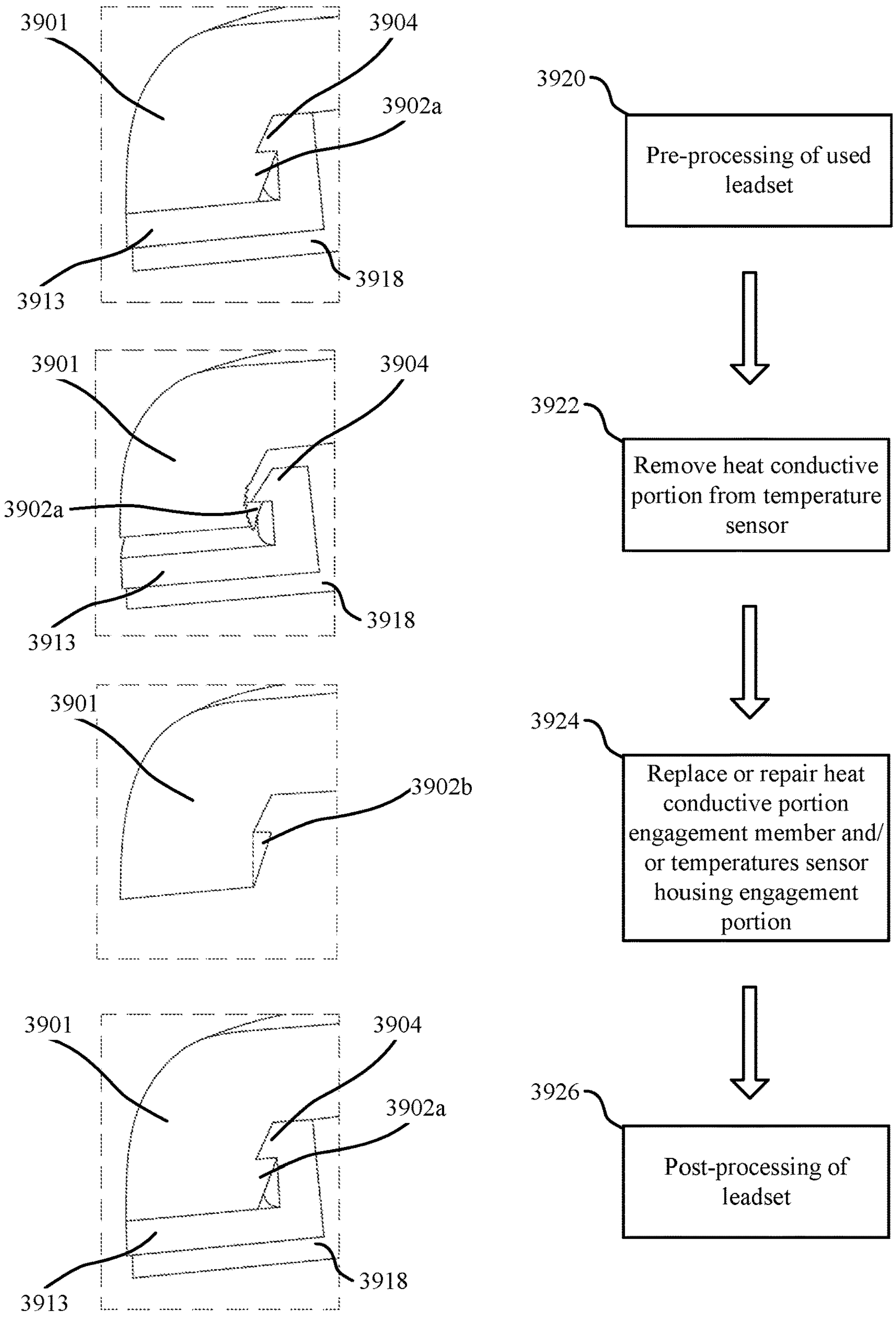
FIG. 39 illustrates a method of reconstructing a sensor system and/or multiparameter lead set according to aspects of the disclosure.

FIG. 39 shows one example method that is usable with oxygen saturation sensor 3316 in FIG. 33 and/or oxygen saturation sensor 3816 in FIG. 38. As noted above with respect to FIGS. 31-38, an oxygen saturation sensor described herein may be refurbished, reconstructed and/or reprocessed via any one of or any combination of the steps described above with respect to FIGS. 31-38. In addition to the steps described above, the steps in FIGS. 39 and 40 may be carried out in addition to the steps described above with respect to FIG. 20 and/or FIGS. 31-38. When the adhereable media portion housing 3913 and/or the adhereable media portion 3918 is removed from the oxygen saturation sensor housing 3901, any one or a combination of the oxygen saturation housing engagement members 3902 and adhereable media portion engagement member 3904 may for example break or otherwise separate or permanently deform or may be configured to break or otherwise be separated or permanently deformed. One example of a method is shown in FIG. 39. In the example shown in FIG. 39 an oxygen saturation sensor and/or a leadset containing or incorporating an oxygen saturation sensor may be subject to pre-processing in step 3920. Pre-processing may include but is not limited to any one or a combination of one or more cleanings, sterilization and/or high level disinfection (HDL) processes. As mentioned above, in some examples, the pre-processing step 2920 may also include replacement of component(s), cable(s), and/or tube(s) if during inspection it is deemed that such replacement is needed.

After pre-processing, the adhereable media portion housing 3913 of the adhereable media portion may be removed for either replacement and/or for replacement or refilling of an adhereable media (e.g., hydrogel or pressure sensitive adhesive) 3918 using any one of the steps, methods, or apparatuses described above. When the adhereable media portion housing 3913 is removed, the oxygen saturation housing engagement members 3902*a* may break or otherwise be removed from the oxygen saturation sensor housing 3901. After the adhereable media portion housing 3913 is removed from the oxygen saturation sensor housing 3901, the oxygen saturation housing engagement members 3902*a* that was broken or otherwise removed during separation may be replaced with replacement oxygen saturation housing engagement members 3902*b* in step 3924. Some examples of replacement may include but are not limited to re-molding, removal of any excess portion of the of the broken oxygen saturation sensor housing engagement portion and adhering or otherwise connecting a new engagement member 3902*b* to the oxygen saturation sensor housing 3901. Some examples of adhering or otherwise connecting a new engagement member may include but are not limited to gluing using an adhesive, resin, or epoxy; ultrasonic or friction welding; melting a portion of the oxygen saturation sensor housing 3901 and/or otherwise partially melting the new engagement member 3902*b*, placing the new engagement member 3902*b* and allowing re-solidification thereof; and/or tapping and threading a new engagement member 3902*b*. In one example, the new engagement member 3902*b* may for example be formed of a material having different properties. For example, the new engagement member 3902*b* may be formed of a material having any one or a combination of a toughness that is greater than the previous oxygen saturation housing engagement members 3902*a*, a flexibility that is greater than the previous oxygen saturation housing engagement members 3902*a*, a stiffness or rigidity that is greater than the previous oxygen saturation housing engagement members 3902*a*. In one example, the new engagement member 3902*b* may for example have an indicator that allows a technician or user to identify that the oxygen saturation sensor has been refurbished, reprocessed and/or refurbished and/or has had the oxygen saturation sensor housing engagement members 3902 replaced. Some examples of indicators include a material with a different color, pattern, and/or texture to name a few examples.

As shown in FIG. 39, once the adhereable portion engagement member and/or oxygen saturation housing engagement portion is replaced, the oxygen saturation sensor and/or leadset having the oxygen saturation sensor connected thereto may be subject to post-processing in step 3926. Some examples of post-processing steps may include but are not limited to: additional cleaning, sterilization and/or high level disinfection (HDL) processes; one or more Ethylene Oxide treatment(s). In some examples the post-processing step 2926 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset and/or temperature sensor may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets.

Figure 40:
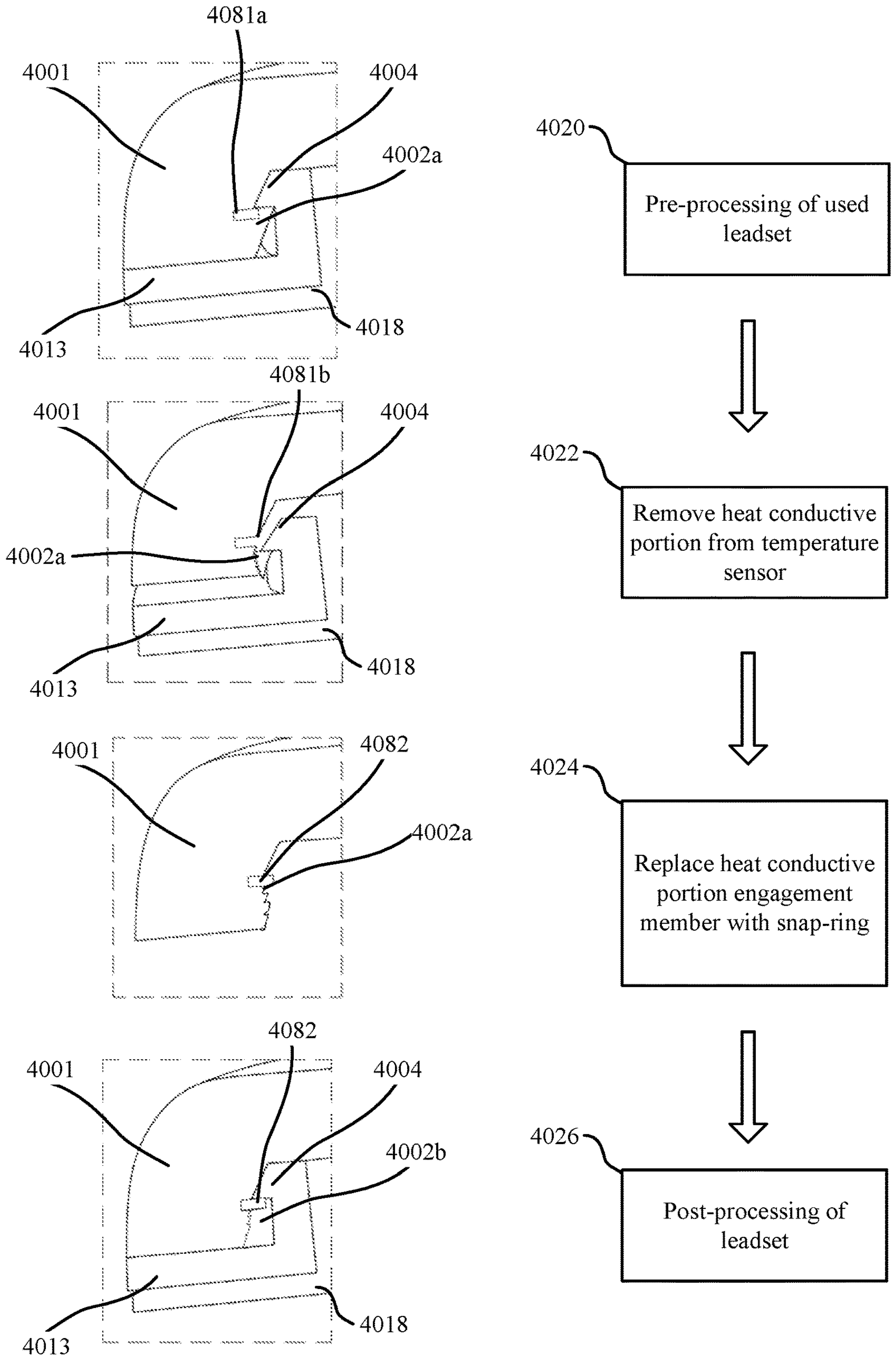
FIG. 40 illustrates a method of reconstructing a sensor system and/or multiparameter lead set according to aspects of the disclosure.

FIG. 40 shows one example method wherein a snap-ring or other engageable replacement oxygen saturation sensor housing engagement member is used to refurbish or repair a broken or otherwise separated oxygen saturation sensor housing engagement member 4002*a*. The aspects described are usable with and may be analogous with the oxygen saturation sensor and aspects usable with oxygen saturation sensor 3316 in FIG. 33 and/or oxygen saturation sensor 3816 in FIG. 38. Further, the method may be usable with sensor 216 in FIG. 2, connector 316 in FIG. 3, connector 416 in FIG. 4, connector 616 in FIG. 6, sensor device 715 in FIG. 7, sensor connector 806*a* and/or sensor 806*b* in FIG. 8, connector 1016 in FIGS. 10A and 10B, connector 1116 in FIG. 11, device 1216 in FIG. 12, device 1316 in FIG. 13, oxygen saturation sensor 3116 in FIGS. 31A-31C, oxygen saturation sensor 3216 in FIG. 32A-32D, and/or oxygen sensor 3300 in FIG. 33, for example. In addition to the steps described above, the steps in FIGS. 39 and 40 may be carried out in addition to the steps described above with respect to FIG. 20 and/or FIGS. 31-38. When the adhereable media portion housing 3913 and/or the adhereable media portion 3918 is removed from the oxygen saturation sensor housing 3901, any one or a combination of the oxygen saturation housing engagement members 3902 and adhereable media portion engagement member 3904 may for example break or otherwise separate or permanently deform or may be configured to break or otherwise be separated or permanently deformed.

In one aspect of the disclosure, the oxygen sensor housing 4001 may for example include a channel or opening 4081*a* therein that is configured to receiveably engage with or receive a portion of a snap-ring or other engagement feature of a replacement oxygen saturation sensor engagement member 3082 after previous oxygen saturation sensor housing engagement members 3002*a* are broken or otherwise removed.

As shown in step 4020 FIG. 40, the adhereable media portion housing 4013 and/or the adhereable media portion 4018 is removed from the oxygen saturation sensor housing 4001, any one or a combination of the oxygen saturation sensor housing engagement members 4002 and adhereable media portion engagement member(s) 4004 may for example break or otherwise separate or permanently deform, or may be configured to break or otherwise be separated or permanently deformed. In the example shown in FIG. 40 a oxygen saturation sensor and/or a leadset containing or incorporating a oxygen saturation sensor may be subject to pre-processing in step 4020. Pre-processing may include but is not limited to any one or a combination of one or more cleanings, sterilization and/or high level disinfection (HDL) processes. As mentioned above, in some examples, the pre-processing step 4020 may also include replacement of component(s), cable(s), and/or tube(s) if during inspection it is deemed that such replacement is needed.

After pre-processing, the media portion housing 4013 of the adhereable media portion may be removed for either replacement and/or for replacement or refilling of an adhereable media (e.g., hydrogel or pressure sensitive adhesive) 4018 using any one of the steps, methods, or apparatuses described above. When the adhereable media portion is removed, the oxygen saturation sensor housing engagement members 4002*a* may break or otherwise be removed from the oxygen saturation sensor housing 4001, which may expose the channel or opening 4081*b* as shown in FIG. 40. After the adhereable media portion is removed from the oxygen saturation sensor housing 4001, a snap ring 4082 or other replacement engagement member may be installed into the channel or opening 4081*b* as shown in step 4024. In one example, the snap ring 4082 or other replacement engagement member may be installed via a tool that compresses the snap ring to decrease the other diameter thereof. Once the snap ring 4082 or other replacement engagement member is aligned within the channel or opening 4081 the snap ring may 4082 may be released, thus casing the outer diameter of the snap ring 4082 to increase and be captively engaged with the channel or opening 4081*b*.

The new engagement member or snap ring 4082 may for example be formed of a material having different properties. For example, the new engagement member 4082 may be formed of a material having any one or a combination of a toughness that is greater than the oxygen saturation sensor housing engagement members 4002*a*, a flexibility that is greater than the previous oxygen saturation sensor housing engagement members 4002*a*, a stiffness or rigidity that is greater than the previous oxygen saturation sensor housing engagement members 4002*a*. In one example, the replacement engagement member or snap ring 4082 may for example be formed of a metal such as stainless steel. In one example, the new engagement member 4082 may for example have an indicator that allows a technician or user to identify that the oxygen saturation sensor housing has been refurbished, reprocessed and/or reconstructed and/or has had the oxygen saturation sensor housing engagement members 4002*a* replaced. Some examples of indicators include a material with a different color, pattern, and/or texture to name a few examples.

As shown in FIG. 40, once the adhereable portion engagement member and/or oxygen saturation sensor housing engagement portion is replaced, the oxygen saturation sensor and/or leadset having the oxygen saturation sensor connected thereto may be subject to post-processing in step 4026. Some examples of post-processing steps may include but are not limited to: additional cleaning, sterilization and/or high level disinfection (HDL) processes; one or more Ethylene Oxide treatment(s). In some examples the post-processing step 3026 may also include testing and/or replacement of component(s), cable(s), and/or tube(s) if it is deemed that such replacement is needed. Further in some aspects cables and/or tubes of the leadset may reconnected or otherwise bundled and/or joined as described throughout the disclosure to form a leadset with a bundled or otherwise connected length of cable(s) and/or tube(s). In some aspects the leadset and/or oxygen saturation sensor may be packaged or otherwise be prepared for the end user, which includes but is not limited to preparation for shipping. While general steps are noted above, it is understood that the aforementioned process may be varied without departing from the scope of the present disclosure. For example, high level disinfecting (HLD)/sterilization may be repeated after the lead set is repackaged, or the lead set may be high level disinfecting (HLD) and/or sterilized only after the leads are repackaged, to name one example alternative. The aforementioned reprocessing, reconstructing, and/or refurbishment process in combination with the various other features of the lead set described herein may provide for a reduction in waste and/or cost by allowing for efficient reprocessing, reconstructing, and/or refurbishment of a lead set by allowing individual components and/or leads to be selectively replaced if damaged or worn and/or allows for efficient high level disinfecting (HLD) or sterilization only of selected lead sets.

f. Methods of Connecting Monitoring Lead Sets to a Patient

Figure 41:
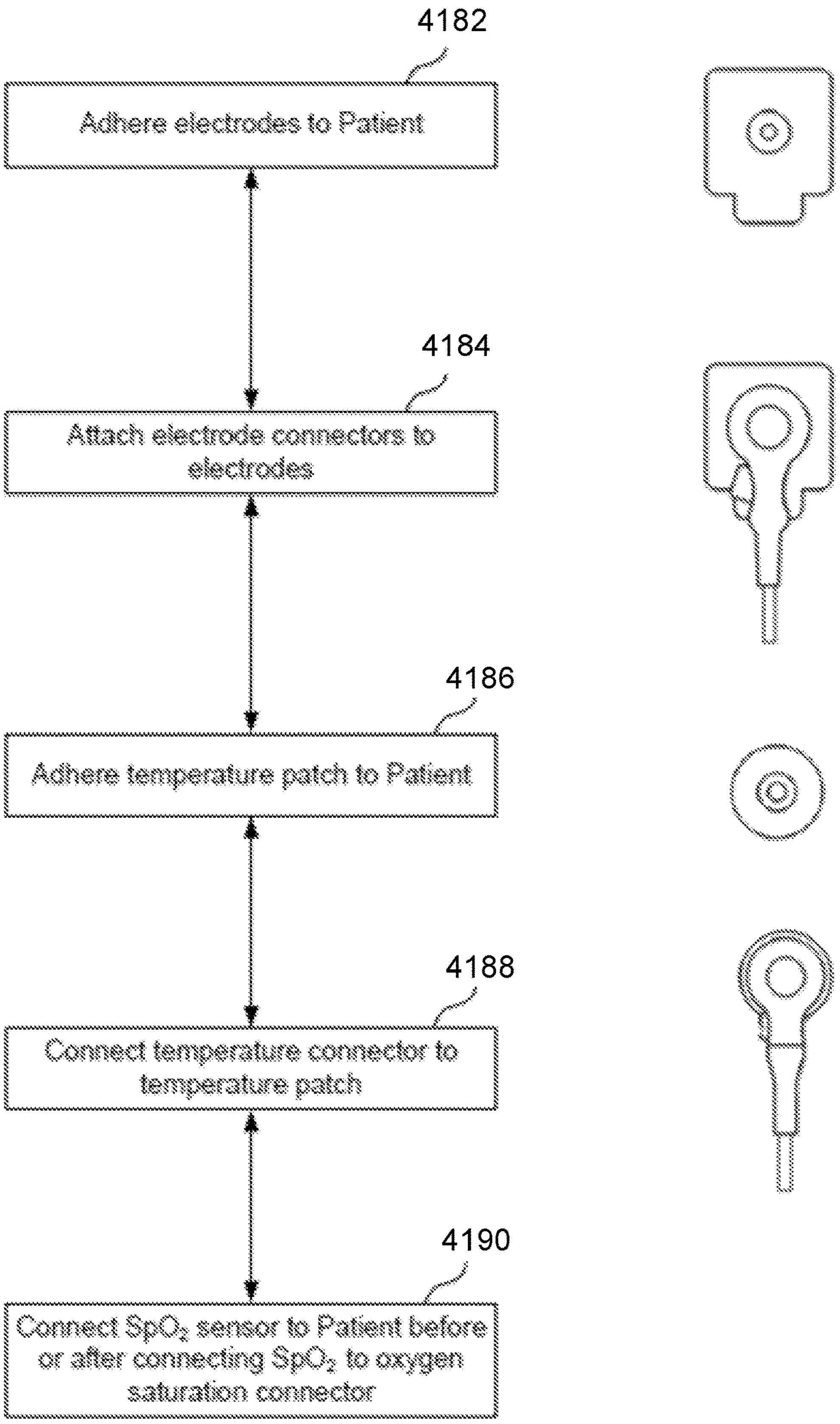
FIG. 41 illustrates an example method of connecting a multiparameter lead set to a patient according to aspects of the present disclosure.

FIG. 41 shows various aspects of one example method of connecting a lead set according to aspects of the present disclosure. The aforementioned example method of connection may be described in instructions provided with the lead set. The instructions may be provided as a pamphlet or as written instructions on the packaging of the lead set and/or as digital content (provided by accessing information on a network, such as a webpage on the Internet). The instructions may also be provided by salesperson via marketing materials to name another non-limiting example. As shown in FIG. 41, at 4182 a single or plurality of electrodes may be adhered to or otherwise emplaced on a patient. At 4184, electrode connectors of the lead set may be connected to respective ones of the single or plurality of electrodes. At 4186, a single or multiple temperature patch(es) or temperature sensing patch(es) or temperature sensor(s) may be adhered or otherwise emplaced on a patient. The temperature sensor(s), patches(s) or combinations thereof describe in step 4118 may include any one or combination of the temperature sensing aspects described herein. At 4188, respective temperature connector(s) or temperature sensing connector(s) may be connected to the single or multiple temperature patch(es). At 4190, a $SpO_2$ sensor may be connected to a patient and the sensor may be connected to the blood oxygen saturation connector of the lead set. In another example, the sensor may be connected to the blood oxygen saturation connector of the lead set before the sensor is connected to the patient. The $SpO_2$ sensor may include any of the oxygen saturation sensor aspects described herein. It is noted that the aforementioned steps are only provided as an example and thus do not necessarily have to occur in the order described above, for example, any electrodes and temperature patches or temperature sensing patches may be connected to the patient prior to the electrode connectors and temperature connector being connected to the respective temperature patch or electrodes, to name another non-limiting example.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the present disclosure. Therefore, the present disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

Some further aspects are provided in the clauses below.

Clause 1: A multiparameter lead set, comprising: a first patient lead for monitoring a first health indicator of a patient, the first patient lead extending between a first lead distal end and a first lead proximal end, wherein the first patient lead further comprises: a first patient connector at the first lead distal end that is configured to be attached to a patient for monitoring the first health indicator of the patient; a first lead connector at the first lead proximal end; and a first lead interconnection feature; a second patient lead for monitoring a second health indicator of the patient, the second patient lead extending between a second lead distal end and a second lead proximal end, wherein the second patient lead further comprises: a second patient connector at the second lead distal end that is configured to be attached to the patient for monitoring the second health indicator of the patient; a second lead connector at the second lead proximal end, and a second lead interconnection feature; wherein the first lead interconnection feature and the second lead interconnection feature are interconnectable to removably connect a first portion of the first patient lead to a second portion of the second patient lead; and wherein the first lead connector and the second lead connector are configured to be selectively connected to at least one monitoring device.

Clause 2: The multiparameter lead set of clause 1, wherein the first patient lead comprises a first wire extending between the first patient connector at the first lead distal end and the first lead connector at the first lead proximal end and the second patient lead comprises a second wire extending between the second patient connector at the second lead distal end and the second lead connector at the second lead proximal end.

Clause 3: The multiparameter lead set of clause 1 or clause 2, wherein the first lead interconnection feature is configured so that a first section of the first patient lead that extends along a length of the first wire between the first lead distal end and the first lead proximal end is connectable and removable from a second section of the second patient lead via the second connection feature that extends along an axial direction of extension of the second wire between the second lead distal end and the second lead proximal end.

Clause 4: The multiparameter lead set any of the above clauses, wherein the first lead interconnection feature and the second lead interconnection feature comprise a magnetic interface.

Clause 5: multiparameter lead set of any of the above clauses, wherein the first lead interconnection feature comprises a receiving portion that is configured to selectively captively receive a protrusion of the second lead interconnection feature.

Clause 6: The multiparameter lead set of any of the above clauses, wherein the first lead interconnection feature is a first section of the first lead connector and wherein the first lead connector is connectable to and disconnectable from the second lead connector via the second lead interconnection feature at the second section of the second lead connector.

Clause 7: The multiparameter lead set of any of the above clauses, wherein when the first lead interconnection feature of the first lead connector and the second lead interconnection feature of the second lead connector are connectable to one another to form a single multiparameter connector, wherein the multiparameter connector is selectively connectable to a multiparameter input device that is selectively connectable to the at least one monitoring device.

Clause 8: The multiparameter lead set of any of the above clauses, wherein at least one of the first lead connector and the second lead connector include a patterned terminal that is configured to be received by a respective patterned terminal receiving portion at the multiparameter input device.

Clause 9: The multiparameter lead set of any of the above clauses, wherein the patterned terminal provides at least one of a structural rigidity to the patterned terminal or shielding of an individual lead of the patterned terminal from unintended contact.

Clause 10: The multiparameter lead set of any of the above clauses, wherein the first patient lead comprises a wire extending between the first patient connector at the first lead distal end and the first lead connector at the first lead proximal end and the second patient lead comprises a tube extending between and providing fluid communication between the second patient connector at the second lead distal end and the second lead connector at the second lead proximal end.

Clause 11: The multiparameter lead set of any of the above clauses, wherein the first lead interconnection feature is configured so that a first section of the first patient lead that extends along an axial direction of extension of the wire between the first lead distal end and the first lead proximal end is connectable to and disconnectable from a second section of the second patient lead via the second lead interconnection feature that extends along an axial direction of extension of the tube between the second lead distal end and the second lead proximal end.

Clause 12: The multiparameter lead set of any of the above clauses, wherein the first interconnection feature and the second interconnection feature comprise a magnetic interface.

Clause 13: The multiparameter lead set of any of the above clauses, wherein the first lead interconnection feature comprises a receiving portion that is configured to selectively captively receive a protrusion of the second lead interconnection feature.

Clause 14: The multiparameter lead set of any of the above clauses, wherein the first lead interconnection feature is a first section of the first lead connector and wherein the first lead connector is connectable to and disconnectable from the second lead connector via the second lead interconnection feature at the second section of the second lead connector.

Clause 15: The multiparameter lead set of any of the above clauses, wherein when the first lead interconnection feature of the first lead connector and the second lead interconnection feature of the second lead connector are interconnectable to form a single multiparameter connector, wherein the multiparameter connector is selectively connectable to a multiparameter input device that is selectively connectable to the at least one monitoring device.

Clause 16: A method of monitoring at least two health indicators of a patient via a monitoring device, the method comprising: connecting a first patient connector of a first patient lead to the patient, wherein the first patient lead is for monitoring a first of the at least two health indicators of the patient and includes a first lead interconnection feature that is configured to be connectable to and disconnectable from a second patient lead via a first interconnection feature of the first patient lead and a second lead interconnection feature of the second patient lead; connecting a second patient connector of the second patient lead to the patient, wherein the second patient lead is for monitoring a second of the at least two health indicators of the patient; connecting the first lead interconnection feature to the second lead interconnection feature or partially disconnecting the first interconnection feature from the second interconnection feature; connecting a first lead connector of the first lead and a second lead connector of the second lead to at least one monitoring device; and receiving, by the monitoring device, at least one of the two health indicators.

Clause 17: The method of any of the above clauses, wherein the first lead interconnection feature and the second lead interconnection feature comprise a magnetic interface.

Clause 18: The method of any of the above clauses, wherein the first lead interconnection feature comprises a receiving portion that is configured to selectively captively receive a protrusion of the second lead interconnection feature.

Clause 19: The method of any of the above clauses, wherein the first patient lead is for monitoring electrical activity of a patient's heart and the second patient lead is for monitoring a patients temperature.

Clause 20: The method of any of the above clauses, wherein the first patient lead further comprises a wire connecting the first patient connector to the first lead connector and the second patient lead further comprises a tube for providing a fluid path between the second patient connector to the at least one monitoring interface.

Clause 21: A method of assembling or reconstructing a multiparameter lead set, wherein the lead set comprises a first type of patient lead for monitoring a first health indicator of a patient and a second type of patient lead for monitoring a second health indicator of a patient that is connectable to and disconnectable from the first type of patient lead, wherein the first type of patient lead comprises a first patient connector and a first lead connector and the second type of patient lead comprises a second patient connector and a second lead connector, wherein the method of assembling or reconstructing comprises: selecting a plurality of leads for the lead set for assembling or reconstructing, wherein the plurality of leads comprises selecting one of the first type of patient lead and one of the second type of patient lead; disconnecting the one of the first type of patient lead and the one of the second type of patient lead if the one of the first type of patient lead and one of the second type of patient lead are not already separated; and sanitizing or sterilizing the one of the first type of patient lead and the one of the second type of lead.

Clause 22: The method of clause 21, further comprising packaging the one of the first type of patient lead and the second type of lead.

Clause 23: The method of any of the above clauses, wherein the method of assembling or reconstructing further comprises re-connecting the one of the first type of patient lead to the one of the second type of patient lead.

Clause 24: The method of any of the above clauses, wherein the first type of patient lead is for monitoring a heart electrical activity of a patient and the second type of patient lead is for monitoring a temperature of the patient.

Clause 25: The method of any of the above clause, wherein the first type of patient lead is for monitoring a heart electrical activity of a patient and the second type of patient lead is for monitoring a blood oxygen saturation of the patient.

Clause 26: A temperature sensing device comprising: a housing connected to or connectable to a first end of a cable for providing a temperature detection signal to a monitoring device; a temperature sensor within the housing, wherein the temperature sensor is configured to be in electrical communication with the cable; and a connection portion, wherein the connection portion is configured to connect to a heat conductive material body that is adherable to a patient's skin so that the heat conductive material body is in thermal communication with the temperature sensor.

Clause 27: The temperature sensing device of clause 26, wherein the temperature sensor placed in thermal communication with a patients skin when the connection portion of the temperature sensing device is connected to the heat conductive material body.

Clause 28: The temperature sensing device of any of the above clauses, wherein the wherein the heat conductive material body is attachable to a patient's body via a hydrogel, wherein the connection portion is configured to connect to a heat conductive material body that is adherable to a patient's body so that the heat conductive material body is in thermal communication with the temperature sensor.

Clause 29: The temperature sensing device of any of the above clauses, wherein the housing is connected to the cable and the cable further comprises a connection feature that extends along a length of the cable, wherein the connection feature is configured to be connected to or disconnected from a second cable.

Clause 30: The temperature sensing device of any of the above clauses, wherein the connection feature is a magnetic interface.

Clause 31: The temperature sensing device any of the above clause, wherein the connection feature comprises one of a receiving portion that is configured to selectively captively receive a protrusion of a second connection feature of the second cable or a protrusion configured be selectively captively received by a receiving portion of the second cable.

Clause 32: The temperature sensing device any of the above clauses, wherein the housing of the temperature sensing device is configured to rotate with respect to the heat conductive material body when the housing is connected to the heat conductive body and the heat conductive body is adhered to a patient's skin.

Clause 33: A heat conductive apparatus configured to be connected to a temperature sensing device housing, the heat conductive apparatus further comprising: a connection feature configured to be removably connected to temperature sensing device housing while allowing for rotational movement between the heat conductive apparatus and the temperature sensing device housing; a sensor contact portion configured to interface and provide a thermal path between a patient's skin and the sensor; an adhereable portion configured to adhere to a patient's skin and provide thermal communication between the patient's skin the sensor interface portion; and a release portion configured to be removably adhered to the adhereable portion.

Clause 34: The heat conductive apparatus of clause 33, wherein the adhereable portion and the sensor contact portion include a hydrogel, wherein the hydrogel provides the thermal communication between the patient's skin and the sensor.

Clause 35: A temperature sensing device comprising: a housing connected to or connectable to a first end of a cable for providing a temperature detection signal to a monitoring device; a temperature sensor within the housing, wherein the temperature sensor is configured to be in electrical communication with the cable; and a heat conductive material body that is adhereable to a patient's skin so that the heat conductive material body is in thermal communication with the temperature sensor.

Clause 36: The temperature sensing device of clause 35, wherein the temperature sensor is embedded within the heat conductive material body.

Clause 37: The temperature sensing device of any of the above clauses, wherein the housing further comprises a first insulating cover.

Clause 38: The temperature sensing device of any of the above clauses, wherein the housing further comprises a second insulating cover, wherein the second insulating cover is configured to provide thermal insulation to the heat conductive material body.

Clause 39: The temperature sensing device of any of the above clauses, wherein the housing further comprises an electrical connection portion configured to provide an electrical connection between the temperature sensor and the first end of the cable.

Clause 40: The temperature sensing device of any of the above clauses, wherein the electrical connection portion is connected to the first insulating cover and the second insulating cover.

Clause 41: The temperature sensing device of any of the above clauses, wherein the wherein the heat conductive material body is a hydrogel that is adhereable to the patient's skin.

Clause 42: The temperature sensing device of any of the above clauses. wherein the housing is disconnectably connected to the cable and the cable further comprises a lead interconnection feature that extends along a length of the cable, wherein the lead interconnection feature is configured to be connected to or disconnected from a second cable.

Clause 43: The temperature sensing device of any one of the above clauses, wherein the lead interconnection feature includes a magnetic interface.

Clause 44: The temperature sensing device of any of the above clauses, wherein the lead interconnection feature comprises one of a receiving portion that is configured to selectively captively receive a protrusion of a second lead interconnection feature of the second cable or a protrusion configured be selectively captively received by a receiving portion of the second cable.

Clause 45: A method of monitoring a patient temperature using a temperature detection device that is configured be in signal communication with a monitoring device, wherein the temperature detection device has a patient connection surface that is connectable to the patients skin, the method comprising: adhering a hydrogel heat conductive material body to a patient's skin, wherein the heat conductive material body is configured to be in thermal communication with a sensing portion of the temperature detection device; and connecting a lead to the monitoring device, wherein the lead provides signal communication between the sensing portion of the temperature detection device and the monitoring device.

Clause 46: A method of reconstructing a multiparameter lead set, wherein the lead set comprises a first type of patient lead for monitoring a first health indicator of a patient and a second type of lead for monitoring a second health indicator of a patient, wherein the first type of patient lead comprises a first patient connector and a first lead connector and the second type of patient lead comprises a second patient connector and a second lead connector, wherein the method of reconstructing comprises: applying a new adhesive media portion to the second patient connector, wherein the adhesive media portion comprises a patient contact surface configured to be placed in contact with a patient's skin.

Clause 47: The method of clause 47, wherein the first type of patient lead provides capability to monitor a heart electrical activity of a patient and the second type of patient lead provides capability to monitor a blood oxygen saturation of the patient.

Clause 48: The method of any of the above clauses, further comprising: removing an existing or used adhesive media portion before applying the adhesive media portion to the second patient connector.

Clause 49: The method of any of the above clauses, wherein at least one of the existing or used adhesive media portion and the adhesive media portion comprises a hydrogel that forms the patient contact surface.

Clause 50: The method any of the above clauses, wherein a release layer is emplaced on the patient contact surface of the hydrogel.

Clause 51: The method of any of the above clauses, wherein the hydrogel has a removable release layer covering the patient contact surface.

Clause 52: The method of any of the above clauses, wherein the hydrogel of the second patient connector is sealed or partially sealed within a low moisture vapor transmission pouch.

Clause 53: The method of any of the above clauses, wherein the multiparameter lead set is sealed or packaged in a pouch.

Clause 54: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 55: The method of any of the above clauses, wherein replacing the adhesive media portion further comprises: installing or replacing an engagement feature of the second patient connector and connecting an adhesive media portion engagement feature with the engagement feature.

Clause 56: The method of any of the above clauses, wherein when removal of an existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 57: The method of any of the above clauses, wherein the replacement engagement feature is receiveably engaged with a channel in the second patient connector.

Clause 58: The method of any of the above clauses, wherein the replacement engagement feature is molded or adhered to an inner wall of the second patient connector.

Clause 59: The method of any of the above clauses, wherein the adhesive media portion further comprises an emitter, a receiver, and a connection portion configured to provide signal communication between the emitter and receiver and the second type of patient lead via a second patient lead connection portion, wherein the connection portion and the second patient lead connection portion are configured to provide signal communication therebetween when the adhesive media portion engagement feature is engaged with the replacement engagement feature.

Clause 60: The method of any of the above clauses, wherein the second patient connector comprises an emitter portion and a receiver portion and wherein replacing the adhesive media portion comprises aligning an opening in the adhesive media portion with one of the emitter portion and a receiver portion so that the majority of the said one of the emitter portion and receiver portion is unobstructed by the adhesive media portion.

Clause 61: The method of any of the above clauses, wherein the adhesive media portion comprises a pressure sensitive adhesive, wherein the pressure sensitive adhesive forms at least a portion of the patient contact surface.

Clause 62: The method of any of the above clauses, wherein the pressure sensitive adhesive has a removable release layer at least partially covering the patient contact surface.

Clause 63: The method of any of the above clauses, wherein a release layer is applied to the patient contact surface of the pressure sensitive adhesive.

Clause 64: The method of any of the above clauses, wherein the pressure sensitive adhesive has a removable release layer covering the patient contact surface.

Clause 65: The method of any of the above clauses, wherein the hydrogel is applied to a flexible circuit of the second patient connector.

Clause 66: The method of any of the above clauses, wherein the pressure sensitive adhesive is applied to a flexible circuit of the second patient connector.

Clause 67: The method of any of the above clauses, wherein the first type of patient lead provides capability to monitor a heart electrical activity of a patient and the second type of patient lead provides capability to monitor a temperature of the patient.

Clause 68: The method of any of the above clauses, further comprising: removing an existing or used adhesive media portion before applying the adhesive media portion to the second patient connector.

Clause 69: The method of any of the above clauses, wherein at least one of the existing or used adhesive media portion and the adhesive media portion comprises a hydrogel that forms the patient contact surface.

Clause 70: The method of any of the above clauses, wherein a release layer is emplaced on the patient contact surface of the hydrogel.

Clause 71: The method of any one of the above clauses, wherein the hydrogel has a removable release layer covering the patient contact surface.

Clause 72: The method of any of the above clauses, wherein the hydrogel of the second patient connector is sealed or partially sealed within a low moisture vapor transmission pouch.

Clause 73: The method of any of the above clauses, wherein the multiparameter lead set is sealed or packaged in a pouch.

Clause 74: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 75: The method of any of the above clauses, wherein replacing the adhesive media portion further comprises: installing or replacing an engagement feature of the second patient connector and connecting an adhesive media portion engagement feature with the engagement feature.

Clause 76: The method of any of the above clauses, wherein when removal the existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 77: The method of any of the above clauses, wherein the replacement engagement feature is receiveably engaged with a channel in the second patient connector.

Clause 78: The method of any of the above clauses, wherein the replacement engagement feature is molded or adhered to an inner wall of the second patient connector.

Clause 79: The method of any of the above clauses, wherein the adhesive media portion further comprises thermistor, and a connection portion configured to provide signal communication between thermistor and the second type of patient lead via a second patient lead connection portion, wherein the connection portion and the second patient lead connection portion are configured to provide signal communication therebetween when the adhesive media portion engagement feature is engaged with the replacement engagement feature.

Clause 80: The method of any of the above clauses, wherein the second patient connector comprises a temperature sensor, wherein replacing the adhesive media portion comprises embedding the temperature sensor within an adhesive media within the adhesive media portion.

Clause 81: The method of any of the above clauses, wherein the temperature sensor is a thermistor.

Clause 82: The method of any of the above clauses, wherein the adhesive media portion comprises a pressure sensitive adhesive, wherein the pressure sensitive adhesive forms at least a portion of the patient contact surface.

Clause 83: The method of claim any of the above clauses, wherein the pressure sensitive adhesive has a removable release layer at least partially covering the patient contact surface.

Clause 84: The method of any of the above clauses, wherein a release layer is applied to the patient contact surface of the pressure sensitive adhesive.

Clause 85: The method of any of the above clauses, wherein the pressure sensitive adhesive has a removable release layer covering the patient contact surface.

Clause 86: A method of producing a multiparameter lead set, wherein the lead set comprises a first type of patient lead for monitoring a first health indicator of a patient and a second type of lead for monitoring a second health indicator of a patient, wherein the first type of patient lead comprises a first patient connector and a first lead connector and the second type of patient lead comprises a second patient connector and a second lead connector, wherein the method of producing comprises: applying an adhesive media portion to the second patient connector, wherein the adhesive media portion comprises a patient contact surface configured to be placed in contact with a patient's skin.

Clause 87: The method of clause 86, wherein the first type of patient lead provides capability to monitor a heart electrical activity of a patient and the second type of patient lead provides capability to monitor a blood oxygen saturation of the patient.

Clause 88: The method of any of the above clauses further comprising: applying the adhesive media portion to a flex circuit of the second patient connector; and connecting the second type of lead to the flex circuit.

Clause 89: The method of any of the above clauses, wherein the second type of lead set is connected to the flex circuit by soldering individual wires of the second type of lead to the flex circuit.

Clause 90: The method of any of the above clauses, wherein the second type of lead set is connected to the flex circuit by connecting a lead connector of the second type of lead to a flex circuit connector of the flex circuit.

Clause 91: The method of any of the above clauses, wherein the method further comprises applying a cover over the flex circuit and a portion of the second type of lead.

Clause 92: The method of any of the above clauses, wherein the method further comprises at least partially wrapping a portion of the cover around a portion of the second type of lead.

Clause 93: The method of any of the above clauses, wherein the cover is adhered to at least a portion of the flex circuit and the second type of lead.

Clause 94: The method of any of the above clauses, wherein the adhesive media portion is a hydrogel.

Clause 95: The method of any of the above clauses, wherein the hydrogel is applied and solidified to the second patient connector.

Clause 96: The method of any of the above clauses, wherein the hydrogel is at least partially contained by a release layer when solidified.

Clause 97: The method of any of the above clauses, wherein the adhesive media portion is a pressure sensitive adhesive.

Clause 98: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 99: The method of any of the above clauses, wherein the adhesive media portion further comprises an adhesive media portion engagement feature, and wherein applying the adhesive media portion to the second patient connector comprises engaging the adhesive media portion engagement feature with a patient connector engagement feature of the second patient connector.

Clause 100: The method of any of the above clauses, wherein the first type of patient lead provides capability to monitor a heart electrical activity of a patient and the second type of patient lead provides capability to monitor a temperature of the patient.

Clause 101: The method of any of the above clauses, further comprising: applying the adhesive media portion to a flex circuit of the second patient connector; and connecting the second type of lead to the flex circuit.

Clause 102: The method of any of the above clauses, wherein the second type of lead set is connected to the flex circuit by soldering individual wires of the second type of lead to the flex circuit.

Clause 103: The method of any of the above clauses, wherein the second type of lead set is connected to the flex circuit by connecting a lead connector of the second type of lead to a flex circuit connector of the flex circuit.

Clause 104: The method of any of the above clauses, wherein the method further comprises applying a cover over the flex circuit and a portion of the second type of lead.

Clause 105: The method of any of the above clauses, wherein the method further comprises at least partially wrapping a portion of the cover around a portion of the second type of lead.

Clause 106: The method of any of the above clauses, wherein the cover is adhered to at least a portion of the flex circuit and the second type of lead.

Clause 107: The method any of the above clauses, wherein the adhesive media portion is a hydrogel.

Clause 108: The method of claim any of the above clauses wherein the hydrogel is applied and solidified to the second patient connector with a temperature sensor of the second patient connector embedded therein.

Clause 109: The method of any of the above clauses, wherein the hydrogel is at least partially contained by the release layer when solidified.

Clause 110: The method of any of the above clauses, wherein the adhesive media portion is a pressure sensitive adhesive.

Clause 111: The method of any of the above clauses, wherein the multiparameter leadset is sealed or packaged in a pouch and disinfected via at least one of a gamma sterilization treatment, an ethylene oxide gas sterilization treatment, or a hydrogen peroxide gas sterilization treatment.

Clause 112: The method of any of the above clauses, wherein the adhesive media portion further comprises an adhesive media portion engagement feature, and wherein applying the adhesive media portion to the second patient connector comprises engaging the adhesive media portion engagement feature with a patient connector engagement feature of the second patient connector.

Clause 113: A method of reconstructing a multiparameter lead set, wherein the lead set comprises a first type of patient lead for monitoring a first health indicator of a patient and a second type of lead for monitoring a second health indicator of a patient, wherein the first type of patient lead comprises a first patient connector and a first lead connector and the second type of patient lead comprises a second patient connector and a second lead connector, wherein the first patient connector is reconstructed by at least one step selected from a group consisting of: cleaning, sanitizing or high level disinfecting, replacing an adhereable media portion, replacing the connector, replacing a component, replacing a cover, or inspecting or testing the first patient connector; wherein the second patient connector is reconstructed by a method other than one consisting of a cleaning step, sanitization step, or high level disinfection step.

Clause 114: The method of clause 113, wherein the method of reconstructing comprises: applying a new adhesive media portion to the second patient connector, wherein the adhesive media portion comprises a patient contact surface configured to be placed in contact with a patient's skin.

Clause 115: The method of any of the above clauses, wherein the first type of patient lead provides capability to monitor a heart electrical activity of a patient and the second type of patient lead provides capability to monitor a blood oxygen saturation of the patient.

Clause 116: The method of any of the above clauses, further comprising: removing an existing or used adhesive media portion before applying the adhesive media portion to the second patient connector.

Clause 117: The method of any of the above clauses, wherein at least one of the existing or used adhesive media portion and the adhesive media portion comprises a hydrogel that forms the patient contact surface.

Clause 118: The method of any of the above clauses, wherein a release layer is emplaced on the patient contact surface of the hydrogel.

Clause 119: The method of any of the above clauses, wherein the hydrogel has a removable release layer covering the patient contact surface.

Clause 120: The method of any of the above clauses, wherein the second patient connector is sealed or partially sealed within a low moisture vapor transmission pouch.

Clause 121: The method of any of the above clauses, wherein the multiparameter lead set is sealed or packaged in a pouch.

Clause 122: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 123: The method of any of the above clauses, wherein replacing the adhesive media portion further comprises: installing or replacing an engagement feature of the second patient connector and connecting an adhesive media portion engagement feature with the engagement feature.

Clause 124: The method of any of the above clauses, wherein when removal of an existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 126: The method of any of the above clauses, wherein the replacement engagement feature is receiveably engaged with a channel in the second patient connector.

Clause 127: The method of any of the above clauses, wherein the replacement engagement feature is molded or adhered to an inner wall of the second patient connector.

Clause 128: The method of any of the above clauses, wherein the adhesive media portion further comprises an emitter, a receiver, and a connection portion configured to provide signal communication between the emitter and receiver and the second type of patient lead via a second patient lead connection portion, wherein the connection portion and the second patient lead connection portion are configured to provide signal communication therebetween when the adhesive media portion engagement feature is engaged with the replacement engagement feature.

Clause 129: The method of any of the above clauses, wherein the second patient connector comprises an emitter portion and a receiver portion and wherein replacing the adhesive media portion comprises aligning an opening in the adhesive media portion with one of the emitter portion and a receiver portion so that the majority of the said one of the emitter portion and receiver portion is unobstructed by the adhesive media portion.

Clause 130: The method of any of the above clauses, wherein the adhesive media portion comprises a pressure sensitive adhesive, wherein the pressure sensitive adhesive forms at least a portion of the patient contact surface.

Clause 131: The method of any of the above clauses, wherein the pressure sensitive adhesive has a removable release layer at least partially covering the patient contact surface.

Clause 132: The method of any of the above clauses, wherein a release layer is applied to the patient contact surface of the pressure sensitive adhesive.

Clause 133: The method of any of the above clauses, wherein the pressure sensitive adhesive has a removable release layer covering the patient contact surface.

Clause 134: The method of any of the above clauses, wherein the hydrogel is applied to a flexible circuit of the second patient connector.

Clause 135: The method of any of the above clauses, wherein the pressure sensitive adhesive is applied to a flexible circuit of the second patient connector.

Clause 136: The method of any of the above clauses, wherein the first type of patient lead provides capability to monitor a heart electrical activity of a patient and the second type of patient lead provides capability to monitor a temperature of the patient.

Clause 137: The method of any of the above clauses, further comprising: removing an existing or used adhesive media portion before applying the adhesive media portion to the second patient connector.

Clause 138: The method of any of the above clauses, wherein at least one of the existing or used adhesive media portion and the adhesive media portion comprises a hydrogel that forms the patient contact surface.

Clause 139: The method of any of the above clauses, wherein a release layer is emplaced on the patient contact surface of the hydrogel.

Clause 140: The method of any of the above clauses, wherein the hydrogel has a removable release layer covering the patient contact surface.

Clause 141: The method of any of the above clauses, wherein the second patient connector is sealed or partially sealed within a low moisture vapor transmission pouch.

Clause 142: The method of any of the above clauses, wherein the multiparameter lead set is sealed or packaged in a pouch.

Clause 143: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 144: The method of any of the above clauses, wherein replacing the adhesive media portion further comprises: installing or replacing an engagement feature of the second patient connector and connecting an adhesive media portion engagement feature with the engagement feature.

Clause 145: The method of any of the above clauses, wherein when removal the existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 146: The method of any of the above clauses, wherein the replacement engagement feature is receiveably engaged with a channel in the second patient connector.

Clause 147: The method of any of the above clauses, wherein the replacement engagement feature is molded or adhered to an inner wall of the second patient connector.

Clause 148: The method of any of the above clauses, wherein the adhesive media portion further comprises thermistor, and a connection portion configured to provide signal communication between thermistor and the second type of patient lead via a second patient lead connection portion, wherein the connection portion and the second patient lead connection portion are configured to provide signal communication therebetween when the adhesive media portion engagement feature is engaged with the replacement engagement feature.

Clause 149: The method of any of the above clauses, wherein the second patient connector comprises a temperature sensor, wherein replacing the adhesive media portion comprises embedding the temperature sensor within an adhesive media within the adhesive media portion.

Clause 150: The method of any of the above clauses, wherein the temperature sensor is a thermistor.

Clause 151: The method of any of the above clauses, wherein the adhesive media portion comprises a pressure sensitive adhesive, wherein the pressure sensitive adhesive forms at least a portion of the patient contact surface.

Clause 152: The method of any of the above clauses, wherein the pressure sensitive adhesive has a removable release layer at least partially covering the patient contact surface.

Clause 152: The method of any of the above clauses, wherein a release layer is applied to the patient contact surface of the pressure sensitive adhesive.

Clause 153: The method of any of the above clauses, wherein the pressure sensitive adhesive has a removable release layer covering the patient contact surface.

Clause 154: A system for monitoring at least two patient health indicators, the system comprising: a monitoring device; a multiparameter lead set configured to provide a first patient heath indicator signal and a second patient health indicator signal, comprising: a first patient lead for monitoring a first health indicator of a patient, the first patient lead extending between a first lead distal end and a first lead proximal end, wherein the first patient lead further comprises: a first patient connector at the first lead distal end that is configured to be attached to a patient for monitoring the first health indicator of the patient; a first lead connector at the first lead proximal end, wherein the multiparameter lead set further comprises: a second patient lead for monitoring a second health indicator of the patient, the second patient lead extending between a second lead distal end and a second lead proximal end, wherein the second patient lead further comprises: a second patient connector at the second lead distal end that is configured to be attached to the patient for monitoring the second health indicator of the patient; a second lead connector at the second lead proximal end; and wherein the first lead connector and the second lead connector are configured to be selectively connected to at least one monitoring device.

Clause 155: The system of clause 154, wherein the first patient lead further comprises a first lead interconnection feature and a second patient lead further comprises a second lead interconnection feature, wherein the first lead interconnection feature and the second lead interconnection feature are interconnectable to removably connect a first portion of the first patient lead to a second portion of the second patient lead.

Clause 156: The system of any of the above clauses, wherein the first patient lead comprises a first wire extending between the first patient connector at the first lead distal end and the first lead connector at the first lead proximal end and the second patient lead comprises a second wire extending between the second patient connector at the second lead distal end and the second lead connector at the second lead proximal end.

Clause 157: The system of any of the above clauses, wherein the first lead interconnection feature is configured so that a first section of the first patient lead that extends along a length of the first wire between the first lead distal end and the first lead proximal end is connectable and removable from a second section of the second patient lead via the second connection feature that extends along an axial direction of extension of the second wire between the second lead distal end and the second lead proximal end.

Clause 158: The system of any of the above clauses, wherein the first lead interconnection feature and the second lead interconnection feature comprise a magnetic interface.

Clause 159: The system of any of the above clauses, wherein the first lead interconnection feature comprises a receiving portion that is configured to selectively captively receive a protrusion of the second lead interconnection feature.

Clause 160: The system of any of the above clauses, wherein the first lead interconnection feature is a first section of the first lead connector and wherein the first lead connector is connectable to and disconnectable from the second lead connector via the second lead interconnection feature at the second section of the second lead connector.

Clause 161: The system of any of the above clauses, wherein when the first lead interconnection feature of the first lead connector and the second lead interconnection feature of the second lead connector are connectable to one another to form a single multiparameter connector, wherein the multiparameter connector is selectively connectable to a multiparameter input device that is selectively connectable to the at least one monitoring device.

Clause 162: The system of any of the above clauses, wherein at least one of the first lead connector and the second lead connector include a patterned terminal that is configured to be received by a respective patterned terminal receiving portion at the multiparameter input device.

Clause 163: The system of any of the above clauses, wherein the patterned terminal provides at least one of a structural rigidity to the patterned terminal or shielding of an individual lead of the patterned terminal from unintended contact.

Clause 164: The system of any of the above clauses, wherein the first patient lead comprises a wire extending between the first patient connector at the first lead distal end and the first lead connector at the first lead proximal end and the second patient lead comprises a tube extending between and providing fluid communication between the second patient connector at the second lead distal end and the second lead connector at the second lead proximal end.

Clause 165: The system of any of the above clauses, wherein the first lead interconnection feature is configured so that a first section of the first patient lead that extends along an axial direction of extension of the wire between the first lead distal end and the first lead proximal end is connectable to and disconnectable from a second section of the second patient lead via the second lead interconnection feature that extends along an axial direction of extension of the tube between the second lead distal end and the second lead proximal end.

Clause 166: The system of any of the above clauses, wherein the first interconnection feature and the second interconnection feature comprise a magnetic interface.

Clause 167: The system of any of the above clauses wherein the first lead interconnection feature comprises a receiving portion that is configured to selectively captively receive a protrusion of the second lead interconnection feature.

Clause 168: The system of any of the above clauses, wherein the first lead interconnection feature is a first section of the first lead connector and wherein the first lead connector is connectable to and disconnectable from the second lead connector via the second lead interconnection feature at the second section of the second lead connector.

Clause 169: The system of any of the above clauses, wherein when the first lead interconnection feature of the first lead connector and the second lead interconnection feature of the second lead connector are interconnectable to form a single multiparameter connector, wherein the multiparameter connector is selectively connectable to a multiparameter input device that is selectively connectable to the at least one monitoring device.

Clause 170: The system of any of the above clauses, wherein the second patient connector is a patient temperature sensor comprising: a housing connected at or connectable to the second lead distal end and providing a temperature detection signal to the monitoring device; a temperature sensor within the housing, wherein the temperature sensor is configured to be in electrical communication with the monitoring device; and a heat conductive material body that is adhereable to a patient's skin so that the heat conductive material body is in thermal communication with the temperature sensor.

Clause 171: The system of any of the above clauses, wherein the heat conductive material body comprises a hydrogel.

Clause 172: The system of any of the above clauses, wherein the temperature sensor is embedded within the heat conductive material body.

Clause 173: The system of any of the above clauses, wherein the first type of patient lead provides capability to monitor a heart electrical activity of a patient.

Clause 174: The system of any of the above clauses, wherein the second patient lead comprises at least five patient connectors for monitoring heart electrical activity of a patient.

Clause 176: The system of any of the above clauses, wherein the heat conducive material body is rotatable with respect to the housing.

Clause 177: The system of any of the above clauses, further comprising a lubricant between at least a portion of the heat conductive material body and the housing.

Clause 178: The system of any of the above clauses, wherein the temperature sensor further comprises a rotatable electrical connector connecting the thermistor to the temperature sensor housing.

Clause 179: The system of any of the above clauses, wherein the temperature sensor further comprises a first temperature sensor body electrical terminal and a second temperature sensor body electrical terminal, wherein the first temperature sensor body electric terminal is configured to contact a first heat conductive body electrical terminal and the second temperature sensor electrical terminal is configured to contact a second heat conductive body electrical terminal.

Clause 180: The system of any of the above clauses, wherein the temperature sensor further comprises a well body configured to contain the hydrogel therein.

Clause 181: The system of any of the above clauses, wherein the second patient connector is a blood oxygen saturation sensor comprising: an oxygen saturation sensor body at or connectable to the second lead distal end and providing an blood oxygen saturation signal to the monitoring device; wherein the oxygen saturation sensor has an emission portion and a receiving portion that are in electrical communication with the cable; and an adhereable material body that is adhereable to a patient's skin, wherein emplacing the adhereable material body on a patients skin locates the emission portion and receiving portion with respect to the patient's skin.

Clause 182: The system of any of the above clauses, wherein the adhereable material body is configured to be re-adhereable after removal form a patients skin.

Clause 183: The system of any of the above clauses, wherein the adhereable material body comprises a hydrogel.

Clause 184: The system of any of the above clauses, wherein the adhereable material body is rotatable with respect to the oxygen saturation sensor body.

Clause 185: The system of any of the above clauses, wherein the adhereable material body has an opening corresponding to the emission portion and the receiving portion of the oxygen saturation sensor.

Clause 186: The system of any of the above clauses, wherein the first type of patient lead provides capability to monitor a heart electrical activity of a patient.

Clause 187: The system of any of the above clauses, wherein the second patient lead comprises at least five patient connectors for monitoring heart electrical activity of a patient.

Clause 188: The system of any of the above clauses, wherein the oxygen saturation sensor further comprises a rotatable electrical connector connecting the emission portion and the receiving portion to the to the oxygen saturation sensor body.

Clause 189: The system of any of the above clauses, wherein the oxygen saturation sensor further comprises a well body configured to contain the hydrogel therein.

Clause 190: A method of reconstructing a multiparameter lead set, wherein the lead set comprises a first type of patient lead for monitoring a first health indicator of a patient and a second type of lead for monitoring a second health indicator of a patient, wherein the first type of patient lead comprises a first patient connector and a first lead connector and the second type of patient lead comprises a second patient connector and a second lead connector, wherein the first patient connector is reprocessed and the second patient connector is reconstructed.

Clause 191: The method of clause 190, wherein reprocessing comprises at least one step selected from a group consisting of: cleaning, sanitizing or high level disinfecting, replacing an adhereable media portion, replacing the connector, replacing a component, replacing a cover, or inspecting or testing the first patient connector.

Clause 192: The method of any of the above clauses, wherein the method of reconstructing the second patient connector comprises at least one from a group consisting of: replacing an adhereable media portion, replacing the connector, replacing a component, or replacing a cover.

Clause 193: The method of any of the above clauses, wherein the method of reconstructing comprises: applying a new adhesive media portion to the second patient connector, wherein the adhesive media portion comprises a patient contact surface configured to be placed in contact with a patient's skin.

Clause 194: The method of any of the above clauses, wherein the first type of patient lead provides capability to monitor a heart electrical activity of a patient and the second type of patient lead provides capability to monitor a blood oxygen saturation of the patient.

Clause 195: The method of any of the above clauses, further comprising: removing an existing or used adhesive media portion before applying the adhesive media portion to the second patient connector.

Clause 196: The method of any of the above clauses, wherein at least one of the existing or used adhesive media portion and the adhesive media portion comprises a hydrogel that forms the patient contact surface.

Clause 197: The method of any of the above clauses, wherein a release layer is emplaced on the patient contact surface of the hydrogel.

Clause 198: The method of any of the above clauses, wherein the hydrogel has a removable release layer covering the patient contact surface.

Clause 199: The method of any of the above clauses, wherein the second patient connector is sealed or partially sealed within a low moisture vapor transmission pouch.

Clause 200: The method of any of the above clauses, wherein the multiparameter lead set is sealed or packaged in a pouch.

Clause 201: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 202: The method of any of the above clauses, wherein replacing the adhesive media portion further comprises: installing or replacing an engagement feature of the second patient connector and connecting an adhesive media portion engagement feature with the engagement feature.

Clause 203: The method of any of the above clauses, wherein when removal of an existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 204: The method of any of the above clauses, wherein the replacement engagement feature is receiveably engaged with a channel in the second patient connector.

Clause 205: The method of any of the above clauses, wherein the replacement engagement feature is molded or adhered to an inner wall of the second patient connector.

Clause 206: The method of any of the above clauses, wherein the adhesive media portion further comprises an emitter, a receiver, and a connection portion configured to provide signal communication between the emitter and receiver and the second type of patient lead via a second patient lead connection portion, wherein the connection portion and the second patient lead connection portion are configured to provide signal communication therebetween when the adhesive media portion engagement feature is engaged with the replacement engagement feature.

Clause 207: The method of any of the above clauses, wherein the second patient connector comprises an emitter portion and a receiver portion and wherein replacing the adhesive media portion comprises aligning an opening in the adhesive media portion with one of the emitter portion and a receiver portion so that the majority of the said one of the emitter portion and receiver portion is unobstructed by the adhesive media portion.

Clause 208: The method of any of the above clauses, wherein the adhesive media portion comprises a pressure sensitive adhesive, wherein the pressure sensitive adhesive forms at least a portion of the patient contact surface.

Clause 209: The method of any of the above clauses, wherein the pressure sensitive adhesive has a removable release layer at least partially covering the patient contact surface:

Clause 210: The method of any of the above clauses, wherein a release layer is applied to the patient contact surface of the pressure sensitive adhesive.

Clause 211: The method of any of the above clauses, wherein the pressure sensitive adhesive has a removable release layer covering the patient contact surface.

Clause 212: The method of any of the above clauses, wherein the hydrogel is applied to a flexible circuit of the second patient connector.

Clause 213: The method of any of the above clauses, wherein the pressure sensitive adhesive is applied to a flexible circuit of the second patient connector.

Clause 214: The method of any of the above clauses, wherein the first type of patient lead provides capability to monitor a heart electrical activity of a patient and the second type of patient lead provides capability to monitor a temperature of the patient.

Clause 215: The method of any of the above clauses, further comprising: removing an existing or used adhesive media portion before applying the adhesive media portion to the second patient connector.

Clause 216: The method of any of the above clauses, wherein at least one of the existing or used adhesive media portion and the adhesive media portion comprises a hydrogel that forms the patient contact surface.

Clause 217: The method of any of the above clauses, wherein a release layer is emplaced on the patient contact surface of the hydrogel:

Clause 218: The method of any of the above clauses, wherein the hydrogel has a removable release layer covering the patient contact surface.

Clause 219: The method of any of the above clauses, wherein the second patient connector is sealed or partially sealed within a low moisture vapor transmission pouch.

Clause 220: The method of any of the above clauses, wherein the multiparameter lead set is sealed or packaged in a pouch.

Clause 221: The method of any of the above clauses, wherein the multiparameter lead set is sealed or packaged in a pouch and disinfected via at least one of a gamma sterilization treatment, an ethylene oxide gas sterilization treatment, or a hydrogen peroxide gas sterilization treatment.

Clause 222: The method of any of the above clauses, wherein replacing the adhesive media portion further comprises: installing or replacing an engagement feature of the second patient connector and connecting an adhesive media portion engagement feature with the engagement feature.

Clause 223: The method of any of the above clauses, wherein when removal the existing or used adhesive media portion causes the removal or breakage of a patient connector engagement feature, a replacement engagement feature is installed into the second patient connector, and wherein the method further comprises: engaging an adhesive media portion engagement feature with the replacement engagement feature.

Clause 224: The method of any of the above clauses, wherein the replacement engagement feature is receiveably engaged with a channel in the second patient connector.

Clause 225: The method of any of the above clauses, wherein the replacement engagement feature is molded or adhered to an inner wall of the second patient connector.

Clause 226: The method of any of the above clauses, wherein the adhesive media portion further comprises thermistor, and a connection portion configured to provide signal communication between thermistor and the second type of patient lead via a second patient lead connection portion, wherein the connection portion and the second patient lead connection portion are configured to provide signal communication therebetween when the adhesive media portion engagement feature is engaged with the replacement engagement feature.

Clause 227: The method of any of the above clauses, wherein the second patient connector comprises a temperature sensor, wherein replacing the adhesive media portion comprises embedding the temperature sensor within an adhesive media within the adhesive media portion.

Clause 228: The method of any of the above clauses, wherein the temperature sensor is a thermistor.

Clause 229: The method of any of the above clauses, wherein the adhesive media portion comprises a pressure sensitive adhesive, wherein the pressure sensitive adhesive forms at least a portion of the patient contact surface.

Clause 230: The method of any of the above clauses, wherein the pressure sensitive adhesive has a removable release layer at least partially covering the patient contact surface.

Clause 231: The method of any of the above clauses, wherein a release layer is applied to the patient contact surface of the pressure sensitive adhesive.

Clause 232: The method of any of the above clauses, wherein the pressure sensitive adhesive has a removable release layer covering the patient contact surface.

Clause 233: The method of any of the above clauses, wherein the second patient connector is reprocessed by at least one step selected from a group consisting of: a cleaning step, a sanitization step, or a high level disinfection step.

What is claimed is:

1. A multiparameter leadset with a single patient connector having a plurality of monitoring contacts and configured to interface with a monitoring device for monitoring a plurality of health indicators of a patient, the multiparameter leadset comprising:

an electrocardiogram (ECG) monitoring patient lead for electrocardiogram (ECG) monitoring, the electrocardiogram (ECG) monitoring patient lead extending between a first lead distal end and a first lead proximal end, wherein the first lead distal end comprises a plurality of ECG leads that are configured to be attached to the patient, and the first lead proximal end includes at least a first monitoring contact;

a second monitoring patient lead, wherein the second monitoring patient lead is associated with a second health indicator of the patient with a second monitoring contact at a second lead proximal end and a second health indicator connector that is configured to be connected to a second health indicator monitoring sensor, wherein the second health indicator of the patient is associated with a health indicator of the plurality of health indicators independent from the electrocardiogram (ECG) monitoring patient lead; and a third monitoring patient lead, wherein the third monitoring patient lead is associated with a third health indicator of the patient with a third monitoring contact at a third lead proximal end and a third health indictor connector that is configured to be connected to a third health indicator monitoring sensor, wherein the third health indicator of the patient is associated with a health indicator of the plurality of health indicators independent from the electrocardiogram (ECG) monitoring and the second health indicator of the patient, wherein the single patient connector comprises at least one of a flat style connector, a printed circuit board (PCB) card edge, a flat style connector, or a PCB receiving input device interface with the first monitoring contact, the second monitoring contact, and the third monitoring contact thereon, and wherein the single patient connector is configured to interface with the monitoring device through the single patient connector which connects to the monitoring device through a multiparameter input device, wherein the first monitoring contact, the second monitoring contact, and the third monitoring contact interface at a solo port with the single patient connector, and provide combined monitoring based on ECG, the second health indicator, and the third health indicator, by providing continuity or signal communication with the monitoring device when the patient connector is connected to the multiparameter input device, wherein the multiparameter leadset further comprises a first lead interconnection feature of the second monitoring patient lead and a second lead interconnection feature of the third monitoring patient lead, the first lead interconnection feature and the second lead interconnection feature being interconnectable to removably connect a first portion of the second monitoring patient lead to a second portion of the third monitoring patient lead so that at least the second and third monitoring patient leads are selectively connectable to and disconnectable from each other, at the first and second lead interconnection features, such that the single patient connector remains connected to the monitoring device and maintains signal communication for each of the ECG monitoring patient lead, the second monitoring patient lead, and the third monitoring patient lead that remains connected to the single patient connector.

2. The multiparameter leadset of claim 1, wherein the second health indicator is the patient's blood oxygen saturation.

3. The multiparameter leadset of claim 2, wherein the second health indicator connector is configured to be connected to a patient blood oxygen monitoring sensor.

4. The multiparameter leadset of claim 2, wherein the third health indicator connector is configured to be connected to a patient temperature monitoring sensor.

5. The multiparameter leadset of claim 2, wherein the second health indicator connector and the third health indicator connector are configured to be removably connected to one another via the interconnection features, the interconnection features each further comprising:

a received portion; and a receiving portion configured to removeably receive the received portion.

6. The multiparameter leadset of claim 5, wherein the receiving portion is configured to captively receive and engage with the received portion.

7. The multiparameter leadset of claim 1, wherein the third health indicator is the patient's temperature.

8. The multiparameter leadset of claim 1, further comprising an interconnection member, wherein the ECG patient lead, second patient lead, and third patient lead are configured to be separated or re-joined via the interconnection member.

9. The multiparameter leadset of claim 8, wherein the interconnection member comprises the interconnection features that extend along a length the ECG patient lead, the second patient lead, and the third patient lead.

10. The multiparameter leadset of claim 1, wherein the single patient connector comprises:

a single flat style connector or PCB with the first monitoring contact, the second monitoring contact, wherein the second monitoring contact provides signal communication with the second health indicator connector, and the third monitoring contact, wherein the third monitoring contact provides signal communication with the third health indicator connector.

11. The multiparameter leadset of claim 1, wherein the ECG patient lead comprises at least one first wire extending between the single patient connector at the first lead distal end and the first monitoring contact at the first lead proximal end, the second patient lead comprises at least one second wire extending between the single patient connector at a second patient lead distal end and the second monitoring contact at the second patient lead proximal end, and the third patient lead comprises at least one third wire extending between the third patient connector at a third patient lead distal end and the third monitoring contact at the third patient lead proximal end.

12. The multiparameter leadset of claim 11, wherein the at least one first wire, at least one second wire and at least one third wire are connected along at least a portion of their lengths thereof to form a connected series of wires.

13. The multiparameter leadset of claim 12, wherein the at least one first wire, at least one second wire, and at least one third wire are connectable to and disconnectable from one another along the portion of their lengths.

14. The multiparameter leadset of claim 1, wherein the plurality of ECG leads comprises at least one of three electrode connectors, five electrode connectors, six electrode connectors, ten electrode connectors, or twelve electrode connectors, wherein each of the electrode connectors are configured to be connected to an electrode that is configured to be emplaced on a patient's skin.

15. The multiparameter leadset of claim 1, wherein the single patient connector is configured to plug into a multiparameter input device connector at a distal end of the multiparameter input device, wherein the multiparameter input device further comprises one or more monitoring connectors at a proximal end for providing continuity with one or more monitoring devices for ECG monitoring, monitoring the second health indicator, and monitoring the third health indicator.

16. The multiparameter leadset of claim 1, wherein the single patient connector is configured to plug into a multiparameter input device connector at a distal end of the multiparameter input device.

17. The multiparameter leadset of claim 1, wherein the plurality of ECG leads are configured to be removeably connected to one or more electrode patches emplaced on a patient's skin.

18. The multiparameter leadset of claim 1, further comprising a fourth monitoring patient lead, wherein the fourth monitoring patient lead is associated with monitoring a patient's blood pressure.

19. The multiparameter leadset of claim 18, wherein the fourth patient lead comprises a fourth health indicator connector, wherein the fourth health indicator connector is configured to connect to a non-invasive blood pressure monitoring device.

* * * * *